(12) United States Patent
Mathias et al.

(10) Patent No.: US 8,076,356 B2
(45) Date of Patent: Dec. 13, 2011

(54) TRIAZOLOPYRIDINYLSULFANYL DERIVATIVES AS P38 MAP KINASE INHIBITORS

(75) Inventors: John Paul Mathias, Sandwich (GB); David Simon Millan, Sandwich (GB); Russell Andrew Lewthwaite, Sandwich (GB); Christopher Phillips, Sandwich (GB)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 12/371,719

(22) Filed: Feb. 16, 2009

(65) Prior Publication Data

US 2009/0239899 A1   Sep. 24, 2009

Related U.S. Application Data

(63) Continuation of application No. 11/201,823, filed on Aug. 10, 2005, now Pat. No. 7,511,057.

(60) Provisional application No. 60/691,559, filed on Jun. 17, 2005, provisional application No. 60/606,228, filed on Aug. 31, 2004, provisional application No. 60/606,256, filed on Aug. 31, 2004.

(30) Foreign Application Priority Data

Aug. 12, 2004   (GB) ................................ 0418015.4

(51) Int. Cl.
*A61K 31/437* (2006.01)
*A61P 11/06* (2006.01)
(52) U.S. Cl. ........................................ 514/303
(58) Field of Classification Search .................... 514/303
See application file for complete search history.

(56) References Cited

U.S. PATENT DOCUMENTS

| | | | | |
|---|---|---|---|---|
| 3,050,525 | A | 8/1962 | Bicking ........................ | 260/296 |
| 3,754,887 | A | 8/1973 | Brantley .......................... | 71/74 |
| 4,183,854 | A | 1/1980 | Crossley ........................ | 548/195 |
| 6,043,246 | A | 3/2000 | Fukami et al. ................ | 514/252 |
| 6,106,864 | A | 8/2000 | Dolan et al. ................... | 424/488 |
| 6,339,099 | B1 | 1/2002 | Lam et al. ..................... | 514/378 |
| 6,387,900 | B1 | 5/2002 | Pevarello et al. .......... | 514/236.5 |
| 6,514,977 | B1 | 2/2003 | Anantanarayan et al. ........................ | 514/254.01 |
| 6,525,046 | B1 | 2/2003 | Cirillo et al. ................ | 514/227.8 |
| 6,617,324 | B1 | 9/2003 | Naraian et al. .............. | 514/235.8 |
| 2002/0025963 | A1 | 2/2002 | Lam et al. ..................... | 514/249 |
| 2003/0069258 | A1 | 4/2003 | Lam et al. ................... | 514/260.1 |
| 2003/0134843 | A1 | 7/2003 | Lubisch et al. .......... | 514/217.07 |
| 2003/0195221 | A1 | 10/2003 | Cai et al. ..................... | 514/258.1 |
| 2004/0063772 | A1 | 4/2004 | Quan et al. ..................... | 514/406 |
| 2004/0176325 | A1 | 9/2004 | Munson et al. ................. | 514/81 |
| 2004/0180896 | A1 | 9/2004 | Munson et al. ................ | 514/248 |
| 2004/0192653 | A1 | 9/2004 | Munson et al. ................. | 514/81 |
| 2005/0203072 | A1 | 9/2005 | Rudolph et al. ............. | 514/171 |

FOREIGN PATENT DOCUMENTS

| | | |
|---|---|---|
| EP | 1291345 | 3/2003 |
| JP | 2001247569 | 9/2001 |
| WO | WO 9111172 | 8/1991 |
| WO | WO 9402518 | 2/1994 |
| WO | WO 9625157 | 8/1996 |
| WO | WO 9740028 | 10/1997 |
| WO | WO 9852937 | 11/1998 |
| WO | WO 9852940 | 11/1998 |
| WO | WO 9852941 | 11/1998 |
| WO | WO 9855148 | 12/1998 |
| WO | WO 9932106 | 7/1999 |
| WO | WO 9958523 | 11/1999 |
| WO | WO 0005999 | 2/2000 |
| WO | WO 0031063 | 6/2000 |
| WO | WO 0031065 | 6/2000 |
| WO | WO 0035298 | 6/2000 |
| WO | WO 0040243 | 7/2000 |
| WO | WO 0043384 | 7/2000 |
| WO | WO 0157038 | 8/2001 |
| WO | WO 02072579 | 9/2002 |

(Continued)

OTHER PUBLICATIONS

Ma N et al., Zhonghua nei ke za zhi [Chinese journal of internal medicine], (Aug. 1999) vol. 38, No. 8, pp. 523-526.*
Hodge et al., Clinical and experimental immunology, 2007, vol. 150, No. 1, pp. 22-29.*
Toghe et al., Eur. J. Immunol. (2007), vol. 37, pp. 768-779.*
Russo et al., Clinical Science (2005), vol. 109, pp. 135-142.*
Yasuda et al., Respiratory Medicine (1998), vol. 92, pp. 993-999.*
Zhang Jinnoug et al., Journal of Huazhong University of Science and technology (2007), vol. 27(5), pp. 505-507.*
Escott et al., British journal of Pharmacology (2000), vol. 131, pp. 173-176.*

(Continued)

*Primary Examiner* — D M Seaman
*Assistant Examiner* — Niloofar Rahmani
(74) *Attorney, Agent, or Firm* — A. David Joran; John A. Wichtowski; Robert T. Ronau

(57) ABSTRACT

A compound of formula (I), or a pharmaceutical acceptable salt and/or solvate (including hydrate) thereof;

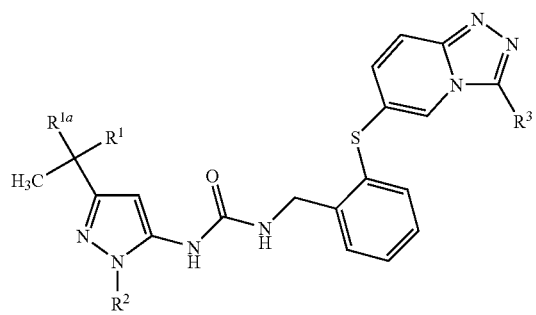

Figure 1:
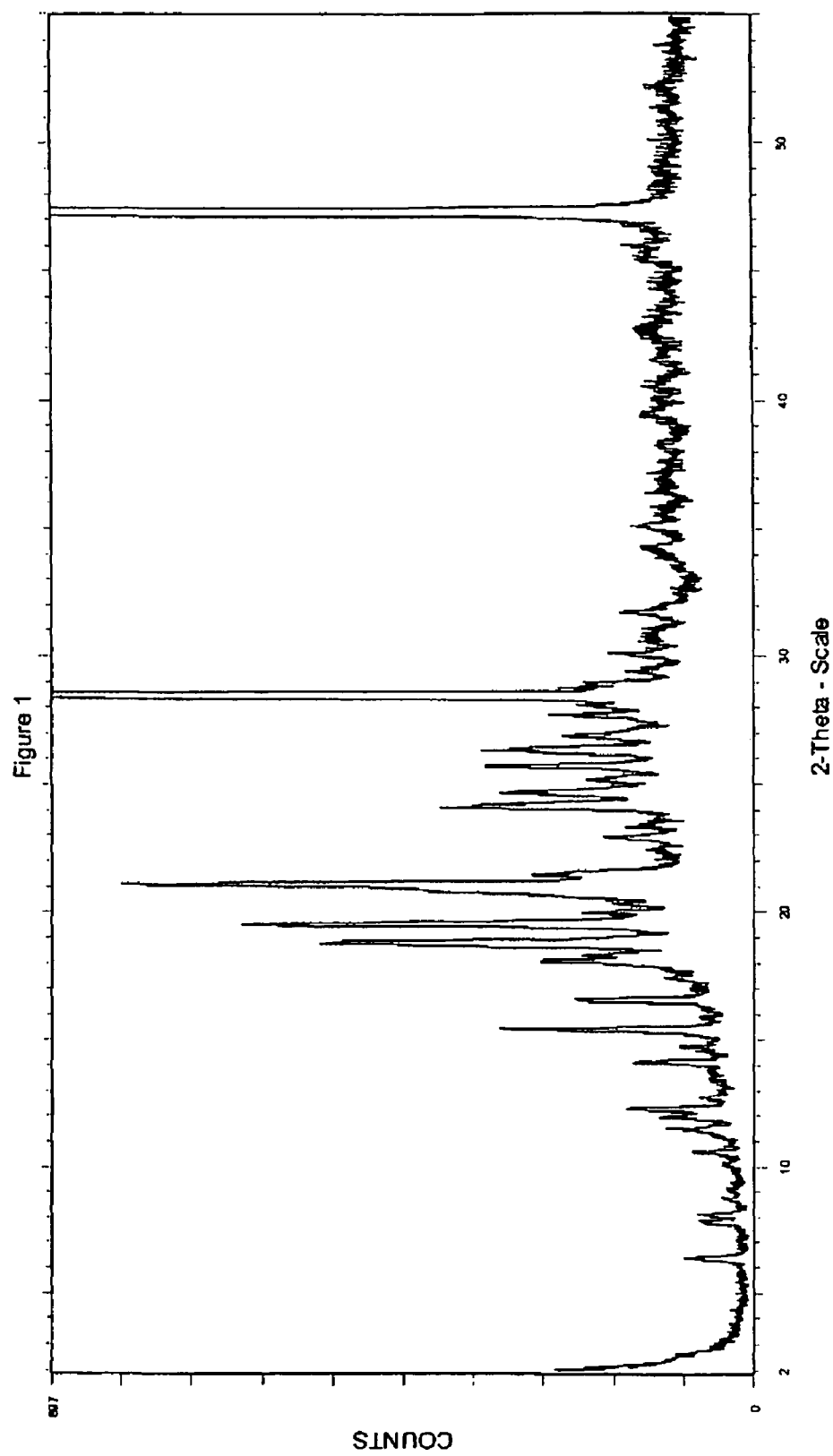
Figure 2:
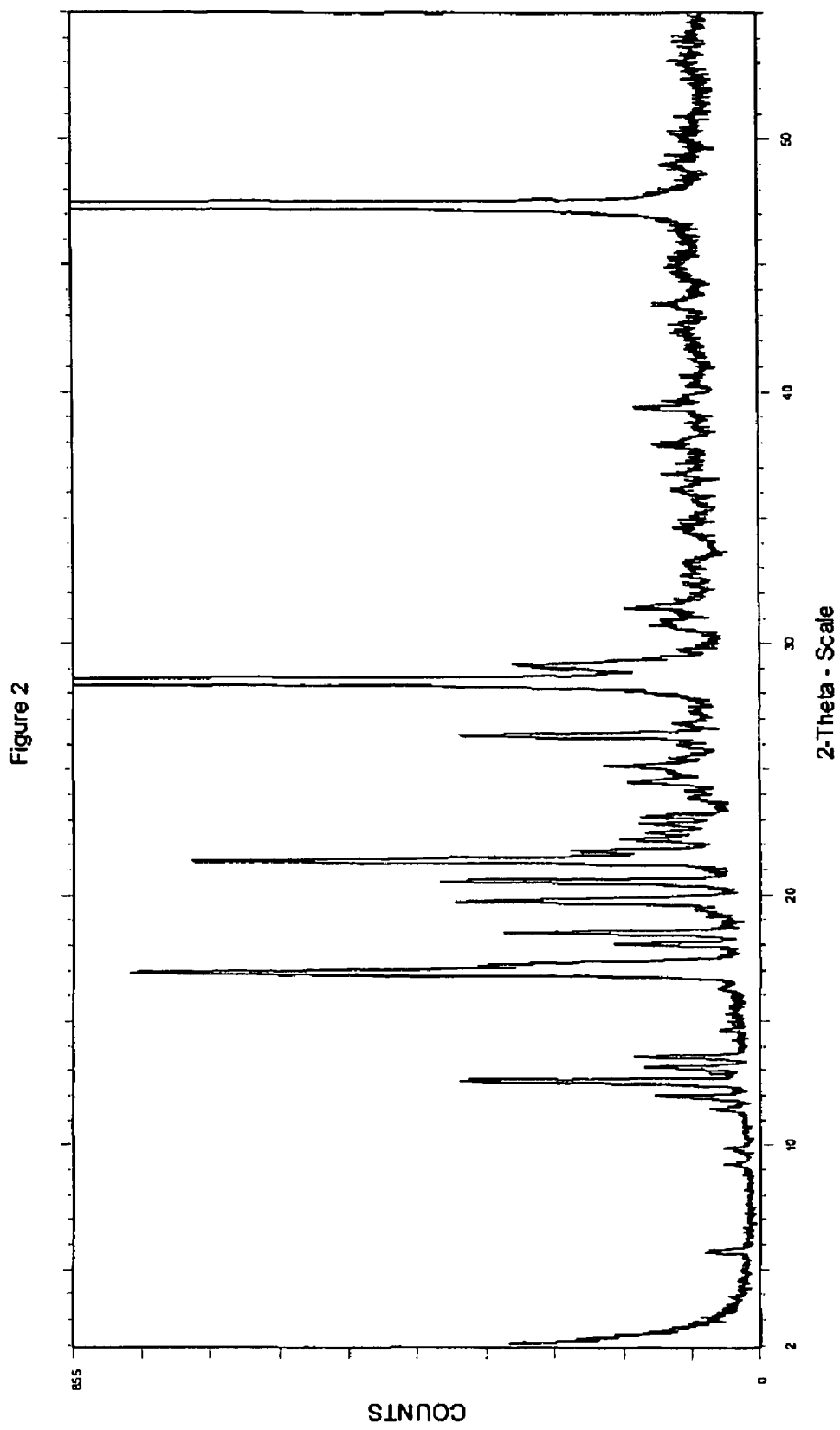
Figure 3:
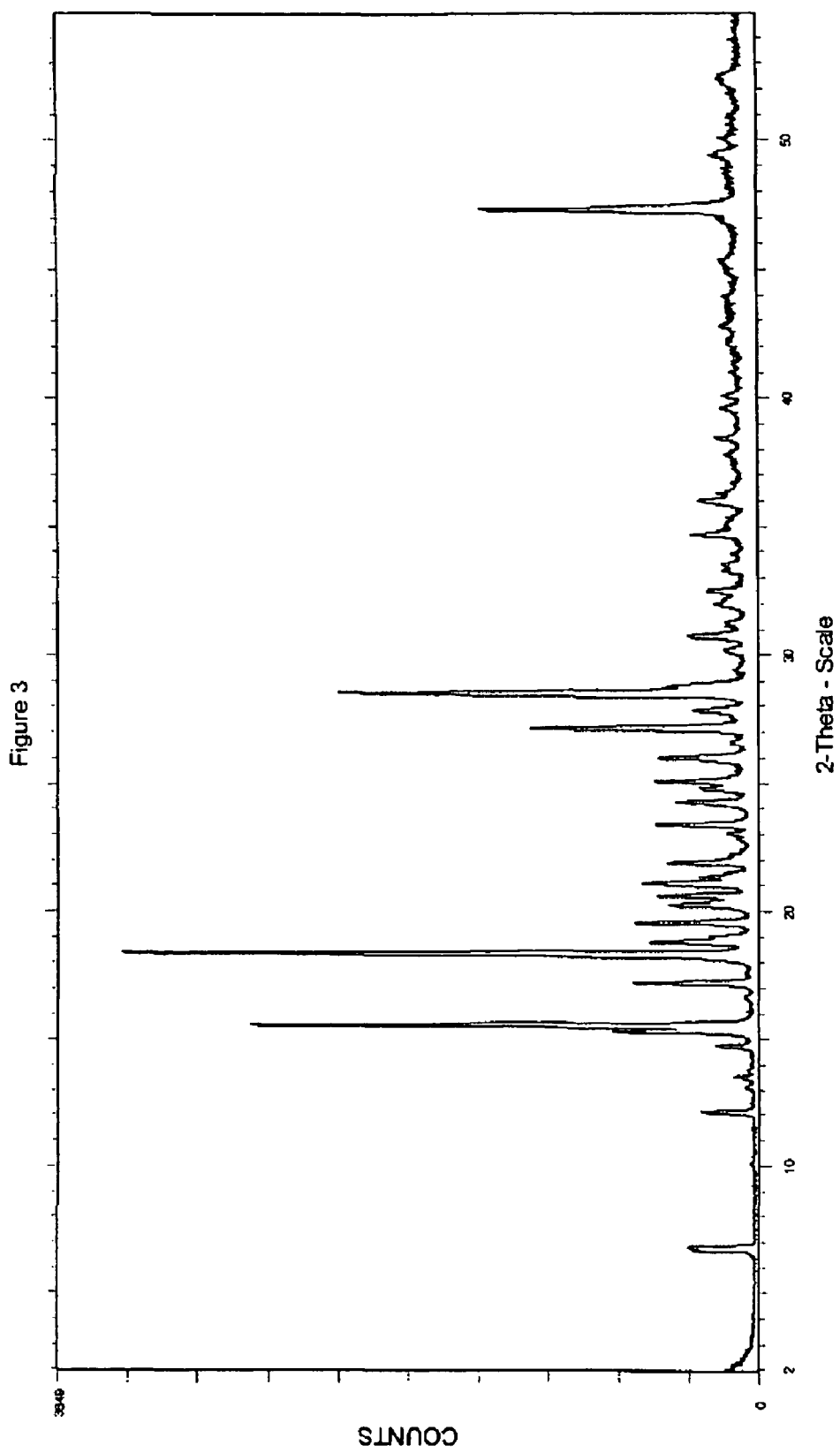
Figure 4:
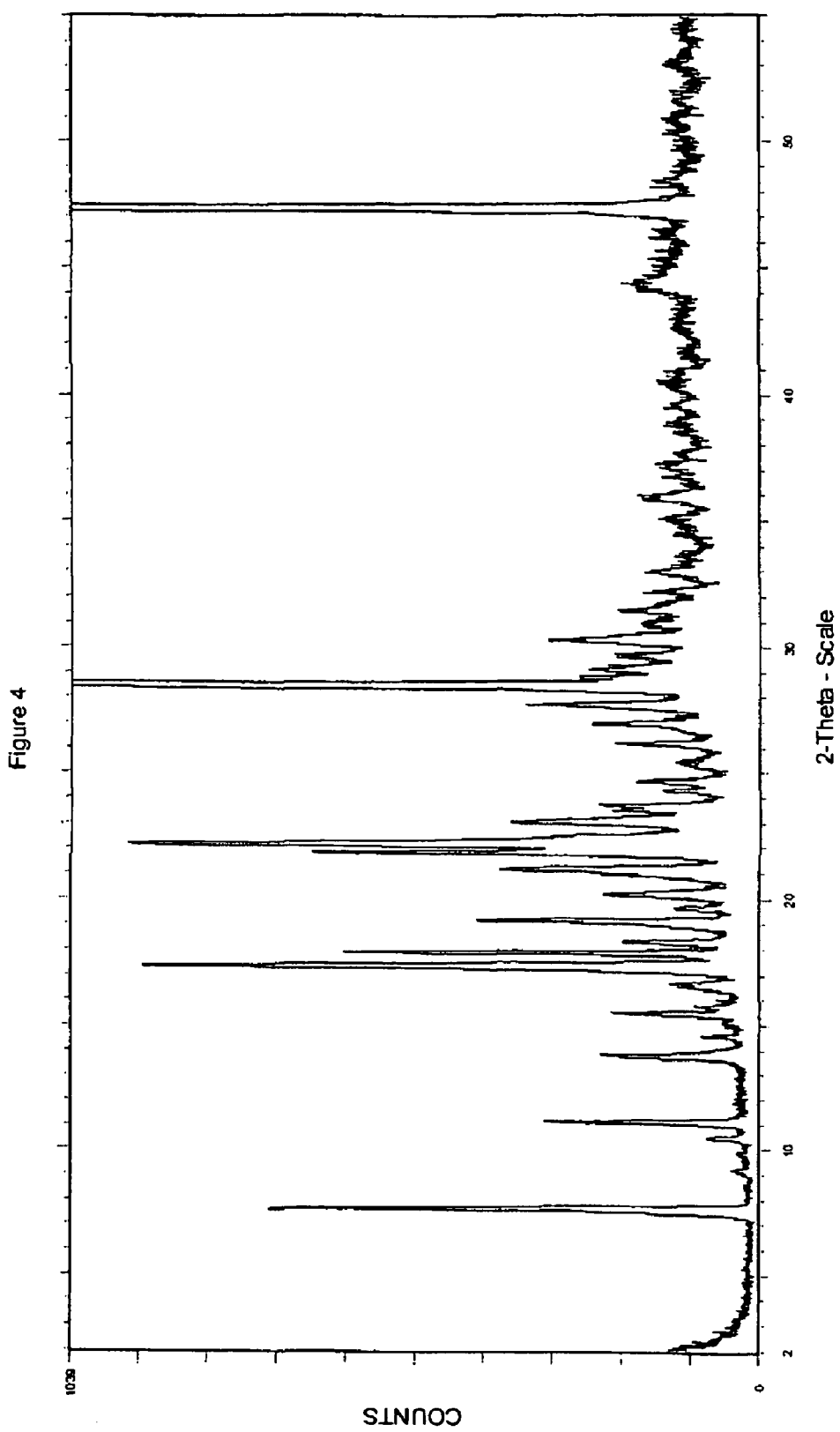
Figure 5:
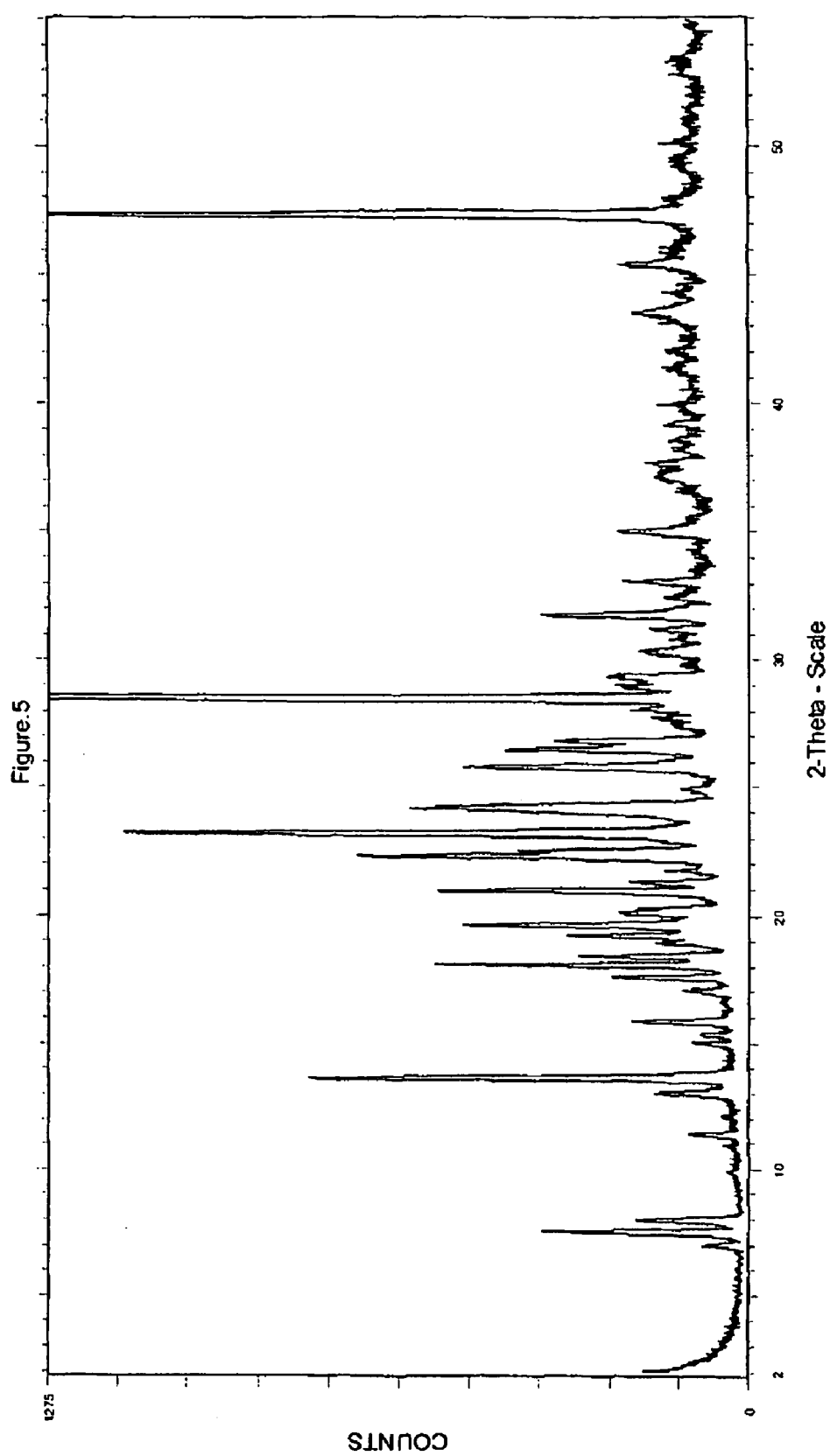
Figure 6:
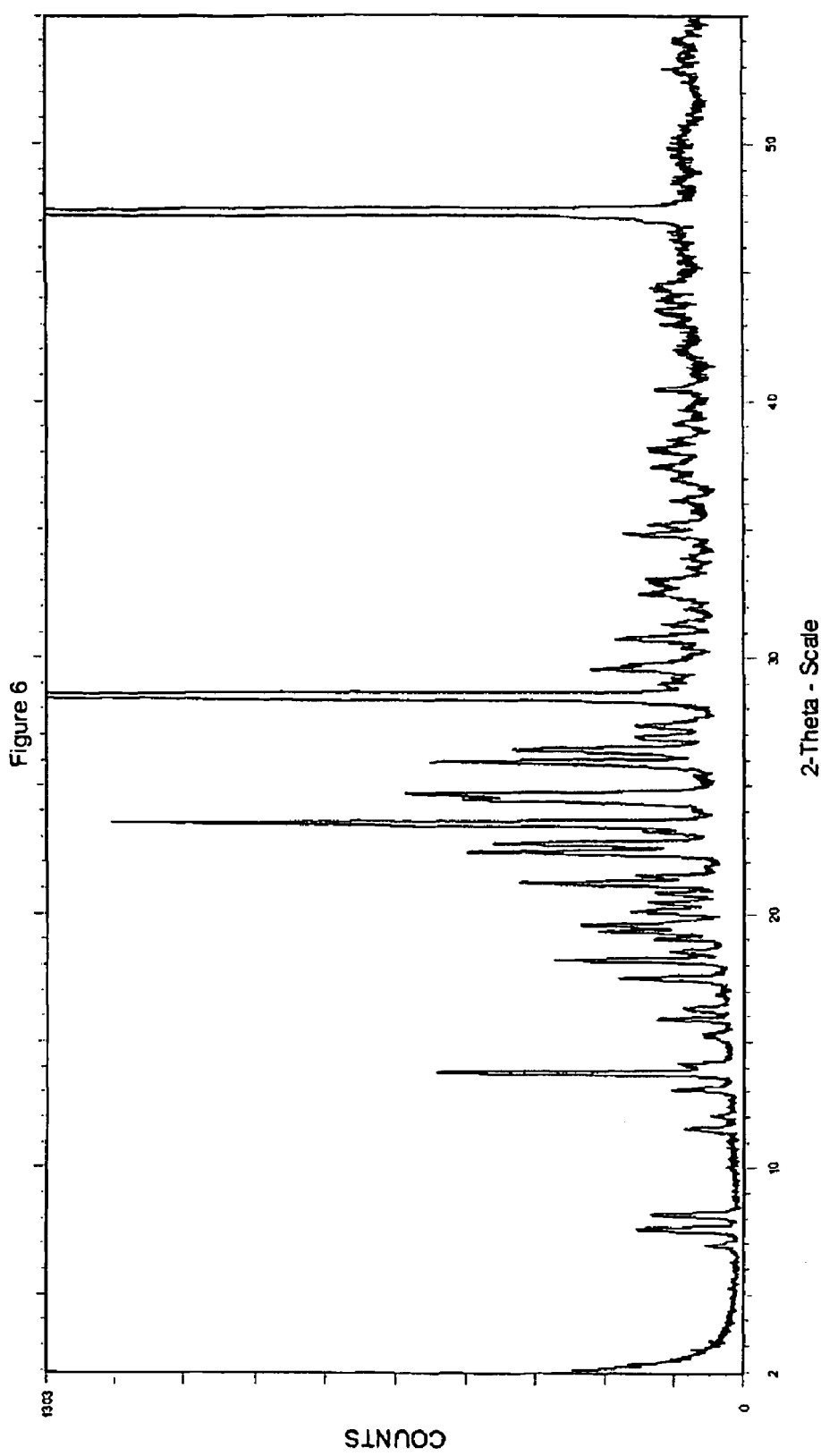

and the use of a compound of formula (I) in the treatment of a TNF-mediated disease, disorder, or condition, or a p38-mediated disease, disorder, or condition, in particular the allergic and non-allergic airways diseases, more particularly obstructive or inflammatory airways diseases, preferably chronic obstructive pulmonary disease.

6 Claims, 6 Drawing Sheets

FOREIGN PATENT DOCUMENTS

| WO | WO 03005999   | 1/2003  |
|----|---------------|---------|
| WO | WO 03044021   | 5/2003  |
| WO | WO 03059891   | 7/2003  |
| WO | WO 03068223   | 8/2003  |
| WO | WO 03068230   | 8/2003  |
| WO | WO 03087087   | 10/2003 |
| WO | WO 03104223   | 12/2003 |
| WO | WO 2004004720 | 1/2004  |
| WO | WO 2004072072 | 8/2004  |
| WO | WO 2004078116 | 9/2004  |
| WO | WO 2004087677 | 10/2004 |
| WO | WO 2004100946 | 11/2004 |
| WO | WO 2004048948 | 6/2005  |

OTHER PUBLICATIONS

Ma N et al., Zhonghua nei ke za zhi [Chinese journal of internal medicine], (Aug. 1999) vol. 38, No. 8, pp. 523-526 (translation).*
Mellor, et al., "Expression of the type 2 receptor for cysteinyl leukotrienes (CysLT2R) by human mast cells: Functional distinction from CysLT1R", Proceedings of the National Academy of Sciences of the United States of America, 2003, pp. 11589-11593, vol. 100(20).
Regan, et al., "Pyrazole Urea-Based Inhibitors of p38 Map Kinase: From Lead Compounds to Clinical Candidate", Journal of Medicinal Chemistry, 2002, pp. 2994-3008, vol. 45, No. 14.
Haleblian, John K., "Characterization of Habits and Crystalline Modification of Solids and Their Pharmaceutical Applications", Journal of Pharmaceutical Sciences, Aug. 1975, pp. 1269-1288, vol. 64, No. 8.
Liang, Alfred, et al., "Fast-dissolving intraoral drug delivery systems", Expert Opinion it Therapeutic Patents, WO2001, pp. 981-986, vol. 11, No. 6.
*English equivalent to AP200557105 A (2005).
Underwood et al., Journal of Physiology (2000), 279 (5, Pt. 1), L895-L908.
Underwood et al., Journal of Pharmacology and Experimental Therapeutics (2000), 293(1), 281-288.
Adcock et al., Biodrugs (2004), 18(3), 167-180.
Underwood et al., Progress in Respiratory Research (2001), 31 (New Drugs for Asthma, Allergy and COPD), 342-345.
*WO 99/32106 is equivalent to EP1047418.
Dominguez et al., Expert Opinion Ther. Patents, 15(7), pp. 801-816, 2005.
Jerome et al., Bioorganic & Medicinal Chem. Letters, 20, pp. 469-473, 2010.
Regan et al., J. Med. Chem., 46, pp. 4676-4686, 2003.
White et al., J. Med. Chem., 39, pp. 4382-4395, 1996.
Vicentini et al., Heterocycles, 32(4), pp. 727-734, 1991.
Kroe et al., J. Med. Chem., 46, pp. 4669-4675, 2003.
McCurdy et al., Journal of Medicinal Chemistry, 45(14), pp. 2887-2890.
Regan, Bioorganic & Medicinal Chemistry Letters, 13, pp. 3101-3104, 2003.
Saklatvala, Current Opinion in Pharmacology, 4, pp. 372-377, 2004.
Schieven, Current Topics in Medicinal Chemistry, 5, pp. 921-928, 2005.
Wadsworth, The Journal Of Pharmacology and Experimental Therapeutics, 291(2), pp. 680-687, 1999.
Zhou et al., Clinical Immunology, 90(3), pp. 232-238, 1999.
Zu et al., Journal of Immunology, 160, pp. 1982-1989, 1998.
Chem. Abstract, 116(21), May 1992, abstract No. 214456r.
Newton et al., BioDrugs, 17(2), pp. 113-129, 2003.
Barnes et al., Current Opinion Pharmacology, 4(3), p. 263-272, 2004.
Beisswen er et al., Respiration, 71(4), p. 402-409, 2004.
Hashimoto et al., The Journal of Pharmacology and Experimental Therapeutics, 293(2), p. 370-375, 2000.
Underwood et al., Am. J. Physiol. Lung Cell Mol. Physiol., 279(5), p. L895-L902, 2000.
Vuillemenot et al., Am. J. Respir. Cell Mol. Biol., 30(4), pp. 438-448, 2004.
Shum et al., American Journal Of Respiratory and Critical Care Medicine, 162(5), p. 1925-1931, 2000.
Choi et al., Tuberculosis and Respiratory Diseases, 45(6), p. 1236-1251, 1998.
Blease et al., Expert Opinion Emerging Drugs, 8(1), pp. 71-81, 2003.
Johnson et al., Science, 298(5600), p. 1911-1912, 2002.
Underwood et al., J. Pharmacol. Exp. Ther. 293(1), p. 281-288, 2000.
Irusen et al., J. Allergy Clin. Immunol. 109(4), p. 649-657, 2002.
Donnelly et al., Drugs, 63(19), p. 1973-1998, 2003.
Bayer AG, Expert Opinion On Therapeutic Patents, 13(10), p. 1663-1666, 2003.
Barnes, Respiration, 68(5), p. 441-448, 2001.
Sethi et al., Chest, 118(6), p. 1557-1565, 2000.
Zhang et al., Am. J. Respir. Cell Mol. Biol., 24(2), p. 123-131, 2001.
Yoshinari et al., Crit. Care Med., 29(3), p. 628-634, 2001.
Dunican et al., Shock, 14(3), p. 284-289, 2000.
Matsuoka et al., Am. J. Physiol. Lung Cell Mol. Physiol, 283(1), p. L103-L112, 2002.
Churg et al., Am. J. Respir. Crit. Care Med., 166(6), p. 849-854, 2002.
Fujita et al., Am. J. Physiol. Lung Cell Mol. Physiol., 280(1), p. L39-L49, 2001.
Churg et al., Am. J. Respir Crit. Care Med., 170(5), p. 492-498, 2004.
Barnes et al., Ann. 1st Super Sanita, 39(4), p. 573-582, 2003.
Barnes et al., Novartis Found Symp, 234, p. 255-272, 2001.
Denham et al., Crit. Care Med., 28(7), p. 2567-2572, 2000.
Jeffery, European Respiratory Review, 7(4), p. 111-118, 1997.

* cited by examiner

SEQUENCE LISTING

<160> NUMBER OF SEQ ID NOS: 2

<210> SEQ ID NO 1
<211> LENGTH: 31
<212> TYPE: DNA
<213> ORGANISM: Homo sapiens

<400> SEQUENCE: 1
gatcgaggat tcatgtctca ggagaggccc a                31

<210> SEQ ID NO 2
<211> LENGTH: 30
<212> TYPE: DNA
<213> ORGANISM: Homo sapiens

<400> SEQUENCE: 2
gatcgaggat tctcaggact ccatctcttc                  30

TRIAZOLOPYRIDINYLSULFANYL DERIVATIVES AS P38 MAP KINASE INHIBITORS

This application is a continuation of U.S. patent application Ser. No. 11/201,823, filed Aug. 10, 2005, which claims priority to U.S. Provisional Application Nos. 60/606,228, filed Aug. 31, 2004; 60/606,256, filed Aug. 31, 2004; and 60/691,559, filed Jun. 17, 2005.

This invention relates to triazolopyridinylsulfanyl derivatives. More particularly, this invention relates to pyrazolyl-[(triazolopyridinylsulfanyl)-benzyl]-urea derivatives and to processes for the preparation of, intermediates used in the preparation of, compositions containing and the uses of, such derivatives.

The triazolopyridinylsulfanyl derivatives of the present invention are inhibitors of p38 mitogen activated protein kinase ("p38 MAPK", "p38 kinase" or "p38"), particularly p38α kinase, and are inhibitors of tumor necrosis factor ("TNF") production, particularly TNFα. They have a number of therapeutic applications, particularly in the treatment of allergic and non-allergic airways diseases, more particularly obstructive or inflammatory airways diseases such as chronic obstructive pulmonary disease ("COPD").

Mitogen activated protein kinases (MAP) constitute a family of proline-directed serine/threonine kinases that activate their substrates by dual phosphorylation. The kinases are activated by a variety of signals, including nutritional and osmotic stress, UV light, growth factors, endotoxin, and inflammatory cytokines. The p38 MAP kinase group is a MAP family of various isoforms, including p38α, p38β, and p38γ. These kinases are responsible for phosphorylating and activating transcription factors (e.g., ATF2, CHOP, and MEF2C), as well as other kinases (e.g., MAPKAP-2 and MAPKAP-3). The p38 isoforms are activated by bacterial lipopolysaccharide, physical and chemical stress, and proinflammatory cytokines, including tumor necrosis factor ("TNF") and interleukin-1 ("IL-1"). The products of the p38 phosphorylation mediate the production of inflammatory cytokines, including TNF.

TNF is a cytokine produced primarily by activated monocytes and macrophages. Excessive or unregulated TNF production (particularly TNF-α) has been implicated in mediating a number of diseases, and it is believed that TNF can cause or contribute to the effects of inflammation in general.

IL-8 is another pro-inflammatory cytokine, which is produced by mononuclear cells, fibroblasts, endothelial cells, and keratinocytes. This cytokine is associated with conditions including inflammation. IL-1 is produced by activated monocytes and macrophages, and is involved in inflammatory responses. IL-1 plays a role in many pathophysiological responses, including rheumatoid arthritis, fever, and reduction of bone resorption.

TNF, IL-1, and IL-8 affect a wide variety of cells and tissues, and are important inflammatory mediators of a wide variety of conditions. Compounds which inhibit p38 kinase will inhibit IL-1, IL-8, and TNF synthesis in human monocytes.

P38 kinase inhibitors are well known to the person skilled in the art. J. Med. Chem. 2002, 45, 2994-3008 discloses certain pyrazole urea compounds as inhibitors of p38 kinase. International patent application PCT/IB02/00424 (WO 02/072579) discloses triazolopyridines as inhibitors of MAP kinases, preferably p38 kinase.

International patent application PCT IB2004/000363 (WO 2004/072072), publication date 26 Aug. 2004, discloses triazolo-pyridines useful as anti-inflammatory compounds for treating certain diseases. This is incorporated by reference in its entirety.

The compounds of the present invention are potentially useful in the treatment of a wide range of disorders. In addition to the treatment of obstructive or inflammatory airways diseases, it is believed that the compounds of the present invention can be used to treat TNF/p38 mediated diseases such as: asthma, chronic or acute bronchoconstriction, bronchitis, acute lung injury and bronchiectasis, inflammation generally (e.g. inflammatory bowel disease), arthritis, neuroinflammation, pain, fever, fibrotic diseases, pulmonary disorders and diseases (e.g., hyperoxic alveolar injury), cardiovascular diseases, post-ischemic reperfusion injury and congestive heart failure, cardiomyopathy, stroke, ischemia, reperfusion injury, renal reperfusion injury, brain edema, neurotrauma and brain trauma, neurodegenerative disorders, central nervous system disorders, liver disease and nephritis, gastrointestinal conditions, ulcerative diseases, ophthalmic diseases, opthalmological conditions, glaucoma, acute injury to the eye tissue and ocular traumas, diabetes, diabetic nephropathy, skin-related conditions, myalgias due to infection, influenza, endotoxic shock, toxic shock syndrome, autoimmune disease, graft rejection, bone resorption diseases, multiple sclerosis, psoriasis, disorders of the female reproductive system, pathological (but non-malignant) conditions, such as hemaginomas, angiofibroma of the nasopharynx, and avascular necrosis of bone, benign and malignant tumors/neoplasia including cancer, leukaemia, lymphoma, systemic lupus erthrematosis (SLE), angiogenesis including neoplasia, hemorrhage, coagulation, radiation damage, and/or metastasis. Chronic release of active TNF can cause cachexia and anorexia, and TNF can be lethal.

TNF has also been implicated in infectious diseases. These include, for example, malaria, mycobacterial infection and meningitis. These also include viral infections, such as HIV, influenza virus, and herpes virus, including herpes simplex virus type-1 (HSV-1), herpes simplex virus type-2 (HSV-2), cytomegalovirus (CMV), varicella-zoster virus (VZV), Epstein-Barr virus, human herpesvirus-6 (HHV-6), human herpesvirus-7 (HHV-7), human herpesvirus-8 (HHV-8), pseudorabies and rhinotracheitis, among others.

The treatment of obstructive or inflammatory airways diseases is a preferred use. All forms of obstructive or inflammatory airways diseases are potentially treatable with the compounds of the present invention, in particular an obstructive or inflammatory airways disease that is a member selected from the group consisting of chronic eosinophilic pneumonia, COPD, COPD that includes chronic bronchitis, pulmonary emphysema or dyspnea associated or not associated with COPD, COPD that is characterized by irreversible, progressive airways obstruction, adult respiratory distress syndrome (ARDS), exacerbation of airways hyper-reactivity consequent to other drug therapy and airways disease that is associated with pulmonary hypertension.

There is a need to provide new TNF inhibitors/p38 kinase inhibitors that are good drug candidates. Preferably, the new TNF inhibitors/p38 kinase inhibitors show good potency, high levels of selectivity over other related protein kinases, have properties particularly suitable for providing effective treatment via the inhalation route, are suitable for the treatment of allergic and non-allergic airways diseases (particularly obstructive or inflammatory airways diseases), are non-toxic and demonstrate few side-effects, have physical properties suitable for administration by inhalation, exist in a physical form that is stable and non-hygroscopic, and/or are easily formulated.

According to one aspect of the present invention, there is provided a compound of formula (I):

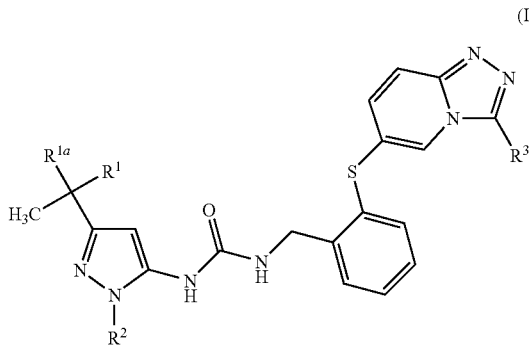

or a pharmaceutical acceptable salt and/or solvate (including hydrate) thereof,
wherein
$R^1$ is $CH_3$, $S(O)_pCH_3$, $S(O)_pCH_2CH_3$, $CH_2CH_3$, H or $CH_2S(O)_pCH_3$;
$R^{1a}$ is $CH_3$ or $CH_2CH_3$, wherein $CH_3$ and $CH_2CH_3$ are each optionally substituted with one or more hydroxy substituents;
$R^2$ is heteroaryl, heterocyclyl, aryl, or carbocyclyl;
$R^3$ is heteroaryl, heterocyclyl, aryl, carbocyclyl or $R^7$;
$R^7$ is ($C_1$-$C_6$)alkyl (optionally substituted with one or more substituents independently selected from OH, halo, $NR^5R^6$, ($C_1$-$C_6$)alkoxy, —$S(O)_p$($C_1$-$C_6$)alkyl, $CO_2H$, $CONR^5R^6$, heteroaryl, heterocyclyl, aryl, carbocyclyl, aryloxy, carbocyclyloxy, heteroaryloxy and heterocyclyloxy);
p is 0, 1 or 2;
$R^5$ and $R^6$ are each independently selected from H and ($C_1$-$C_6$)alkyl, said ($C_1$-$C_4$)alkyl being optionally substituted with one or more substituents independently selected from OH and halo,
or $R^5$ and $R^6$, together with the nitrogen to which they are attached form a piperazinyl, piperidinyl, morpholinyl or pyrrolidinyl group, (said piperazinyl, piperidinyl, morpholinyl and pyrrolidinyl each being optionally substituted by one or more OH)
each "aryl" independently means phenyl or naphthyl, said phenyl or naphthyl being optionally substituted with one or more substituents independently selected from halo, —CN, —$CO_2H$, OH, $CONR^5R^6$, $NR^5R^6$, $R^8$ and $R^9$, and preferably, said phenyl or naphthyl being optionally substituted with one or more substituents independently selected from halo, —CN, —$CO_2H$, OH, $CONR^5R^6$, $R^8$ and $R^9$;
each $R^8$ is independently selected from ($C_1$-$C_6$)alkyl, ($C_1$-$C_6$)alkoxy, —$CO_2$($C_1$-$C_6$)alkyl, —$S(O)_p$($C_1$-$C_6$)alkyl, —CO($C_1$-$C_6$)alkyl and ($C_3$-$C_7$)cycloalkyl;
each $R^8$ is optionally substituted with one or more substituents independently selected from:
($C_1$-$C_6$)alkoxy (optionally substituted with one or more substituents independently selected from OH, halo, $CO_2H$, $CONR^5R^6$ and $NR^5R^6$),
—$S(O)_p$($C_1$-$C_6$)alkyl (optionally substituted with one or more substituents independently selected from OH, halo, $CO_2H$, $CONR^5R^6$ and $NR^5R^6$),
OH,
halo,
$NR^5R^6$,
$CO_2H$
$CONR^5R^6$, and
$R^9$;

each $R^9$ is heteroaryl$^2$, heterocyclyl$^2$, aryl$^2$, carbocyclyl$^2$, aryl$^2$oxy, carbocyclyl$^2$oxy, heteroaryl$^2$oxy or heterocyclyl$^2$oxy;
"aryl$^2$", means phenyl or naphthyl, said phenyl or naphthyl being optionally substituted with one or more substituents independently selected from halo, —CN, —$CO_2H$, OH, $NR^5R^6$, and $CONR^5R^6$, and preferably, said phenyl or naphthyl being optionally substituted with one or more substituents independently selected from halo, —CN, —$CO_2H$, OH and $CONR^5R^6$;
"carbocyclyl" means a mono or bicyclic, saturated or partially unsaturated ring system containing from 3 to 10 ring carbon atoms, optionally substituted with one or more substituents independently selected from halo, —CN, —$CO_2H$, OH, $NR^5R^6$, $CONR^5R^6$, $R^8$ and $R^9$, and preferably, optionally substituted with one or more substituents independently selected from halo, —CN, —$CO_2H$, OH, $CONR^5R^6$, $R^8$ and $R^9$;
"carbocyclyl$^2$" means a mono or bicyclic, saturated or partially unsaturated ring system containing from 3 to 10 ring carbon atoms, optionally substituted with one or more substituents independently selected from halo, —CN, —$CO_2H$, $NR^5R^6$, OH and $CONR^5R^6$, and preferably, optionally substituted with one or more substituents independently selected from halo, —CN, —$CO_2H$, OH and $CONR^5R^6$,
examples of "carbocyclyl" and "carbocyclyl$^2$" are groups such as: indanyl, indenyl, cyclopropyl, cyclobutyl, cyclopentyl, cyclohexyl, cyclohexenyl, cycloheptyl and tetrahydronaphthyl;
each "heterocyclyl", and "heterocyclyl$^2$", independently, means a 3- to 10-membered, saturated or partially unsaturated, mono or bicyclic group comprising 1, 2, 3 or 4 ring heteroatoms independently selected from N, O, and S. Examples of "heterocyclyl" and "heterocyclyl$^2$" are groups such as: tetrahydrofuranyl, tetrahydrothiophenyl, pyrrolidinyl, tetrahydropyranyl, tetrahydrothiopyranyl, piperidinyl, 1,4-dioxanyl, 1,4-oxathianyl, morpholinyl, 1,4-dithianyl, piperazinyl, 3,4-dihydro-2H-pyranyl, 5,6-dihydro-2H-pyranyl, 2H-pyranyl, 1,2,3,4-tetrahydropyridinyl, 1,2,5,6-tetrahydropyridinyl, dihydroindolyl and dihydrobenzofuranyl.
each "heteroaryl", and each "heteroaryl$^2$", independently, means a 5 to 10 membered, mono or bicyclic, aromatic group comprising 1, 2, 3 or 4 ring heteroatoms independently selected from N, O, and S (wherein the total number of ring S atoms does not exceed 1, and the total number of ring O atoms does not exceed 1), and includes the groups:
pyrrolyl, furanyl, thiophenyl, pyrazolyl, imidazolyl, isoxazolyl, oxazolyl, isothiazolyl, thiazolyl, 1,2,3-triazolyl, 1,3,4-triazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, tetrazolyl, pyridyl, pyridazinyl, pyrimidinyl, pyrazinyl, benzofuranyl, benzothiophenyl, indolyl, benzimidazolyl, indazolyl, benzotriazolyl, pyrrolo[2,3-b]pyridinyl, pyrrolo[2,3-c]pyridinyl, pyrrolo[3,2-c]pyridinyl, pyrrolo[3,2-b]pyridinyl, imidazo[4,5-b]pyridinyl, imidazo[4,5-c]pyridinyl, pyrazolo[4,3-d]pyridinyl, pyrazolo[4,3-c]pyridinyl, pyrazolo[3,4-c]pyridinyl, pyrazolo[3,4-b]pyridinyl, isoindolyl, purinyl, indolininyl, imidazol[1,2-a]pyridinyl, imidazo[1,5-a]pyridinyl, pyrazolo[1,5-a]pyridinyl, pyrrolo[1-2,b]pyridazinyl, imidazo[1,2-c]pyrimidinyl, quinolinyl, isoquinolinyl, cinnolinyl, quinazolinyl, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]

pyrazinyl, pyrido[3,4-b]pyrazinyl, pyrimido[5,4-d]pyrimidinyl, pyrazino[2,3-b]pyrazinyl, pyrimido[4,5-d]pyrimidinyl;

each "heterocyclyl" and each "heteroaryl" group is, independently, optionally substituted on one or more ring carbon atoms with one or more substituents independently selected from halo, —CN, —CO$_2$H, OH, NR$^5$R$^6$, CONR$^5$R$^6$, R$^8$ and R$^9$, and preferably, optionally substituted on one or more ring carbon atoms with one or more substituents independently selected from halo, —CN, —CO$_2$H, OH, CONR$^5$R$^6$, R$^8$ and R$^9$, and optionally substituted on one or more ring nitrogen atoms with one or more substituents independently selected from H and (C$_1$-C$_6$)alkyl;

each "heterocyclyl$^2$" and each "heteroaryl$^2$" group is, independently, optionally substituted on one or more ring carbon atoms with one or more substituents independently selected from halo, —CN, —CO$_2$H, NR$^5$R$^6$, OH and CONR$^5$R$^6$, and preferably, optionally substituted on one or more ring carbon atoms with one or more substituents independently selected from halo, —CN, —CO$_2$H, OH and CONR$^5$R$^6$, and optionally substituted on one or more ring nitrogen atoms with one or more substituents independently selected from H and (C$_1$-C$_6$)alkyl;

"alkyl" and "alkoxy" groups, including groups incorporating said moieties, may be straight chain or branched where the number of carbon atoms allows. "(C$_1$-C$_4$)alkyl" or "(C$_1$-C$_6$)alkyl" denotes a straight) chain or branched group containing respectively from 1 to 4 or from 1 to 6 carbon atoms. This also applies if they carry substituents or occur as substituents of other radicals, for example in (C$_1$-C$_6$)alkoxy radicals, —CO$_2$(C$_1$-C$_6$)alkyl radicals, —CO(C$_1$-C$_6$)alkyl radicals, or —S(O)$_p$(C$_1$-C$_6$)alkyl radicals. Examples of suitable (C$_1$-C$_4$)alkyl or (C$_1$-C$_6$)alkyl radicals are methyl, ethyl, n-propyl, iso-propyl, n-butyl, iso-butyl, sec-butyl, tert-butyl, pentyl and hexyl. Examples of suitable (C$_1$-C$_6$)alkoxy radicals are methoxy, ethoxy, n-propyloxy, iso-propyloxy, n-butyloxy, iso-butyloxy, sec-butyloxy, tert-butyloxy, pentyloxy and hexyloxy. "halogen" or "halo" is taken to mean a halogen atom selected from the group consisting of fluorine, chlorine and bromine.

It is to be appreciated that all references herein to "treatment", "treat" or "treating" include curative, palliative and/or prophylactic treatment.

"compounds of the invention" or "a compound of the invention" as used herein means compounds, or a compound, of formula (I), or a pharmaceutically acceptable salt and/or solvate thereof, and includes all polymorphs and crystal habits thereof, prodrugs and isomers thereof (including optical, geometric and tautomeric isomers), and mixtures thereof, as hereinafter defined and isotopically-labeled compounds of formula I.

It has now been found that the compounds of formula (I) are p38 inhibitors/inhibitors of TNF production, are particularly useful for the treatment of a TNF mediated, and/or p38 mediated, disease, disorder, or condition, and are particularly suitable for administration via the inhalation route.

In another aspect of the invention there is provided a compound of formula (I), or a pharmaceutically acceptable salt and/or solvate (including hydrate) thereof, wherein
R$^1$ is CH$_3$, SCH$_3$, SCH$_2$CH$_3$, CH$_2$CH$_3$, H or CH$_2$SCH$_3$;
R$^{1a}$ is CH$_3$ or CH$_2$CH$_3$;
and wherein
R$^2$, R$^3$, R$^7$, p, R$^5$, R$^6$, "aryl", R$^8$, R$^9$, "aryl$^2$", "carbocyclyl", "carbocyclyl$^2$", "heterocyclyl", "heterocyclyl$^2$", "heteroaryl" and "heteroaryl$^2$", are all as defined above.

Preferably, R$^1$ is CH$_3$, SCH$_3$, SCH$_2$CH$_3$ or CH$_2$SCH$_3$, and more preferably R$^1$ is CH$_3$ or SCH$_3$.

In an alternative embodiment, preferably R$^1$ is CH$_3$, SCH$_3$, CH$_2$CH$_3$ or CH$_2$SCH$_3$, and more preferably R$^1$ is CH$_3$, CH$_2$CH$_3$ or CH$_2$SCH$_3$.

Preferably, R$^{1a}$ is CH$_3$.

Preferably, R$^2$ is pyridyl, tetrahydronaphthyl or aryl, said pyridyl, tetrahydronaphthyl and aryl each being optionally substituted with one or more substituents independently selected from the group consisting of:
halo,
—CN,
—CO$_2$H
OH,
CONR$^5$R$^6$
(C$_1$-C$_6$)alkyl (said (C$_1$-C$_6$)alkyl being optionally substituted with one or more substituents independently selected from OH, NR$^5$R$^6$, aryl$^2$ and halo),
—S(O)$_p$(C$_1$-C$_6$)alkyl (said —S(O)$_p$(C$_1$-C$_6$)alkyl being optionally substituted with one or more substituents independently selected from OH, aryl$^2$ and halo),
(C$_1$-C$_6$)alkoxy (said (C$_1$-C$_6$)alkoxy being optionally substituted with one or more substituents independently selected from OH, aryl$^2$ and halo),
—CO$_2$(C$_1$-C$_6$)alkyl (said —CO$_2$(C$_1$-C$_6$)alkyl being optionally substituted with one or more substituents independently selected from OH, aryl$^2$ and halo),
(C$_3$-C$_7$)cycloalkyl (said (C$_3$-C$_7$)cycloalkyl being optionally substituted with one or more substituents independently selected from OH and halo),
pyridyl, and
aryl$^2$, More preferably, R$^2$ is:
3-pyridyl (optionally substituted with one or more substituents independently selected from OH, —S(C$_1$-C$_6$)alkyl, (C$_1$-C$_6$)alkoxy, CF$_3$ and halo), or
phenyl (optionally substituted with one or more substituents independently selected from (C$_1$-C$_6$)alkyl, OH, —S(C$_1$-C$_6$)alkyl, (C$_1$-C$_6$)alkoxy, CN, CF$_3$ and halo).

Yet more preferably, R$^2$ is phenyl (optionally substituted with one or more substituents independently selected from methyl, ethyl, OH, CN, CF$_3$, Cl, F, —SCH$_3$ and —OCH$_3$).

Even more preferably, R$^2$ is 3-hydroxyphenyl, 4-hydroxyphenyl, phenyl, 3,4-dichlorophenyl, 4-methylphenyl, 3-methoxyphenyl, 4-hydroxy-3-methylphenyl, 3-methylphenyl or 4-hydroxy-3-chlorophenyl.

In an alternative embodiment, R$^2$ is preferably pyridyl or aryl,
said pyridyl and aryl each being optionally substituted with one or more substituents independently selected from the group consisting of:
halo,
—CN,
—CO$_2$H
OH,
CONR$^5$R$^6$
(C$_1$-C$_6$)alkyl (said (C$_1$-C$_6$)alkyl being optionally substituted with one or more substituents independently selected from OH, NR$^5$R$^6$ and halo),
(C$_1$-C$_6$)alkoxy (said (C$_1$-C$_6$)alkoxy being optionally substituted with one or more substituents independently selected from OH, CO$_2$H, aryl$^2$ and halo),
More preferably, R$^2$ is:
3-pyridyl (optionally substituted with one or more substituents independently selected from OH, (C$_1$-C$_6$)alkyl, (C$_1$-C$_6$)alkoxy and CF$_3$), or
phenyl (optionally substituted with one or more substituents independently selected from (C$_1$-C$_6$)alkyl, OH, —S(C$_1$-C$_6$)alkyl (wherein said —S(C$_1$-C$_6$)alkyl is optionally substituted with OH), $(C_1-C_6)$alkoxy (wherein said $(C_1-C_6)$alkoxy is optionally substituted with OH), CN, $CF_3$ and halo).

Even more preferably, $R^2$ is phenyl optionally substituted with one or more substituents independently selected from $(C_1-C_4)$alkyl, OH, —$S(C_1-C_4)$alkyl (wherein said —$S(C_1-C_4)$alkyl is optionally substituted with OH), $(C_1-C_4)$alkoxy (wherein said $(C_1-C_4)$alkoxy is optionally substituted with OH), CN, $CF_3$ and halo).

Yet more preferably, $R^2$ is phenyl (optionally substituted with one or more substituents independently selected from methyl, ethyl, OH, CN, $CF_3$, Cl, F and —$OCH_2CH_2OH$).

Yet even more preferably, $R^2$ is phenyl substituted with one or two substituents independently selected from OH, Cl, CN, methyl and —$OCH_2CH_2OH$.

Preferably, when $R^2$ is substituted phenyl, the substitution is at the 3- and/or 4-positions of said phenyl.

In another preferred embodiment, when $R^2$ is phenyl substituted with a hydroxyethoxy substituent, said hydroxyethoxy substituent is at the 3 (meta) position of the phenyl.

In a particularly preferred embodiment of the invention, $R^2$ is substituted phenyl according to any one of the embodiments or preferences herein, wherein the $R^2$ phenyl is substituted with at least one hydroxy substituent, or at least one hydroxyethoxy substituent, more preferably at least one hydroxy substituent.

In a preferred embodiment of the invention, $R^2$ is phenyl substituted by:
3-chloro and 4-hydroxy, 3-cyano and 4-hydroxy, 3-hydroxy, 4-hydroxy, 3-hydroxyethoxy, 3-hydroxy and 4-chloro, or 3-hydroxy and 4-cyano.

In another embodiment, $R^2$ is preferably, 3-hydroxyphenyl, 4-hydroxyphenyl, phenyl, 4-methylphenyl, 3-methylphenyl, —$OCH_2CH_2OH$ or 4-hydroxy-3-chlorophenyl.

Preferably, $R^3$ is pyridyl or aryl, wherein the pyridyl and aryl are each optionally substituted with one or more substituents independently selected from the group consisting of:
halo,
—CN,
—$CO_2H$
OH,
$CONR^5R^6$
$(C_1-C_6)$alkyl (said $(C_1-C_6)$alkyl being optionally substituted with one or more substituents independently selected from OH, $NR^5R^6$, aryl$^2$ and halo),
—$S(O)_p(C_1-C_6)$alkyl (said —$S(O)_p(C_1-C_6)$alkyl being optionally substituted with one or more substituents independently selected from OH, aryl$^2$ and halo),
$(C_1-C_6)$alkoxy (said $(C_1-C_6)$alkoxy being optionally substituted with one or more substituents independently selected from OH, aryl$^2$ and halo),
—$CO_2(C_1-C_6)$alkyl (said —$CO_2(C_1-C_6)$alkyl being optionally substituted with one or more substituents independently selected from OH, aryl$^2$ and halo),
$(C_3-C_7)$cycloalkyl (said $(C_3-C_7)$cycloalkyl being optionally substituted with one or more substituents independently selected from OH and halo),
pyridyl, and
aryl$^2$,
or, alternatively, $R^3$ is preferably $(C_1-C_6)$alkyl, optionally substituted with one or more substituents independently selected from OH, halo, and $(C_1-C_6)$alkoxy.

More preferably, $R^3$ is aryl, optionally substituted with one or more substituents independently selected from the group consisting of:
halo,
OH,
$(C_1-C_6)$alkyl (said $(C_1-C_6)$alkyl being optionally substituted with one or more substituents independently selected from OH and halo),
$(C_1-C_6)$alkoxy (said $(C_1-C_6)$alkoxy being optionally substituted with one or more substituents independently selected from OH and halo),
or $R^3$ is $(C_1-C_6)$alkyl.

Even more preferably, $R^3$ is phenyl (optionally substituted with one or more substituents independently selected from:
Cl, F, OH, methyl, ethyl, isopropyl, $CF_3$, methoxy, ethoxy (said methoxy and ethoxy each being optionally substituted by OH),
or $R^3$ is isopropyl.

In an alternative embodiment, $R^3$ is preferably pyridyl or aryl, wherein the pyridyl and aryl are each optionally substituted with one or more substituents independently selected from the group consisting of:
halo,
—CN,
—$CO_2H$
OH,
$CONR^5R^6$
$(C_1-C_6)$alkyl (said $(C_1-C_6)$alkyl being optionally substituted with one or more substituents independently selected from OH, $NR^5R^6$, aryl$^2$ and halo),
—$S(O)_p(C_1-C_6)$alkyl (said —$S(O)_p(C_1-C_6)$alkyl being optionally substituted with one or more substituents independently selected from OH, aryl$^2$ and halo),
$(C_1-C_6)$alkoxy (said $(C_1-C_6)$alkoxy being optionally substituted with one or more substituents independently selected from OH, aryl$^2$ and halo),
—$CO_2(C_1-C_6)$alkyl (said —$CO_2(C_1-C_6)$alkyl being optionally substituted with one or more substituents independently selected from OH, aryl$^2$ and halo),
$(C_3-C_7)$cycloalkyl (said $(C_3-C_7)$cycloalkyl being optionally substituted with one or more substituents independently selected from OH and halo),
or, alternatively, $R^3$ is preferably $(C_1-C_6)$alkyl, optionally substituted with one or more substituents independently selected from OH, halo, and $(C_1-C_6)$alkoxy.

More preferably, $R^3$ is aryl, optionally substituted with one or more substituents independently selected from the group consisting of:
halo,
OH,
CN,
$(C_1-C_8)$alkyl (said $(C_1-C_6)$alkyl being optionally substituted with one or more substituents independently selected from OH and halo),
$(C_1-C_6)$alkoxy (said $(C_1-C_6)$alkoxy being optionally substituted with one or more substituents independently selected from OH and halo),
—S—$(C_1-C_6)$alkyl (said —S—$(C_1-C_6)$alkyl being optionally substituted with one or more substituents independently selected from OH and halo),
or $R^3$ is $(C_1-C_6)$alkyl.

Even more preferably, $R^3$ is phenyl (optionally substituted with one or more substituents independently selected from: CN, Cl, F, OH, methyl, ethyl, isopropyl, $CF_3$, —S—$(C_1-C_4)$ alkyl (said —S—$(C_1-C_4)$alkyl being optionally substituted by OH), methoxy, ethoxy (said ethoxy being optionally substituted by OH), or $R^3$ is isopropyl.

Yet even more preferably, $R^3$ is phenyl substituted with one or two substituents independently selected from Cl, F, CN, OH, —S-methyl, OCH$_3$, —SCH$_2$CH$_2$OH and —OCH$_2$CH$_2$OH.

In a particularly preferred embodiment of the invention, $R^3$ is substituted phenyl according to any one of the embodiments or preferences herein, wherein the $R^3$ phenyl is substituted with at least one hydroxy substituent, or at least one hydroxyethoxy substituent, more preferably at least one hydroxy substituent.

In another particularly preferred embodiment of the invention, $R^3$ is phenyl substituted with:
2-hydroxy and 5-chloro,
2-hydroxy and 3-chloro,
3-hydroxy and 2-chloro,
5-hydroxy and 2-chloro,
3-cyano and 4-hydroxy,
2-hydroxy, or
2-OCH$_2$CH$_2$OH.

Preferably, when $R^3$ is substituted phenyl and at least one substituent is —S—(C$_1$-C$_6$)alkyl, —S—(C$_1$-C$_4$)alkyl or —SCH$_2$CH$_2$OH, the —S—(C$_1$-C$_6$)alkyl, —S—(C$_1$-C$_4$) alkyl or —SCH$_2$CH$_2$OH is present at the ortho position (position 2-) of the phenyl.

More preferably $R^3$ is phenyl substituted with at least one substituent selected independently from —S-methyl and —SCH$_2$CH$_2$OH, wherein said —S-methyl or —SCH$_2$CH$_2$OH is present at the ortho position (position 2) of the phenyl.

Preferably, $R^5$ and $R^6$ are independently selected from H, methyl and ethyl.

Preferably, "aryl" and "aryl$^2$" are phenyl (optionally substituted with one or more substituents independently selected from halo, —CN, OH, and $R^8$).

Preferably, $R^8$ is (C$_1$-C$_6$)alkyl, (C$_1$-C$_6$)alkoxy or (C$_3$-C$_7$) cycloalkyl (each (C$_1$-C$_6$)alkyl, (C$_1$-C$_6$)alkoxy and (C$_3$-C$_7$) cycloalkyl being optionally substituted with one or more substituents independently selected from OH and halo).

More preferred $R^8$ groups are CF$_3$, methyl, methoxy, ethyl, ethoxy, —OCH$_2$CH$_2$OH, —SCH$_2$CH$_2$OH, S-Me and cyclopropyl.

Preferably, p is 0.

Preferably, $R^9$ is heteroaryl$^2$, heterocyclyl$^2$, aryl$^2$, aryl$^2$oxy or heteroaryl$^2$oxy;

More preferably, $R^9$ is heteroaryl$^2$ or aryl$^2$.

Even more preferably, $R^9$ is pyridyl or phenyl (said pyridyl or phenyl being optionally substituted by one or more OH or halo).

Even more preferably, $R^9$ is phenyl.

Another particularly preferred embodiment of the invention is the compound of formula (I) according to any one of the embodiments or preferences herein, wherein at least one of $R^2$ and $R^3$ is substituted phenyl, wherein said substituted phenyl is substituted with at least one hydroxy substituent or at least one hydroxyethoxy substituent, more preferably at least one hydroxy substituent.

Preferably, "carbocyclyl" and "carbocyclyl$^2$" are each independently selected from cyclopropyl, cyclobutyl, cyclopentyl and cyclohexyl (each cyclopropyl, cyclobutyl, cyclopentyl and cyclohexyl optionally substituted with one or more OH).

Preferably, "heterocyclyl" and "heterocyclyl$^2$" are each independently selected from pyrrolidinyl, tetrahydropyranyl, tetrahydrothiopyranyl, piperidinyl, morpholinyl, 1,4-dithianyl and piperazinyl (each pyrrolidinyl, tetrahydropyranyl, tetrahydrothiopyranyl, piperidinyl, morpholinyl, 1,4-dithianyl and piperazinyl optionally substituted with one or more OH).

Preferably, "heteroaryl", and "heteroaryl$^2$", are each independently selected from pyrazolyl, imidazolyl, tetrazolyl, pyridyl, pyridazinyl, pyrimidinyl, isoquinolinyl and pyrazinyl (each pyrazolyl, imidazolyl, tetrazolyl, pyridyl, pyridazinyl, pyrimidinyl, isoquinolinyl and pyrazinyl being optionally substituted with one or more OH).

More preferably, "heteroaryl" is pyridyl or isoquinolinyl, each optionally substituted with one or more OH.

According to another embodiment, a compound of formula (I), or a pharmaceutically acceptable salt and/or solvate (including hydrate) thereof, wherein:
$R^1$ is CH$_3$, SCH$_3$, CH$_2$CH$_3$ or CH$_2$SCH$_3$;
$R^{1a}$ is CH$_3$;
$R^2$ is pyridyl, isoquinolinyl or phenyl, said phenyl being optionally substituted with one or more substituents independently selected from SCH$_3$, Cl, F, Br, ethyl, methyl, methoxy, OH, benzyloxy, CF$_3$, CO$_2$H, CO$_2$Et, CN, —OCO$_2$H, hydroxyethoxy, and —C(O)NHCH$_3$; and
$R^3$ is isopropyl or phenyl, said phenyl being optionally substituted with one or more substituents independently selected from Cl, OH, F, benzyloxy, methoxy, hydroxyethoxy, isopropyl, methyl, ethyl, SCH$_3$, CO$_2$H, hydroxyethylthio and CN; is preferred.

According to a further embodiment, a compound of formula (I), or a pharmaceutically acceptable salt and/or solvate (including hydrate) thereof, wherein:
$R^1$ is CH$_3$, SCH$_3$, or CH$_2$SCH$_3$;
$R^{1a}$ is CH$_3$;
$R^2$ is phenyl, said phenyl being optionally substituted with one or more substituents independently selected from SCH$_3$, Cl, OH, CN and hydroxyethoxy; and
$R^3$ is isopropyl or phenyl, said phenyl being optionally substituted with one or more substituents independently selected from Cl, OH, hydroxyethoxy, SCH$_3$, hydroxyethylthio and CN; is more preferred.

In another embodiment there is provided a compound of formula (I) wherein each $R^1$, $R^{1a}$, $R^2$ and $R^3$ substituent is independently selected from the substituents as defined in any of the preferred or alternative embodiments herein, including any combination of said preferred or alternative embodiments.

A preferred group of compounds is that in which each substituent is as specified in the Examples below.

Preferably, the compound of formula (I) is selected from a compound as specified in the Examples below.

A preferred group of compounds is that in which each substituent is as specified in the list[1] below.

Preferably, the compound of formula (I) is selected from the list[1]:

list[1]:
N-{3-tert-Butyl-1-[4-(methylthio)phenyl]-1H-pyrazol-5-yl}-N'-{2-[(3-isopropyl[1,2,4]triazolo[4,3-a]pyridin-6-yl)thio]benzyl}urea,
N-{3-tert-butyl-1-[3-(methylthio)phenyl]-1H-pyrazol-5-yl}-N'-{2-[(3-isopropyl[1,2,4]triazolo[4,3-a]pyridin-6-yl)thio]benzyl}urea,
N-[3-tert-butyl-1-(3,4-dichlorophenyl)-1H-pyrazol-5-yl]-N'-{2-[(3-isopropyl[1,2,4]triazolo[4,3-a]pyridin-6-yl)thio]benzyl}urea,
ethyl 4-(3-tert-butyl-5-{[({2-[(3-isopropyl[1,2,4]triazolo[4,3-a]pyridin-6-yl)thio]benzyl}amino)carbonyl]amino}-1H-pyrazol-1-yl)benzoate, ethyl 3-(3-tert-butyl-5-{[({2-[(3-isopropyl[1,2,4]triazolo[4,3-a]pyridin-6-yl)thio]benzyl}amino)carbonyl]amino}-1H-pyrazol-1-yl)benzoate, N-[3-tert-butyl-1-(4-cyanophenyl)-1H-pyrazol-5-yl]-N'-{2-[(3-isopropyl[1,2,4]triazolo[4,3-a]pyridin-6-yl)thio]benzyl}urea, N-[3-tert-butyl-1-(3-cyanophenyl)-1H-pyrazol-5-yl]-N'-{2-[(3-isopropyl[1,2,4]triazolo[4,3-a]pyridin-6-yl)thio]benzyl}urea, N-(3-tert-butyl-1-phenyl-1H-pyrazol-5-yl)-N'-{2-[(3-isopropyl[1,2,4]triazolo[4,3-a]pyridin-6-yl)thio]benzyl}urea.

N-[3-tert-butyl-1-(4-methylphenyl)-1H-pyrazol-5-yl]-N'-{2-[(3-isopropyl[1,2,4]triazolo[4,3-a]pyridin-6-yl)thio]benzyl}urea, N-[3-tert-butyl-1-(4-methoxyphenyl)-1H-pyrazol-5-yl]-N'-{2-[(3-isopropyl[1,2,4]triazolo[4,3-a]pyridin-6-yl)thio]benzyl}urea, N-[3-tert-butyl-1-(4-methoxy-3-methylphenyl)-1H-pyrazol-5-yl]-N'-{2-[(3-isopropyl[1,2,4]triazolo[4,3-a]pyridin-6-yl)thio]benzyl}urea, N-[3-tert-butyl-1-(3-methoxyphenyl)-1H-pyrazol-5-yl]-N'-{2-[(3-isopropyl[1,2,4]triazolo[4,3-a]pyridin-6-yl)thio]benzyl}urea, N-[3-tert-Butyl-1-(4-methylphenyl)-1H-pyrazol-5-yl]-N'-(2-{[3-(2-chloro-4-hydroxyphenyl)[1,2,4]triazolo[4,3-a]pyridin-6-yl]thio}benzyl)urea, N-[3-tert-Butyl-1-(4-methylphenyl)-1H-pyrazol-5-yl]-N'-(2-{[3-(2-chloro-5-hydroxyphenyl)[1,2,4]triazolo[4,3-a]pyridin-6-yl]thio}benzyl)urea, N-{3-[1,1-Dimethyl-2-<methylthio)ethyl]-1-phenyl-1H-pyrazol-5-yl}-N'-{2-[(3-isopropyl[1,2,4]triazolo[4,3-a]pyridin-6-yl)thio]benzyl}urea, N-[3-[1,1-dimethyl-2-(methylthio)ethyl]-1-(4-methylphenyl)-1H-pyrazol-5-yl]-N'-{2-[(3-isopropyl[1,2,4]triazolo[4,3-a]pyridin-6-yl)thio]benzyl}urea, N-{2-[(3-isopropyl[1,2,4]triazolo[4,3-a]pyridin-6-yl)thio]benzyl}-N'-{3-[1-methyl-1-(methylthio)ethyl]1-phenyl-1H-pyrazol-5-yl}urea, N-{1-[2-(benzyloxy)phenyl]-3-[1-methyl-1-(methylthio)ethyl]-1H-pyrazol-5-yl}-N'-{2-[(3-isopropyl[1,2,4]triazolo[4,3-a]pyridin-6-yl)thio]benzyl}urea, N-{1-(4-chlorophenyl)-3-[1-methyl-1-(methylthio)ethyl]-1H-pyrazol-5-yl}-N'-{2-[(3-isopropyl[1,2,4]triazolo[4,3-a]pyridin-6-yl)thio]benzyl}urea, N-{2-[(3-isopropyl[1,2,4]triazolo[4,3-a]pyridin-6-yl)thio]benzyl}-N'-{3-[1-methyl-1-(methylthio)ethyl]-1-[4-(trifluoromethyl)phenyl]-1H-pyrazol-5-yl}urea, N-[2-({3-[2-benzyloxy)phenyl][1,2,4]triazolo[4,3-a]pyridin-6-yl}thio)benzyl]-N'-{3-[1-methyl-1-(methylthio)ethyl]-1-phenyl-1H-pyrazol-5-yl}urea, N-[2-({3-[2-(benzyloxy)phenyl][1,2,4]triazolo[4,3-a]pyridin-6-yl}thio)benzyl]-N'-{1-(4-chlorophenyl)-3-[1-methyl-1-(methylthio)ethyl]-1H-pyrazol-5-yl}urea, N-[2-({3-[2-(benzyloxy)phenyl][1,2,4]triazolo[4,3-a]pyridin-6-yl}thio)benzyl]-N'-{3-[1-methyl-1-(methylthio)ethyl]-1-[4-(trifluoromethyl)phenyl]-1H-pyrazol-5-yl}urea, N-[3-tert-Butyl-1-(3-hydroxyphenyl)-1H-pyrazol-5-yl]-N'-{2-[(3-isopropyl[1,2,4]triazolo[4,3-a]pyridin-6-yl)thio]benzyl}urea, N-[3-tert-Butyl-1-(4-hydroxy-3-methylphenyl)-1H-pyrazol-5-yl]-N'-{2-[(3-isopropyl[1,2,4]triazolo[4,3-a]pyridin-6-yl)thio]benzyl}urea, N-{1-(3-Hydroxyphenyl)-3-[1-methyl-1-(methylthio)ethyl]-1H-pyrazol-5-yl}-N'-{2-[(3-isopropyl[1,2,4]triazolo[4,3-a]pyridin-6-yl)thio]benzyl}urea, N-(2-{[3-(2-hydroxyphenyl)[1,2,4]triazolo[4,3-a]pyridin-6-yl]thio}benzyl)-N'-{3-[1-methyl-1-(methylthio)ethyl]-1-phenyl-1H-pyrazol-5-yl}urea, N-{1-(4-chlorophenyl)-3-[1-methyl-1-(methylthio)ethyl]-1H-pyrazol-5-yl}-N'-(2-{[3-(2-hydroxyphenyl)[1,2,4]triazolo[4,3-a]pyridin-6-yl]thio}benzyl)urea, N-(2-{[3-(2-hydroxyphenyl)[1,2,4]triazolo[4,3-a]pyridin-6-yl]thio}benzyl)-N'-{3-[1-methyl-1-(methylthio)ethyl]-1-[4-(trifluoromethyl)phenyl]-1H-pyrazol-5-yl}urea 3-(3-tert-Butyl-5-{3-[2-(3-isopropyl-[1,2,4]triazolo[4,3-a]pyridin-6-ylsulfanyl)-benzyl]-ureido}-pyrazol-1-yl)-benzoic acid, 4-(3-tert-butyl-5-{[({2-[(3-isopropyl[1,2,4]triazolo[4,3-a]pyridin-6-yl)thio]benzyl}amino)carbonyl]amino}-1H-pyrazol-1-yl)benzoic acid, N-[3-tert-Butyl-1-(4-hydroxyphenyl)-1H-pyrazol-5-yl]-N'-{2-[(3-isopropyl[1,2,4]triazolo[4,3-a]pyridin-6-yl)thio]benzyl}urea, N-[3-tert-Butyl-1-(3-methylphenyl)-1H-pyrazol-5-yl]-N'-{2-[(3-isopropyl[1,2,4]triazolo[4,3-a]pyridin-6-yl)thio]benzyl}urea, N-(3-tert-butyl-1-pyridin-3-yl-1H-pyrazol-5-yl)-N'-{2-[(3-isopropyl[1,2,4]triazolo[4,3-a]pyridin-6-yl)thio]benzyl}urea, N-(2-{[3-(2-hydroxyphenyl)[1,2,4]triazolo[4,3-a]pyridin-6-yl]thio}benzyl)-N'-{3-[1-methyl-1-(methylthio)ethyl]-1-pyridin-3-yl-1H-pyrazol-5-yl}urea, N-{2-[(3-isopropyl[1,2,4]triazolo[4,3-a]pyridin-6-yl)thio]benzyl}-N'-[3-[1-methyl-1-(methylthio)ethyl]1-(4-methylphenyl)-1H-pyrazol-5-yl]urea, N-[3-tert-Butyl-1-(4-methylphenyl)-1H-pyrazol-5-yl]-N'-(2-{[3-(2-hydroxyphenyl)[1,2,4]triazolo[4,3-a]pyridin-6-yl]thio}benzyl)urea, N-(2-{[3-(2-Hydroxyphenyl)[1,2,4]triazolo[4,3-a]pyridin-6-yl]thio}benzyl)-N'-[3-[1-methyl-1-(methylthio)ethyl]-1-(4-methylphenyl)-1H-pyrazol-5-yl]urea, N-(2-{[3-(2-hydroxy-4-methylphenyl)[1,2,4]triazolo[4,3-a]pyridin-6-yl]thio}benzyl)-N'-[3-[1-methyl-1-(methylthio)ethyl]-1-(4-methylphenyl)-1H-pyrazol-5-yl]urea, N-{2-[(3-isopropyl[1,2,4]triazolo[4,3-a]pyridin-6-yl)thio]benzyl}-N'-[3-[1-methyl-1-(methylthio)ethyl]-1-(3-methylphenyl)-1H-pyrazol-5-yl]urea, N-[3-tert-Butyl-1-(3-methylphenyl)-1H-pyrazol-5-yl]-N'-(2-{[3-(2-hydroxyphenyl)[1,2,4]triazolo[4,3-a]pyridin-6-yl]thio}benzyl)urea, N-(2-{[3-(2-hydroxyphenyl)[1,2,4]triazolo[4,3-a]pyridin-6-yl]thio}benzyl)-N'-[3-[1-methyl-1-(methylthio)ethyl]-1-(3-methylphenyl)-1H-pyrazol-5-yl]urea, N-(2-{[3-(2-hydroxy-4-methylphenyl)[1,2,4]triazolo[4,3-a]pyridin-6-yl]thio}benzyl)-N-[3-[1-methyl-1-(methylthio)ethyl]-1-(3-methylphenyl)-1H-pyrazol-5-yl]urea, N-[3-tert-Butyl-1-(3-methylphenyl)-1H-pyrazol-5-yl]-N'-(2-{[3-(2-hydroxy-4-methylphenyl)[1,2,4]triazolo[4,3-a]pyridin-6-yl]thio}benzyl)urea, N-{3-[1,1-dimethyl-2-(methylthio)ethyl]-1-phenyl-1H-pyrazol-5-yl}-N'-(2-{[3-(2-hydroxyphenyl)[1,2,4]triazolo[4,3-a]pyridin-6-yl]thio}benzyl)urea, N-(2-{[3-(2-hydroxy-4-methylphenyl)[1,2,4]triazolo[4,3-a]pyridin-6-yl]thio}benzyl)-N'-{3-[1-methyl-1-(methylthio)ethyl]-1-phenyl-1H-pyrazol-5-yl}urea, N-[3-[1,1-dimethyl-2-(methylthio)ethyl]-1-(4-methylphenyl)-1H-pyrazol-5-yl]-N'-(2-{[3-(2-hydroxyphenyl)[1,2,4]triazolo[4,3-a]pyridin-6-yl]thio}benzyl)urea, N-[3-[1,1-dimethyl-2-(methylthio)ethyl]-1-(3-methylphenyl)-1H-pyrazol-5-yl]-N'-(2-{[3-(2-hydroxyphenyl)[1,2,4]triazolo[4,3-a]pyridin-6-yl]thio}benzyl)urea, N-[3-[1,1-dimethyl-2-(methylthio)ethyl]-1-(4-hydroxyphenyl)-1H-pyrazol-5-yl]-N'-{2-[(3-isopropyl[1,2,4]triazolo[4,3-a]pyridin-6-yl)thio]benzyl}urea, N-[3-[1,1-dimethyl-2-(methylthio)ethyl]-1-(3-hydroxyphenyl)-1H-pyrazol-5-yl]-N'-{2-[(3-isopropyl[1,2,4]triazolo[4,3-a]pyridin-6-yl)thio]benzyl}urea, N-[3-tert-Butyl-1-(4-chlorophenyl)-1H-pyrazol-5-yl]-N'-(2-{[3-(2-hydroxyphenyl)[1,2,4]triazolo[4,3-a]pyridin-6-yl]thio}benzyl)urea, N-[3-tert-Butyl-1-(4-chlorophenyl)-1H-pyrazol-5-yl]-N'-(2-{[3-(2-hydroxy-4-methylphenyl)[1,2,4]triazolo[4,3-a]pyridin-5-yl]thio}benzyl)urea, N-[1-(4-chlorophenyl)-3-[1-methyl-1-(methylthio)ethyl]-1H-pyrazol-5-yl]-N'-(2-{[3-(2-hydroxy-4-methylphenyl)[1,2,4]triazolo[4,3-a]pyridin-6-yl]thio}benzyl)urea, N-[3-tert-butyl-1-(3-ethylphenyl)-1H-pyrazol-5-yl]-N'-(2-{[3-(2-hydroxyphenyl)[1,2,4]triazolo[4,3-a]pyridin-6-yl]thio}benzyl)urea, N-[3-tert-butyl-1-(3-ethylphenyl)-1H-pyrazol-5-yl]-N'-(2-{[3-(2-hydroxy-4-methylphenyl)[1,2,4]triazolo[4,3-a]pyridin-6-yl]thio}benzyl)urea, N-{1-(3-ethylphenyl)-3-[1-methyl-1-(methylthio)ethyl]1H-pyrazol-5-yl}-N'-(2-{[3-(2-hydroxy-4-methylphenyl)[1,2,4]triazolo[4,3-a]pyridin-6-yl]thio}benzyl)urea, N-{3-tert-butyl-1-[4-(trifluoromethyl)phenyl]-1H-pyrazol-5-yl}-N'-(2-{[3-(2-hydroxyphenyl)[1,2,4]triazolo[4,3-a]pyridin-6-yl]thio}benzyl)urea, N-{3-tert-butyl-1-[4-(trifluoromethyl)phenyl]-1H-pyrazol-5-yl}-N'-(2-{[3-(2-hydroxy-4-methylphenyl)[1,2,4]triazolo[4,3-a]pyridin-6-yl]thio}benzyl)urea, N-(2-{[3-(2-hydroxy-4-methylphenyl)[1,2,4]triazolo[4,3-a]pyridin-6-yl]thio}benzyl)-N'-{3-[1-methyl-1-(methylthio)ethyl]-1-[4-(trifluoromethyl)phenyl]-1H-pyrazol-5-yl}urea, N-{2-[(3-isopropyl[1,2,4]triazolo[4,3-a]pyridin-6-yl)thio]benzyl}-N'-{3-[1-methyl-1-(methylthio)ethyl]-1-[3-(trifluoromethyl)phenyl]-1H-pyrazol-5-yl}urea, N-(2-{[3-(2-hydroxyphenyl)[1,2,4]triazolo[4,3-a]pyridin-6-yl]thio}benzyl)-N'-{3-[1-methyl-1-(methylthio)ethyl]-1-[3-(trifluoromethyl)phenyl]-1H-pyrazol-5-yl}urea, N-{3-tert-butyl-1-[3-(trifluoromethyl)phenyl]-1H-pyrazol-5-yl}-N'-(2-{[3-(2-hydroxyphenyl)[1,2,4]triazolo[4,3-a]pyridin-6-yl]thio}benzyl)urea N-{3-tert-butyl-1-[3-(trifluoromethyl)phenyl]-1H-pyrazol-5-yl}-N'-(2-{[3-(2-hydroxy-4-methylphenyl)[1,2,4]triazolo[4,3-a]pyridin-6-yl]thio}benzyl)urea, N-(2-{[3-(2-hydroxy-4-methylphenyl)[1,2,4]triazolo[4,3-a]pyridin-6-yl]thio}benzyl)-N'-{3-[1-methyl-1-(methylthio)ethyl]-1-[3-(trifluoromethyl)phenyl]-1H-pyrazol-5-yl}urea, N-{1-(4-cyclopropylphenyl)-3-[1-methyl-1-(methylthio)ethyl]-1H-pyrazol-5-yl}-N'-{2-[(3-isopropyl[1,2,4]triazolo[4,3-a]pyridin-6-yl)thio]benzyl}urea, N-{1-(4-cyclopropylphenyl)-3-[1-methyl-1-(methylthio)ethyl]-1H-pyrazol-5-yl}-N'-(2-{[3-(2-hydroxyphenyl)[1,2,4]triazolo[4,3-a]pyridin-6-yl]thio}benzyl)urea, N-[3-tert-butyl-1-(4-cyclopropylphenyl)-1H-pyrazol-5-yl]-N'-(2-{[3-(2-hydroxyphenyl)[1,2,4]triazolo[4,3-a]pyridin-6-yl]thio}benzyl)urea, N-[3-tert-butyl-1-(4-cyclopropylphenyl)-1H-pyrazol-5-yl]-N'-(2-{[3-(2-hydroxy-4-methylphenyl)[1,2,4]triazolo[4,3-a]pyridin-6-yl]thio}benzyl)urea, N-{1-(4-cyclopropylphenyl)-3-[1-methyl-1-(methylthio)ethyl]-1H-pyrazol-5-yl}-N'-(2-{[3-(2-hydroxy-4-methylphenyl)[1,2,4]triazolo[4,3-a]pyridin-6-yl]thio}benzyl)urea, N-{1-(3-cyclopropylphenyl)-3-[1-methyl-1-(methylthio)ethyl]-1H-pyrazol-5-yl}-N'-{2-[(3-isopropyl[1,2,4]triazolo[4,3-a]pyridin-6-yl)thio]benzyl}urea, N-{1-(3-cyclopropylphenyl)-3-[1-methyl-1-(methylthio)ethyl]-1H-pyrazol-5-yl}-N'-(2-{[3-(2-hydroxyphenyl)[1,2,4]triazolo[4,3-a]pyridin-6-yl]thio}benzyl)urea, N-[3-tert-butyl-1-(3-cyclopropylphenyl)-1H-pyrazol-5-yl]-N'-(2-{[3-(2-hydroxyphenyl)[1,2,4]triazolo[4,3-a]pyridin-6-yl]thio}benzyl)urea, N-[3-tert-butyl-1-(3-cyclopropylphenyl)-1H-pyrazol-5-yl]-N'-(2-{[3-(2-hydroxy-4-methylphenyl)[1,2,4]triazolo[4,3-a]pyridin-6-yl]thio}benzyl)urea, N-{1-(3-cyclopropylphenyl)-3-[1-methyl-1-(methylthio)ethyl]-1H-pyrazol-5-yl}-N'-(2-{[3-(2-hydroxy-4-methylphenyl)[1,2,4]triazolo[4,3-a]pyridin-6-yl]thio}benzyl)urea, N-{1-(3,5-dimethylphenyl)-3-[1-methyl-1-(methylthio)ethyl]-1H-pyrazol-5-yl}-N'-{2-[(3-isopropyl)[1,2,4]triazolo[4,3-a]pyridin-6-yl)thio]benzyl}urea, N-{1-(3,5-dimethylphenyl)-3-[1-methyl-1-(methylthio)ethyl]-1H-pyrazol-5-yl}-N'-(2-{[3-(2-hydroxyphenyl)[1,2,4]triazolo[4,3-a]pyridin-6-yl]thio}benzyl)urea.

N-[3-tert-butyl-1-(3,5-dimethylphenyl)-1H-pyrazol-5-yl]-N'-(2-{[3-(2-hydroxyphenyl)[1,2,4]triazolo[4,3-a]pyridin-6-yl]thio}benzyl)urea, N-[3-tert-butyl-1-(3,5-dimethylphenyl)-1H-pyrazol-5-yl]-N'-(2-{[3-(2-hydroxy-4-methylphenyl)[1,2,4]triazolo[4,3-a]pyridin-6-yl]thio}benzyl)urea, N-{1-(3,5-dimethylphenyl)-3-[1-methyl-1-(methylthio)ethyl]-1H-pyrazol-5-yl}-N'-(2-{[3-(2-hydroxy-4-methylphenyl)[1,2,4]triazolo[4,3-a]pyridin-6-yl]thio}benzyl)urea, N-{1-(4-hydroxyphenyl)-3-[1-methyl-1-(methylthio)ethyl]-1H-pyrazol-5-yl}-N'-{2-[(3-isopropyl[1,2,4]triazolo[4,3-a]pyridin-6-yl)thio]benzyl}urea, N-[3-tert-butyl-1-(4-hydroxyphenyl)-1H-pyrazol-5-yl]-N'-(2-{[3-(2-chlorophenyl)[1,2,4]triazolo[4,3-a]pyridin-6-yl]thio}benzyl)urea, N-{1-(4-hydroxyphenyl)-3-[1-methyl-1-(methylthio)ethyl]-1H-pyrazol-5-yl}-N'-(2-{[3-(2-methylphenyl)[1,2,4]triazolo[4,3-a]pyridin-6-yl]thio}benzyl)urea, N-[3-tert-butyl-1-(3-hydroxyphenyl)-1H-pyrazol-5-yl]-N'-(2-{[3-(2-chlorophenyl)[1,2,4]triazolo[4,3-a]pyridin-6-yl]thio}benzyl)urea, N-{1-(3-hydroxyphenyl)-3-[1-methyl-1-(methylthio)ethyl]-1H-pyrazol-5-yl}-N'-(2-{[3-(2-methylphenyl)[1,2,4]triazolo[4,3-a]pyridin-6-yl]thio}benzyl)urea, N-[3-tert-butyl-1-(3-chloro-hydroxyphenyl)-1H-pyrazol-5-yl]-N'-{2-[(3-isopropyl[1,2,4]triazolo[4,3-a]pyridin-6-yl)thio]benzyl}urea, N-{1-(3-chloro-4-hydroxyphenyl)-3-[1-methyl-1-(methylthio)ethyl]-1H-pyrazol-5-yl}-N'-{2-[(3-isopropyl[1,2,4]triazolo[4,3-a]pyridin-6-yl)thio]benzyl}urea, N-[3-tert-butyl-1-(3-chloro-4-hydroxyphenyl)-1H-pyrazol-5-yl]-N'-(2-{[3-(2-chlorophenyl)[1,2,4]triazolo[4,3-a]pyridin-6-yl]thio}benzyl)urea, N-{1-(3-chloro-4-hydroxyphenyl)-3-[1-methyl-1-(methylthio)ethyl]-1H-pyrazol-5-yl}-N'-(2-{[3-(2-methylphenyl)[1,2,4]triazolo[4,3-a]pyridin-6-yl]thio}benzyl)urea, N-[3-tert-butyl-1-(4-chloro-3-hydroxyphenyl)-1H-pyrazol-5-yl]-N'-{2-[(3-isopropyl[1,2,4]triazolo[4,3-a]pyridin-6-yl)thio]benzyl}urea, N-{1-(4-chloro-3-hydroxyphenyl)-3-[1-methyl-1-(methylthio)ethyl]-1H-pyrazol-5-yl}-N'-{2-[(3-isopropyl[1,2,4]triazolo[4,3-a]pyridin-6-yl)thio]benzyl}urea, N-[3-tert-butyl-1-(4-chloro-3-hydroxyphenyl)-1H-pyrazol-5-yl]-N'-(2-{[3-(2-chlorophenyl)[1,2,4]triazolo[4,3-a]pyridin-6-yl]thio}benzyl)urea, N-{1-(4-chloro-3-hydroxyphenyl)-3-[1-methyl-1-(methylthio)ethyl]-1H-pyrazol-5-yl}-N'-(2-{[3-(2-methylphenyl)[1,2,4]triazolo[4,3-a]pyridin-6-yl]thio}benzyl)urea, N-{1-(4-hydroxy-3-methylphenyl)-3-[1-methyl-1-(methylthio)ethyl]-1H-pyrazol-5-yl}-N'-{2-[(3-isopropyl[1,2,4]triazolo[4,3-a]pyridin-6-yl)thio]benzyl}urea, N-[3-tert-butyl-1-(4-hydroxy-3-methylphenyl)-1H-pyrazol-5-yl]-N'-(2-{[3-(2-chlorophenyl)[1,2,4]triazolo[4,3-a]pyridin-6-yl]thio}benzyl)urea, N-{1-(4-hydroxy-3-methylphenyl)-3-[1-methyl-1-(methylthio)ethyl]-1H-pyrazol-5-yl}-N'-(2-{[3-(2-methylphenyl)[1,2,4]triazolo[4,3-a]pyridin-6-yl]thio}benzyl)urea, N-[3-tert-butyl-1-(3-hydroxy-4-methylphenyl)-1H-pyrazol-5-yl]-N'-{2-[(3-isopropyl[1,2,4]triazolo[4,3-a]pyridin-6-yl)thio]benzyl}urea, N-{1-(3-hydroxy-4-methylphenyl)-3-[1-methyl-1-(methylthio)ethyl]-1H-pyrazol-5-yl}-N'-{2-[(3-isopropyl[1,2,4]triazolo[4,3-a]pyridin-6-yl)thio]benzyl}urea, N-[3-tert-butyl-1-(3-hydroxy-4-methylphenyl)-1H-pyrazol-5-yl]-N'-(2-{[3-(2-chlorophenyl)[1,2,4]triazolo[4,3-a]pyridin-6-yl]thio}benzyl)urea, N-{1-(3-hydroxy-4-methylphenyl)-3-[1-methyl-1-(methylthio)ethyl]-1H-pyrazol-5-yl}-N'-(2-{[3-(2-methylphenyl)[1,2,4]triazolo[4,3-a]pyridin-6-yl]thio}benzyl)urea, N-[3-tert-butyl-1-(4-ethyl-3-hydroxyphenyl)-1H-pyrazol-5-yl]-N'-{2-[(3-isopropyl[1,2,4]triazolo[4,3-a]pyridin-6-yl)thio]benzyl}urea, N-{1-(4-ethyl-3-hydroxyphenyl)-3-[1-methyl-1-(methylthio)ethyl]-1H-pyrazol-5-yl}-N'-{2-[(3-isopropyl[1,2,4]triazolo[4,3-a]pyridin-6-yl)thio]benzyl}urea, N-[3-tert-butyl-1-(4-ethyl-3-hydroxyphenyl)-1H-pyrazol-5-yl]-N'-(2-{[3-(2-chlorophenyl)[1,2,4]triazolo[4,3-a]pyridin-6-yl]thio}benzyl)urea, N-{1-(4-ethyl-3-hydroxyphenyl)-3-[1-methyl-1-(methylthio)ethyl]-1H-pyrazol-5-yl}-N'-(2-{[3-(2-methylphenyl)[1,2,4]triazolo[4,3-a]pyridin-6-yl]thio}benzyl)urea, N-(2-{[3-(2-chloro-4-hydroxyphenyl)[1,2,4]triazolo[4,3-a]pyridin-6-yl]thio}benzyl)-N'-[3-[1-methyl-1-(methylthio)ethyl]-1-(3-methylphenyl)-1H-pyrazol-5-yl]urea, N-(2-{[3-(2-chloro-4-hydroxyphenyl)[1,2,4]triazolo[4,3-a]pyridin-6-yl]thio}benzyl)-N'-[3-[1-methyl-1-(methylthio)ethyl]-1-(4-methylphenyl)-1H-pyrazol-5-yl]urea, N-[3-tert-butyl-1-(3-methylphenyl)-1H-pyrazol-5-yl]-N'-(2-{[3-(2-chloro-4-hydroxyphenyl)[1,2,4]triazolo[4,3-a]pyridin-6-yl]thio}benzyl)urea, N-(2-{[3-(2-chloro-5-hydroxyphenyl)[1,2,4]triazolo[4,3-a]pyridin-6-yl]thio}benzyl)-N'-[3-[1-methyl-1-methylthio)ethyl]-1-(3-methylphenyl)-1H-pyrazol-5-yl]urea, N-(2-{[3-(2-chloro-5-hydroxyphenyl)[1,2,4]triazolo[4,3-a]pyridin-6-yl]thio}benzyl)-N'-[3-[1-methyl-1-(methylthio)ethyl]-1-(4-methylphenyl)-1H-pyrazol-5-yl]urea, N-[3-tert-butyl-1-(3-methylphenyl)-1H-pyrazol-5-yl]-N'-(2-{[3-(2-chloro-5-hydroxyphenyl)[1,2,4]triazolo[4,3-a]pyridin-6-yl]thio}benzyl)urea, N-[3-tert-butyl-1-(4-hydroxyphenyl)-1H-pyrazol-5-yl]-N'-{2-[(3-phenyl[1,2,4]triazolo[4,3-a]pyridin-6-yl)thio]benzyl}urea, N-[3-tert-butyl-1-(3-hydroxyphenyl)-1H-pyrazol-5-yl]-N'-{2-[(3-phenyl[1,2,4]triazolo[4,3-a]pyridin-6-yl)thio]benzyl}urea, N-{1-(4-hydroxyphenyl)-3-[1-methyl-1-(methylthio)ethyl]-1H-pyrazol-5-yl}-N'-{2-[(3-phenyl[1,2,4]triazolo[4,3-a]pyridin-6-yl)thio]benzyl}urea, N-{3-(2-hydroxy-1,1-dimethylethyl)-1-[3-(2-hydroxyethoxy)phenyl]-1H-pyrazol-5-yl}-N'-(2-{[3-(2-hydroxyphenyl)[1,2,4]triazolo[4,3-a]pyridin-6-yl]thio}benzyl)urea N-[3-tert-butyl-1-(3-hydroxyphenyl)-1H-pyrazol-5-yl]-N'-[2-({3-[2-(methylsulfinyl)phenyl][1,2,4]triazolo[4,3-a]pyridin-6-yl}thio)benzyl]urea N-[3-[1,1-dimethyl-2-(methylsulfinyl)ethyl]-1-(3-fluorophenyl)-1H-pyrazol-5-yl]-N'-(2-{[3-(2-hydroxyphenyl)[1,2,4]triazolo[4,3-a]pyridin-6-yl]thio}benzyl)urea and N-(1-(3-hydroxyphenyl)-3-[1-methyl-1-(methylthio)ethyl]-1H-pyrazol-5-yl)-N'-{2-[(3-phenyl[1,2,4]triazolo[4,3-a]pyridin-6-yl)thio]benzyl}urea, and the salts, and/or solvates thereof.

Pharmaceutically acceptable salts of the compounds of formula (I) include the acid addition and base salts thereof.

Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate, adipate, cyclamate, tannate, pyroglutamate, xinafoate (1-hydroxynaphthalene-2-carboxylate) and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see *Handbook of Pharmaceutical Salts: Properties, Selection, and Use* by Stahl and Wermuth (Wiley-VCH, Weinheim, Germany, 2002).

Pharmaceutically acceptable salts of compounds of formula (I) may be prepared by one or more of three methods:
(i) by reacting the compound of formula (I) with the desired acid or base;
(ii) by removing an acid- or base-labile protecting group from a suitable precursor of the compound of formula (I) or by ring-opening a suitable cyclic precursor, for example, a lactone or lactam, using the desired acid or base; or
(iii) by converting one salt of the compound of formula (I) to another by reaction with an appropriate acid or base or by means of a suitable ion exchange column.

All three reactions are typically carried out in solution. The resulting salt may precipitate out and be collected by filtration or may be recovered by evaporation of the solvent. The degree of ionisation in the resulting salt may vary from completely ionised to almost non-ionised.

The compounds of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts.

Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288, by Haleblian (August 1975).

Hereinafter all references to compounds of formula (I) include references to salts, solvates, hydrates and complexes thereof and to solvates and complexes of salts thereof.

The compounds of the invention include compounds of formula (I) as hereinbefore defined, including all polymorphs and crystal habits thereof, prodrugs and isomers thereof (including optical, geometric and tautomeric isomers) as hereinafter defined and isotopically-labeled compounds of formula (I).

As indicated, so-called 'pro-drugs' of the compounds of formula (I) are also within the scope of the invention. Thus certain derivatives of compounds of formula (I) which may have little or no pharmacological activity themselves can, when administered into or onto the body, be converted into compounds of formula (I) having the desired activity, for example, by hydrolytic cleavage. Such derivatives are referred to as 'prodrugs'. Further information on the use of prodrugs may be found in *Pro-drugs as Novel Delivery Systems*, Vol. 14, ACS Symposium Series (T. Higuchi and W. Stella) and *Bioreversible Carriers in Drug Design*, Pergamon Press, 1987 (ed. E. B. Roche, American Pharmaceutical Association).

Prodrugs in accordance with the invention can, for example, be produced by replacing appropriate functionalities present in the compounds of formula (I) with certain moieties known to those skilled in the art as 'pro-moieties' as described, for example, in *Design of Prodrugs* by H. Bundgaard (Elsevier, 1985).

Some examples of prodrugs in accordance with the invention include
(i) where the compound of formula I contains a carboxylic acid functionality (—COOH), an ester thereof, for example, a compound wherein the hydrogen of the carboxylic acid functionality of the compound of formula (I) is replaced by $(C_1-C_8)$alkyl;
(ii) where the compound of formula (I) contains an alcohol functionality (—OH), an ether thereof, for example, a compound wherein the hydrogen of the alcohol functionality of the compound of formula (I) is replaced by $(C_1-C_6)$alkanoyloxymethyl; and
(iii) where the compound of formula (I) contains a primary or secondary amino functionality (—NH$_2$ or —NHR where R≠H), an amide thereof, for example, a compound wherein, as the case may be, one or both hydrogens of the amino functionality of the compound of formula (I) is/are replaced by $(C_1-C_{10})$alkanoyl.

Further examples of replacement groups in accordance with the foregoing examples and examples of other prodrug types may be found in the aforementioned references.

Moreover, certain compounds of formula (I) may themselves act as prodrugs of other compounds of formula (I).

Also included within the scope of the invention are metabolites of compounds of formula (I), that is, compounds formed in vivo upon administration of the drug. Some examples of metabolites in accordance with the invention include
(i) where the compound of formula (I) contains a $(C_1-C_6)$alkyl group, the hydroxy$(C_1-C_6)$alkyl derivative thereof. For example where the compound of formula (I) contains a methyl group, the hydroxymethyl derivative thereof (—CH$_3$→—CH$_2$OH);

(ii) where the compound of formula (I) contains an alkoxy group, an hydroxy derivative thereof (—OR→—OH);
(iii) where the compound of formula (I) contains a tertiary amino group, a secondary amino derivative thereof (—NR$^5$R$^6$→—NHR$^5$ or —NHR$^6$);
(iv) where the compound of formula (I) contains a secondary amino group, a primary derivative thereof (—NHR$^5$→—NH$_2$);
(v) where the compound of formula (I) contains a phenyl moiety, a phenol derivative thereof (-Ph→-PhOH);
(vi) where the compound of formula (I) contains an amide group, a carboxylic acid derivative thereof (—CONH$_2$→COOH); and
(vii) where the compound of formula (I) contains a S—$(C_1-C_6)$alkyl group, the S(O)$(C_1-C_6)$alkyl derivative thereof. For example, where the compound of formula (I) contains a S-methyl group, the S(O)methyl derivative thereof, and where the compound of formula (I) contains an alkyl-S-alkyl group, the alkyl-S(O)-alkyl derivative thereof.

In another aspect of the invention there is provided the active metabolites of the compounds of formula (I), wherein "active" means having an IC$_{50}$ (TNFα screen) of less than 1000 nM, and preferably an IC$_{50}$ (TNFα screen) of less than 100 nM. Preferably, there is provided a compound of formula (I) which contains a S(O)$(C_1-C_6)$alkyl group, or a hydroxy group.

Compounds of formula (I) containing one or more asymmetric carbon atoms can exist as two or more stereoisomers. Where structural isomers are interconvertible via a low energy barrier, tautomeric isomerism ('tautomerism') can occur. This can take the form of proton tautomerism in compounds of formula (I) containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of formula (I), including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (I) contains an acidic or basic moiety, a base or acid such as 1-phenylethylamine or tartaric acid. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine, Concentration of the eluate affords the enriched mixture.

Stereoisomeric conglomerates may be separated by conventional techniques known to those skilled in the art—see, for example, *Stereochemistry of Organic Compounds* by E. L. Eliel and S. H. Wilen (Wiley, New York, 1994).

The present invention includes all pharmaceutically acceptable isotopically-labelled compounds of formula (I) wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, nitrogen, such as $^{13}$N and $^{15}$N, oxygen, such as $^{15}$O, $^{17}$O and $^{18}$O, and sulphur, such as $^{35}$S.

Certain isotopically-labelled compounds of formula (I), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labelled compounds of formula (I) can generally be prepared by conventional techniques known to those skilled in the art or by processes analogous to those described in the accompanying Examples and Preparations using an appropriate isotopically-labelled reagent in place of the non-labelled reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Also within the scope of the invention are novel intermediates as herein defined, all salts, solvates and complexes thereof and all solvates and complexes of salts thereof as defined herein for compounds of formula (I). The invention includes all polymorphs of the aforementioned species and crystal habits thereof.

When preparing compounds of formula (I) in accordance with the invention, it is open to a person skilled in the art to routinely select the form of intermediate compound which provides the best combination of features for this purpose. Such features include the melting point, solubility, processability and yield of the intermediate form and the resulting ease with which the product may be purified on isolation.

The crystal structures of the compounds of example numbers 80, 26, 93, 73, 63 and 60 were analyzed using powder X-ray diffraction ("PXRD").

Illustrative PXRD patterns for these compounds are shown in FIGS. 1-6 containing 15% silicon internal reference standard.

FIG. 1: Example 80
FIG. 2: Example 26
FIG. 3: Example 93
FIG. 4: Example 73
FIG. 5: Example 63
FIG. 6: Example 60

The X-ray diffraction data were collected at room temperature using a Bruker AXS D4 powder X-ray diffractometer (Cu Kα radiation) fitted with an automatic sample changer, a theta-theta goniometer, automatic beam divergence slits, a secondary monochromator and a scintillation counter. Samples were prepared for analysis by mixing the compound with a silicon powder internal reference at 15% content by weight. The powders were mounted on a 12 mm diameter silicon wafer specimen holder. The sample was rotated while being irradiated with Copper Kα1 X-rays (wavelength=1.5406 Ångstroms) with the X-ray tube operated at 40 kV/40 mA. The analyses were performed with the goniometer running in continuous mode set for a 5 second count per 0.02° step over a two theta range of 2° to 55°. The peaks obtained were aligned against the silicon reference standard (ICDD reference number 001-0791).

As will be appreciated by the skilled crystallographer, the relative intensities of the various peaks reported in the Tables and Figures below may vary due to a number of factors such as orientation effects of crystals in the X-ray beam or the purity of the material being analyzed or the degree of crystallinity of the sample. The peak positions may also shift for variations in sample weight but the peak positions will remain substantially as defined in the Figures. The skilled crystallographer also will appreciate that measurements using a different wavelength will result in different shifts according to the Bragg equation—$n\lambda=2d \sin \theta$. Such further PXRD patterns generated by use of alternative wavelengths are considered to be alternative representations of the PXRD patterns of the crystalline materials of the present invention and as such are within the scope of the present invention.

Tables 1-6 list the corresponding main diffraction peaks in terms of 2θ values and intensities for the compounds excluding those peaks that can be assigned to the silicon reference standard. All 2θ values are to +/−0.1 degree.

Table 1 lists the Example 80 peaks having a relative intensity greater than 33.0%.

Table 2 lists the Example 26 peaks having a relative intensity greater than 36.5%.

Table 3 lists the Example 93 peaks having a relative intensity greater than 15.5%.

Table 4 lists the Example 73 peaks having a relative intensity greater than 34.0%.

Table 5 lists the Example 63 peaks having a relative intensity greater than 35.7%.

Table 6 lists the Example 60 peaks having a relative intensity greater than 36.4%.

TABLE 1

Ex 80 Relative Intensity at least 33.0%

| Angle 2-Theta (degrees) | Relative Intensity |
|---|---|
| 15.4 | 39.2 |
| 18.0 | 34.7 |
| 18.8 | 68.6 |
| 19.5 | 81.1 |
| 21.1 | 100.0 |
| 21.5 | 33.9 |
| 24.1 | 50.3 |
| 24.7 | 40.7 |
| 25.7 | 42.6 |
| 26.4 | 42.0 |
| 27.8 | 33.0 |

TABLE 2

Ex 26 Relative Intensity at least 36.5%

| Angle 2-Theta (degrees) | Relative Intensity |
|---|---|
| 12.5 | 46.9 |
| 16.9 | 100.0 |
| 17.2 | 39.6 |
| 18.5 | 39.2 |
| 19.7 | 45.6 |
| 20.5 | 49.9 |
| 21.3 | 89.9 |
| 26.3 | 47.5 |
| 29.2 | 36.5 |

TABLE 3

Ex 93 Relative Intensity at least 15.5%

| Angle 2-Theta (degrees) | Relative Intensity |
|---|---|
| 15.5 | 79.1 |
| 17.2 | 19.4 |
| 18.3 | 100.0 |
| 18.8 | 16.5 |
| 19.5 | 19.1 |
| 20.6 | 15.6 |
| 21.1 | 18.0 |
| 23.4 | 15.8 |
| 25.0 | 15.6 |
| 26.0 | 15.5 |
| 27.1 | 35.1 |

TABLE 4

Ex 73: Relative Intensity at least 34.0%

| Angle 2-Theta (degrees) | Relative Intensity |
|---|---|
| 7.6 | 77.1 |
| 11.0 | 34.7 |
| 17.3 | 98.9 |
| 17.8 | 65.4 |
| 19.1 | 45.5 |
| 21.1 | 40.3 |
| 21.8 | 70.7 |
| 22.1 | 100.0 |
| 23.0 | 39.2 |
| 27.7 | 36.9 |
| 30.3 | 34.0 |

TABLE 5

Ex 63: Relative Intensity at least 35.7%

| Angle 2-Theta (degrees) | Relative Intensity |
|---|---|
| 13.6 | 70.6 |
| 18.1 | 49.6 |
| 19.6 | 45.2 |
| 21.0 | 50.0 |
| 22.3 | 62.7 |
| 22.5 | 35.7 |
| 23.2 | 100.0 |
| 24.2 | 53.1 |
| 25.8 | 44.7 |
| 26.5 | 39.4 |

TABLE 6

Ex 60: Relative Intensity at least 36.4%

| Angle 2-Theta (degrees) | Relative Intensity |
|---|---|
| 13.7 | 49.1 |
| 21.2 | 36.4 |
| 22.4 | 44.8 |
| 22.7 | 40.6 |
| 23.5 | 100.0 |
| 24.5 | 45.3 |
| 24.6 | 53.4 |
| 25.9 | 50.0 |
| 26.4 | 36.9 |

In a further aspect of the invention, there is provided a compound of example number 80, 26, 93, 73, 63 or 60, having the crystal structure as illustrated in the Figures and/or as defined in the Tables herein. The invention is by no means limited to said solid forms.

Compounds of formula (I) may be prepared, in a known manner, in a variety of ways. The following routes illustrate such ways of preparing these compounds; the skilled man wilt appreciate that other routes may be equally as practicable. In the following schemes, unless otherwise stated, the substituents are as defined above with reference to the compounds of formula (I) above, and "PdCl$_2$(dppf).CH$_2$Cl$_2$" is 1,1-bis(diphenylphosphino)ferrocene palladium (II) chloride 1:1 dichloromethane complex "DBU" is 1,8-diazabicyclo[5.4.0]undec-7-ene "BOC" means tert-butoxycarbonyl;

"CBz" means benzyloxycarbonyl

"Et" means ethyl

"Me" means methyl

"Pd" means palladium, and

"eq" means mole equivalent(s)

"iPr" means isopropyl.

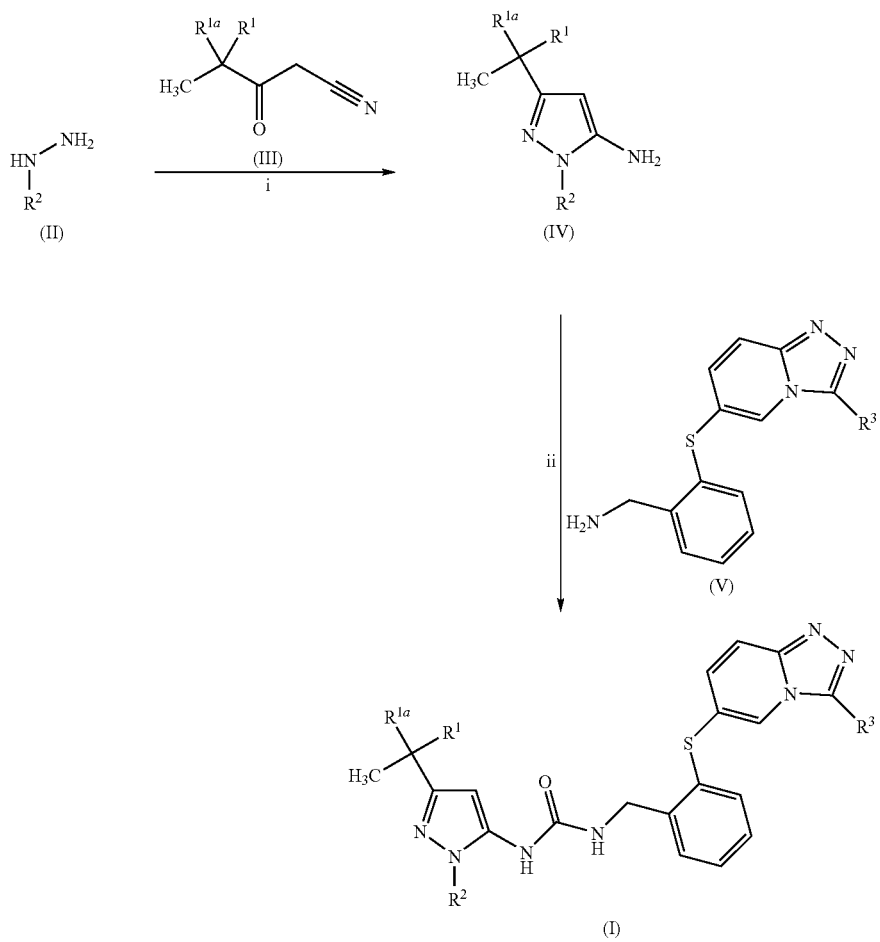

Compounds of general formula (II) are either commercially available or can be prepared as shown in scheme 2.

Compounds of general formula (III) are either commercially available (e.g. when $R^{1a}$=Me and $R^1$=Me) or can be prepared as shown in scheme 3.

Compounds of general formula (IV) can be prepared from compounds of formula (II) and (III) by process step i—cyclocondensation of compound (II) and compound (III) optionally in the presence of a suitable acid catalyst such as hydrochloric acid, optionally in the presence of a suitable base such as Hünig's base, triethylamine or pyridine, in a suitable solvent such as methanol or ethanol, at elevated temperature for 3-24 hours. Typical conditions comprise of 1.0-1.3 equivalents of compound (II) and 1.0-1.1 equivalents of compound (III) in the presence of hydrochloric acid, in ethanol, heated under reflux for 3-24 hours.

Additionally, compounds of general formula (IV) can be obtained by direct condensation of compounds of formula (VII) with compounds of formula (III), in EtOH/HCl.

Compounds of general formula (V) can be prepared as shown in scheme 4.

Compounds of formula (I) can be prepared from compounds (IV) and (V) by process step ii—urea formation is achieved by reaction of compound (IV) in the presence of a suitable carbonyl source such as N,N'-carbonyldiimidazole, phenylchloroformate or bis(trichloromethyl)carbonate and a suitable base such as Hünig's base or pyridine, in a suitable solvent such as dichloromethane or 1,4 dioxane, under ambient conditions for 48 hours, followed by addition of compound (V). Typical conditions comprise of either:
  a) 1.0 equivalent of compound (IV) and 5.0-6.0 equivalents of N,N'-carbonyldiimidazole in dichloromethane, under ambient conditions for 24 hours,
  b) 0.25-0.80 equivalents of compound (V), 0.25-1.25 equivalents of Hünig's base in dichloromethane or 1,4 dioxane, under ambient conditions for 24 hours, or
  c) 1 equivalent of compound (IV) and 1 equivalent of phenylchloroformate in THF/pyridine, followed by 0.8-1 equivalent of compound (V) in DMSO.

When $R^2$ is aryl or heteroaryl, compounds of general formula (II) may be prepared as shown in scheme 2.

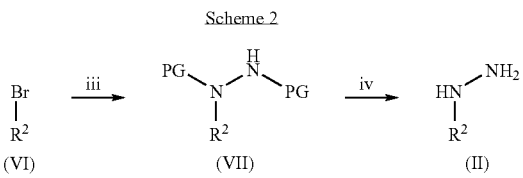

Where $R^2$—Br is not available, the compound of formula (II) could be prepared from the corresponding aniline derivative by diazotisation followed by reduction, using conditions well-known in the chemical literature.

PG is a suitable protecting group such as BOC or CBz and preferably BOC.

Where $R^2$ is, or includes, a phenol, the skilled person will appreciate that it may be necessary to use a protecting group, typically benzyloxy or methyloxy.

Compounds of general formula (VI) are commercially available.

Compounds of general formula (II) can be prepared from compounds of general formula (VI), via compound (VII), by process steps (iii) and (iv).

Step (iii)—is achieved by formation of a suitable organometallic reagent e.g. arylMgBr, heteroarylMgBr, arylLi, or heteroarylLi, optionally prepared in situ under standard Grignard conditions or by reaction with a suitable alkyl lithium, e.g. $^n$BuLi, in a suitable solvent such as tetrahydrofuran or diethyl ether, at a temperature between –100° C. to 25° C., for 1-18 hours. The intermediate compound (VII) is formed by subsequent nucleophilic attack of a suitably protected diazocarboxylate compound, preferably di-tert-butyldiazocarboxylate, by arylMgBr/heteroarylMgBr/arylLi/heteroarylLi, in a suitable solvent such as tetrahydrofuran or diethyl ether, at –78° C. for 0.5-1.0 hours.

Step (iv)—Deprotection of compound (VII) using standard methodology as described in "Protecting Groups in Organic Synthesis" by T. W. Greene and P. Wutz. When PG=BOC, typical conditions involve saturation of intermediate (VII) with a suitable acid such as hydrochloric acid or trifluoroacetic acid, in a suitable solvent such as isopropyl alcohol, 1,4-dioxane or diethyl ether, under ambient conditions for 2-18 hours.

More preferably, compounds of general formula (II) can be prepared from compounds of formula (VI) by a combination of steps iii and iv in a one-pot synthesis. Typical conditions comprise of a) 1.0 equivalent of compound (VI), 1.1 equivalents of magnesium turnings and a single crystal of iodine in tetrahydrofuran, at room temperature for 18 hours, followed by addition of di-tert-butyldiazocarboxylate at –78° C., for 30 minutes.

b) Saturation with hydrochloride gas in isopropyl alcohol, under ambient conditions for 0.5-1.0 hours.

When $R^2$ represents heterocyclyl or carbocyclyl, compounds of general formula (II) may be prepared according to scheme 2.1.

Scheme 2.1

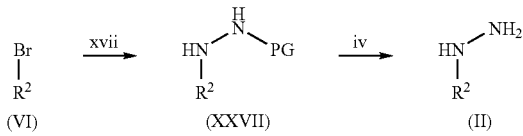

Step (xvii)—Compounds of formula (XXVII) may be prepared from compounds of formula (VI) by reaction with a suitable protected hydrazine (e.g. BOC—NHNH$_2$) in the presence of a suitable alkali metal base (e.g. $K_2CO_3$ or $Na_2CO_3$) in a suitable solvent such as acetonitrile or N,N-dimethylformamide at between ambient temperature and 60° C. for upto 48 hours.

Compounds of formula (II) may be prepared from compounds of formula (XXVII) using the methods described previously for step iv.

Compounds of general formula (III) may be prepared according to schemes 3.1 and 3.2.

When $R^1=-(CH_2)_nSR^b$, compounds of formula (III) can be prepared as shown in scheme 3.1. $R^b$ represents methyl or ethyl.

n represents 0 or 1.

Scheme 3.1

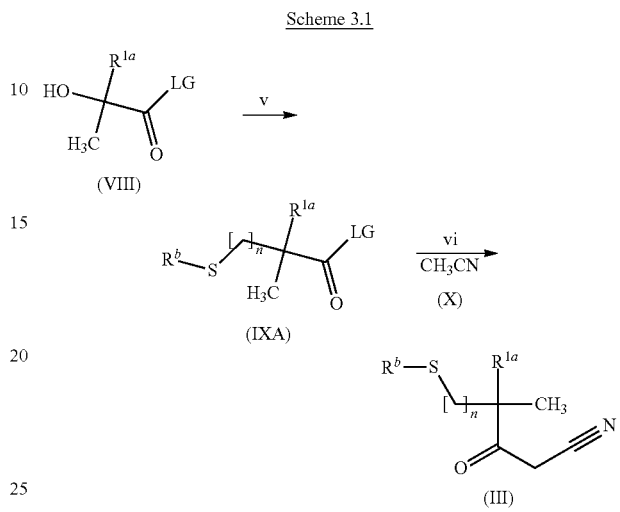

LG is a suitable leaving group, e.g. OR' or Cl and is preferably OR'.

R' represents $C_1$-$C_4$ alkyl, and preferably $C_1$-$C_2$ alkyl.

When R'=Et or Me, compounds of formula (VIII) are commercially available.

When n=1, compounds of formula (IXA) can be prepared from compounds of formula (VIII) by process step v—nucleophilic substitution. The reaction proceeds via the formation of an intermediate containing a suitable leaving group LG', such as mesylate or tosylate by reaction of compound (VIII) with mesyl chloride/anhydride or tosyl chloride, in the presence of a suitable base such as Hünig's base, triethylamine or pyridine, in a suitable solvent such as dichloromethane or diethyl ether, at low temperature for 1-2 hours. Concentration in vacuo is followed by the addition 1,4-dioxane or toluene and methanethiol sodium salt, heating under reflux for 24 hours. Typical conditions comprise of a) 1.0 eq of compound (VIII), 1.0-1.2 eq of Hünig's base, and 1.1 eq of methane sulfonyl chloride in dichloromethane, at 0° C. for 1-2 hours.

b) 1.1 eq methanethiol sodium salt in 1,4-dioxane, heating under reflux for 24 hours.

When n=0, compounds of formula (IXA) are commercially available

Compound (III) can be prepared from compounds of formula (IXA) by process step vi—reaction with acetonitrile (X). Treatment of (X) with a suitable base such as sodium hydride or lithium diisopropylamide, followed by quench of the intermediate anion with compound (IXA), in a suitable solvent such as tetrahydrofuran, at elevated temperature for 3 hours provides compounds of formula (III). Typical conditions comprise of 1.3 eq acetonitrile, 1.3 eq sodium hydride (60% dispersion in mineral oil) and 1.0 equivalent of compound (IXA) in tetrahydrofuran, heated under reflux for 3 hours.

When $R^{1a}$ represents H, $CH_3$ or $CH_2CH_3$, compounds of formula (III) may be prepared as shown in scheme 3.2.

Scheme 3.2

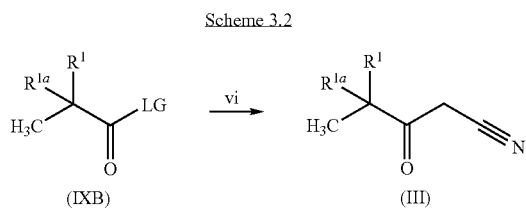

LG is a suitable leaving group, e.g. OR' or Cl and is preferably OR'.
R' represents $C_1$-$C_4$ alkyl, and preferably $C_1$-$C_2$ alkyl.

Compounds of formula (III) may be prepared from compounds of formula (IXB) by process step vi, as described previously.

Compounds of formula (IXB) are either available commercially, or may be prepared by analogy with the methods of Julia et. al. Bull. Soc. Chim. Fr. 1996; 133(1); 15-24, or Chuit et. al. Tetrahedron 1980; 36(16), 2305-10.

Compounds of formula (V) may be prepared as shown in scheme 4

Scheme 4

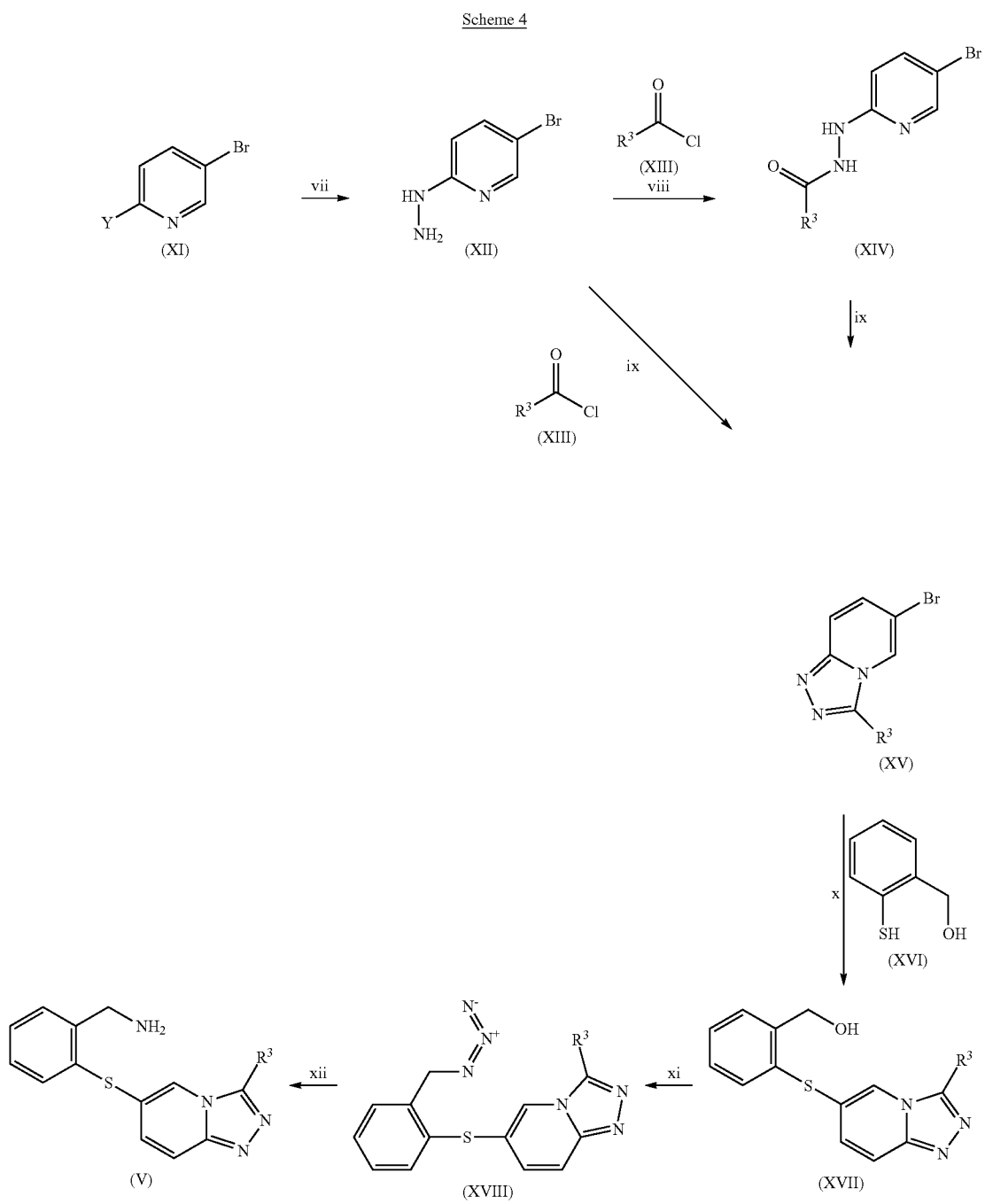

When Y=halogen and is preferably bromo, compounds of general formula (XI) are commercially available.

Compounds of formula (XII) can be prepared from compounds of formula (XI) by process step vii—reaction with hydrazine monohydrate, optionally in a suitable solvent such as methanol or ethanol, at elevated temperature for 18-72 hours. Typical conditions comprise 1.0 eq of compound (XI) and an excess of hydrazine monohydrate heated to 70° C. for 72 hours.

Compounds of formula (XIV) can be prepared from compounds of formula (XII) by process step viii—reaction with a suitable alkoyl chloride $R^3C(O)Cl$ (XIII), in the presence of a suitable base such as Hünig's base, triethylamine or pyridine in a suitable solvent such as dichloromethane or diethyl ether, at low temperature for 1-2 hours. Typical conditions comprise of 1.0 eq of compound (XII), 1.0 eq of $R^3C(O)Cl$ (XIII) and 5.0 eq Hünig's base in dichloromethane, at a temperature between 0-5° C. for 1-2 hours.

Compounds of formula (XV) can be prepared from compounds of formula (XIV) by process step ix—cyclisation. This is achieved by use of a suitable dehydrating agent such as phosphorus oxychloride or phosphorus (V) oxide in sulfuric acid, at elevated temperature for 18-24 hours. Typical conditions comprise of 1.0 equivalent of compound (XIV) in an excess of phosphorus oxychloride, at 75°G for 18-24 hours.

Alternatively, compounds of formula (XV) can be prepared directly from compounds of formula (XII) by process step ix. This cyclisation is achieved by reaction with an excess of compound (XIII) and heated, for example at 95° C., for 18-24 hours.

Compounds of formula (XVII) can be prepared from compounds of formula (XV) by process step x—Pd catalysed cross coupling reaction with 2-mercaptobenzyl alcohol (XVI), in the presence of a suitable catalyst such as $PdCl_2$(dppf).$CH_2Cl_2$, in the presence of a suitable base such as cesium carbonate or potassium carbonate, in a suitable solvent such as N,N-dimethylformamide or 1,4-dioxane, at elevated temperature for 2-48 hours. Typical conditions comprise of 1.0 eq compound (XV), 1.2-1.4 eq cesium carbonate, 1.3 eq 2-mercaptobenzyl alcohol (XVI) and 0.1 eq $PdCl_2$(dppf).$CH_2Cl_2$ in N,N-dimethylformamide, at elevated temperature for 18 hours.

Compounds of formula (XVIII) can be prepared from compounds of formula (XVII) by process step xi—azide formation. This proceeds by reaction of compound (XVII) with a suitable base such as DBU or sodium hydride, followed by reaction with a suitable azide such as diphenylphosphoryl azide in a suitable solvent such as toluene or tetrahydrofuran, at a temperature between 0-25° C. for 18-24 hours. Typical conditions comprise of 1.0 eq of compound (XVII), 1.2 eq of DBU and 1.2 eq diphenylphosphoryl azide in toluene at 0-25° C. for 24 hours.

Compounds of formula (V) can be prepared from compounds of formula (XVIII) by process step xii—reduction of compound (XVIII) with a suitable reducing agent such as triphenyl phosphine/water, tin chloride or catalytic hydrogenation, in a suitable solvent such as tetrahydrofuran or ethanol, between ambient and elevated temperature. Typical conditions comprise of 1.0 eq compound (XVIII), 1.2 eq triphenylphosphine and 1.2 eq of water in tetrahydrofuran, at room temperature for 40 hours and at 50° C. for 5 hours.

Alternatively, compounds of formula (V) can also be prepared as shown in scheme 5

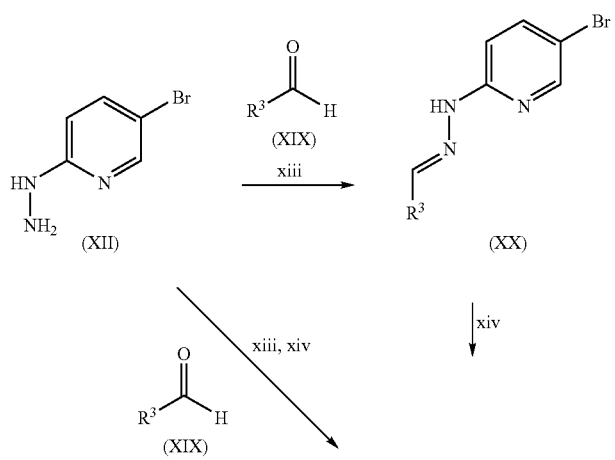

-continued

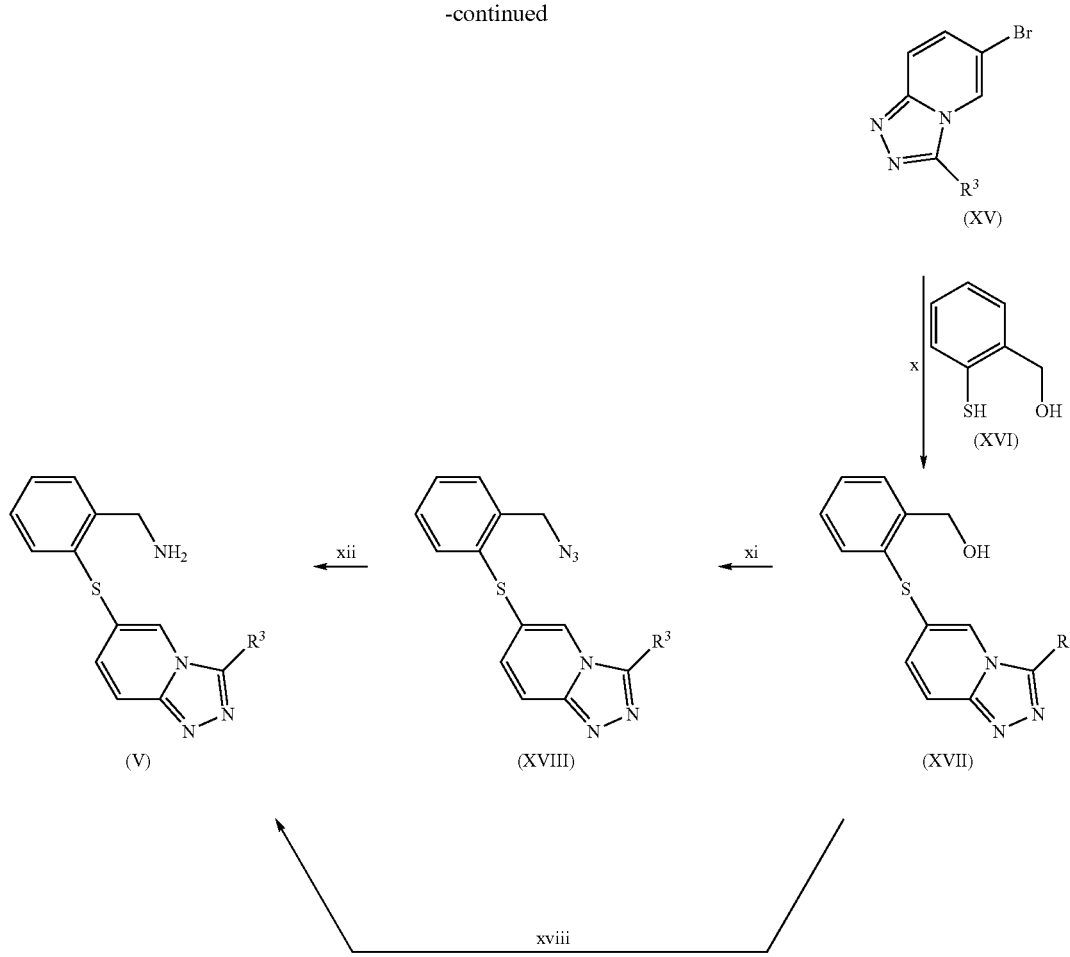

Compounds of formula (XII) can be prepared as described in scheme 4.

Compounds of formula (XIX) are either commercially available or can be prepared as described in scheme 6

Compounds of formula (XX) can be prepared from compounds of formula (XII) and (XIX) by process step xiii—condensation of hydrazine (XII) and aldehyde (XIX) in a suitable solvent such as methanol, ethanol or toluene, at elevated temperature for 0.5-1 hour. Typical conditions comprise of 1 eq of compound (XII) and 1 eq of compound (XIX) in ethanol, heated at reflux for 0.5-1.0 hour.

Compounds of formula (XV) can be prepared from compounds of formula (XX) by process step xiv—cyclisation of compound (XX) in the presence of a suitable oxidising agent such as (diacetoxyiodo)benzene, cerium (IV) ammonium nitrate or 2,3-dichloro-5,6-dicyano-1,4-benzoquinone in a suitable solvent such as ethyl acetate, dichloromethane or acetonitrile, under ambient conditions for 18-24 hours. Typical conditions comprise of 1.0 eq of compound (XX) and 1.2 eq of (diacetoxyiodo)benzene in dichloromethane, at room temperature for 24 hours.

Alternatively, compounds of formula (XV) can be prepared from compound (XII) by process steps xiii and xiv in a one-pot synthesis. Typical conditions comprise of 1 eq of compound (XII) and 1 eq of compound (XIX) in ethanol, heated at reflux for 0.5-1.0 hour, followed by addition of 1.2 eq of (diacetoxyiodo)benzene and dichloromethane, at room temperature for 24 hours.

Compounds of formula (XVII) can be prepared from compounds of formula (XV) and (XVI) by process step x as described in scheme 4.

Compounds of formula (XVIII) can be prepared from compounds of formula (XVII) by process step xi as described in scheme 4.

Compounds of formula (V) can be prepared from compounds of formula (XVIII) by process step xii as described in scheme 4.

Alternatively, compounds of formula (V) can be also be prepared from compounds of formula (XVII) by process step xviii—The reaction proceeds via the formation of an intermediate containing a suitable leaving group such as mesylate or tosylate by reaction of compound (VIII) with mesyl chloride/anhydride or tosyl chloride, in the presence of a suitable base such as Hünig's base, triethylamine or pyridine, in a suitable solvent such as dichloromethane or diethyl ether, at low to ambient temperature for 1-4 hours. The resulting intermediate is then treated with a suitable source of ammonia, typically 7M ammonia in methanol, under ambient conditions for 18-72 hours. Typical conditions comprise of 1.0 eq of compound (XVII), 3.0-4.0 eq of Hünig's base, and 2.0-3.0 eq of methane sulfonyl anhydride in dichloromethane, at 25° C. for 1-4 hours. Excess 7M ammonia in methanol is added and reaction is stirred at ambient temperature for 18-72 hours.

Alternatively compounds of formula (V) can be prepared from compounds of formula (XV) and compound of formula (XXVII) where PG is a protecting group, such as BOC. Typical conditions comprise of 1 eq of compound (XV), 1.2 eq of compound (XXVII), 1.2 eq of anhydrous cesium carbonate, 3 eq of cesium fluoride, 0.1 eq of PdCl$_2$(dppf).CH$_2$Cl$_2$ in dimethylformamide as solvent at 80-100° C. for 2-48 h.

The product of this reaction is then subject to acid-mediated removal of the BOC group to afford compounds of formula (V).

Compounds of formula (XXVII) can be prepared from compounds of formula (XXVIII) by process step xix (Scheme 5.1). The reaction proceeds by a palladium-catalysed insertion of the sulfide into an aromatic-bromine bond.

Typical conditions comprise of 1 eq of compound (XXVIII), 1 eq of potassium tri(isopropyl)silylsulfide (formed from 1 eq of potassium tert-butoxide and 1 eq of triisopropylsilanethiol in toluene), 1 eq of PdCl$_2$(dppf).CH$_2$Cl$_2$ in toluene as solvent at 100° C. for 0.5 to 2 h.

Scheme 5.1

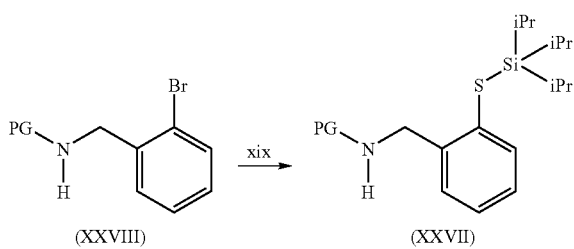

Where R$^3$ is, or includes, a phenol, the skilled person will appreciate that it may be necessary to use a protecting group, typically benzyloxy or methyloxy.

Scheme 6

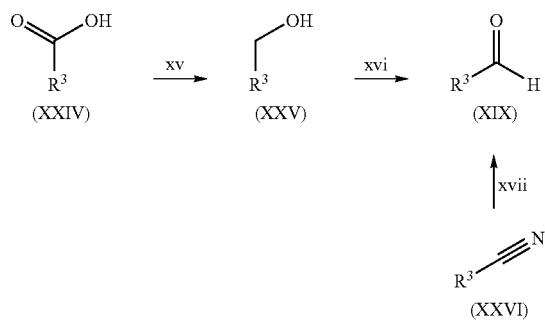

Compounds of formula (XXIV) are commercially available

Compounds of formula (XXV) can be prepared from compounds of formula (XXIV) by process step xv—reduction with a suitable reducing agent such as lithium aluminium hydride, diisobutylaluminium hydride or sodium borohydride in a suitable solvent such as tetrahydrofuran or methanol, at elevated temperature for 6-18 hours. Typical conditions comprise of 1.0 eq of compound (XXIV) and 1.0-1.2 eq of lithium aluminium hydride in tetrahydrofuran, at reflux for 6 hours.

Compounds of formula (XIX) can be prepared from compounds of formula (XXV) by process step xvi—oxidation with a suitable oxidising agent such as manganese dioxide, potassium permanganate or oxalyl chloride/dimethylsulfoxide, in a suitable solvent such as acetone, dichloromethane or dimethylsulfoxide, at from −80 to +80° C. for 3-18 hours.

Typical conditions comprise of 1.0 eq of compound (XXV) and 0.5 eq of manganese dioxide in acetone, heated under reflux for 3 hours.

Alternatively, compounds of formula (XIX) can be prepared from commercial compounds of formula (XXVI) by process step xvii—reduction of nitrile by diisobutylaluminium hydride in a suitable solvent such as tetrahydrofuran, at low temperature. Typical conditions comprise of
  a) 1.0 equivalent of compound (XXVI) and 1.0-2.0 equivalents of diisobutylaluminium hydride in tetrahydrofuran, at −78° C. for 1 hour,
  b) excess hydrochloric acid and water at 0° C.

It will be appreciated by those skilled in the art that it may be necessary or desirable at any stage in the synthesis of compounds of formula (I) to protect one or more sensitive groups in the molecule so as to prevent undesirable side reactions. In particular, it may be necessary or desirable to protect phenol groups. The protecting groups used in the preparation of compounds of formula (I) may be used in a conventional manner. See, for example, those described in 'Protective Groups in Organic Synthesis' by Theodora W Green and Peter G M Wuts, third edition, (John Wiley and Sons, 1999), in particular chapter 2, pages 17-245 ("Protection for the Hydroxyl Group"). Alternatively, the protected phenols are available commercially. Removal of such groups can be achieved using conventional methods.

It will be still further appreciated that compounds of formula (I) may also be converted to alternative compounds of formula (I) using standard chemical reactions and transformations. For example, when X (wherein X is a group as shown in the Examples and Preparations herein) is an ester, compounds of formula (I) can undergo saponification to give the carboxylic acid derivative. When X=aryloxy, compound (I) can undergo de-alkylation using boron tribromide or HBr/acetic acid to give the corresponding phenol. Furthermore when X=OH, hydroxyalkoxy derivatives can be prepared by reaction with 2-(2-bromoethoxy)tetrahydro-2H-pyran followed by de-protection of the primary alcohol, using boron tribromide or para-toluenesulfonic acid.

In another embodiment of the invention, there is provided a process for making a compound of formula (I), wherein the substituents are as defined in claim 1 and the description related to the processes, which comprises the steps:

i: cyclocondensation of a compound of formula (II) and a compound of formula (III) to make a compound of formula (IV):

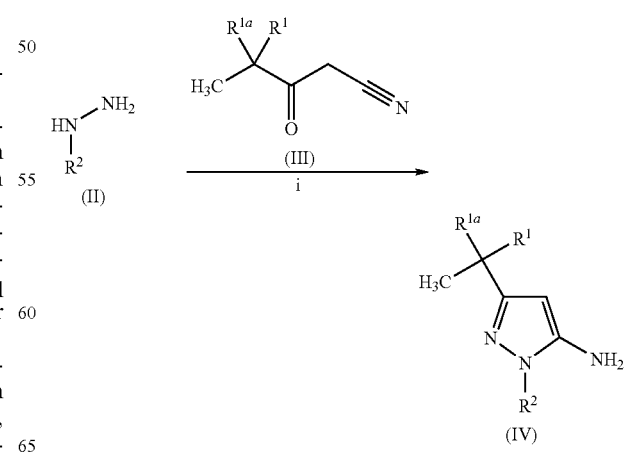

and/or ii: urea formation, by reaction of a compound of formula (IV) with a compound of formula (V), in the presence of a suitable carbonyl source.

In another embodiment of the invention, there is provided a process for making a compound of formula (V), wherein the substituents are as defined in the description related to the processes, which comprises the steps:

xi: azide formation, by reaction of a compound of formula (XVII), with a suitable base, followed by reaction with a suitable azide, to form a compound of formula (XVIII)

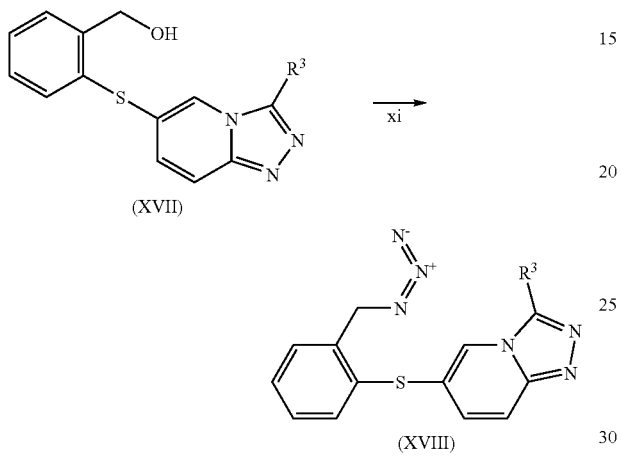

and/or xii: reduction of a compound of formula (XVIII) to form a compound of formula (V)

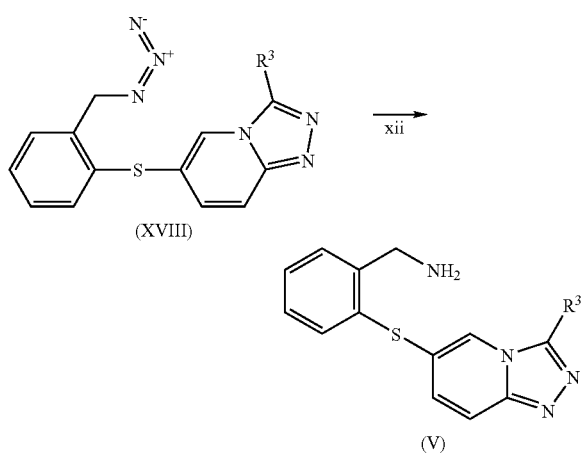

In another embodiment of the invention, there is provided a novel process as described herein.

In another embodiment of the invention, there is provided an intermediate compound of formula (IV), (V), (XVII) or (XVIII), wherein the substituents are as described herein.

In another embodiment of the invention, there is provided a novel intermediate compound of a formula as described herein.

Another aspect of the invention is a compound of formula (I) as described herein, or a salt and/or solvate thereof, for use in medicine.

Another aspect of the invention is a compound of formula (I) as described herein, or a salt and/or solvate thereof, for use in treating a disease, disorder, or condition selected from the group consisting of:

1. asthma of whatever type, etiology, or pathogenesis, in particular asthma that is a member selected from the group consisting of atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, non-atopic asthma, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome and branchiolytis, 2. chronic or acute bronchoconstriction, chronic bronchitis, small airways obstruction, and emphysema, 3. obstructive or inflammatory airways diseases of whatever type, etiology, or pathogenesis, in particular an obstructive or inflammatory airways disease that is a member selected from the group consisting of chronic eosinophilic pneumonia, chronic obstructive pulmonary disease (COPD), COPD that includes chronic bronchitis, pulmonary emphysema or dyspnea associated or not associated with COPD, COPD that is characterized by irreversible, progressive airways obstruction, adult respiratory distress syndrome (ARDS), exacerbation of airways hyper-reactivity consequent to other drug therapy and airways disease that is associated with pulmonary hypertension, 4. bronchitis of whatever type, etiology, or pathogenesis, in particular bronchitis that is a member selected from the group consisting of acute bronchitis, acute laryngotracheal bronchitis, arachidic bronchitis, catarrhal bronchitis, croupus bronchitis, dry bronchitis, infectious asthmatic bronchitis, productive bronchitis, *staphylococcus* or streptococcal bronchitis and vesicular bronchitis, 5. acute lung injury, 6. bronchiectasis of whatever type, etiology, or pathogenesis, in particular bronchiectasis that is a member selected from the group consisting of cylindric bronchiectasis, sacculated bronchiectasis, fusiform bronchiectasis, capillary bronchiectasis, cystic bronchiectasis, dry bronchiectasis and follicular bronchiectasis.

A further aspect of the invention is the use of a compound of formula (I) as described herein, or a salt and/or solvate thereof, in the manufacture of a medicament for the treatment of a disease, disorder, or condition disclosed in paragraphs 1-6 above.

A further aspect of the invention is the use of a compound of formula (I) as described herein, or a salt and/or solvate thereof, in the manufacture of a medicament for the treatment of a p38-mediated disease, disorder or condition or a TNF-mediated disease, disorder, or condition.

Another aspect of the invention is a compound of formula (I) as described herein, or a salt and/or solvate thereof, for use in treating a p38-mediated disease, disorder or condition or a TNF-mediated disease, disorder, or condition.

The present invention provides a method of treating a mammal, including a human being, with an effective amount of a compound of formula (I), or a pharmaceutically acceptable salt or solvate thereof.

More precisely, the present invention provides a method of treating a p38-mediated disease, disorder or condition or a TNF-mediated disease, disorder, or condition in a mammal, including a human being, in particular a disease disorder, or condition listed above, comprising administering said mammal with an effective amount of a compound of formula (I), or a salt and/or solvate thereof.

Preferably, the present invention provides a compound of formula (I), or a pharmaceutically acceptable salt or solvate thereof, for use in treating obstructive or inflammatory airways diseases of whatever type, etiology, or pathogenesis, in particular an obstructive or inflammatory airways disease that is a member selected from the group consisting of chronic eosinophilic pneumonia, chronic obstructive pulmonary disease (COPD), COPD that includes chronic bronchitis, pulmonary emphysema or dyspnea associated or not associated with COPD, COPD that is characterized by irreversible, progressive airways obstruction, adult respiratory distress syndrome (ARDS), exacerbation of airways hyper-reactivity consequent to other drug therapy and airways disease that is associated with pulmonary hypertension, or asthma of whatever type, etiology, or pathogenesis, in particular asthma that is a member selected from the group consisting of atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, non-atopic asthma, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome and bronchiolytis.

More preferably, the present invention provides a compound of formula (I), or a pharmaceutically acceptable salt or solvate thereof, for use in treating chronic obstructive pulmonary disease (COPD).

Preferably, the present invention provides the use of a compound of formula (I), or a pharmaceutically acceptable salt or solvate thereof, in the manufacture of a medicament for treating obstructive or inflammatory airways diseases of whatever type, etiology, or pathogenesis, in particular an obstructive or inflammatory airways disease that is a member selected from the group consisting of chronic eosinophilic pneumonia, chronic obstructive pulmonary disease (COPD), COPD that includes chronic bronchitis, pulmonary emphysema or dyspnea associated or not associated with COPD, COPD that is characterized by irreversible, progressive airways obstruction, adult respiratory distress syndrome (ARDS), exacerbation of airways hyper-reactivity consequent to other drug therapy and airways disease that is associated with pulmonary hypertension, or asthma of whatever type, etiology, or pathogenesis, in particular asthma that is a member selected from the group consisting of atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, non-atopic asthma, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome and bronchiolytis.

More preferably, the present invention provides the use of a compound of formula (I), or a pharmaceutically acceptable salt or solvate thereof, in the manufacture of a medicament for treating chronic obstructive pulmonary disease (COPD).

As used herein, the term "TNF-mediated disease", or "TNF-mediated disorder" or "TNF-mediated condition" refers to any disease, disorder, or condition (particularly any pathological conditions), respectively, in which TNF plays a role, either by control of TNF itself, or by TNF causing another monokine to be released, such as, for example, IL-1, IL-6, and/or IL-8. A disease state in which, for instance, IL-1 is a major component and whose production or action is exacerbated or secreted in response to TNF, would therefore be considered a disorder mediated by TNF.

As used herein, the term "p38-mediated disease", or "p38-mediated disorder" or "p38-mediated condition" refers to any disease, disorder, or condition (particularly any pathological conditions), respectively, in which p38 plays a role, either by control of p38 itself, or by p38 causing another monokine to be released, such as, for example, IL-1, IL-6, and/or IL-8. A disease state in which, for instance, IL-1 is a major component and whose production or action is exacerbated or secreted in response to p38, would therefore be considered a disorder mediated by p38.

The compounds of the invention can be used in the treatment of a TNF-mediated disease, disorder, or condition, or a p38-mediated disease, disorder or condition, in particular the allergic and non-allergic airways diseases disclosed above, but also in the treatment of p38- or TNF-mediated conditions such as:

(a) inflammation;
(b) arthritis, such as rheumatoid arthritis, spondyloarthropathies, gouty arthritis, osteoarthritis, systemic lupus erythematosus arthritis, juvenile arthritis, osteoarthritis, and gouty arthritis;
(c) neuroinflammation;
(d) pain (i.e., use of the compounds as analgesics), such as neuropathic pain;
(e) fever (i.e., use of the compounds as antipyretics);
(f) pulmonary sarcoisosis, and silicosis;
(g) cardiovascular diseases, such as atherosclerosis, myocardial infarction (such as post-myocardial infarction indications), thrombosis, congestive heart failure, cardiac reperfusion injury, and complications associated with hypertension and/or heart failure such as vascular organ damage;
(h) cardiomyopathy;
(i) stroke, such as ischemic and hemorrhagic stroke;
(j) ischemia, such as brain ischemia and ischemia resulting from cardiac/coronary bypass;
(k) reperfusion injury;
(l) renal reperfusion injury;
(m) brain edema;
(n) neurotrauma and brain trauma, such as closed head injury;
(O) neurodegenerative disorders;
(p) central nervous system disorders (these include, for example, disorders having an inflammatory or apoptotic component), such as Alzheimer's disease, Parkinson's disease, Huntington's Disease, amyotrophic lateral sclerosis, spinal cord injury, and peripheral neuropathy;
(q) liver disease and nephritis;
(r) gastrointestinal conditions, such as inflammatory bowel disease, Crohn's disease, gastritis, irritable bowel syndrome, and ulcerative colitis;
(s) ulcerative diseases, such as gastric ulcer;
(t) ophthalmic diseases, such as retinitis, retinopathies (such as diabetic retinopathy), uveitis, ocular photophobia, non-glaucomatous optic nerve atrophy, and age-related macular degeneration (ARMD) (such as ARMD-atrophic form);

(u) opthalmological conditions, such as corneal graft rejection, ocular neovascularization, retinal neovascularization (such as neovascularization following injury or infection), and retrolental fibroplasia;
(v) glaucoma, such as primary open angle glaucoma (POAG), juvenile onset primary open-angle glaucoma, angle-closure glaucoma, pseudoexfoliative glaucoma, anterior ischemic optic neuropathy (AION), ocular hypertension, Reiger's syndrome, normal tension glaucoma, neovascular glaucoma, ocular inflammation, and corticosteroid-induced glaucoma;
(w) acute injury to the eye tissue and ocular traumas, such as post-traumatic glaucoma, traumatic optic neuropathy, and central retinal artery occlusion (CRAO);
(x) diabetes;
(y) diabetic nephropathy;
(z) skin-related conditions, such as psoriasis, eczema, burns, dermatitis, keloid formation, scar tissue formation, and angiogenic disorders;
(aa) viral and bacterial infections, such as sepsis, septic shock, gram negative sepsis, malaria, meningitis, opportunistic infections, cachexia secondary to infection or malignancy, cachexia secondary to acquired immune deficiency syndrome (AIDS), AIDS, ARC (AIDS related complex), pneumonia, rhinovirus infections, and herpes virus;
(bb) myalgias due to infection;
(cc) influenza;
(dd) endotoxic shock;
(ee) toxic shock syndrome;
(ff) autoimmune disease, such as graft vs. host reaction and allograft rejections;
(gg) bone resorption diseases, such as osteoporosis;
(hh) multiple sclerosis;
(ii) disorders of the female reproductive system, such as endometriosis;
(jj) pathological, but non-malignant, conditions, such as hemaginomas (such as infantile hemaginomas), angiofibroma of the nasopharynx, and avascular necrosis of bone;
(kk) benign and malignant tumors/neoplasia including cancer, such as colorectal cancer, brain cancer, bone cancer, epithelial cell-derived neoplasia (epithelial carcinoma) such as basal cell carcinoma, adenocarcinoma, gastrointestinal cancer such as lip cancer, mouth cancer, esophageal cancer, small bowel cancer and stomach cancer, colon cancer, liver cancer, bladder cancer, pancreas cancer, ovarian cancer, cervical cancer, lung cancer, breast cancer, skin cancer such as squamus cell and basal cell cancers, prostate cancer, renal cell carcinoma, and other known cancers that affect epithelial cells throughout the body;
(ll) leukemia;
(mm) lymphoma, such as B cell lymphoma;
(nn) systemic lupus erthrematosis (SLE);
(oo) angiogenesis including neoplasia;
(pp) metastasis;
(qq) a fibrotic disease;
(rr) hemorrhage;
(ss) coagulation;
(tt) acute phase responses like those seen with infections and sepsis and during shock (e.g., (uu) septic shock, hemodynamic shock, etc.);
(vv) anorexia;
(ww) mycobacterial infection;
(xx) pseudorabies,
(yy) rhinotracheitis,
(zz) HIV,
(aaa) influenza virus,
(bbb) herpes virus, including herpes simplex virus type-1 (HSV-1), herpes simplex virus type-2 (HSV) 2).
(ccc) cytomegalovirus (CMV),
(ddd) varicella-zoster virus (VZV),
(eee) Epstein-Barr virus,
(fff) human herpesvirus-6 (HHV-6),
(ggg) human herpesvirus-7 (HHV-7), human herpesvirus-8 (HHV-8).

In another embodiment of the invention, there is a compound of formula (I), or a salt and/or solvate thereof, for use in treating a disease, disorder, or condition, selected from the list (a) to (ggg) above.

A further embodiment of the invention is the use of a compound of formula (I), or a salt and/or solvate thereof, in the manufacture of a medicament for treating a disease, disorder, or condition selected from the list (a) to (ggg) above.

A yet further embodiment of the invention is a method of treating a disease, disorder, or condition selected from the list (a) to (ggg) above, in a mammal, including a human being, comprising administering said mammal with an effective amount of a compound of formula (I), or a salt and/or solvate thereof.

The compounds of the invention can also be used in the treatment of a p38- or TNF-mediated disease such as smoke-induced airway inflammation, inflammation enhanced cough, for the control of myogenesis, for treating mucin overproduction, and/or for treating mucus hypersecretion.

As TNF-β has close structural homology with TNF-α (also known as cachectin), and because each induces similar biologic responses and binds to the same cellular receptor, the synthesis of both TNF-α and TNF-β tend to be inhibited by the compounds of this invention and thus are herein referred to collectively as "TNF" unless specifically delineated otherwise.

A compound of formula (I), or a pharmaceutically acceptable salt and/or solvate thereof, as mentioned above, can be administered according to the invention to animals, preferably to mammals, and in particular to humans, as pharmaceuticals.

The compound can be administered per se, in a mixture with one or more other compounds of the invention, or in the form of pharmaceutical preparation, which, as active constituent contains an efficacious dose of at least one compound of the invention, in addition to customary pharmaceutically innocuous excipients and/or additives.

The compounds of the invention intended for pharmaceutical use may be administered as crystalline or, amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term 'excipient' is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in *Remington's Pharmaceutical Sciences,* 19th Edition (Mack Publishing Company, 1995).

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nanoparticulates, gels, solid solution, liposome, films, ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in Pharmaceutical Dosage Forms: Tablets, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of the invention, a film-forming polymer, a binder, a solvent, a humectant, a plasticiser, a stabiliser or emulsifier, a viscosity-modifying agent and a solvent. Some components of the formulation may perform more than one function.

The compounds of the invention may be water-soluble or insoluble. A water-soluble compound typically comprises from 1 weight % to 80 weight %, more typically from 20 weight % to 50 weight %, of the solutes. Less soluble compounds may comprise a greater proportion of the composition, typically up to 88 weight % of the solutes. Alternatively, the compounds of the invention may be in the form of multi-particulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Pharmaceutical Technology On-line, 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

The compounds of the invention may also be administered topically to the skin or mucosa, that is, dermally or transdermally.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 μg to 20 mg of the compound of the invention per actuation and the actuation volume may vary from 1 μl to 100 μl. A typical formulation may comprise a compound of the invention, propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 0.001 mg to 10 mg of the compound of the invention. The overall daily dose will typically be in the range 0.001 mg to 40 mg which may be administered in a single dose or, more usually, as divided doses throughout the day.

In another embodiment of the invention, the compounds of the invention are preferably administered by inhalation. More preferably, the compounds of the invention are administered by inhalation with a dry powder inhaler or a metered dose inhaler, most preferably with a dry powder inhaler.

The compounds of the invention may be administered rectally or vaginally, for example, in the form of a suppository, pessary, or enema.

The compounds of the invention may also be administered directly to the eye or ear, typically in the form of drops of a micronised suspension or solution in isotonic, pH-adjusted, sterile saline.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

In another embodiment of the invention, there is provided a pharmaceutical composition comprising a compound of formula (I), or a salt and/or solvate thereof, and a pharmaceutically acceptable diluent, carrier or adjuvant.

In another aspect of the invention, there is provided a kit, including:
a. a compound of formula (I), or a salt and/or solvate thereof,
b. instructions for treating an obstructive or inflammatory airways disease, and
c. packaging for containing a and b.

Preferably, the obstructive or inflammatory airways disease is COPD.

In an alternative embodiment, the instructions in b. are for treating asthma.

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus another aspect of the invention is a kit comprising two or more separate pharmaceutical compositions, at least one of which contains a compound of the invention in accordance with the invention, and means for separately retaining said compositions, such as a container, divided bottle, or divided foil packet. An example of such a kit is the familiar blister pack used for the packaging of tablets, capsules and the like.

The kit of the invention may be particularly suitable for administering different dosage forms, for example parenteral, for administering the separate compositions at different dosage intervals, or for titrating the separate compositions against one another. To assist compliance, the kit typically comprises directions for administration and may be provided with a so-called memory aid.

For administration to human patients, the total daily dose of the compounds of the invention is typically in the range 0.01 mg to 10 mg depending, of course, on the mode of administration. For example, an inhaled daily dose may only require from 0.01 mg to 5 mg. The total daily dose may be administered in single or divided doses and may, at the physician's discretion, fall outside of the typical range given herein.

These dosages are based on an average human subject having a weight of about 65 kg to 70 kg. The physician will readily be able to determine doses for subjects whose weight falls outside this range, such as infants and the elderly.

According to another embodiment of the present invention, the compounds of the invention can also be used as a combination with one or more additional therapeutic agents to be co-administered to a patient to obtain some particularly desired therapeutic end result such as the treatment of pathophysiologically-relevant disease processes including, but not limited to (i) bronchoconstriction, (ii) inflammation, (iii) allergy, (iv) tissue destruction, (v) signs and symptoms such as breathlessness, cough. The second and more additional therapeutic agents may also be a compound of the invention, or one or more TNF inhibitors and/or p38 inhibitors known in the art. More typically, the second and more therapeutic agents will be selected from a different class of therapeutic agents.

As used herein, the terms "co-administration", "co-administered" and "in combination with", referring to the compounds of the invention and one or more other therapeutic agents, is intended to mean, and does refer to and include the following:

- simultaneous administration of such combination of compound(s) of the invention) and therapeutic agent(s) to a patient in need of treatment, when such components are formulated together into a single dosage form which releases said components at substantially the same time to said patient,
- substantially simultaneous administration of such combination of compound(s) of the invention and therapeutic agent(s) to a patient in need of treatment, when such components are formulated apart from each other into separate dosage forms which are taken at substantially the same time by said patient, whereupon said components are released at substantially the same time to said patient,
- sequential administration of such combination compound(s) of the invention and therapeutic agent(s) to a patient in need of treatment, when such components are formulated apart from each other into separate dosage forms which are taken at consecutive times by said patient with a significant time interval between each administration, whereupon said components are released at substantially different times to said patient; and
- sequential administration of such combination of compound(s) of the invention and therapeutic agent(s) to a patient in need of treatment, when such components are formulated together into a single dosage form which releases said components in a controlled manner whereupon they are concurrently, consecutively, and/or overlappingly administered at the same and/or different times by said patient, where each part may be administered by either the same or different route.

Suitable examples of other therapeutic agents which may be used in combination with the compound(s) of the invention, or pharmaceutically acceptable salts, solvates or compositions thereof, include, but are by no means limited to:

(a) 5-Lipoxygenase (5-LO) inhibitors or 5-lipoxygenase activating protein (FLAP) antagonists,
(b) Leukotriene antagonists (LTRAs) including antagonists of $LTB_4$, $LTC_4$, $LTD_4$, and $LTE_4$,
(c) Histamine receptor antagonists including H1 and H3 antagonists,
(d) $\alpha_1$- and $\alpha_2$-adrenoceptor agonist vasoconstrictor sympathomimetic agents for decongestant use,
(e) muscarinic M3 receptor antagonists or anticholinergic agents,
(f) PDE inhibitors, e.g. PDE3, PDE4 and PDE5 inhibitors,
(g) Theophylline,
(h) Sodium cromoglycate,
(i) COX inhibitors both non-selective and selective COX-1 or COX-2 inhibitors (NSAIDs),
(j) Oral and inhaled glucocorticosteroids, such as DAGR (dissociated agonists of the corticoid receptor)
(k) Monoclonal antibodies active against endogenous inflammatory entities,
(l) β2 agonists, including long-acting 62 agonists
(m) Adhesion molecule inhibitors including VLA-4 antagonists,
(n) Kinin-$B_1$- and $B_2$-receptor antagonists,
(o) Immunosuppressive agents,
(p) Inhibitors of matrix metalloproteases (MMPs),
(q) Tachykinin $NK_1$, $NK_2$ and $NK_3$ receptor antagonists,
(r) Elastase inhibitors,
(s) Adenosine A2a receptor agonists,
(t) Inhibitors of urokinase,
(u) Compounds that act on dopamine receptors, e.g. D2 agonists,
(v) Modulators of the NFκB pathway, e.g. IKK inhibitors,
(w) modulators of cytokine signalling pathways such as syk kinase, or JAK kinase inhibitors,
(x) Agents that can be classed as mucolytics or anti-tussive, and
(y) Antibiotics.

According to the present invention, combination of the compounds of the invention with:
- H3 antagonists,
- Muscarinic M3 receptor antagonists,
- PDE4 inhibitors,
- glucocorticosteroids,
- Adenosine A2a receptor agonists,
- β2 agonists
- Modulators of cytokine signalling pathways such as syk kinase, or,
- Leukotriene antagonists (LTRAs) including antagonists of $LTB_4$, $LTC_4$, $LTD_4$, and $LTE_4$, are preferred.

According to the present invention, combination of the compounds of the invention with:
- glucocorticosteroids, in particular inhaled glucocorticosteroids with reduced systemic side effects, including prednisone, prednisolone, flunisolide, triamcinolone acetonide, beclomethasone dipropionate, budesonide, fluticasone propionate, ciclesonide, and mometasone furoate and mometasone furoate monohydrate,
- muscarinic M3 receptor antagonists or anticholinergic agents including in particular ipratropium salts, namely ipratropium bromide, tiotropium salts, namely tiotropium bromide, oxitropium salts, namely oxitropium bromide, perenzepine, and telenzepine,
- or β2 agonists, in particular long-acting β2 agonists, including salmeterol, formoterol, QAB-149 and CHF-4226.

are further preferred.

Preferably, the compounds of the invention exhibit slow-offset binding kinetics to p38.

In another preferred embodiment, when the compounds are administered via the inhalation route, they are rapidly metabolised when they have moved out of the lung.

More preferably, the compounds of the invention are metabolised to compounds that are less active than the compound administered.

In another embodiment of the invention there is provided a compound, use, method or composition, substantially as described herein.

Assay: TNFα Screen

The anti-inflammatory properties of the compounds of the invention are demonstrated by their ability to inhibit TNFα release from human peripheral blood mononuclear cells. Venous blood is collected from healthy volunteers and the mononuclear cells purified by centrifugation through Histopaque (Ficoll) cushions. TNFα production from these cells is stimulated by addition of lipopolysaccharide. After 18 hours incubation in the presence of LPS, the cell supernatant is removed and the concentration of TNFα in the supernatant determined by ELISA. Addition of the compounds of the invention reduces the amount of TNFα produced. An $IC_{50}$ is determined which is equal to the concentration of compound that gives 50% inhibition of TNFα production as compared to the LPS stimulated control wells.

The examples were tested in the assay described above and were found to have an $IC_{50}$ (TNFα screen) of less than 1000 nM, and for most of the tested compounds, were found to have an $IC_{50}$ (TNFα screen) of even less than 100 nM.

The examples tested were found to have an $IC_{50}$ (p38 assay) of less than 1000 nM, and for most of the tested compounds, they were found to have an $IC_{50}$ (p38 assay) of even less than 100 nM.

In the present invention, the term "active", "potent" or "potency" means that the compounds of formula (I) show TNF activity which is less than 1000 nM as measured by the TNF assay described herein.

p38 Kinase Assay:

Cloning of Human p38a:

The coding region of the human p38a cDNA was obtained by PCR-amplification from RNA isolated from the human monocyte cell line THP.1. First strand CDNA was synthesized from total RNA as follows: 2 μg of RNA was annealed to 100 ng of random hexamer primers in a 10 μl reaction by heating to 70° C. for 10 minutes followed by 2 minutes on ice. cDNA was then synthesized by adding 1 μl of RNAsin (Promega, Madison Wis.), 2 μl of 50 mM dNTP's, 4 μl of 5× buffer, 2 μl of 100 mM DTT and 1 μl (200 U) of Superscript II™ AMV reverse transcriptase. Random primer, dNTP's and Superscript II™ reagents were all purchased from Life-Technologies, Gaithersburg, Mass. The reaction was incubated at 42° C. for 1 hour. Amplification of p38 cDNA was performed by aliquoting 5 μl of the reverse transcriptase reaction into a 100 μl PCR reaction containing the following: 80 μl $dH_2O$, 2 μl 50 mM dNTP's, 1 μl each of forward and reverse primers (50 pmol/μl), 10 μl of 10× buffer and 1 μl Expand™ polymerase (Boehringer Mannheim). The PCR primers incorporated Bam HI sites onto the 5' and 3' end of the amplified fragment, and were purchased from Genosys. The sequences of the forward and reverse primers were 5'-GATC-GAGGATTCATGTCTCAGGAGAGGCCCA-3' and 5'GATCGAGGATTCTCAGGACTCCATCTCTTC-3' respectively. The PCR amplification was carried out in a DNA Thermal Cycler (Perkin Elmer) by repeating 30 cycles of 94° C. for 1 minute, 60° C. for 1 minute and 68° C. for 2 minutes. After amplification, excess primers and unincorporated dNTP's were removed from the amplified fragment with a Wizard™ PCR prep (Promega) and digested with Bam HI (New England Biolabs). The Bam HI digested fragment was ligated into BamHI digested pGEX 2T plasmid DNA (PharmaciaBiotech) using T-4 DNA ligase (New England Biolabs) as described by T. Maniatis, Molecular Cloning: A Laboratory Manual, 2nd ed. (1989). The ligation reaction was transformed into chemically competent E. coli DH10B cells purchased from Life-Technologies following the manufacturer's instructions. Plasmid DNA was isolated from the resulting bacterial colonies using a Promega Wizard™ miniprep kit. Plasmids containing the appropriate Bam HI fragment were sequenced in a DNA Thermal Cycler (Perkin Elmer) with Prism™ (Applied Biosystems Inc.). cDNA clones were identified that coded for both human p38a isoforms (Lee et al. Nature 372, 739). One of the clones that contained the cDNA for p38a-2 (CSB-2) inserted in the cloning site of PGEX 2T, 3' of the GST coding region was designated pMON 35802. The sequence obtained for this clone is an exact match of the cDNA clone reported by Lee et al. This expression plasmid allows for the production of a GST-p38a fusion protein.

Expression of Human p38a

GST/p38a fusion protein was expressed from the plasmid pMON 35802 in E. coli, stain DH10B (Life Technologies, Gibco-BRL). Overnight cultures were grown in Luria Broth (LB) containing 100 mg/ml ampicillin. The next day, 500 ml of fresh LB was inoculated with 10 ml of overnight culture, and grown in a 2 liter flask at 37° C. with constant shaking until the culture reached an absorbance of 0.8 at 600 nm. Expression of the fusion protein was induced by addition of isopropyl b-D-thiogalactosidase (IPTG) to a final concentration of 0.05 mM. The cultures were shaken for three hours at room temperature, and the cells were harvested by centrifugation. The cell pellets were stored frozen until protein purification.

Purification of P38 Kinase-Alpha

All chemicals were from Sigma Chemical Co. unless noted. Twenty grams of E. coli cell pellet collected from five 1 L shake flask fermentations was resuspended in a volume of PBS (140 mM NaCl, 2.7 mM KCl, 10 mM $Na_2HPO_4$, 1.8 mM $KH_2PO_4$, pH 7.3) up to 200 ml. The cell suspension was adjusted to 5 mM DTT with 2 M DTT and then split equally into five 50 ml Falcon conical tubes. The cells were sonnicated (Ultrasonics model W375) with a 1 cm probe for 3.times.1 minutes (pulsed) on ice. Lysed cell material was removed by centrifugation (12,000×g, 15 minutes) and the clarified supernatant applied to glutathione-sepharose resin (Pharmacia).

Glutathione-Sepharose Affinity Chromatography

Twelve ml of a 50% glutathione sepharose-PBS suspension was added to 200 ml clarified supernatant and incubated batchwise for 30 minutes at room temperature. The resin was collected by centrifugation (600.times.g, 5 min) and washed with 2.times.150 ml PBS/1% Triton X-100, followed by 4.times.40 ml PBS. To cleave the p38 kinase from the GST-p38 fusion protein, the glutathione-sepharose resin was resuspended in 6 ml PBS containing 250 units thrombin protease (Pharmacia, specific activity>7500 units/mg) and mixed gently for 4 hours at room temperature. The glutathione-sepharose resin was removed by centrifugation (600.times.g, 5 min) and washed 2.times.6 ml with PBS. The PBS wash fractions and digest supernatant containing p38 kinase protein were pooled and adjusted to 0.3 mM PMSF.

Mono Q Anion Exchange Chromatography

The thrombin-cleaved p38 kinase was further purified by FPLC-anion exchange chromatography. Thrombin-cleaved sample was diluted 2-fold with Buffer A (25 mM HEPES, pH 7.5, 25 mM beta-glycerophosphate, 2 mM DTT, 5% glycerol) and injected onto a Mono Q HR 10/10 (Pharmacia) anion exchange column equilibrated with Buffer A. The column was eluted with a 160 ml 0.1 M-0.6 M NaCl/Buffer A gradient (2 ml/minute flowrate). The p38 kinase peak eluting at 200 mM NaCl was collected and concentrated to 3-4 ml with a Filtron 10 concentrator (Filtron Corp.).

Sephacryl S100 Gel Filtration Chromatography

The concentrated Mono Q-p38 kinase purified sample was purified by gel filtration chromatography (Pharmacia HiPrep 26/60 Sephacryl S100 column equilibrated with Buffer B (50 mM HEPES, pH 7.5, 50 mM NaCl, 2 mM DTT, 5% glycerol)). Protein was eluted from the column with Buffer B at a 0.5 ml/minute flowrate and protein was detected by absorbance at 280 nm. Fractions containing p38 kinase (detected by SDS-polyacrylamide gel electrophoresis) were pooled and frozen at −80° C. Typical purified protein yields from 5 L E. coli shake flasks fermentations were 35 mg p38 kinase.

Kinetics Assays

Association Kinetics:

SKF-86002 (from Calbiochem; KD ~200 nM) gives an increase in fluorescence upon binding to p38a (as monitored by an excitation at 340 nm and emission at 420 nm). SKF-86002 (1-2 uM) was preincubated with p38a (20-60 nM) for 5-10 min at room temperature in a buffer consisting of 20 mM Bis-Tris, 2 mM EDTA, 500 mM NaCl, 0.01% NaN3, 0.15% NOG and 5% DMSO. The sample compound (20-100 nM) was then added and the change in fluorescence monitored. As SKF dissociated from its binding site on p38a, the SKF was replaced by the sample compound and a decrease in fluorescence was observed on a time scale proportional to the association rate of the compound. Using the known binding kinetics of SKF-86002, the association rate of the compound was measured.

Dissociation Kinetics:

Sample compounds (50 or 100 nM) were preincubated with p38a (37 nM protein or 21 nM as determined by active site titration) overnight at room temperature in a buffer consisting of 20 mM Bis-Tris, 2 mM EDTA, 0.01% NaN3, 0.15% NOG, 500 mM NaCl and 5% DMSO. The following day, SKF 86002 was added to a final concentration of 50 uM. The fluorescence increase observed upon the binding of SKF 86002 to p38a was monitored by excitation at 340 nm and emission at 420 nm, and the dissociation rate was measured.

Data:

The following data were generated using the TNF screen disclosed herein.

| Example | TNF IC50 nM |
|---|---|
| 26 | 1.6 |
| 33 | 2.0 |
| 34 | 1.3 |
| 36 | 4.8 |
| 37 | 2.8 |
| 44 | 1.1 |
| 45 | 1.4 |
| 46 | 0.8 |
| 51 | 0.7 |
| 54 | 0.7 |
| 55 | 0.9 |
| 57 | 1.2 |
| 58 | 1.6 |
| 59 | 1.3 |
| 60 | 1.4 |
| 63 | 1.4 |
| 64 | 0.9 |
| 68 | 2.3 |
| 70 | 0.9 |
| 71 | 3.0 |
| 73 | 0.9 |
| 74 | 4.0 |
| 76 | 0.8 |
| 77 | 2.7 |
| 78 | 0.8 |
| 80 | 1.1 |
| 81 | 1.8 |
| 86 | 0.8 |
| 87 | 0.6 |
| 93 | 1.1 |
| 94 | 0.9 |
| 95 | 0.6 |
| 97 | 0.6 |
| 98 | 0.4 |
| 100 | 1.1 |
| 102 | 1.7 |
| 104 | 1.0 |
| 105 | 0.6 |
| 109 | 1.2 |
| 114 | 3.6 |
| 116 | 3.2 |
| 118 | 15.7 |
| 124 | 4.6 |
| 125 | 80.0 |
| 128 | 3.7 |
| 132 | 4.5 |
| 136 | 1.0 |
| 139 | 3.2 |
| 140 | 1.8 |
| 141 | 1.4 |
| 142 | 2.2 |
| 143 | 1.2 |
| 144 | 1.2 |
| 145 | 0.9 |
| 151 | 1.4 |
| 152 | 4.9 |
| 153 | 4.8 |
| 179 | 1.5 |
| 180 | 21.0 |
| 181 | 2.7 |
| 182 | 0.7 |

EXAMPLES AND PREPARATIONS

Nuclear magnetic resonance (NMR) data were obtained using Varian Unity Inova-400, Varian Unity Inova-300 or Bruker AC300 spectrometers and are quoted in parts per million from tetramethylsilane. Mass spectral (MS) data were obtained on a Finnigan Mat. TSQ 7000 or a Fisons Instruments Trio 1000. The calculated and observed ions quoted refer to the isotopic composition of lowest mass. For column chromatography on silica gel, Kieselgel 60, 230-400 mesh, from E. Merck, Darmstadt was used, unless otherwise specified. Kieselgel 60 $F_{254}$ plates from E. Merck were used for TLC, and compounds were visualised using UV light, 5% aqueous potassium permanganate or Dragendorff's reagent (oversprayed with aqueous sodium nitrite). Water content was determined on a Mitsubishi CA100 (Coulometric Karl Fisher Titrator). Other measurements were taken using standard equipment. $PdCl_2(dppf).CH_2Cl_2$ is 1,1-bis(diphenylphosphino)ferrocene palladium (II) chloride 1:1 dichloromethane complex.

DBU is 1,8-diazabicyclo[5.4.0]undec-7-ene.

Preparation 1

2,2-Dimethyl-3-methylsulfanyl-propionic acid methyl ester

N,N-Diisopropylethylamine (15.5 g, 0.12 mol) was added to a solution of methyl 2,2-dimethyl-3-hydroxypropionate (13.2 g, 0.1 mol) in dichloromethane (150 mL) and the solution was cooled to 0° C. Methane sulfonyl chloride (12.6 g, 0.11 mol) was then added dropwise and the mixture was stirred at 0° C. for 90 minutes. The reaction mixture was then diluted with 0.5M hydrochloric acid (100 mL) and the layers were separated. The aqueous was extracted with dichloromethane (2×50 mL) and the combined organic solution was dried over magnesium sulfate and concentrated in vacuo. Methanethiol sodium salt (7.7 g, 0.11 mol) was added to a solution of the residue in dioxan (100 mL) and the mixture was heated under reflux for 24 hours. The mixture was then diluted with ethyl acetate (250 mL), washed with water and brine, dried over magnesium sulfate and concentrated in

Preparation 2

4,4-Dimethyl-5-methylsulfanyl-3-oxo-pentanenitrile

A suspension of sodium hydride (60% dispersion in mineral oil, 1.20 g, 30 mmol) in tetrahydrofuran (20 mL) was brought to reflux. A solution of the product of preparation 1 (3.84 g, 23.7 mmol) in acetonitrile (1.56 mL, 30 mmol) was added and the mixture was heated under reflux for 3 hours. The cooled reaction mixture was then diluted with water, acidified with 2M hydrochloric acid (30 mL) and extracted with dichloromethane (3×50 mL). The combined organic extracts were dried over magnesium sulfate, concentrated in vacuo and the residue was purified by column chromatography on silica gel, eluting with dichloromethane to afford the title compound as a pale yellow oil in 67% yield, 2.70 g.

Preparation 3

4-Methyl-4-methylsulfanyl-3-oxo-pentanenitrile

The title compound was prepared from ethyl 2-methyl-2-(methylthio)propionate and acetonitrile, using a method similar to that of preparation 2, as a colourless oil in 81% yield.

Preparation 4

(3-Methylsulfanyl-phenyl)-hydrazine

Magnesium turnings (0.79 g, 33 mmol) and a single crystal of iodine were added to a solution of 3-bromothioanilsole (6.11 g, 30 mmol) in tetrahydrofuran (50 mL) and the mixture was stirred at room temperature for 18 hours. The mixture was cooled to −78° C. and di-tertbutyldiazocarboxylate (6.91 g, 30 mmol) was added. The mixture was stirred at −78° C. for 30 minutes and was then quenched by the addition of 1M citric acid (40 mL). The reaction mixture was allowed to warm to room temperature and was extracted with ethyl acetate (250 mL). The organic solution was washed with brine and water, dried over magnesium sulfate and concentrated in vacuo. The residue was re-dissolved in isopropyl alcohol (200 mL) and the solution was saturated with hydrogen chloride gas. The mixture was then allowed to cool to room temperature and was concentrated in vacuo. The residue was taken up in water, basified with saturated sodium hydrogen carbonate solution and extracted with dichloromethane:methanol, 90:10, (4×50 mL). The combined organic solution was dried over magnesium sulfate concentrated in vacuo and the residue was purified by column chromatography on silica gel, eluting with dichloromethane:methanol, 100:0 to 70:30, to afford the title compound as a dark orange liquid in 36% yield.

Preparation 5 di-tert-Butyl 1-(4-methoxy-3-methylphenyl)hydrazine-1,2-dicarboxylate $^n$Butyllithium (2.5M in hexanes, 23.9 mL, 59.75 mmol) was added to a solution of 4-bromo-2-methylanisole (10 g, 49.74 mmol) in tetrahydrofuran (150 mL) cooled to −78° C., and the mixture was stirred at this temperature for 1 hour. A solution of di-tert-butyldiazocarboxylate (13.74 g, 59.68 mmol) in tetrahydrofuran (50 mL) was then added dropwise and the mixture was stirred at −78° C. for one hour and then at room temperature for 2 hours. The reaction was quenched with water (25 mL), concentrated in vacuo to low volume and partitioned between diethyl ether (300 mL) and brine (300 mL). The aqueous layer was separated and re-extracted with diethyl ether (2×100 mL), and the combined organic solution was dried over sodium sulphate and concentrated in vacuo. Purification of the residue by column chromatography on silica gel, eluting with heptanes:ethyl acetate, 75:25, afforded the title compound as a pale yellow solid in 62% yield, 10.93 g.

Preparation 6

(4-Methoxy-3-methylphenyl)hydrazine hydrochloride

4M Hydrochloric acid in 1,4-dioxane (37.5 mL, 150 mmol) was added dropwise to a solution of the product of preparation 5 (10.75 g, 30.50 mmol) in 1,4-dioxane (12.5 mL) and the mixture was stirred for 48 hours at room temperature. The mixture was then concentrated in vacuo and the residue was stirred in diethyl ether at 0° C. for 30 minutes. The precipitate was filtered off, washing through with diethyl ether, and the solid was dried under vacuum at 40° C. for 6 hours to afford the title compound in 94% yield, 5.43 g.

Preparation 7

3-tert-Butyl-1-[4-(methylthio)phenyl]-1H-pyrazol-5-amine

Concentrated hydrochloric acid (1 mL) was added dropwise to a mixture of 4-methylthiophenyl hydrazine (2 g, 10.5 mmol) and 4,4-dimethyl-3-oxopentane nitrile (1.44 g, 11.5 mmol) in ethanol (30 mL) and the mixture was heated under reflux for 18 hours. The cooled mixture was then diluted with ethyl acetate, washed with saturated sodium hydrogen carbonate solution, dried over magnesium sulfate and concentrated in vacuo. The residue was purified by column chromatography on silica gel, eluting with dichloromethane:methanol, 100:0 to 97:3 to afford the title compound as a yellow oil that crystallised on standing (2.59 g, 95% yield).

Preparations 8 to 19

The following compounds, of the general formula shown below were prepared by a method similar to that described for preparation 7, using the appropriate hydrazine and nitrile starting materials. The reactions were monitored by tlc analysis and were heated under reflux for 3-24 hours.

Compounds of formula:

(with R1, phenyl-X,Y substituents, NH2)

| No. | X | Y | Data | Yield |
|---|---|---|---|---|

Compounds of formula (Preps. 8-13):

| No. | X | Y | Data | Yield |
|---|---|---|---|---|
| 8 | SCH₃ | H | LRMS: m/z APCl 261 [MH]⁺ | 77% |
| 9 | Cl | Cl | LRMS: m/z APCl 284 [MH]⁺ | 68% |
| 10 | H | CO₂CH₂CH₃ | LRMS: m/z APCl 288 [MH]⁺ | 55% |
| 11 | CO₂CH₂CH₃ | H | LRMS: m/z APCl 288 [MH]⁺ | 28% |
| 12 | H | CN | m/z APCl 241 [MH]⁺ | 52% |
| 13 | CN | H |  | 58% |

Compounds of formula (preps. 14 and 15):

| No. | X | Y | Data | Yield |
|---|---|---|---|---|
| 14 | H | CH₃ | m/z APCl 276 [MH]⁺ | 57% |
| 15 | H | H | m/z APCl 262 [MH]⁺ | 48% |

Compounds of formula (preps 16-19):

| No. | X | Y | Data | Yield |
|---|---|---|---|---|
| 16 | H | H | m/z APCl 248 [MH]⁺ | 72% |
| 17 | O—CH₂Ph | H | m/z APCl 354 [MH]⁺ | 54% |
| 18 | H | CF₃ | m/z ES 316 [MH]⁺ | 55% |
| 19 | H | Cl | m/z ES 282 [MH]⁺ | 20% |

Preparations 14-19: Purification achieved by column chromatography on silica gel, eluting with dichloromethane:ethyl acetate. 80:20

Preparation 20

5-tert-Butyl-2-phenyl-2H-pyrazol-3-ylamine

N,N-Diisopropylethylamine (1.7 mL, 7.99 mmol) was added to a mixture of phenyl hydrazine hydrochloride (1.5 g, 10.39 mmol) and 4,4-dimethyl-3-oxopentane nitrile (1.0 g, 7.99 mmol) in ethanol (15 mL) and the mixture was heated under reflux for 18 hours. The cooled mixture was then concentrated to low volume and partitioned between ethyl acetate and saturated sodium hydrogen carbonate solution. The organic layer was separated, dried over sodium sulfate and concentrated in vacuo. The residue was purified by column chromatography on silica gel, eluting with heptanes:ethyl acetate, 75:25, to afford the title compound as a pale orange oil that crystallised on standing (1.21 g, 70% yield).

Preparations 21 to 24

The following compounds, of the general formula shown below were prepared by a method similar to that described for preparation 20, using the appropriate hydrazine and nitrile starting materials. The reactions were monitored by tlc analysis and were heated under reflux for 3-24 hours.

| No. | X | Y | Data | Yield |
|---|---|---|---|---|
| 21 | H | CH₃ | LRMS: m/z API-ES 230.7 [MH]⁺ | 79% |
| 22 | H | O—CH₃ | LRMS: m/z API-ES 246.6 [MH]⁺ | 58% |
| 23 | CH₃ | OCH₃ | LRMS: m/z API-ES 260 [MH]⁺ | 84% |
| 24 | O—CH₃ | H | LRMS: m/z API-ES 246.7 [MH]⁺ | 99% |

Preparation 25

(5-Bromo-pyridin-2-yl)-hydrazine

2-Chloro-5-bromopyridine (64 g, 333 mmol) was suspended in hydrazine monohydrate (250 mL) and the mixture was heated at 70° C. for 72 hours. The reaction mixture was then diluted with water (750 mL) and the resulting precipitate was filtered off and azeotroped, firstly with toluene (×2) then dichloromethane (×2), to afford the title compound as a pale brown solid in 83% yield, 52 g.

Preparation 26

4-Chloro-3-hydroxymethyl-phenol

Lithium aluminium hydride (1M in diethyl ether, 25 mL, 25 mmol) was added to an ice-cooled solution of 2-chloro-5- hydroxy-benzoic acid (4 g, 23.2 mmol) in tetrahydrofuran (200 mL) and the mixture was heated under reflux for 6 hours. The mixture was then diluted with a mixture of water/tetrahydrofuran, acidified with 1M hydrochloric acid, and extracted with ethyl acetate. The organic solution was dried over sodium sulphate and concentrated in vacuo to afford the title compound in quantitative yield, 4.3 g.

Preparation 27

2-Chloro-5-hydroxy-benzaldehyde

Manganese dioxide (11 g, 125 mmol) was added to a suspension of the product of preparation 26 (4 g, 25.2 mmol) in acetone (25 mL) and the mixture was heated to reflux for 3 hours. The reaction mixture was then cooled to room temperature and concentrated in vacuo. The residue was dissolved in dichloromethane:methanol, 95:5, passed through a pad of silica and concentrated in vacuo to afford the title compound as a solid in 81% yield, 3.17 g Preparation 28

2-Chloro-4-hydroxy-benzaldehyde

Diisobutylaluminium hydride (1M in hexane, 240 mL, 240 mmol) was added to a solution of 2-chloro-4-hydroxybenzonitrile (15 g, 97.7 mmol) in tetrahydrofuran (200 mL), cooled to −78° C., and the mixture was stirred at this temperature for 1 hour then at room temperature for 18 hours. The mixture was then cooled to 0° C. and 1M hydrochloric acid (80 mL) was added dropwise. The reaction mixture was diluted with water (200 mL) and filtered, washing through with ethyl acetate (×2). The layers of the filtrate were separated and the organic solution was dried over magnesium sulfate and concentrated in vacuo, Trituration of the residue with dichloromethane afforded the title compound as a solid in 84% yield, 12.92 g.

Preparation 29

Isobutyric acid N'-(5-bromo-pyridin-2-yl)-hydrazide

N,N-Diisopropylethylamine (137 g, 1.06 mol) was added to a suspension of the product of preparation 25 (40 g, 213 mmol) in dichloromethane (100 mL) and the solution was cooled to 0° C. Isobutyryl chloride (22.7 g, 213 mmol) was then added dropwise and the mixture was stirred at 0° C. for 2 hours. The reaction mixture was quenched with water and the resulting solid was filtered off and dried for 48 hours in air. The solid was then re-crystallised from methanol/N,N-diisopropylethylamine, 25:75, to afford the title compound as a white crystalline solid in 85% yield, 1.16 g.

Preparation 30

2-(Benzyloxy)benzaldehyde(5-bromopyridin-2-yl) hydrazone

A mixture of 2-benzyloxybenzaldehyde and the product of preparation 25 (10 g, 53.2 mmol) in ethanol (350 mL) was heated at 80° C. for 15 minutes. The resulting precipitate was filtered off, washing through with ethanol, and dried under vacuum for 18 hours to afford the title compound as a white solid in 94% yield.

Preparation 31

6-Bromo-3-isopropyl-[1,2,4]triazolo[4,3-a]pyridine

A suspension of the product of preparation 29 (16 g, 62 mmol) in phosphorus oxychloride (320 mL) was heated at 75° C. for 18 hours. The reaction mixture was then concentrated in vacuo and the residue was dissolved in water, basified with 2M sodium hydroxide solution and extracted with ethyl acetate. The organic solution was dried over sodium sulfate and concentrated in vacuo. Trituration of the residue in ethyl acetate/methanol, 98:2, afforded the title compound in 75% yield, 11.23 g.

Preparation 32

3-(6-Bromo-[1,2,4]triazolo[4,3-a]pyridin-3-yl)-4-chloro-phenol

A mixture of the product of preparations 27 (3.1 g, 19.7 mmol) and 25 (3.7 g, 19.7 mmol) in ethanol (75 mL) was heated under reflux for 1 hour. The mixture was then cooled to room temperature, diluted with ethanol (75 mL) and iodobenzene diacetate (6.30 g, 19.7 mmol) was added. The reaction mixture was then stirred at room temperature for 18 hours. The mixture was concentrated in vacuo, triturated with a mixture of ethyl acetate and methanol and filtered off. The residue was further purified by column chromatography on silica gel, eluting with dichloromethane:methanol, 90:10, to afford the title compound in 15% yield, 0.95 g Preparation 33

4-(6-Bromo-[1,2,4]triazolo[4,3-a]pyridin-3-yl)-3-chloro-phenol

The title compound was prepared from the products of preparations 28 and 25, using a method similar to that of preparation 32, as a solid in 78% yield.

Preparation 34

3-[2-(Benzyloxy)phenyl]-6-bromo[1,2,4]triazolo[4,3-a]pyridine

The title compound was prepared from the product of preparation 30, using a similar method to preparation 33. The title compound was further purified by column chromatography on silica gel, eluting with ethyl acetate:dichloromethane, 50:50, followed by trituration with diethyl ether/ethyl acetate to afford the title compound as a solid in 88% yield.

Preparation 35

[2-(3-Isopropyl-[1,2,4]triazolo[4,3-a]pyridin-6-ylsulfanyl)-phenyl]-methanol

2-Mercaptobenzyl alcohol (12.8 g, 91 mmol) was added to a mixture of the product of preparation 31 (19.8 g, 70 mmol), cesium carbonate (31.9 g, 98 mmol) and 1,1'-bis(diphenylphosphino)ferrocenedichloropalladium(II) dichloromethane adduct (5.7 g, 7.0 mmol) in N,N-dimethylformamide (175 mL) and the reaction mixture was heated to 90° C. for 21 hours. The mixture was then cooled, diluted with water and extracted with ethyl acetate. The organic solution was dried over sodium sulfate, concentrated in vacuo and the residue was purified by column chromatography on silica gel, eluting with ethyl acetate:methanol, 98:2, and triethylamine (one drop per 100 mL of organic solution), to afford the title compound as a brown solid in 33% yield, 7 g.

Preparation 36

4-Chloro-3-(6-{[2-(hydroxymethyl)phenyl]thio}[1,2,4]triazolo[4,3-a]pyridin-3-yl)phenol The title compound was prepared from the product of preparation 32 and 2-mercaptobenzyl alcohol, using a method similar to that of preparation 35, as a pale brown solid in 62% yield.

Preparation 37

3-Chloro-4-(6-{[2-(hydroxymethyl)phenyl]thio}[1,2,4]triazolo[4,3-a]pyridin-3-yl)phenol The title compound was prepared from the product of preparation 33 and 2-mercaptobenzyl alcohol, using a method similar to that of preparation 35, as a pale brown foam in 41% yield.

Preparation 38

[2-({3-[2-(Benzyloxy)phenyl][1,2,4]triazolo[4,3-a]pyridin-6-yl}thio)phenyl]methanol The title compound was prepared from the product of preparation 34 and 2-mercaptobenzyl alcohol, using a method similar to that of preparation 35, as a brown solid in 57% yield.

Preparation 39

6-(2-Azidomethyl-phenylsulfanyl)-3-isopropyl-[1,2,4]triazolo[4,3-a]pyridine 1,8-Diazabicyclo[5.4.0]undec-7-ene (6.4 g, 42.1 mmol) was added to an ice-cold suspension of the product of preparation 35 (10.5 g, 35.1 mmol) and diphenylphosphoryl azide (11.6 g, 42.1 mmol) in toluene (60 mL) and the mixture was stirred at 0° C. for 3 hours and at room temperature for 18 hours. The reaction was then quenched with sodium hydrogen carbonate solution and extracted with ethyl acetate. The organic solution was washed with brine, dried over sodium sulfate and concentrated in vacuo. Purification by column chromatography on silica gel, eluting with ethyl acetate:methanol, 98:2, and triethylamine (one drop per 100 mL of organic solution), then afforded the title compound as a brown oil in 79% yield, 9 g.

Preparation 40

3-(6-{[2-(Azidomethyl)phenyl]thio}[1,2,4]triazolo[4,3-a]pyridin-3-yl)-4-chlorophenyl diphenyl phosphate The title compound was prepared from the product of preparation 36, using a method similar to that of preparation 39, in 84% yield.

Preparation 41

4-(6-{[2-(Azidomethyl)phenyl]thio}[1,2,4]triazolo[4,3-a]pyridin-3-yl)-3-chlorophenol The title compound was prepared from the product of preparation 37, using a method similar to that of preparation 39, as a pale brown foam in 58% yield.

Preparation 42

6-{[2-(azidomethyl)phenyl]thio}-3-[2-(benzyloxy)phenyl][1,2,4]triazolo[4,3-a]pyridine The title compound was prepared from the product of preparation 38, using a method similar to that of preparation 39, as a liquid in 45% yield.

Preparation 43

{2-[(3-Isopropyl[1,2,4]triazolo[4,3-a]pyridin-6-yl)thio]benzyl}amine hydrochloride Triphenylphosphine (10.6 g, 40.3 mmol) and water (0.73 mL, 40.3 mmol) were added to a solution of the product of preparation 39 (10.8 g, 33.6 mmol) in tetrahydrofuran (114 mL) and the mixture was stirred at room temperature for 40 hours, then warmed to 40° C. for 5 hours. The reaction mixture was then cooled to room temperature, diluted with water and extracted with ethyl acetate. The organic solution was washed with brine, dried over sodium sulfate and concentrated in vacuo. The residue was dissolved in dichloromethane and cooled in an ice-bath. 1M Hydrochloric acid in diethyl ether (35 mL) was added dropwise and the mixture was stirred for 18 hours at room temperature. The resulting precipitate was filtered off and dried over phosphorus pentoxide to afford the title compound as a grey solid in 65% yield, 7.24 g.

Preparation 44

3-(6-{[2-(Aminomethyl)phenyl]thio}[1,2,4]triazolo[4,3-a]pyridin-3-yl)-4-chlorophenol hydrochloride The title compound was prepared from the product of preparation 40, using a method similar to that of preparation 43. The crude product was re-dissolved in methanol and saturated with 1M hydrochloric acid in diethyl ether to afford the desired product in quantitative yield.

Preparation 45

4-(6-{[2-(Aminomethyl)phenyl]thio}[1,2,4]triazolo[4,3-a]pyridin-3-yl)-3-chlorophenol hydrochloride The title compound was prepared from the product of preparation 41, using a method similar to that of preparation 43. The crude product was re-dissolved in methanol and saturated with 1M hydrochloric acid in diethyl ether to afford the desired product in 60% yield.

Preparation 46

[2-({3-[2-(benzyloxy)phenyl][1,2,4]triazolo[4,3-a]pyridin-6-yl}thio)benzyl]-amine hydrochloride The title compound was prepared from the product of preparation 42, using a method similar to that of preparation 43. The crude product was re-dissolved in methanol and saturated with 1M hydrochloric acid in diethyl ether to afford the desired product as a white solid in 78% yield.

Preparation 47

4,4-Dimethyl-3-oxohexanenitrile

A suspension of sodium hydride (60% dispersion in mineral oil, 3.18 g, 79.4 mmol) in tetrahydrofuran (60 mL) was heated at 60° C. for 1 hour. The reaction mixture was then cooled to room temperature, acetonitrile (4.2 mL, 79.4 mmol) and 2,2-dimethyl-butyric acid ethyl ester [(7.95 g, 61 mmol), *J. Am. Chem. Soc.,* 1942, 64, 2964] in tetrahydrofuran (100 mL) were added and the mixture was stirred for 4 hours at 25° C. The mixture was then diluted with 1M hydrochloric acid (100 mL) and the aqueous layer was separated and extracted with ethyl acetate. The organic solution was then dried over magnesium sulfate, concentrated in vacuo and the residue was triturated with heptane to afford the title compound as a pale brown solid in 27% yield, 2.3 g.

Preparation 48

1-(Benzyloxy)-3-bromo-5-methylbenzene

A mixture of 3-bromo-5-methylphenol [(40.7 g, 218 mmol) *J. Amer. Chem. Soc.,* 2003, 125, 7792)], benzyl bromide (28.6 mL, 239 mmol) and potassium carbonate (90.2 g, 653 mmol) in acetone (1 L) was heated under reflux for 2 hours. The cooled reaction mixture was then acidified with 2M hydrochloric acid and the aqueous layer was extracted with ethyl acetate. The organic solution was washed with brine (×3), dried over magnesium sulfate and concentrated in vacuo to afford the title compound as a red oil in quantitative yield.

Preparation 49

Benzyl 5-(benzyloxy)-2-chlorobenzoate

The title compound was prepared from 2-chloro-5-hydroxybenzoic acid (US2002/0037905 p15), using a similar method to that described for preparation 46, as an oil in quantitative yield.

Preparation 50

4-(Benzyloxy)-2-chlorobenzonitrile

Potassium carbonate (66.3 g, 480 mmol) was added to a mixture of 2-chloro-4-hydroxybenzonitrile (25 g, 160 mmol) and benzyl bromide (19.3 mL, 161 mmol) in acetonitrile (300 mL) and the mixture was stirred for 18 hours at room temperature. The reaction mixture was then filtered and the filtrate was concentrated in vacuo. Trituration of the residue with heptanes afforded the title compound as an off-white solid in 99% yield, 38.65 g.

Preparation 51

4-(Benzyloxy)-2-chlorobenzaldehyde

The title compound was prepared from the product of preparation 50, using the same method as that described for preparation 28, in 97% yield.

Preparation 52

4-Bromo-1-ethyl-2-methoxybenzene

Methyl iodide (3 mL, 47.3 mmol) was added to a solution of 4-bromo-2-hydroxyacetophenone (9.25 g, 43 mmol) and potassium carbonate (6.54 g, 47.3 mmol) in acetone (20 mL) and the mixture was stirred at room temperature for 18 hours. The reaction mixture was concentrated in vacuo to low volume and diluted with water. The aqueous mixture was extracted with dichloromethane (3×50 mL) and the combined organic solution was washed with water, dried over sodium sulfate and concentrated in vacuo. The residue was dissolved in 1,2-ethanediol (10 mL), hydrazine (19.47 mL, 400 mmol) and potassium hydroxide (7.86 g, 140 mmol) were added and the reaction mixture was heated at 150° C. for 60 hours. The reaction mixture was then quenched with 1M hydrochloric acid and extracted with ethyl acetate (3×20 mL). The combined organic solution was dried over sodium sulfate, concentrated in vacuo and the residue was purified by Kugel Rohr fractional distillation (150° C./0.05 mbar) to provide the title compound as a yellow oil (128 mg).

Preparation 53

N-(3-Chloro-4-methoxyphenyl)-N'-(2,2-dimethylpropanoyl)-2,2-dimethylpropanohydrazide The title compound was prepared from 4-bromo-2-chloro-1-methoxy-benzene (*J. Org. Chem.* 1982, 47, 5270) and di-tert-butyldiazocarboxylate, using the same method as that of preparation 5, as a white powder in 43% yield.

Preparation 54 di-tert-Butyl 1-[3-(benzyloxy)-5-methylphenyl]hydrazine-1,2-dicarboxylate

The title compound was prepared from the product of preparation 48 and di-tert-butyldiazocarboxylate, using the same method as that described for preparation as that of preparation 5, as a yellow liquid in 84% yield.

Preparation 55 di-tert-butyl 1-(3-ethyl-4-methoxyphenyl)hydrazine-1,2-dicarboxylate

The title compound was prepared from 4-bromo-2-ethyl-1-methoxy-benzene and di-tertbutyldiazocarboxylate, using the same method as that described for preparation 53, as a solid in 53% yield.

Preparation 56 di-tert-Butyl 1-(4-ethyl-3-methoxyphenyl)hydrazine-1,2-dicarboxylate

The title compound was prepared from the product of preparation 52 and di-tert-butyldiazocarboxylate, using the same method as that described for preparation 53, as a pale yellow oil in 40% yield.

Preparation 57

(3-Chloro-4-methoxyphenyl)hydrazine hydrochloride

The title compound was prepared from the product of preparation 53, using the same method as that described for preparation 6, as an off-white powder in 93% yield.

Preparation 58

[3-(Benzyloxy)-5-methylphenyl]hydrazine hydrochloride

The title compound was prepared from the product of preparation 54, using the same method as that described for preparation 6, as a solid in 59% yield.

Preparation 59

(3-Ethyl-4-methoxyphenyl)hydrazine hydrochloride

The title compound was prepared from the product of preparation 55, using the same method as that described for preparation 6, as a solid in quantitative yield.

Preparation 60

(4-Ethyl-3-methoxyphenyl)hydrazine hydrochloride

The title compound was prepared from the product of preparation 56, using the same method as that described for preparation 6, as an off-white solid in 85% yield.

Preparations 61 to 86, 88 and 89

The following compounds, of the general formula shown below were prepared by a method similar to that described for preparation 7, using the appropriate commercially available hydrazine and commercially available nitrile starting materials. Where the starting materials are not commercially available, the syntheses are disclosed herein. The reactions were monitored by tlc analysis and were heated under reflux for 3-24 hours.

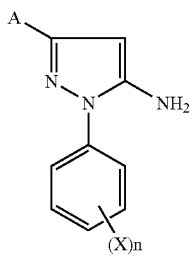

| No. | Data | Yield |
|---|---|---|
| | A = C(CH$_3$)$_3$ | |
| 61 | X = 4-F | 57% |
| 62 | X = 3-F | 94% |
| 63 | X = 3-OCH$_2$Ph | 90% |
| 64 | X = 4-CH$_2$CH$_3$ | 91% |
| 65 | X = 3-CH$_2$CH$_3$ | 78% |
| 66 | X = 3-OCH$_2$Ph, 5-CH$_3$ | 60% |
| 67 | X = 4-OCH$_3$ | 49% |

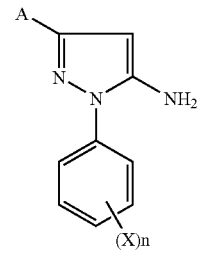

| No. | Data | Yield |
|---|---|---|
| 68 | X = 3-OCH$_3$ | 86% |
| 69 | X = 3-OCH$_3$, 4-Cl | 50% |
| | A = (CH$_2$CH$_3$)C(CH$_3$)$_2$ | |
| 70 | X = 3-OCH$_2$Ph | 91% |
| 71 | X = 4-CH$_3$ | 35% |
| | A = (CH$_3$—S—CH$_2$)C(CH$_3$)$_2$ | |
| 72 | X = 3-OCH$_2$Ph | 71% |
| 73 | X = 4-F | 35% |
| 74 | X = 3-F | 75% |
| 75 | X = 3-F, 4-F | 63% |
| 76 | X = 4-OCH$_2$Ph | 70% |
| | A = (CH$_3$—S)C(CH$_3$)$_2$ | |
| 77 | X = 3-CF$_3$ | 73% |
| 78 | X = 4-F | 62% |
| 79 | X = 3-F | 86% |
| 80 | X = 3-Cl | 50% |
| 81 | X = 3-F, 4-F | 79% |
| 82 | X = 4-CH$_2$CH$_3$ | 79% |
| 83 | X = 3-CH$_2$CH$_3$ | 65% |
| 84 | X = 3-CH$_3$, 4-OCH$_3$ | 25% |
| 85 | X = 4-CH$_3$ | 50% |
| 86 | X = 3-CH$_3$ | quant |
| 88 | X = 3-Br | 52% |
| 89 | X = 3-CH$_3$, 5-CH$_3$ | 73% |

*a* Crude compounds were purified by column chromatography on silica gel, eluting with heptanes:ethyl acetate, 75:25

Preparation 83: was prepared from the product of preparation 3 and (3-ethylphenyl)-hydrazine hydrochloride (EP 177242, p31)

Preparation 84: crude compound was purified by column chromatography on silica gel, eluting with pentane:ethyl acetate, 100:0 to 60:40.

Preparation 86: crude compound was purified by column chromatography on silica gel, eluting with hexane:ethyl acetate, 91:9 to 83:17.

Preparation 87

(4-Chloro-3-methoxyphenyl)hydrazine

Concentrated hydrochloric acid (12 mL) and a solution of sodium nitrite (1.7 g, 24.4 mmol) in water (8 mL) were added to a solution of 4-chloro-3-methoxy aniline (3.86 g, 24.4 mmol) in water (8 mL), at −10° C. The mixture was stirred for 30 minutes and was then added to solution of tin chloride (14.89 g, 66 mmol) in concentrated hydrochloric acid (24 mL) and water (24 mL), cooled to 0° C. The reaction mixture was stirred for 18 hours, allowing the temperature to rise to 25° C. The resulting precipitate was filtered off and the solid was re-crystallised from heptanes/ethyl acetate (33:66) to afford the title compound the title compound as white solid in 72% yield, 3 g

Preparation 90

3-tert-Butyl-1-pyridin-3-yl-1H-pyrazol-5-amine

The title compound was prepared from 4,4-dimethyl-3-oxopentane nitrile and 3-pyridinohydrazide (US2002/0143176, p22), using the same method as that described for preparation 7, as an orange oil in 50% yield.

Preparation 91

3-tert-Butyl-1-pyridin-2-yl-1H-pyrazol-5-amine

The title compound was prepared from 4,4-dimethyl-3-oxopentane nitrile and 2-hydrazinopyridine, using the same method as that described for preparation 7, as a solid in 99% yield.

Preparation 92

1-[4-(benzyloxy)phenyl]-3-[1-methyl-1-(methylthio)ethyl]-1H-pyrazol-5-amine

Concentrated hydrochloric acid (2 mL) was added dropwise to a suspension of [4-(benzyloxy)phenyl]hydrazine hydrochloride (3.19 g, 12.74 mmol) and the product of preparation 3 (2 g, 12.74 mmol) in ethanol (50 mL) and the mixture was heated under reflux for 2 hours. Water was then added (5 mL) and the reaction mixture was heated under reflux for a further 16 hours. The cooled mixture was then diluted with ethyl acetate, washed with saturated sodium hydrogen carbonate solution, dried over magnesium sulfate and concentrated in vacuo. The residue was purified by column chromatography on silica gel, eluting with dichloromethane:ethyl acetate, 100:0 to 85:15, to afford the title compound as an orange oil that crystallised on standing (2.79 g, 62% yield).

Preparations 93 to 97

The following compounds, of the general formula shown below were prepared by a method similar to that described for preparation 20, using the appropriate commercially available hydrazine and commercially available nitrile starting materials. Where the starting materials are not commercially available, the syntheses are disclosed herein. The reactions were monitored by tlc analysis and were heated under reflux for 3-24 hours.

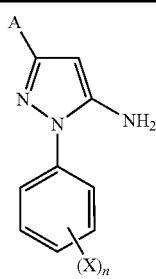

| No. | Data | Yield |
|---|---|---|
| | A = C(CH$_3$)$_3$ | |
| 93 | X = 4-CH$_3$ | 57% |
| 94 | X = 3-Cl, 4-OCH$_3$ | 48% |

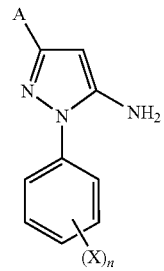

| No. | Data | Yield |
|---|---|---|
| 95 | X = 3-F, 4-F | 18% |
| 96 | X = 3-CH$_2$CH$_3$, 4-OCH$_3$ | 65% |
| 97 | X = 3-OCH$_3$, 4-CH$_2$CH$_3$ | 27% |

Preparation 93: The crude compound was triturated with heptane: diethyl ether 66:33.

Preparation 98

[4-(5-Amino-3-tert-butyl-1H-pyrazol-1-yl)phenyl]methanol

Lithium aluminium hydride (1M in tetrahydrofuran, 1.83 mL, 1.83 mmol) was added to an ice-cold solution of 4-[5-amino-3-(1,1-dimethylethyl)-1H-pyrazol-yl]-benzoic acid methyl ester [(0.25 g, 0.92 mmol), WO2004060306, p134] in tetrahydrofuran (5 mL), and the mixture was stirred at 0° C. for 1 hour. The reaction was then quenched with water (0.35 mL) and 1M sodium hydroxide solution (0.35 mL) followed by further water (1 mL). The mixture was then extracted with diethyl ether, (10 mL) and the organic solution was dried over sodium sulfate and concentrated in vacuo to afford the title compound as red oil in 98% yield, 220.1 mg.

Preparation 99

3-tert-Butyl-1-[4-({[tert-butyl(dimethyl)silyl]oxy}methyl)phenyl]-1H-pyrazol-5-amine A mixture of the product of preparation 98 (0.5 g, 2.04 mmol), tert-butyldimethylsilyl chloride (0.34 g, 2.25 mmol) and imidazole (0.18 g, 2.55 mmol) in N,N-dimethylformamide (2 mL) was stirred at room temperature for 18 hours. The reaction mixture was then diluted with methanol (1 mL) and stirred for 15 minutes at room temperature. The mixture was diluted further with sodium hydrogen carbonate solution (20 mL) and extracted with ethyl acetate (3×15 mL). The combined organic solution was dried over sodium sulfate, concentrated in vacuo and the residue was purified by column chromatography on silica gel, eluting with heptanes:ethyl acetate, 85:15, 75:25, to afford the title compound as a colourless solid in 30% yield, 220.5 mg.

Preparation 100

3-tert-Butyl-1-(3-{[tert-butyl(dimethyl)silyl]oxy}-4-methylphenyl)-1H-pyrazol-5-amine The title compound was prepared from 5-[5-amino-3-(1,1-dimethylethyl)-1H-pyrazol-1-yl]-2-methylphenol hydrochloride (WO 03/005999, p81-p82) and tert-butyldimethylsilyl chloride, using the same method as that described for preparation 99, as a solid in 86% yield.

Preparation 101

3-(5-Amino-3-tert-butyl-1H-pyrazol-1-yl)phenol

Boron tribromide (1M in dichloromethane, 12 mL, 12 mmol) was added dropwise to an ice-cold solution of the product of preparation 63 (1.28 g, 4 mmol) in dichloromethane (50 mL) and the mixture was stirred for 30 minutes, allowing the temperature to rise to 25° C. The reaction mixture was then diluted with methanol (20 mL) and water, basified with 0.88 ammonia and extracted with dichloromethane (3×50 mL). The combined organic solution was dried over magnesium sulfate concentrated in vacuo and the residue was purified by column chromatography on silica gel, eluting with dichloromethane:ethyl acetate, 100:0 to 80:20, to afford the title compound as a pale yellow foam in 89% yield, 825 mg.

Preparation 102

4-{5-Amino-3-[1-methyl-1-(methylthio)ethyl]-1H-pyrazol-1-yl}phenol

The title compound was prepared from the product of preparation 76, using a similar method to that described for preparation 101, as a white solid in 40% yield.

Preparation 103

N-{1-[4-(Benzyloxy)phenyl]-3-tert-butyl-1H-pyrazol-5-yl}benzamide

The title compound was prepared from the product of 244 and phenyl chloroformate, using the same method as that described for preparation 116, as a brown oil in quantitative yield.

Preparation 104

1-(4-{[tert-Butyl(dimethyl)silyl]oxy}phenyl)-3-[1-methyl-1-(methylthio)ethyl]-1H-pyrazol-5-amine The title compound was prepared from the product of preparation 102 and tert-butyldimethylsilyl chloride, using the same method as that described for preparation 99, as a yellow oil in 48% yield.

Preparation 105

1-(3-{[tert-Butyl(dimethyl)silyl]oxy}phenyl)-3-[1-methyl-1-(methylthio)ethyl]-1H-pyrazol-5-amine The title compound was prepared from the product of preparation 110 and tert-butyldimethylsilyl chloride, using the same method as that described for preparation 99, as a red oil in 49% yield.

Preparation 106

3-tert-Butyl-1-(3-{[tert-butyl(dimethyl)silyl]oxy}phenyl)-1H-pyrazol-5-amine

The title compound was prepared from the product of preparation 101 and tert-butyldimethylsilyl chloride using the same method as that described for preparation 99, as a colourless oil in 34% yield.

Preparation 107

3-{5-Amino-3-[1,1-dimethyl-2-(methylthio)ethyl]-1H-pyrazol-1-yl}-phenol

The title compound was prepared from the product of preparation 72, using the same method as that described for preparation 101, as a yellow solid in 18% yield.

Preparation 108

3-[5-Amino-3-(1,1-dimethylpropyl)-1H-pyrazol-1-yl]-phenol

A solution of boron tribromide (1.7 mL, 17.9 mmol) in dichloromethane (20 mL) was added dropwise to an ice-cold solution of the product of preparation 70 (1.20 g, 3.6 mmol) in dichloromethane (15 mL) and the mixture was stirred for 90 minutes, allowing the temperature to rise to 25° C. Dimethylamine (40% in water, 5 mL) was then added dropwise and the mixture was stirred for 1 hour at room temperature. The aqueous layer was separated, extracted with ethyl acetate and the organic solution was dried over magnesium sulfate and concentrated in vacuo. Purification of the residue by column chromatography on silica gel, eluting with heptanes:ethyl acetate, 100:0 to 50:50, afforded the title compound as a yellow foam in 49% yield, 390 mg.

Preparation 109

2-(6-{[2-(Aminomethyl)phenyl]thio}[1,2,4]triazolo[4,3-a]pyridin-3-yl)phenol

The product of preparation 46 (3.43 g, 7.22 mmol) was suspended in hydrobromic acid (5.7M in glacial acetic acid, 7 mL, 40 mmol) and the mixture was stirred at room temperature for 18 hours. The reaction mixture was diluted with diethyl ether (150 mL), stirred at room temperature for 15 minutes and then filtered off. The residue was partitioned between dichloromethane and saturated sodium hydrogen carbonate solution and the resulting precipitate was filtered off and re-dissolved in dichloromethane:methanol, (90:10, 400 mL), The aqueous layer of the filtrate was separated and extracted three times with dichloromethane:methanol, (90:10). The extracts were then combined with the solution of dissolved residue, dried over magnesium sulfate and concentrated in vacuo. Trituration of the residue with diethyl ether afforded the title compound as a solid in 96% yield, 2.40 g.

Preparation 110

3-{5-Amino-3-[1-methyl-1-(methylthio)ethyl]-1H-pyrazol-1-yl}phenol

The title compound was prepared from the product of preparation 87, using the same method as that described for preparation 109, as a white foam in 44% yield.

Preparation 111

3-tert-Butyl-1-{3-[2-(tetrahydro-2H-pyran-2-yloxy)ethoxy]phenyl}-1H-pyrazol-5-amine A mixture of the product of preparation 101 (750 mg, 3.25 mmol), 2-(2-bromoethoxy)tetrahydro-2H-pyran (1.02 g, 4.88 mmol) and potassium carbonate (690 mg, 5 mmol) in N,N-dimethylformamide (10 mL) was stirred at 60° C. for 4

Preparation 112

3-[1-Methyl-1-(methylthio)ethyl]-1-{3-[2-(tetrahydro-2H-pyran-2-yloxy)ethoxy]phenyl}-1H-pyrazol-5-amine The title compound was prepared from the product of preparation 110 and 2-(2-bromoethoxy)tetrahydro-2H-pyran, using the same method as that described for preparation 111, as an orange oil in 94% yield.

Preparation 113

3-[1,1-Dimethyl-2-(methylthio)ethyl]-1-{3-[2-(tetrahydro-2H-pyran-2-yloxy)ethoxy]phenyl}-1H-pyrazol-5-amine The title compound was prepared from the product of preparation 107 and 2-(2-bromoethoxy)tetrahydro-2H-pyran, using the same method as that described for preparation 111, as a yellow oil in 71% yield.

Preparation 114

3-(1,1-Dimethylpropyl-1-{3-[2-(tetrahydro-2H-pyran-2-yloxy)ethoxy]phenyl}-1H-pyrazol-5-amine The title compound was prepared from the product of preparation 108 and 2-(2-bromoethoxy)tetrahydro-2H-pyran, using the same method as that described for preparation 111, as a yellow oil in 71% yield.

Preparation 115

3-[1-Methyl-1-(methylthio)ethyl]-1-{4-[2-(tetrahydro-2H-pyran-2-yloxy)ethoxy]phenyl}-1H-pyrazol-5-amine The title compound was prepared from the product of preparation 102 and 2-(2-bromoethoxy)tetrahydro-2H-pyran, using the same method as that described for preparation 111, as a yellow oil in 82% yield.

Preparation 116

Phenyl(3-tert-butyl-1-{3-[2-(tetrahydro-2H-pyran-2-yloxy)ethoxy]phenyl}-1H-pyrazol-5-yl)carbamate Phenylchloroformate (1.94 g, 12.4 mmol) was added to an ice-cooled solution of the product of preparation 111 (4.05 g, 11.3 mmol) and pyridine (1.09 mL, 13.5 mmol) in tetrahydrofuran (50 mL) and the mixture was stirred at 0° C. for 5 minutes and at room temperature for 20 minutes. The reaction mixture was then diluted with ethyl acetate, washed with water, 5% citric acid and saturated sodium hydrogen carbonate solution, dried over magnesium sulfate and concentrated in vacuo to afford the title compound as a yellow oil in 86% yield, 5.22 g.

Preparation 117

Phenyl (3-[1-methyl-1-(methylthio)ethyl]-1-{3-[2-(tetrahydro-2H-pyran-2-yloxy)ethoxy]phenyl}-1H-pyrazol-5-yl)carbamate The title compound was prepared from the product of preparation 112 and phenylchloroformate, using the same method as that described for preparation 116, as an orange oil in quantitative yield.

Preparation 118

Phenyl {1-[3-(benzyloxy)phenyl]-3-tert-butyl-1H-pyrazol-5-yl}carbamate

The title compound was prepared from the product of preparation 63 and phenylchloroformate, using the same method as that described for preparation 116, as a brown solid in 94% yield.

Preparation 119

Phenyl[3-tert-butyl-1-(3-{[tert-butyl(dimethyl)silyl]oxy}phenyl)-1H-pyrazol-5-yl]-carbamate The title compound was prepared from the product of preparation 106 and phenylchloroformate, using the same method as that described for preparation 116, as a clear oil in quantitative yield.

Preparation 120

Phenyl {1-(3-{[tertbutyl(dimethyl)silyl]oxy}phenyl)-3-[1-methyl-1-(methylthio)ethyl]-1H-pyrazol-5-yl}carbamate The title compound was prepared from the product of preparation 105 and phenylchloroformate, using the same method as that described for preparation 116, as a red oil in quantitative yield.

Preparation 121

N-[2-({3-2-(benzyloxy)phenyl[1,2,4]triazolo[4,3-a]pyridine-6-yl}thio)benzyl]-N'-[3-tert-butyl-1-(4-fluorophenyl)-1H-pyrazol-5-yl]urea The product of preparation 61 (117 mg, 0.50 mmol) was added to a solution of N,N'-carbonyldiimidazole (405 mg, 2.50 mmol) in dichloromethane (20 mL) and the mixture was stirred at room temperature for 16 hours. The reaction mixture was then diluted with water and extracted with dichloromethane (3×20 mL). The combined organic solution was dried over magnesium sulfate and concentrated in vacuo. The product of preparation 46 (142 mg, 0.30 mmol) was added to a solution of the residue and N-ethyldiisopropylamine (129 mg, 1 mmol) in dichloromethane (10 mL) and the mixture was stirred for 45 minutes at room temperature. The reaction mixture was then diluted with ethyl acetate, washed with 0.5M hydrochloric acid and brine, dried over magnesium sulfate and concentrated in vacuo. The residue was purified by column chromatography on silica gel, eluting with ethyl acetate:methanol, 100:0 to 90:10, to afford the title compound as a glass in 90% yield, 189 mg.

Preparation 122

N-[2-({3-2-(benzyloxy)phenyl[1,2,4]triazolo[4,3-a]
Pyridine-6-yl}thio)benzyl]-N'-(3-tert-butyl-1-{3-[2-
(tetrahydro-2H-pyran-2-yloxy)ethoxy]phenyl}-1H-
pyrazol-5-yl)urea The product of preparation 111 (180 mg, 0.50 mmol) was added to a solution of N,N'-carbonyldiimidazole (405 mg, 2.50 mmol) in dichloromethane (20 mL) and the mixture was stirred at room temperature for 18 hours. The reaction mixture was then diluted with water and extracted with dichloromethane (3×20 mL). The combined organic solution was dried over magnesium sulfate and concentrated in vacuo. The product of preparation 46 (167 mg, 0.35 mmol) was added to a solution of the residue and N-ethyldiisopropylamine (0.17 mL, 1 mmol) in dichloromethane (10 mL) and the mixture was stirred for 1 hour at room temperature. The reaction mixture was then diluted with ethyl acetate, washed with 0.1N citric acid and brine, dried over magnesium sulfate and concentrated in vacuo. The residue was purified by column chromatography on silica gel, eluting with ethyl acetate:methanol, 95:5, to afford the title compound in 95% yield, 273 mg.

Preparations 123 to 166

The following compounds, of the general formula shown below were prepared by a method similar to that described for preparation 121, using the appropriate amine, N,N'-carbonyldiimidazole and the appropriate aminopyrazole starting materials, which are available from the syntheses disclosed herein or are commercially available. The reactions were monitored by tlc analysis and were stirred at room temperature for 20-72 hours.

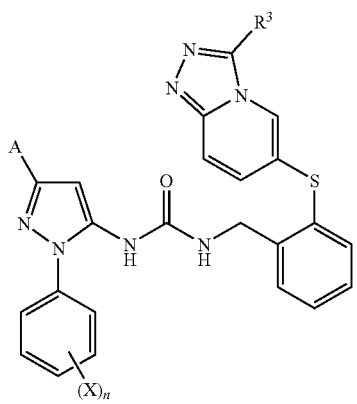

| No. | Data | Yield |
|---|---|---|
| | A = C(CH$_3$)$_3$ | |
| 123 | X = 3-(benzyloxy)phenyl, R$^3$ = 2-hydroxyphenyl | 72% |
| 124 | X = 4-CH$_3$; R$^3$ = 2-(benzyloxy)phenyl | 82% |
| 125 | X = 3-CH$_3$; R$^3$ = 2-(benzyloxy)-5-chlorophenyl | 78% |
| 126 | X = 4-CH$_2$CH$_3$; R$^3$ = 2-(benzyloxy)phenyl | 80% |
| 127 | X = 3-CH$_2$CH$_3$; R$^3$ = 2-(benzyloxy)phenyl | 86% |
| 128 | X = 3-Cl, 4-Cl; R$^3$ = 2-(benzyloxy)phenyl | 73% |
| 129 | X = 3-CN; R$^3$ = 2-(benzyloxy)phenyl | 87% |
| 130 | X = 4-CN; R$^3$ = 2-(benzyloxy)phenyl | 58% |
| 131 | X = H; R$^3$ = 2-(benzyloxy)phenyl | 77% |
| 132 | X = 3-OCH$_2$Ph; 5-CH$_3$; R$^3$ = HC(CH$_3$)$_2$ | 48% |
| 133 | X = 3-CH$_2$CH$_3$, 4-OCH$_3$; R$^3$ = HC(CH$_3$)$_2$ | 42% |

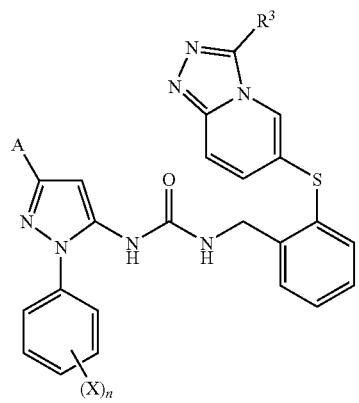

| No. | Data | Yield |
|---|---|---|
| 134 | X = 3-OCH$_3$, 4-CH$_2$CH$_3$; R$^3$ = HC(CH$_3$)$_2$ | 17% |
| 135 | X = 3-F, 4-F; R$^3$ = 2-(benzyloxy)phenyl | 34% |
| 136 | X = 4-({[tert-butyl(dimethyl)silyl]oxy}methyl); R$^3$ = HC(CH$_3$)$_2$ | 58% |
| 137 | X = 3-{[tert-butyl(dimethyl)silyl]oxy}, 4-CH$_3$; R$^3$ = HC(CH$_3$)$_2$ | 66% |
| 138 | X = 4-OCH$_3$; R$^3$ 2-(benzyloxy)phenyl | 84% |
| 139 | X = 3-OCH$_3$; R$^3$ 2-(benzyloxy)phenyl | 69% |
| 140 | X = 3-OCH$_3$, 4-Cl; R$^3$ = HC(CH$_3$)$_2$<br>A = (CH$_3$—CH$_2$)C(CH$_3$)$_2$ | 58% |
| 141 | X = 4-CH$_3$; R$^3$ = 2-(benzyloxy)phenyl<br>A = (CH$_3$—S—CH$_2$)C(CH$_3$)$_2$ | 36% |
| 142 | X = H; R$^3$ = 2-(benzyloxy)phenyl | 86% |
| 143 | X = 4-CH$_3$; R$^3$ = 2-(benzyloxy)phenyl | 78% |
| 144 | X = 4-F; R$^3$ = 2-(benzyloxy)phenyl | 77% |
| 145 | X = 3-F; R$^3$ = 2-(benzyloxy)phenyl | 78% |
| 146 | X = 3-F, 4-F; R$^3$ = 2-(benzyloxy)phenyl | 44% |
| 147 | X = 3-benzyloxy; R$^3$ = CH(CH$_3$)$_2$ | 87% |
| 148 | X = 4-benzyloxy; R$^3$ = CH(CH$_3$)$_2$ | 72% |
| 149 | X = 4-CH$_3$; R$^3$ = 2-(benzyloxy)-5-chloro-phenyl<br>A = (CH$_3$—S)C(CH$_3$)$_2$ | 75% |
| 150 | X = 3-CF$_3$; R$^3$ = 2-(benzyloxy)phenyl | 70% |
| 151 | X = 4-benzyloxy; R$^3$ = 2-(benzyloxy)phenyl | 56% |
| 152 | X = 4-F; R$^3$ = 2-(benzyloxy)phenyl | 63% |
| 153 | X = 3-F; R$^3$ = 2-(benzyloxy)phenyl | 70% |
| 154 | X = 3-Cl; R$^3$ = 2-(benzyloxy)phenyl | 46% |
| 155 | X = 3-Br; R$^3$ = 2-(benzyloxy)phenyl | 28% |
| 156 | X = 3-F; 4-F; R$^3$ = 2-(benzyloxy)phenyl | 61% |
| 157 | X = 4-ethyl; R$^3$ = 2-(benzyloxy)phenyl | 83% |
| 158 | X = 3-ethyl; R$^3$ = 2-(benzyloxy)phenyl | 76% |
| 159 | X = 3-methyl; 4-methoxy; R$^3$ = 2-(benzyloxy)phenyl | 93% |
| 160 | X = 3-benzyloxy; R$^3$ = 2-methylphenyl | 12% |
| 161 | X = 3-[2-(tetrahydro-2H-pyran-2-yloxy)ethoxy]; R$^3$ = HC(CH$_3$)$_2$ | 88% |
| 162 | X = 3-[2-(tetrahydro-2H-pyran-2-yloxy)ethoxy]; R$^3$ = 2-chlorophenyl | 36% |
| 163 | X = 4-{[tert-butyl(dimethyl)silyl]oxy}; R$^3$ = 2-fluorophenyl | 48% |
| 164 | X = 3-CH$_3$, 5-CH$_3$; R$^3$ = 2-(benzyloxy)phenyl | 72% |
| 165 | X = 3-CH$_3$; R$^3$ = 2-(benzyloxy)-5-chlorophenyl | 72% |
| 166 | X = 4-CH$_3$; R$^3$ = 2-(benzyloxy)-5-chlorophenyl | 60% |

$^a$Crude compounds were purified further by trituration with diethyl ether.

Preparations 124, 132 and 133: crude compounds were purified by column chromatography on silica gel, eluting with dichloromethane: 7M methanolic ammonia, 100:0 to 97.5:2.5. This was followed by further purification using reversed phase column chromatography on C18 silica gel, eluting with water/7M methanolic ammonia (98:2):acetonitrile/7M methanolic ammonia (98:2), 75:25 to 25:75.

Preparation 134: crude compound was purified by column chromatography on silica gel, eluting with dichloromethane: 7M methanolic ammonia/dichloromethane (10:90), 100:0 to 50:50. This was followed by further purification by trituration with dichloromethane:methanol:diethyl ether.

Preparation 160: prepared from the products of preparations 17 and 206

Preparation 163: prepared from the products of preparations 104 and 214

Preparation 165 and 166: were prepared from the appropriate aminopyrazoles and the product of preparation 208. The crude compounds were purified by column chromatography on silica gel, eluting with hexane:ethyl acetate, 90:10, followed by pentane:ethyl acetate, 80:20 to 20:80, followed by ethyl acetate:methanol, 100:0 to 50:50.

Preparation 167

N-[2-({3-2-(benzyloxy)phenyl[1,2,4]triazolo[4,3-a]pyridin-6-yl}thio)benzyl]-N'-(3-tert-butyl-1-pyridin-3-yl-1H-pyrazol-5-yl)urea The title compound was prepared from the product of preparations 46 and 90, using the same method as that described for preparation 121, in 15% yield.

Preparation 168

N-[2-({3-2-(benzyloxy)phenyl[1,2,4]triazolo[4,3-a]pyridin-6-yl}thio)benzyl]-N'-(3-tert-butyl-1-pyridin-2-yl-1H-pyrazol-5-yl)urea The title compound was prepared from the product of preparations 46 and 91, using the same method as that described for preparation 121, in 63% yield.

Preparation 169

N-[2-({3-2-(benzyloxy)phenyl[1,2,4]triazolo[4,3-a]pyridin-6-yl}thio)benzyl]-N'-(3-[1,1-dimethyl-2-(methylthio)ethyl]-1-{3-[2-(tetrahydro-2H-pyran-2-yloxy)ethoxy]phenyl}-1H-pyrazol-5-yl)urea Pyridine (64 μL, 0.8 mmol) and phenylchloroformate (110 mg, 0.70 mmol) were added sequentially to an ice-cooled solution of the product of preparation 113 (250 mg, 0.62 mmol) in tetrahydrofuran (10 mL) and the mixture was stirred at 0° C. for 10 minutes and at room temperature for 40 minutes. The reaction mixture was then diluted with ethyl acetate, washed with water, dried over magnesium sulfate and concentrated in vacuo. The residue was dissolved in dimethylsulfoxide (5 mL), the product of preparation 46 (332 mg, 0.70 mmol) and N,N-ethyldiisopropylamine (0.17 mL, 1 mmol) were added and the mixture was stirred at 50° C. for 90 minutes, The reaction mixture was then cooled to room temperature, diluted with water and washed with 0.1M citric acid, saturated sodium hydrogen carbonate solution. The organic solution was dried over magnesium sulfate and concentrated in vacuo to afford the title compound as a yellow foam in quantitative yield, 614 mg.

Preparation 170

N-[2-({3-2-(benzyloxy)phenyl[1,2,4]triazolo[4,3-a]pyridin-6-yl}thio)benzyl]-N'-(3-(1,1-dimethylpropyl)-1-{3-[2-(tetrahydro-2H-pyran-2-yloxy)ethoxy]phenyl}-1H-pyrazol-5-yl)urea The title compound was prepared from the products of preparations 114 and 46, using the same method as that described for preparation 169. The crude compound was purified by column chromatography on silica gel, eluting with dichloromethane:ethyl acetate, 100:0 to 30:70, to afford the desired product as a white foam in 59% yield.

Preparation 171

N-{1-[3-(Benzyloxy)phenyl]-3-tert-butyl-1H-pyrazol-5-yl}-N'-(2-{[3-(2-methylphenyl)[1,2,4]triazolo[4,3-a]pyridin-6-yl]thio}benzyl)urea The title compound was prepared from the products of preparations 63 and 206, using the same method as that described for preparation 169. The crude compound was purified by column chromatography using a 12 g ISCO silica cartridge, eluting with ethyl acetate, to afford the desired product in 43% yield.

Preparation 172

N-(2-{[3-(2-Hydroxyphenyl)[1,2,4]triazolo[4,3-a]pyridin-6-yl]thio}benzyl)-N'-[3-[1-methyl-1-methylthio)ethyl]-1-(4-methylphenyl)-1H-pyrazol-5-yl]urea The title compound was prepared from the products of preparations 85 and 109, using the same method as that described for preparation 169. The crude compound was purified by column chromatography on silica gel, eluting with dichloromethane:methanol, 95:5, to afford the desired product in 33% yield.

Preparation 173

N-{2-[(3-Isopropyl[1,2,4]triazolo[4,3-a]pyridin-6-yl)thio]benzyl}-N'-(3-[1-(methylthio)ethyl]-1-{3-[2-(tetrahydro-2H-pyran-2-yloxy)ethoxy]phenyl}-1H-pyrazol-5-yl)urea A mixture of the product of example 26 (89 mg, 0.15 mmol), 2-(2-bromoethoxy)tetrahydro-2H-pyran (36 mg, 0.17 mmol) and potassium carbonate (28 mg, 0.2 mmol) in N,N-dimethylformamide (2 mL) was stirred at room temperature for 18 hours and heated at 60° C. for 12 hours. The reaction mixture was then cooled to room temperature diluted with ethyl acetate and washed with water and brine. The organic solution was then dried over magnesium sulfate concentrated in vacuo and the residue was purified by column chromatography on silica gel, eluting with dichloromethane:methanol:0.88 ammonia, 100:0:0 to 94:6:1, to afford the title compound as a glass in 67% yield.

Preparation 174

N-{1-[3-(Benzyloxy)phenyl]-3-tert-butyl-1H-pyrazol-5-yl}-N'-{2-[(3-{2-[2-(tetrahydro-2H-pyran-2-yloxy)ethoxy]phenyl}[1,2,4]triazolo[4,3-a]pyridin-6-yl)thio]benzyl}urea The title compound was prepared from the product of preparation 123 and 2-<2-bromoethoxy)tetrahydro-2H-pyran, using the same method as that described for preparation 111, as a white foam in 75% yield.

Preparation 175

N-(3-tert-Butyl-1-{4-[2-tetrahydro-2H-pyran-2-yloxy)ethoxy]phenyl}-1H-pyrazol-5-yl)-N'-(2-{[3-(2-chlorophenyl)[1,2,4]triazolo[4,3-a]pyridin-6-yl]thio}benzyl)urea The title compound was prepared from the product of preparation 257 and 2-(2-bromoethoxy)tetrahydro-2H-pyran, using the same method as that described for preparation 111, as a pale yellow foam in 45% yield.

Preparation 176

[5-(Benzyloxy)-2-chlorophenyl]methanol

The title compound was prepared from the product of preparation 49, using the same method as that described for preparation 26. The crude compound was triturated with diethyl ether to afford the desired product as a white solid in 91% yield.

Preparation 177

5-(Benzyloxy)-2-chlorobenzaldehyde

The title compound was prepared from the product of preparation 176, using a similar method as that described for preparation 27. The crude compound was re-crystallised from isopropyl ether to afford the desired product as a solid in 67% yield.

Preparations 178 to 183

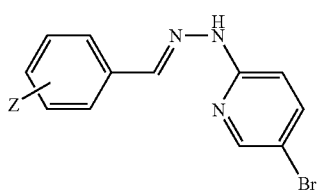

The following compounds, of the general formula shown below were prepared by a method similar to that described for preparation 30, using the product of preparation 25 and the appropriate commercially available aldehyde. For preparation 182, the starting material 4-benzyloxy-2-chloro benzaldehyde was prepared as described in J. Chem. Soc. Perkin Trans 1990, (2), 253.

| No. | Data | Yield |
|---|---|---|
| 178 | Z = 2-ethyl | 84% |
| 179 | Z = 2-methyl | Quant |
| 180 | Z = 2-(methylthio) | 89% |
| 181 | Z = 2-chloro | 98% |
| 182 | Z = 2-chloro, 4-benzyloxy | 89% |
| 183 | Z = 2-benzyloxy, 5-chloro | 94% |

Preparation 184

6-Bromo-3-(2-ethylphenyl)[1,2,4]triazolo[4,3-a]pyridine (Diacetoxyiodo)benzene (6.95 g, 22 mmol) was added to a solution of the product of preparation 178 (5.46 g, 18 mmol) in dichloromethane (200 mL) and the mixture was stirred at room temperature for 18 hours. The reaction mixture was then concentrated in vacuo and the residue was purified by column chromatography on silica gel, eluting with ethyl acetate:dichloromethane, 50:50, to afford the title compound as a solid in quantitative yield.

Preparation 185

6-Bromo-3-(2-chlorophenyl)[1,2,4]triazolo[4,3-a]pyridine

The title compound was prepared from the product of preparation 181, using the same method as that described for preparation 184. The crude compound was further purified by trituration with ethyl acetate to afford the desired product in 73% yield.

Preparation 186

6-Bromo-3-[2-(methylthio)phenyl][1,2,4]triazolo[4,3-a]pyridine (Diacetoxyiodo)benzene (500 mg, 1.55 mmol) was added to an ice-cooled solution of the product of preparation 180 (500 mg, 1.55 mmol) and the mixture was stirred for 6 hours, allowing the temperature to rise to 25° C. Further (diacetoxyiodo)benzene (500 mg, 1.55 mmol) was added and stirring continued for 18 hours at room temperature. The reaction mixture was then concentrated in vacuo and the residue was purified by column chromatography on silica gel, eluting with ethyl acetate to afford the title compound as a white solid in 68% yield.

Preparation 187

6-Bromo-3-(2-methylphenyl)[1,2,4]triazolo[4,3-a]pyridine

Ammonium eerie nitrate (35 g, 63.76 mmol) was added to a solution of the product of preparation 179 (9.25 g, 31.88 mmol) in ethanol (190 mL) and dichloromethane (60 mL) and the mixture was stirred for 72 hours at room temperature. The reaction mixture was then concentrated in vacuo and the residue was partitioned between ethyl acetate (200 mL) and water (100 mL). The organic solution was separated, washed with water (4×100 mL), dried over sodium sulfate and concentrated in vacuo. Purification of the residue by column chromatography on silica gel, eluting with pentane:ethyl acetate, 75:25, followed by dichloromethane:ethanol, 50:50, afforded the title compound in 21% yield, 1.94 g.

Preparation 188

6-Bromo-3-(2-fluorophenyl)[1,2,4]triazolo[4,3-a]pyridine

The title compound was prepared from 2-fluorobenzaldehyde and the product of preparation 25, using the same method as that described for preparation 32, as a white powder in 54% yield.

Preparation 189

6-Bromo-3-(2-methoxyphenyl)[1,2,4]triazolo[4,3-a]pyridine

A mixture of 2-methoxybenzaldehyde (10 g, 73.4 mmol) and the product of preparation 25 (13.8 g, 73.4 mmol) in dichloromethane (10 mL) and ethanol (100 mL) was heated to 65° C. for 5 minutes. The mixture was then cooled to room temperature and filtered off. The residue was re-dissolved in dichloromethane (50 mL) and ethanol (50 mL), iodobenzene diacetate (23.66 g, 73.4 mmol) was added and the reaction mixture was then stirred at room temperature for 90 minutes. The mixture was concentrated in vacuo and the residue was triturated three times with diethyl ether to afford the title compound as a white solid in 64% yield, 14.2 g.

Preparation 190

6-Bromo-3-(2-chloro-3-methoxyphenyl)[1,2,4]triazolo[4,3-a]pyridine

A mixture of 2-chloro-3-methoxybenzaldehyde [(10 g, 58.6 mmol), WO 2005/007165, p47] and the product of preparation 25 (11.13 g, 58.6 mmol) in ethanol (70 mL) was heated to 70° C. for 2.5 hours. Iodobenzene diacetate (24.5 g, 76 mmol) was added and the reaction mixture was diluted with ethanol (40 mL) and stirred at room temperature for 18 hours. The resulting precipitate was filtered off, washing through with ethanol, and dried under vacuum to afford the title compound as a solid in 64% yield, 12.70 g

Preparation 191

3-[5-(Benzyloxy)-2-chlorophenyl]-6-bromo[1,2,4]triazolo[4,3-a]pyridine

The title compound was prepared from the product of preparation 177, using a similar method to that described for preparation 190, as a solid in 60% yield.

Preparation 192

3-[4-(Benzyloxy)-2-chlorophenyl]-6-bromo[1,2,4]triazolo[4,3-a]pyridine

A mixture of the product of preparation 182 (53.4 g, 128 mmol) and iodobenzene diacetate (41.3 g, 128 mmol) in dichloromethane (50 mL) and ethyl acetate (50 ml) was stirred at room temperature for 18 hours. The resulting yellow precipitate was filtered off, affording a first portion of title compound. The filtrate was then treated with dichloromethane (50 mL) and diethyl ether (100 mL) and the resulting yellow precipitate was filtered off to afford further title compound, providing a total yield 37.1 g (70%).

Preparation 193

3-[2-(Benzyloxy)-5-chlorophenyl]-6-bromo[1,2,4]triazolo[4,3-a]pyridine

A suspension of the product of preparation 183 (6.2 g, 14.8 mmol) in dichloromethane (300 mL) and ethanol (100 mL) was warmed to 40° C. Iodobenzene diacetate (6.39 g, 19.24 mmol) was added and the mixture was stirred at 40° C. for 10 minutes then allowed to cool to room temperature over 3 hours. The reaction mixture was diluted with dichloromethane (400 mL), washed with 5% sodium bisulphite solution (300 mL) and water (300 mL), dried over magnesium sulfate and concentrated in vacuo. The residue was then triturated with diethyl ether to afford the title compound as a white solid in 92% yield, 5.7 g.

Preparations 194 to 203

The following compounds, of the general formula shown below were prepared by a method similar to that described for preparation 35, using the appropriate starting material and 2-mercaptobenzyl alcohol.

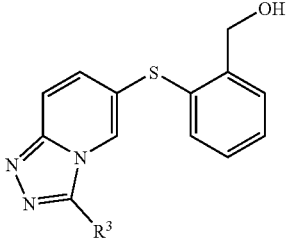

| No. | Data | Yield |
|---|---|---|
| 194 | $R^3$ = 2-ethylphenyl | 75% |
| 195 | $R^3$ = 2-methylphenyl | 77% |
| 196 | $R^3$ = 2-(methylthio)phenyl | 48% |
| 197 | $R^3$ = 2-fluorophenyl | 67% |
| 198 | $R^3$ = 2-methoxyphenyl | 61% |
| 199 | $R^3$ = 2-chlorophenyl | 93% |
| 200 | $R^3$ = 2-chloro-3-methoxyphenyl | 91% |
| 201 | $R^3$ = 2-chloro-4-benzyloxyphenyl | 87% |
| 202 | $R^3$ = 2-chloro-5-benzyloxyphenyl | 71% |
| 203 | $R^3$ = 2-benzyloxy-5-chlorophenyl | 37% |

Preparation 195: The crude compound was purified by column chromatography on silica gel, eluting with ethyl acetate:dichloromethane, 50:50, followed by dichloromethane:methanol, 95:5.

Preparation 196: The crude compound was purified by column chromatography on silica gel, eluting with dichloromethane:ethyl acetate, 40:60 to 0:100.

Preparation 197, 198 and 202: Crude compounds were triturated with diethyl ether

Preparation 204

(2-{[3-(2-Ethylphenyl)[1,2,4]triazolo[4,3-a]pyridin-6-yl]thio}benzyl)amine hydrochloride

Methanesulfonic anhydride (5 g, 29 mmol) was added to a solution of the product of preparation 194 (3.5 g, 9.7 mmol) and N,N-ethyldiisopropylamine (6.8 mL, 38.8 mmol) in dichloromethane (100 mL) and the mixture was stirred at room temperature for 90 minutes. 7M Methanolic ammonia (140 mL) was then added and the mixture was stirred at room temperature for 72 hours. The reaction mixture was then concentrated in vacuo and the residue was dissolved in dichloromethane (200 mL) and washed with sodium hydrogen carbonate solution (2×200 mL) and 2M hydrochloric acid (4×50 mL). The acidic washings were combined, basified with 2M sodium hydroxide to pH8 and extracted with dichloromethane (3×100 mL). The combined organic solution was dried over sodium sulfate, concentrated in vacuo and the residue was re-dissolved in dichloromethane. The resulting solution was cooled in an ice bath and hydrogen chloride gas

Preparation 205

(2-{[3-(2-Chlorophenyl)[1,2,4]triazolo[4,3-a]pyridin-6-yl]thio}benzyl)amine hydrochloride Methanesulfonic anhydride (4.99 g, 28.66 mmol) was added to an ice-cold solution of the product of preparation 199 (5.27 g, 14.33 mmol) and N,N-ethyldiisopropylamine (7.4 mL, 42.99 mmol) in dichloromethane (150 mL) and the mixture was stirred at 0° C. for 10 minutes and at room temperature for 4 hours. 7M Methanolic ammonia (143 mL) was then added and the mixture was stirred at room temperature for 18 hours. The reaction mixture was then concentrated in vacuo and the residue was dissolved in dichloromethane (150 mL) and washed with sodium hydrogen carbonate solution (150 mL) and 2M hydrochloric acid (3×70 mL). The acidic washings were combined, basified with 2M sodium hydroxide (250 mL) and extracted with dichloromethane (4×125 mL). The combined organic solution was dried over magnesium sulfate, concentrated in vacuo and the residue was purified by column chromatography on silica gel, eluting with dichloromethane:methanol:0.88 ammonia, 95:5:0.5, to give an orange foam. This foam was then dissolved in dichloromethane (15 mL) and acidified with hydrochloric acid (4M in dioxane, 3.1 mL). The mixture was azeotroped with methanol and dichloromethane, and the residue was triturated with diethyl ether to afford the title compound as a white solid in 48% yield, 2.82 g

Preparation 206

(2-{[3-(2-methylphenyl)[1,2,4]triazolo[4,3-a]pyridin-6-yl]thio}benzyl)amine

Methanesulfonic anhydride (2.7 g, 15.49 mmol) was added to a solution of the product of preparation 195 (1.8 g, 5.18 mmol) and N,N-ethyldiisopropylamine (3.6 mL, 20.72 mmol) in dichloromethane (50 mL) and the mixture was stirred at room temperature for 1 hour. 7M Methanolic ammonia (140 mL) was then added and the mixture was stirred at room temperature for 72 hours. The reaction mixture was then washed with sodium hydrogen carbonate solution, brine and 2M hydrochloric acid (3×100 mL). The acidic washings were combined, basified with 2M sodium hydroxide to pH8 and extracted with dichloromethane (5×150 mL). The combined organic solution was dried over sodium sulfate and concentrated in vacuo to afford the title compound as an orange gum in 55% yield, 982 mg.

Preparation 207

[2-({3-[2-(Methylthio)phenyl][1,2,4]triazolo[4,3-a]pyridin-6-yl}thio)benzyl]amine The title compound was prepared from the product of preparation 196, using the same method as that described for preparation 206, as a pale orange foam in 49% yield.

Preparation 208

[2-({3-[2-(Benzyloxy)-5-chlorophenyl][1,2,4]triazolo[4,3-a]pyridin-6-yl}thio)benzyl]amine The title compound was prepared from the product of preparation 203, using the same method as that described for preparation 206. The crude compound was purified by column chromatography on silica gel, eluting with dichloromethane:methanol:0.88 ammonia, 97.3:0.2 to 95:5:0.5, to afford the desired compound as a pale brown gum in 52% yield.

Preparation 209

6-{[2-(Azidomethyl)phenyl]thio}-3-(2-fluorophenyl)[1.2.4]triazolo[4,3-a]pyridine The title compound was prepared from the product of preparation 197 and diphenylphosphoryl azide, using a method similar to that of preparation 39, in 95% yield.

Preparation 210

6-{[2-(Azidomethyl)phenyl]thio}-3-(2-methoxyphenyl)[1,2,4]triazolo[4,3-a]pyridine The title compound was prepared from the product of preparation 198 and diphenylphosphoryl azide, using a method similar to that of preparation 39, in 86% yield.

Preparation 211

6-{[2-(azidomethyl)phenyl]thio}3-(2-chloro-3-methoxyphenyl)[1,2,4]triazolo[4,3-a]pyridine The title compound was prepared from the product of preparation 200 and diphenylphosphoryl azide, using a method similar to that of preparation 39. The crude compound was triturated with dichloromethane/diethyl ether to afford the desired product in 59% yield.

Preparation 212

6-{[2-(Azidomethyl)phenyl]thio}-3-[4-(benzyloxy)-2-chlorophenyl][1,2,4]triazolo[4,3-a]pyridine The title compound was prepared from the product of preparation 201 and diphenylphosphoryl azide, using a method similar to that of preparation 39, as a brown foam in quantitative yield.

Preparation 213

6-{[2-(Azidomethyl)phenyl]thio}-3-[5-(benzyloxy)-2-chlorophenyl][1,2,4]triazolo[4,3-a]pyridine The title compound was prepared from the product of preparation 202 and diphenylphosphoryl azide, using a method similar to that of preparation 39, in quantitative yield.

Preparation 214

(2-{[3-(2-Fluorophenyl)[1,2,4]triazolo[4,3-a]Pyridin-6-yl]thio}benzyl)amine hydrochloride Triphenylphosphine (8.53 g, 32.5 mmol) and water (0.58 mL, 32.5 mmol) were added to a solution of the product of preparation 209 (10.2 g, 27.1 mmol) in tetrahydrofuran (100 mL) and the mixture was stirred at room temperature for 18 hours. The reaction mixture was then concentrated in vacuo and the residue was dissolved in dichloromethane (200 mL). Hydrochloric acid (4M in dioxane, 8 mL) was added dropwise and the mixture was stirred for 72 hours at room temperature. The resulting precipitate was filtered off and triturated with dichloromethane to afford the title compound as a solid in 35% yield, 3.7 g.

Preparation 215

(2-{[3-(2-Methoxyphenyl)[1,2,4]triazolo[4,3-a]pyridin-6-yl]thio}benzyl)amine hydrochloride The title compound was prepared from the product of preparation 210, using the same method as that described for preparation 214, as a solid in 52% yield.

Preparation 216

(2-{[3-(2-Chloro-3-methoxyphenyl)[1,2,4]triazolo[4,3-a]pyridin-6-yl]thio}benzyl)amine hydrochloride The title compound was prepared from the product of preparation 211, using the same method as that described for preparation 214, as a solid in 72% yield.

Preparation 217

[2-({3-[4-(benzyloxy)-2-chlorophenyl][1,2,4]triazolo[4,3-a]pyridin-6-yl}thio)benzyl]-amine hydrochloride The title compound was prepared from the product of preparation 212, using a similar method to that described for preparation 214, as a solid in 64% yield.

Preparation 218

[2-({3-[5-(Benzyloxy)-2-chlorophenyl][1,2,4]triazolo[4,3-a]pyridin-6-yl}thio)benzyl]amine The title compound was prepared from the product of preparation 213, using a similar method to that described for preparation 214, as a solid in 85% yield.

Preparation 219

N-(3-tert-Butyl-1-{3-[2-(tetrahydro-2H-pyran-2-yloxy)ethoxy]phenyl}-1H-pyrazol-5-yl)-N'-(2-{[3-(2-fluorophenyl)[1,2,4]triazolo[4,3-a]pyridin-6-yl]thio}benzyl)urea A mixture of the product of preparation 214 (360 mg, 0.93 mmol), the product of preparation 116 (446 mg, 0.93 mmol) and N,N-ethyldiisopropylamine (0.39 mL, 2.23 mmol) in dimethylsulfoxide (4 mL) was stirred at room temperature for 72 hours and at 60° C. for 1 hour. The reaction mixture was then cooled to room temperature, diluted with ethyl acetate (50 mL) and washed with 0.5M hydrochloric acid, saturated sodium hydrogen carbonate solution and brine. The organic solution was dried over sodium sulfate concentrated in vacuo and the residue was purified by column chromatography on silica gel, eluting with dichloromethane:methanol, 99:1 to 93:7, to afford the title compound as a light brown oil in 33% yield, 223 mg.

Preparation 220

N-(3-tert-Butyl-1-{3-[2-tetrahydro-2H-pyran-2-yloxy)ethoxy]phenyl}-1H-pyrazol-5-yl)-N'-(2-{[3-(2-chlorophenyl)[1,2,4]triazolo[4,3-a]pyridin-6-yl]thio}benzyl)urea The title compound was prepared from the products of preparations 205 and 116, using the same method as that described for preparation 219, as a white foam in 45% yield.

Preparation 221

N-(3-tert-butyl-1-{3-[2-(tetrahydro-2H-pyran-2-yloxy)ethoxy]phenyl}-1H-pyrazol-5-yl)-N'-(2-{[3-(2-isopropylphenyl)[1,2,4]triazolo[4,3-a]pyridin-6-yl]thio}benzyl)urea The title compound was prepared from the products of preparation 237 and 116, using the same method as that described for preparation 219, as a white foam in 37% yield.

Preparation 222

N-(3-tert-Butyl-1-{3-[2-(tetrahydro-2H-pyran-2-yloxy)ethoxy]phenyl}-1H-pyrazol-5-yl)-N'-(2-{[3-(2-methoxyphenyl)[1,2,4]triazolo[4,3-a]pyridin-6-yl]thio}benzyl)urea The title compound was prepared from the products of preparations 215 and 116, using the same method as that described for preparation 219, as a white foam in 46% yield.

Preparation 223

N-{1-[3-(Benzyloxy)phenyl]-3-tert-butyl-1H-pyrazol-5-yl}-N'-(2-{[3-(2-chlorophenyl)[1,2,4]triazolo[4,3-a]pyridin-6-yl]thio}benzyl)urea The title compound was prepared from the products of preparations 118 and 205, using the same method as that described for preparation 219, as a pale yellow foam in 59% yield.

Preparation 224

N-{1-[3-(Benzyloxy)phenyl]-3-tert-butyl-1H-pyrazol-5-yl}-N'-[2-({3-2-(benzyloxy)phenyl[1,2,4]triazolo[4,3-a]pyridin-6-yl}thio)benzyl]urea The title compound was prepared from the products of preparations 118 and 46, using the same method as that described for preparation 219, as a white solid in 58% yield.

Preparation 225

N-{1-(3-{[tert-Butyl(dimethyl)silyl]oxy}phenyl)-3-[1-methyl-1-(methylthio)ethyl]-1H-pyrazol-5-yl}-N'-{2-[(3-isopropyl[1,2,4]triazolo[4,3-a]pyridin-6-yl)thio]benzyl}urea The title compound was prepared from the products of preparations 120 and 43, using the same method as that described for preparation 219, as a white foam in 69% yield.

Preparation 226

N-{1-(3-{[tert-Butyl(dimethyl)silyl]oxy}phenyl)-3-[1-methyl-1-(methylthio)ethyl]-1H-pyrazol-5-yl}-N'-(2-{[3-(2-fluorophenyl)[1,2,4]triazolo[4,3-a]pyridin-6-yl]thio}benzyl)urea The title compound was prepared from the products of preparations 120 and 214, using the same method as that described for preparation 219, as an off-white foam in 48% yield.

Preparation 227

N-{1-(3-{[tert-Butyl(dimethyl)silyl]oxy}phenyl)-3-[1-methyl-1-(methylthio)ethyl]-1H-pyrazol-5-yl}-N'-(2-{[3-(2-methoxyphenyl)[1,2,4]triazolo[4,3-a]pyridin-6-yl]thio}benzyl)urea The title compound was prepared from the products of preparations 120 and 215, using the same method as that described for preparation 219, as a white foam in 53% yield.

Preparation 228

N-{1-[3-(Benzyloxy)phenyl]-3-[1-methyl-1-(methylthio)ethyl]-1H-pyrazol-5-yl}-N'-(2-{[3-(2-ethylphenyl)[1,2,4]triazolo[4,3-a]pyridin-6-yl]thio}benzyl)urea The title compound was prepared from the product of preparation 204 and preparation 17, using the same method as that described for preparation 121, in 41% yield.

Preparation 229

N-{1-[3-(Benzyloxy)phenyl]-3-tert-butyl-1H-pyrazol-5-yl}-N'-[2-({3-[2-(methylthio)phenyl][1,2,4]triazolo[4,3-a]pyridin-6-yl}thio)benzyl]urea The title compound was prepared from the product of preparation 207 and 63, using the same method as that described for preparation 121, as a white solid in 52% yield.

Preparation 230

N-{1-[4-(Benzyloxy)phenyl]-3-[1-methyl-1-(methylphenyl)ethyl]1H-pyrazol-5-yl}-N'-(2-{[3-(2-methylphenyl)[1,2,4]triazolo[4,3-a]pyridin-6-yl]thio}benzyl)urea The title compound was prepared from the products of preparations 92 and 206, using the same method as that described for preparation 121, in 19% yield.

Preparation 231

N-[2-({3-[4-(Benzyloxy)-2-chlorophenyl][1,2,4]triazolo[4,3-a]pyridin-6-yl}thio)benzyl]-N'-[3-tert-butyl-1-(3,4-difluorophenyl)-1H-pyrazol-5-yl]urea The title compound was prepared from the products of preparations 95 and 217, using the same method as that described for preparation 121, as a brown powder in 59% yield.

Preparation 232

N-[2-({3-[5-(Benzyloxy)-2-chlorophenyl][1,2,4]triazolo[4,3-a]pyridin-6-yl}thio)benzyl]-N'-[3-tert-butyl-1-(3,4-difluorophenyl)-1H-pyrazol-5-yl]urea The title compound was prepared from the products of preparations 218 and 95, using the same method as that described for preparation 121, as a white powder in 40% yield.

Preparation 234

6-Bromo-3-(2-isopropylphenyl)[1,2,4]triazolo[4,3-a]pyridine

The title compound was prepared from the product of preparation 25 and 2-isopropylbenzaldehyde, using the same method as that described for preparation 189. The crude compound was purified by column chromatography on silica gel, eluting with dichloromethane:methanol, 95:5, to afford the desired product as a yellow liquid in 35% yield.

Preparation 235

[3-(2-isopropylphenyl)[1,2,4]triazolo[4,3-a]pyridin-6-yl]-methanol

The title compound was prepared from the product of preparation 234 and 2-mercaptobenzyl alcohol, using the same method as that described for preparation 35. The crude compound was purified by column chromatography, eluting with dichloromethane:methanol, 95:5, to afford the desired product as a dark brown oil in 45% yield.

Preparation 236

6-{[2-(Azidomethyl)phenyl]thio}-3-(2-isopropylphenyl)[1,2,4]triazolo[4,3-a]pyridine The title compound was prepared from the product of preparation 235 and diphenylphosphoryl azide, using the same method as that described for preparation 39, as a brown oil in 66% yield.

Preparation 237

(2-{[3-(2-Isopropylphenyl)[1,2,4]triazolo[4,3-a]pyridin-6-yl]thio}benzyl)amine hydrochloride The title compound was prepared from the product of preparation 236, using the same method as that described for preparation 214, as a white solid in 805 yield.

Preparation 238

N-(2-{[3-(2-Fluorophenyl)[1,2,4]triazolo[4,3-a]pyridin-6-yl]thio}benzyl)-N'-(3-[1-methyl-1-(methylthio)ethyl]-1-(3-[2-(tetrahydro-2H-pyran-2-yloxy)ethoxy]-phenyl)-1H-pyrazol-5-yl)urea A mixture of the product of preparation 117 (399 mg, 0.78 mmol), the product of preparation 214 (307 mg, 0.78 mmol) and N,N-ethyldiisopropylamine (0.30 mL, 1.70 mmol) in dimethylsulfoxide (2 mL) was stirred at room temperature for 18 hours. The reaction mixture was then diluted with ethyl acetate (50 mL) and washed with 0.5M hydrochloric acid, saturated sodium hydrogen carbonate solution and brine. The organic solution was dried over sodium sulfate concentrated in vacuo and the residue was purified by column chromatography on silica gel, eluting with dichloromethane:methanol, 100:0 to 95:5, to afford the title compound as a white foam in 40% yield, 266 mg.

Preparation 239

N-(2-{[3-(2-Methoxyphenyl)[1,2,4]triazolo[4,3-a]pyridin-6-yl]thio}benzyl)-N'-(3-[1-methyl-1-(methylthio)ethyl]-1-{3-[2-(tetrahydro-2H-pyran-2-yloxy)ethoxy]phenyl}-1H-pyrazol-5-yl)urea The title compound was prepared from the products of preparations 117 and 215, using the same method as that described for the product of preparation 238, as a white foam in 45% yield.

Preparation 240

1-[3-(Benzyloxy)phenyl]-3-(1,1-dimethylpropyl)-1H-pyrazol-5-amine

The title compound was prepared from the product of preparation 47 and 3-benzyloxyphenylhydrazine hydrochloride, using the same method as that described for preparation 7. The crude compound was triturated with diethyl ether to afford the desired product as a pink solid in 91% yield.

Preparation 241

3-[5-Amino-3-(1,1-dimethylpropyl)-1H-pyrazol-1-yl]phenol

The title compound was prepared from the product of preparation 240, using the same method as that described for example 99, as a yellow foam in 49% yield.

Preparation 242

1-(3-{[tert-butyl(dimethyl)silyl]oxy}phenyl)-3-(1,1-dimethylpropyl)-1H-pyrazol-5-amine The title compound was prepared from the product of preparation 241 and tert-butyldimethylsilyl chloride, using the same method as that described for preparation 99, as a solid in 69% yield.

Preparation 243

N-[1-(3-{[tert-Butyl(dimethyl)silyl]oxy}phenyl)-3-(1,1-dimethylpropyl)-1H-pyrazol-5-yl]-N'-[2-({3-[2-methylthio)phenyl][1,2,4]triazolo[4,3-a]pyridin-6-yl}thio)benzyl]urea The title compound was prepared from the products of preparations 242 and 207, using the same method as that described for preparation 169, in 47% yield.

Preparation 244

1-[4-(Benzyloxy)phenyl]-3-tert-butyl-1H-pyrazol-5-amine

The title compound was prepared from 4,4-dimethyl-3-oxopentane nitrile and 4-benzyloxyphenylhydrazine hydrochloride, using the same method as that described for preparation 7, as a pale pink powder in quantitative yield.

Preparation 245

4-(5-Amino-3-tert-butyl-1H-pyrazol-1-yl)phenol

The title compound was prepared from the product of preparation 244, using the same method as that described for example 99, as a brown powder in 72% yield.

Preparation 246

3-tert-Butyl-1-(4-{[tert-butyl(dimethyl)silyl]oxy}phenyl)-1H-pyrazol-5-amine

The title compound was prepared from the product of preparation 245 and tert-butyldimethylsilyl chloride, using the same method as that described for preparation 99, as a white solid in 18% yield.

Preparation 247

Phenyl[3-tert-butyl-1-(4-{[tert-butyl(dimethyl)silyl]oxy}phenyl)-1H-pyrazol-5-yl]carbamate The title compound was prepared from the product of preparation 246 and phenylchloroformate, using the same method as described for preparation 116 in quantitative yield.

Preparation 248

N-[3-tert-Butyl-1-(4-{[tert-butyl(dimethyl)silyl]oxy}phenyl)-1H-pyrazol-5-yl]-N'-(2-{[3-(2-fluorophenyl)[1,2,4]triazolo[4,3-a]pyridin-6-yl]thio}benzyl)urea The title compound was prepared from the products of preparations 214 and 247, using the same method as that described for preparation 219, as a colourless glass in 93% yield.

Preparation 249

4-(Methylthio)benzaldehyde(5-bromopyridin-2-yl)hydrazone

The title compound was prepared from the product of preparation 25 and 4-(methylthio)benzaldehyde, using the same method as that described for preparation 30, as a pale yellow solid in 92% yield.

Preparation 250

6-Bromo-3-[4-(methylthio)phenyl][1,2,4]triazolo[4,3-a]pyridine

The title compound was prepared form the product of preparation 249, using the same method as described for preparation 184, as a white solid in 72% yield.

Preparation 251

[2-({3-[4-(Methylthio)phenyl][1,2,4]triazolo[4,3-a]pyridin-6-yl}thio)phenyl]methanol The title compound was prepared from the product of preparation 250 and 2-mercaptobenzyl alcohol, using the same method as that described for preparation 35, as a white solid in 58% yield.

Preparation 252

[2-({3-[4-(methylthio)phenyl][1,2,4]triazolo[4,3-a]pyridin-6-yl}thio)benzyl]amine hydrobromide Thionyl bromide (235 µL, 3.03 mmol) was added to an ice-cooled solution of the product of preparation 251 (384 mg, 1.01 mmol) in dichloromethane (10 mL) and the mixture was stirred for 1 hour. The reaction mixture was then concentrated in vacuo and the residue was re-dissolved in dichloromethane. The solution was cooled to 0° C., 7M methanolic ammonia (15 mL) was added dropwise and the mixture was stirred for 18 hours at room temperature. The reaction mixture was then concentrated in vacuo and the residue was diluted with dichloromethane, washed with saturated sodium hydrogen carbonate solution, dried over magnesium sulfate and concentrated in vacuo. Purification of the residue by column chromatography on silica get, eluting with methanol:ethyl acetate, 20:80 to 50:50, then afforded the title compound as a pale yellow solid in 40% yield, 154 mg.

Preparation 253

N-{1-[3-(benzyloxy)phenyl]-3-tert-butyl-1H-pyrazol-5-yl}-N'-[2-({3-[4-(methylthio)phenyl][1,2,4]triazolo[4,3-a]pyridin-6-yl}thio)benzyl]urea The title compound was prepared from the products of preparations 252 and 63, using the same method as that described for the product of preparation 121, as a white solid in 65% yield.

Preparation 254

N-[2-({3-[2-(Benzyloxy)phenyl][1,2,4]triazolo[4,3-a]pyridin-6-yl}thio)benzyl]-N'-[3-tert-butyl-1-(3-fluorophenyl)-1H-pyrazol-5-yl]urea The title compound was prepared from the products of preparations 62 and 46, using the same method as that described for preparation 121. The crude compound was triturated with diethyl ether to afford the desired product as a solid in 85% yield.

Preparation 255

N-(2-{[3-(2-isopropylphenyl)[1,2,4]triazolo[4,3-a]pyridin-6-yl]thio}benzyl)-N'-(3-[1-methyl-1-(methylthio)ethyl]-1-{3-[2-(tetrahydro-2H-pyran-2-yloxy)ethoxy]phenyl}-1H-pyrazol-5-yl)urea The title compound was prepared from the products of preparation 237 and 117, using the same method as that described for preparation 219, as a white foam in 48% yield.

Preparation 256

N-{1-[4-(Benzyloxy)phenyl]-3-tert-butyl-1H-pyrazol-5-yl}-N'-(2-{[3-(2-chlorophenyl)[1,2,4]triazolo[4,3-a]pyridin-6-yl]-thio}benzyl)urea The title compound was prepared from the product of preparations 103 and 205, using the same method as that described for preparation 219, as a foam in 74% yield.

Preparation 257

N-[3-tert-Butyl-1-(4-hydroxyphenyl)-1H-pyrazol-5-yl]-N'-(2-{[3-(2-chlorophenyl)[1,2,4]triazolo[4,3-a]pyridin-6-yl]thio}benzyl)urea The title compound was prepared from the product of preparation 256, using the same method as that described for preparation 101. The crude compound was further purified by triturated with diethyl ether to afford the title compound the title compound as a white solid in 47% yield.

Example 1

N-{3-tert-Butyl-1-[4-(methylthio)phenyl]-1H-pyrazol-5-yl}-N'-{2-[(3-isopropyl[1,2,4]triazolo[4,3-a]pyridin-6-yl)thio]benzyl}urea

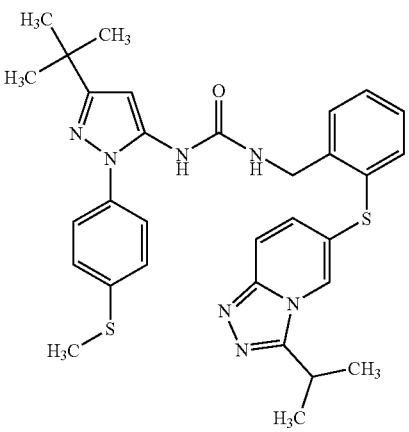

The product of preparation 7 (0.13 g, 0.50 mmol) was added to a solution of N,N'-carbonyldiimidazole (0.49 g, 3.00 mmol) in dichloromethane (10 mL) and the mixture was stirred at room temperature for 20 hours. The reaction mixture was then diluted with brine and stirred vigorously for 15 minutes. The aqueous layer was separated and extracted with dichloromethane (3×15 mL) and the combined organics were dried over sodium sulfate and concentrated in vacuo. The product of preparation 43 (0.15 g, 0.49 mmol) was added to a solution of the residue and N-ethyldiisopropylamine (65 mg, 0.50 mmol) in 1,4-dioxane (10 mL) and the mixture was stirred for 18 hours at room temperature. The reaction mixture was then diluted with ethyl acetate, washed with water (25 mL) and brine (25 mL), dried over sodium sulphate and concentrated in vacuo. The residue was purified by column chromatography on silica gel, eluting with dichloromethane:7M ammonia in methanol, 100:0 to 97.5:2.5. The appropriate fractions were concentrated in vacuo and the residue was re-purified twice using a Flashmaster® silica column, eluting with dichloromethane: 7M ammonia in methanol, 100:0 to 97.5:2.5 to afford the title compound.

$^1$H NMR (300 MHz, CDCl$_3$) δ: 1.20 (d, 6H), 1.40 (s, 9H), 2.29 (s, 3H), 3.15 (m, 1H), 4.50 (d, 2H), 6.30 (s, 1H), 6.72 (d, 1H), 6.80 (d, 2H), 7.05 (d, 2H), 7.21 (m, 5H), 7.48 (d, 1H), 7.65 (S, 1H), 8.15 (s, 1H) LRMS: m/z API-ES 586.7 [MH]$^+$

Examples 2 to 12

The following compounds, of the general formula shown before were prepared by a method similar to that described for example 1, using the product of preparation 43, N,N'-carbonyldiimidazole and the appropriate pyrazole starting material. The reactions were monitored by tlc analysis and were stirred at room temperature for 20-48 hours.

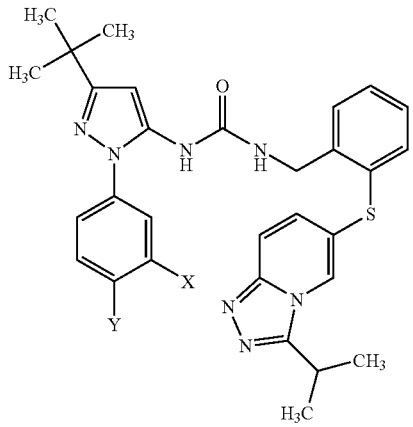

| No. | X | Y | Data | Yield |
|---|---|---|---|---|
| 2 | SCH$_3$ | H | $^1$H NMR (300 MHz, CDCl$_3$) δ: 1.30(m, 15 H), 2.25(s, 3 H), 3.15(m, 1 H), 4.55(d, 2 H), 6.32(s, 1 H), 6.75-7.30(m, 8 H), 7.45(d, 1 H), 7.72(s, 1 H), 8.40 (brs, 1 H) LRMS: m/z API-ES 586.7 [MH]$^+$ | 55% |
| 3 | Cl | Cl | $^1$H NMR (400 MHz, CDCl$_3$) δ: 1.28(m, 15 H), 3.14(m, 1 H), 4.55(d, 2 H), 6.33(s, 1 H), 6.87(d, 1 H), 6.99(d, 1 H), 7.09(d, 1 H), 7.23(m, 1 H), 7.28(m, 3 H), 7.40 (m, 1 H), 7.45(d, 1 H), 7.54(s, 1 H), 7.68(s, 1 H), 8.79(bs, 1 H), LRMS: m/z APCI 608 [MH]$^+$ | 27% |
| 4 | H | CO$_2$CH$_2$CH$_3$ | $^1$H NMR (400 MHz, CDCl$_3$) δ: 1.24-1.33(m, 18 H), 3.14(m, 1 H), 4.26(q, 2 H), 4.54(d, 2 H), 6.33(s, 1 H), 6.85(d, 1 H), 7.03(d, 1 H), 7.19(m, 1 H), 7.26(m, 3 H), 7.43(d, 1 H), 7.49(d, 2 H), 7.71 (m, 3 H), 8.56(s, 1 H) LRMS: m/z APCI 612 [MH]$^+$ Microanalysis: C$_{33}$H$_{37}$N$_7$O$_3$S. 0.1DCM requires (%): C 64.10; H 6.05; N 15.81; found (%) C 63.85; H 6.14, N 15.43. | 46% |
| 5 | CO$_2$CH$_2$CH$_3$ | H | $^1$H NMR (400 MHz, CDCl$_3$) δ: 1.28(m, 18 H), 3.15(m, 1 H), 4.21(q, 2 H), 4.52(d, 2 H), 6.33(s, 1 H), 6.86(d, 1 H), 7.03(bs, 1 H), 7.12(m, 1 H), 7.16-7.27(m, 4 H), 7.40(d, 1 H), 7.59(d, 1 H), 7.66 (d, 1 H), 7.71(s, 1 H), 8.08(s, 1 H), 8.31(s, 1 H), LRMS: m/z APCI 612 [MH]$^+$ | 24% |
| 6 | H | CN | $^1$H NMR (400 MHz, CDCl$_3$) δ: 1.29(m, 15 H), 3.17(m, 1 H), 4.55(d, 2 H), 6.30(s, 1 H), 6.94(d, 1 H), 7.13(d, 1 H), 7.24-7.33(m, 4 H), 7.40(m, 2 H), 7.45(d, 1 H), 7.65(d, 2 H), 7.74(s, 1 H), 8.64(s, 1 H): LRMS: m/z APCI 565 [MH]$^+$ | 52% |
| 7 | CN | H | $^1$H NMR (400 MHz, CD$_3$OD) δ: 1.31(s, 9 H), 1.41(d, 6 H), 3.46 (m, 1 H), 4.50(d, 2 H), 6.27(s, 1 H), 7.20(d, 1 H), 7.25-7.39(m, 4 H), 7.58-7.64(m, 2 H), 7.71(d, 1 H), 7.81(d, 1 H), 7.87(s, 1 H), 8.31(s, 1 H), LRMS: m/z APCI 565 [MH]$^+$ | 58% |
| 8 | H | H | $^1$H NMR (300 MHz, DMSO-d$_6$) δ: 1.21(s, 9 H), 1.35(d, 6 H), 3.55 (m, 1 H), 4.40(d, 2 H), 6.25(s, 1 H), 7.10(d, 1 H), 7.20-7.30(m, 4 H), 7.35(m, 1 H), 7.50(m, 4 H), 7.65(s, 1 H), 7.70(d, 1 H), 8.30(s, 1 H), 8.60(s, 1 H), LRMS: m/z API-ES 540.8 [MH]$^+$ | Quantitative |
| 9 | H | CH$_3$ | $^1$H NMR (300 MHz, DMSO-d$_6$) δ: 1.25(s, 9 H), 1.40(d, 6 H), 2.27 (s, 3 H), 3.55(m, 1 H), 4.40(d, 2 H), 6.20(s, 1 H), 7.00(m, 1 H), 7.10(d, 1 H), 7.20-7.40(m, 8 H), 7.65(d, 1 H), 8.20(s, 1 H), 8.56(s, 1 H), LRMS: m/z API-ES 554.8 [MH]$^+$ | 71% |
| 10 | H | O—CH$_3$ | $^1$H NMR (300 MHz, CDCl$_3$) δ: 1.30(s, 9 H), 1.36(d, 6 H), 3.16 (m, 1 H), 3.68(s, 3 H), 4.54(d, 2 H), 6.27(s, 1 H), 6.42(m, 1 H), 6.66(d, 2 H), 6.85(d, 1 H), 7.17-7.31(m, 7 H), 7.38(d, 1 H), 7.70(s, 1 H), LRMS: m/z API-ES 570.8 [MH]$^+$ | 80% |
| 11 | CH$_3$ | O—CH$_3$ | $^1$H NMR (300 MHz, CDCl$_3$) δ: 1.30(s, 9 H), 1.38(d, 6 H), 2.05(s, 3 H), 3.20(m, 1 H), 3.71(s, 3 H), 4.60(d, 2 H), 6.27(m, 2 H), 6.60(d, 1 H), 6.88(d, 1 H), 7.10 (d, 1 H), 7.16(m, 2 H), 7.20-7.34 (m, 4 H), 7.40(d, 1 H), 7.75(s, 1 H), LRMS: m/z API-ES 584.6 [MH]$^+$ | 49% |
| 12 | O—CH$_3$ | H | $^1$H NMR (300 MHz, CDCl$_3$) δ: 1.30(m, 15 H), 3.15(m, 1 H), 3.62(s, 3 H), 4.55(d, 2 H), 6.32(s, 1 H), 6.55(d, 1 H), 6.85-7.10(m, 5 H), 7.20-7.40(m, 5 H), 7.72(s, 1 H), 8.40(brs, 1 H), LRMS: m/z API-ES 570.8 [MH]$^+$ | 88% |

Example 3: Reaction earned out in dichlorometnane only. Purified using Biotage® silica column, eluting with ethyl acetate.

Example 4: Reaction carried out in dichloromethane only. Purified by ISCO Companion® silica column, eluting with pentane:ethyl acetate, 100:0, 50:50, 20:80.

Example 5: Purified by ISCO Companion® silica column, eluting with ethyl acetate.

Example 9: Crude product is further purified by re-crystallisation from dichloromethane/diethyl ether to afford final compound.

Example 11: Crude compound is further purified using a Flashmaster® silica column, eluting with ethyl acetate.

Example 13

N-[3-tert-Butyl-1-(4-methylphenyl)-1H-pyrazol-5-yl]-N'-(2-{[3-(2-chloro-4-hydroxyphenyl)[1,2,4]triazolo[4,3-a]pyridin-6-yl]thio}benzyl)urea

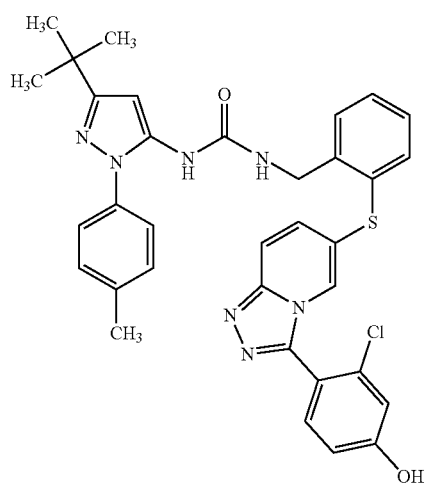

The title compound was prepared from the products of preparation 21 and 45, using a method similar to that of example 1, as a white foam in 54% yield.

$^1$H NMR (300 MHz, CDCl$_3$) δ: 1.30 (s, 9H), 2.40 (s, 3H), 4.45 (d, 2H), 6.30 (s, 1H), 6.85 (dd, 1H), 7.00 (d, 1H), 7.15 (d, 1H), 7.20-7.32 (m, 10H), 7.40 (d, 1H), 7.65 (s, 1H), 7.70 (d, 1H) LRMS: m/z API-ES 638.5 [MH]$^+$

Example 14

N-[3-tert-Butyl-1-(4-methylphenyl)-1H-pyrazol-5-yl]-N'-(2-{[3-(2-chloro-5-hydroxyphenyl)[1,2,4]triazolo[4,3-a]pyridin-6-yl]thio}benzyl)urea

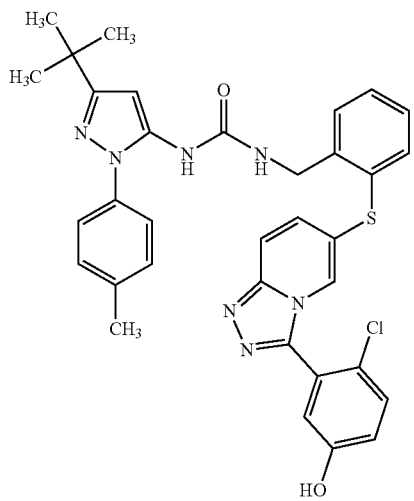

The title compound was prepared from the products of preparation 21 and 44, using a method similar to that of example 1, in 51% yield.

$^1$H NMR (300 MHz, DMSO-d$_6$) δ: 1.25 (s, 9H), 2.30 (s, 3H), 4.35 (d, 2H), 6.20 (s, 1H), 6.95-7.10 (m, 3H), 7.20-7.40 (m, 9H), 7.45 (d, 1H), 7.85 (d, 1H), 7.99 (s, 1H), 8.20 (s, 1H) LRMS: m/z API-ES 638.5 [MH]$^+$

Example 15

N-{3-[1,1-Dimethyl-2-(methylthio)ethyl]-1-phenyl-1H-pyrazol-5-yl}-N'-{2-[(3-isopropyl[1,2,4]triazolo[4,3-a]pyridin-6-yl)thio]benzyl}urea

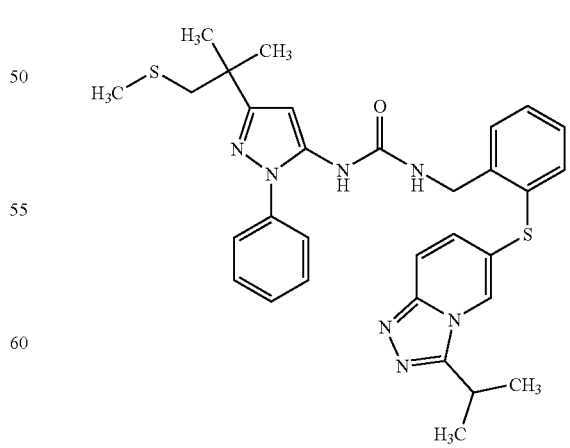

The product of preparation 15 (209 mg, 0.80 mmol) was added to a solution of N,N'-carbonyldiimidazole (810 mg, 5.00 mmol) in dichloromethane (10 mL) and the mixture was stirred at room temperature for 24 hours. The reaction mixture was then diluted with water and extracted with dichloromethane (3×25 mL). The combined organic solution was dried over magnesium sulfate and concentrated in vacuo. The product of preparation 43 (215 mg, 0.64 mmol) was added to a solution of the residue and N-ethyldiisopropylamine (129 mg, 1 mmol) in dichloromethane (10 mL) and the mixture was stirred for 24 hours at room temperature. The reaction mixture was then diluted with 0.1M hydrochloric acid (25 ml) and extracted with dichloromethane (3×25 mL). The combined organic solution was dried over magnesium sulfate and concentrated in vacuo. The residue was purified by column chromatography on silica gel, eluting with ethyl acetate: methanol, 100:0 to 85:15. The appropriate fractions were concentrated in vacuo and the residue was crystallised from ethyl acetate to afford the title compound in 55% yield, 206 mg.

$^1$H NMR (400 MHz, DMSO-$d_6$) δ: 1.29 (s, 6H), 1.34 (d, 6H), 1.97 (s, 3H), 2.77 (s, 2H), 3.55 (m, 1H), 4.40 (d, 2H), 6.29 (s, 1H), 7.02 (t, 1H), 7.10 (d, 1H), 7.26 (m, 4H), 7.38 (t, 1H), 7.46 (m, 4H), 7.70 (d, 1H), 8.35 (s, 1H), 8.60 (s, 1H) LRMS: m/z APCI 586 [MH]$^+$ Microanalysis: $C_{33}H_{35}N_7OS_2$. 0.2H$_2$O requires (%): C, 63.17; H, 6.05; N, 16.63. found (%) C, 63.03; H, 6.00; N, 16.42.

Examples 16 to 20

The following compounds, of the general formula shown below were prepared by a method similar to that described for example 15, using the product of preparation 43, N,N'-carbonyldiimidazole and the appropriate pyrazole starting material. The reactions were monitored by tlc analysis and were stirred at room temperature for 0.5-18 hours.

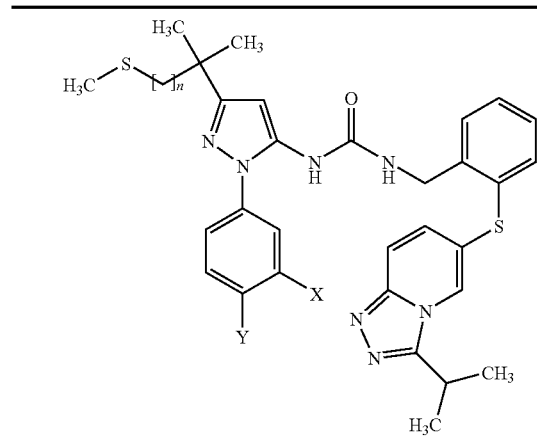

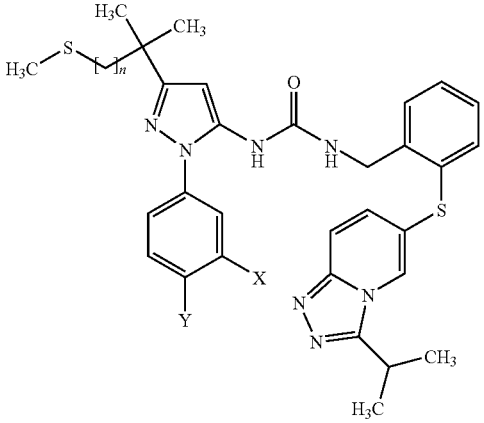

| No | X | Y | n | Data | Yield |
|---|---|---|---|---|---|
| 6 | H | CH$_3$ | 1 | $^1$H NMR (400 MHz, DMSO-$d_6$) δ: 1.28(s, 6 H), 1.34(d, 6 H), 1.96(s, 3 H), 2.34(s, 3 H), 2.76(s, 2 H), 3.55(m, 1 H), 4.39(d, 2 H), 6.26(s, 1 H), 7.00(t, 1 H), 7.10(d, 1 H), 7.23-7.33(m, 8 H), 7.69(d, 1 H), 8.27(s, 1 H), 8.60(s, 1 H), LRMS: m/z APCI 600 [MH]$^+$ Microanalysis: $C_{32}H_{37}N_7OS_2$. requires (%): C 64.08; H 6.22; N 16.35; found (%) C 63.79; H 6.20, N 16.14. | 67% |
| 17 | H | H | 0 | $^1$H NMR (400 MHz, DMSO-$d_6$) δ: 1.33(d, 6 H), 1.57(s, 6 H), 1.89(s, 3 H), 3.55(m, 1 H), 4.40(d, 2 H), 6.36(s, 1 H), 7.06(m, 1 H), 7.10(d, 1 H), 7.26(d, 4 H), 7.40(m, 1 H), 7.48(m, 4 H), 7.70(d, 1 H), 8.38(s, 1 H), 8.60(s, 1 H) LRMS: m/z APCI 572 [MH]$^+$ Microanalysis: $C_{30}H_{37}N_7OS_2$. requires (%): C 63.02; H 5.82; N 17.15; found (%) C 62.75; H 5.80, N 17.09. | 76% |
| 18 | —OCH$_2$Ph | H | 0 | $^1$H NMR (400 MHz, CDCl$_3$) δ: 1.37(d, 6 H), 1.68(s, 6 H), 1.95(s, 3 H), 3.17(m, 1 H), 4.58(d, 2 H), 4.98(s, 2 H), 6.15(bs, 1 H), 6.46(s, 1 H), 6.80(d, 1 H), 6.95(d, 1 H), 7.00(d, 1 H), 7.06(bs, 1 H), 7.09(t, 1 H), 7.17(t, 1 H), 7.23-7.37(m, 9 H), 7.46(s, 1 H), 7.72(s, 1 H) LRMS: m/z APCI 678 [MH]$^+$ Microanalysis: $C_{33}H_{35}N_7OS_2$. 0.2 H$_2$O requires (%): C 63.17; H 6.05; N 16.63; found (%) C 63.03; H 6.00, N 16.42. | 77% |
| 19 | H | Cl | 0 | $^1$H NMR (400 MHz, CDCl$_3$) δ: 1.38(d, 6 H), 1.65(s, 6 H), 1.98(s, 3 H), 3.18(m, 1 H), 4.61(d, 2 H), 6.48(s, 1 H), 7.00-7.65(m, 13 H), m/z ES 606 [MH]$^+$ $C_{33}H_{32}ClN_7OS_2$ requires (%): C 59.44; H 5.32; N 16.17; found (%) C 59.29; H 5.19, N 16.07. | 58% |
| 20 | H | CF$_3$ | 0 | $^1$H NMR (400 MHz, CDCl$_3$) δ: 1.35(d, 6 H), 1.65(s, 6 H), 1.98(s, 3 H), 3.15(m, 1 H), 4.62(d, 2 H), 6.49(s, 1 H), 7.20-7.65(m, 13 H), m/z ES 640 [MH]$^+$ $C_{33}H_{32}F_3N_7OS_2$ 0.4 H$_2$O requires (%): C 57.19; H 4.86; N 15.00; found (%) C 57.55; H 5.11, N 15.15. | 87% |

Examples 21 to 23

The following compounds, of the general formula shown below were prepared by a method similar to that described for example 15, using the product of preparation 46 N,N'-carbonyldiimidazole and the appropriate pyrazole starting material. The reactions were monitored by tlc analysis and were stirred at room temperature for 0.5-18 hours.

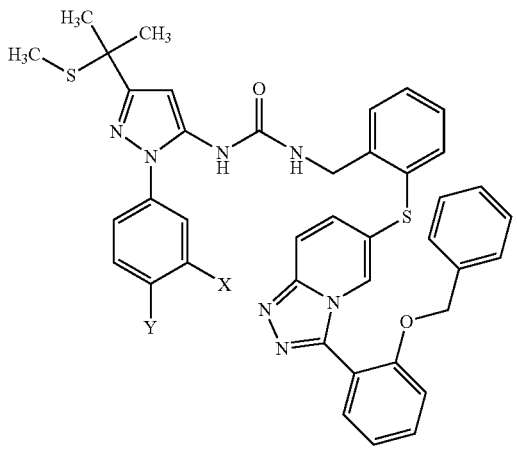

| No | X | Y | Data | Yield |
|----|---|---|------|-------|
| 21 | H | H | ¹H NMR (400 MHz, CDCl₃) δ: 1.66(d, 6 H), 1.34(s, 3 H), 4.51(d, 2 H), 5.02(s, 2 H), 6.20(bs. 1 H), 6.45(s, 1 H), 6.86(d, 1 H), 6.99(d, 1 H), 7.05(t, 1 H), 7.10-7.15(m, 5 H), 7.17-7.28(m, 7 H), 7.35-7.40(m, 3 H), 7.51-7.59(m, 2 H), 7.81(s, 1 H), LRMS: m/z APCI 712 [MH]⁺ | 82% |
| 22 | H | Cl | ¹H NMR (400 MHz, CDCl₃) δ: 1.65(d, 6 H), 1.95(s, 3 H), 4.55(d, 2 H), 5.01(s, 2 H), 6.42(s, 1 H), 6.43(brs, 1 H), 6.90(brs, 1 H), 7.05-7.35(m, 15 H), 7.42-7.60(m, 4 H), 7.72(brs, 1 H) LRMS: m/z ESI 746 [MH]⁺ | 75% |
| 23 | H | CF₃ | ¹H NMR (400 MHz, CDCl₃) δ: 1.65(d, 6 H), 1.95(s, 3 H), 4.55(d, 2 H), 4.97(s, 2 H), 6.49(s, 1 H), 6.71(d, 1 H), 6.82(d, 1 H), 6.91(brs, 1 H), 7.00(brs, 1 H), 7.01-7.32(m, 10 H), 7.40-7.58(m, 4 H), 7.68(s, 1 H) 8.38(brs, 1 H) LRMS: m/z ESI 780 [MH]⁺ | 52% |

Example 24

N-[3-tert-Butyl-1-(3-hydroxyphenyl)-1H-pyrazol-5-yl]-N'-{2-[(3-isopropyl[1,2,4]triazolo[4,3-a]pyridin-6-yl)thio]benzyl}urea

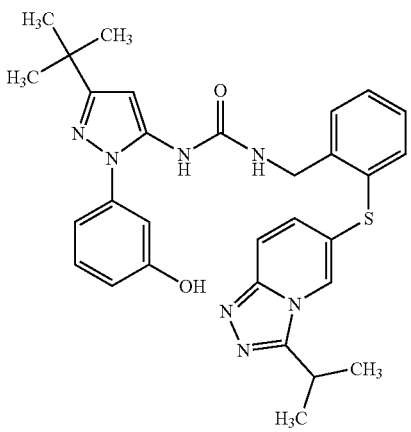

A solution of the product of example 12 (0.26 g, 0.45 mmol) in dichloromethane (5.5 mL) was cooled to 10° C., boron tribromide (1M in dichloromethane, 5.5 mL, 5.50 mmol) was added and the mixture was stirred at room temperature for 18 hours. A solution of ethylenediamine (15% in water, 25 mL) was added dropwise and the mixture was then acidified with 6M hydrochloric acid to pH1. The aqueous layer was separated and extracted with ethyl acetate (3×20 mL) and the combined organic solution was dried over sodium sulphate and concentrated in vacuo. Purification of the residue by column chromatography on silica gel, eluting with dichloromethane:methanol, 96:4 to 92:8, followed by trituration with dichloromethane/diethyl ether afforded the title compound in 35% yield, 88 mg.

¹H NMR (300 MHz, CDCl₃) δ: 1.20 (s, 9H), 1.40 (d, 6H), 3.60 (m, 1H), 4.40 (d, 2H), 6.20 (s, 1H), 6.75 (d, 1H), 6.85 (m, 2H), 7.20 (m, 2H), 7.30 (m, 5H), 7.72 (d, 1H), 8.30 (s, 1H), 8.60 (s, 1H), 9.70 (s, 1H) LRMS: m/z API-ES 556.8 [MH]⁺

Example 25

N-[3-tert-Butyl-1-(4-hydroxy-3-methylphenyl)-1H-pyrazol-5-yl]-N'-{2-[(3-isopropyl[1,2,4]triazolo[4,3-a]pyridin-6-yl)thio]benzyl}urea

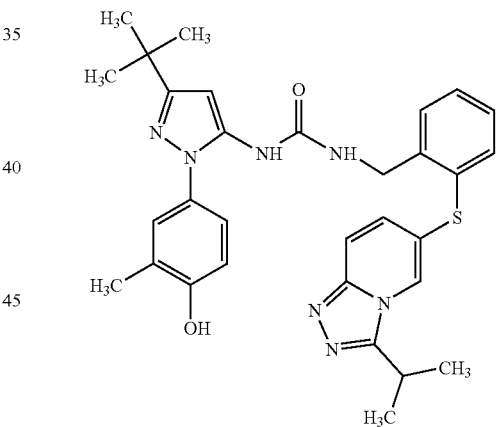

The title compound was prepared from the product of example 11, using a method similar to example 24. The crude compound was purified using a Flashmaster® silica column, eluting with dichloromethane:7M ammonia in methanol, 100:0 to 95:5, to afford the desired product in 84% yield.

¹H NMR (300 MHz, DMSO-d₆) δ: 1.20 (s, 9H), 1.35 (d, 6H), 2.14 (s, 3H), 3.55 (m, 1H), 4.60 (d, 2H), 6.20 (s, 1H), 6.80 (d, 1H), 6.95-7.05 (m, 2H), 7.10 (m, 2H), 7.20-7.34 (m,

4H), 7.70 (d, 1H), 8.10 (s, 1H), 8.60 (s, 1H), 9.60 (bs, 1H) LRMS: m/z API-ES 570.6 [MH]⁺

Example 26

N-{1-(3-Hydroxyphenyl)-3-[1-methyl-1-(methylthio)ethyl]-1H-pyrazol-5-yl}-N'-{2-[(3-isopropyl[1,2,4]triazolo[4,3-a]pyridin-6-yl)thio]benzyl}urea

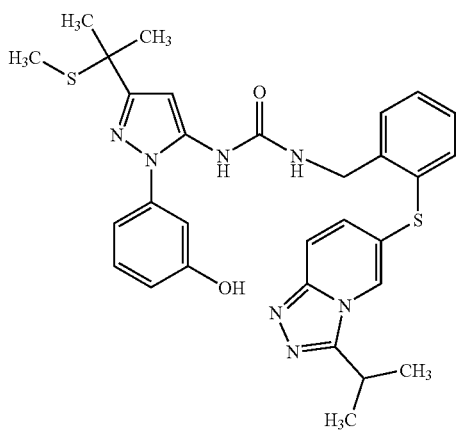

The title compound was prepared from the product of example 18, using a similar method to example 24. The crude product was purified by column chromatography on silica gel, eluting with ethyl acetate:methanol, 100:0 to 90:10. The appropriate fractions were concentrated in vacuo and the residue was re-crystallised from ethyl acetate to afford the title compound as a solid in 55% yield.

$^1$H NMR (400 MHz, DMSO-d$_6$) δ: 1.34 (d, 6H), 1.57 (s, 6H), 1.88 (s, 3H), 3.56 (m, 1H), 4.41 (d, 2H), 6.34 (s, 1H), 6.79 (d, 1H), 6.88 (m, 2H), 7.10 (m, 2H), 7.23-7.30 (m, 5H), 7.70 (d, 1H), 8.35 (s, 1H), 8.60 (s, 1H), 9.79 (s, 1H) LRMS: m/z APCI 588 [MH]⁺

Examples 27 to 29

The following compounds, of the general formula shown below were prepared by a method similar to that described for example 24, using the appropriate urea starting material. The reactions were monitored by tlc analysis and were stirred at room temperature for 0.5-1.0 hours.

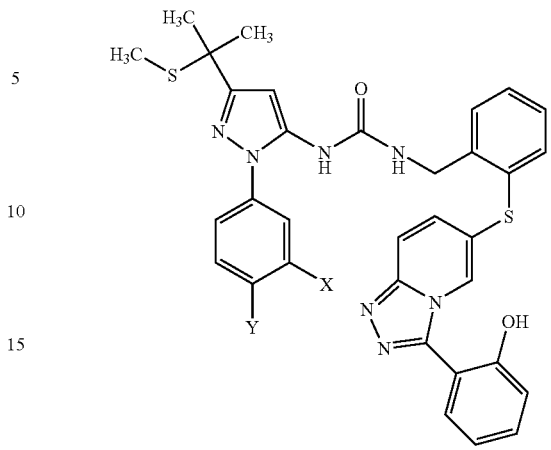

| No | X | Y | Data |
|----|---|---|------|
| 27 | H | H | HRMS: m/z found: 622.2072; C$_{33}$H$_{32}$N$_7$O$_2$S$_2$ requires 622.2053 |
| 28 | H | Cl | HRMS: m/z found: 656.1669; C$_{33}$H$_{30}$ClN$_7$O$_2$S$_2$ requires 656.1664 |
| 29 | H | CF$_3$ | HRMS: m/z found: 690.1927; C$_{33}$H$_{30}$F$_3$N$_7$O$_2$S$_2$ requires 690.1927 |

Example 30

3-(3-tert-Butyl-5-{3-[2-(3-isopropyl-[1,2,4]triazolo[4,3-a]pyridin-6-ylsulfanyl)-benzyl]-ureido}-pyrazol-1-yl)-benzoic acid

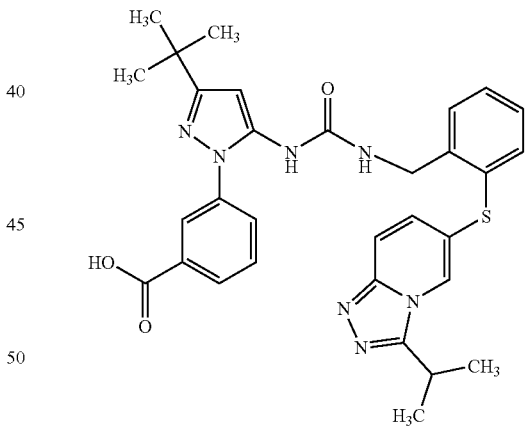

A mixture of the product of example 5 (68.5 mg, 0.11 mmol) and 2M sodium hydroxide solution (1 mL) in dioxan (2 mL) was heated at 90° C. for 18 hours. The solvent was then evaporated under reduced pressure and the aqueous residue was diluted with water (10 mL), acidified with 1M hydrochloric acid to pH3, and extracted with ethyl acetate (2×10 mL). The organic solution was dried over sodium sulfate, concentrated in vacuo and the residue was purified by column chromatography on silica gel, eluting with dichloromethane:methanol:acetic acid, 95:5:0.5. The relevant fractions were concentrated in vacuo and the residue was dried under vacuum at 50° C. to afford the title compound in 27% yield, 16.8 mg.

¹H NMR (400 MHz, CD₃OD) δ: 1.31 (s, 9H), 1.41 (d, 6H), 3.48 (m, 1H), 4.49 (s, 2H), 6.28 (s, 1H), 7.19 (d, 1H), 7.23-7.31 (m, 3H), 7.37 (d, 1H), 7.52-7.65 (m, 3H), 8.02 (d, 1H), 8.11 (s, 1H), 8.27 (s, 1H) LRMS: m/z APCI 582 [MH]⁺ Microanalysis: $C_{31}H_{33}N_7O_3S$. 0.55 DCM requires (%): C, 60.11; H, 5.45; N, 15.55. found (%) C, 59.76; H, 5.57; N, 15.42.

Example 31

4-(3-tert-butyl-5-{[({2-[(3-isopropyl[1,2,4]triazolo[4,3-a]pyridin-6-yl)thio]benzyl}amino)carbonyl]amino}-1H-pyrazol-1-yl)benzoic acid

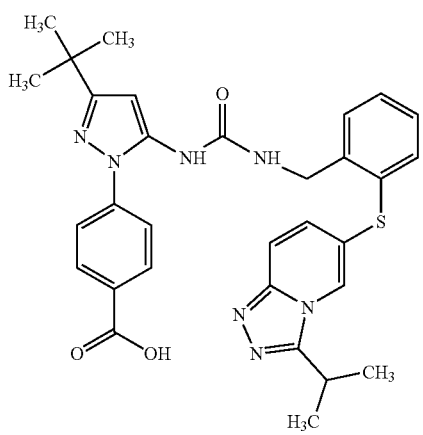

A mixture of the product of example 4 (130 mg, 0.21 mmol) and 2M sodium hydroxide solution (1.5 mL) in dioxan (3 mL) was heated at 90° C. for 16 hours. The mixture was then diluted with ethyl acetate (10 mL) and extracted with sodium hydroxide solution (2×5 mL). The aqueous solution was acidified to pH5 with 1M hydrochloric acid and extracted with ethyl acetate (2×5 mL). The organic solution was dried over sodium sulfate, concentrated in vacuo and the residue was purified by column chromatography on silica gel, eluting with dichloromethane:methanol:acetic acid, 95:5:0.5 to 90:10:1. The relevant fractions were concentrated in vacuo, and the residue was azeotroped with toluene and dried under vacuum at 50° C. to afford the title compound in 6% yield, 7 mg.

¹H NMR (400 MHz, CD₃OD) δ: 1.31 (s, 9H), 1.41 (d, 6H), 3.47 (m, 1H), 4.50 (s, 2H), 6.28 (s, 1H), 7.20 (d, 1H), 7.24-7.39 (m, 4H), 7.53 (d, 2H), 7.59 (d, 1H), 8.09 (d, 2H), 8.27 (s, 1H) LRMS: m/z ES 607 [MNa]⁺

Example 32

N-[3-tert-Butyl-1-(4-hydroxyphenyl)-1H-pyrazol-5-yl]-N'-{2-[(3-isopropyl[1,2,4]triazolo[4,3-a]pyridin-6-yl)thio]benzyl}urea

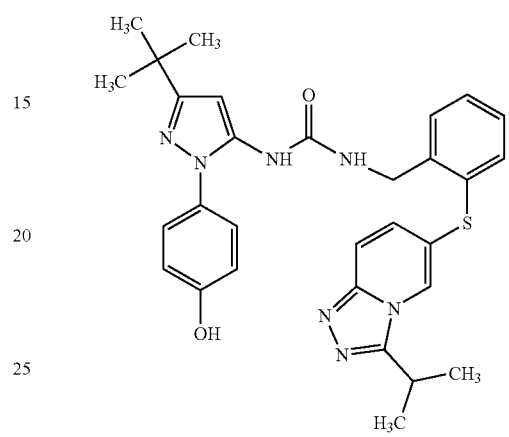

The title compound was prepared from the product of example 10, using a method similar to that described for example 24, as a white powder in 46% yield.

¹H NMR (400 MHz, DMSO-d₆) δ: 1.24 (s, 9H), 1.35 (d, 6H), 3.56 (m, 1H), 4.41 (d, 2H), 6.22 (s, 1H), 6.85 (d, 2H), 7.03 (m, 1H), 7.12 (dd, 1H), 7.19-7.34 (m, 6H), 7.71 (d, 1H), 8.15 (s, 1H), 8.60 (s, 1H), 9.74 (s, 1H); LRMS: m/z API-ES 556.4 [MH]⁺

Example 33

N-[3-tert-Butyl-1-(3-chloro-4-methoxyphenyl)-1H-pyrazol-5-yl]-N'-{2-[(3-isopropyl[1,2,4]triazolo[4,3-a]pyridin-6-yl)thio]-benzyl}urea

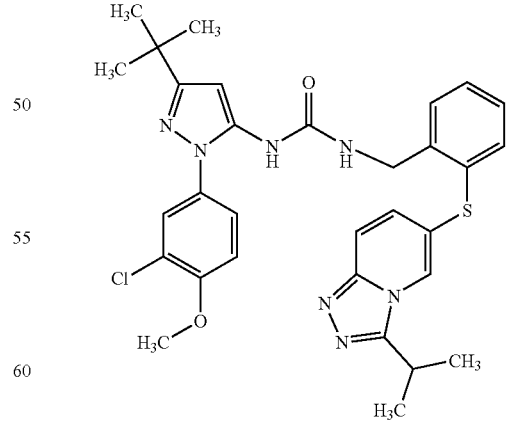

The title compound was prepared from the products of preparations 94 and 43, using the same method as that described for preparation 121. The crude compound was purified by column chromatography on silica gel, eluting with dichloromethane:7M methanolic ammonia, 100:0 to 97.5:2.5. This was followed by further purification using reversed phase column chromatography on C18 silica gel, eluting with water/7M methanolic ammonia (98:2):acetonitrile/7M methanolic ammonia (98:2), 75:25 to 25:75, to afford the desired product as a white solid in 22% yield.

$^1$H NMR (300 MHz, CDCl$_3$) δ: 1.25-1.47 (m, 15H), 3.15 (m, 1H), 3.79 (s, 3H), 4.55 (d, 2H), 6.30 (s, 1H), 6.67 (d, 1H), 6.81 (m, 2H), 7.07 (m, 1H), 7.17-7.31 (m, 4H), 7.36 (m, 1H), 7.42 (m, 1H), 7.66 (s, 1H), 7.94 (m, 1H); LCMS m/z 604/606 [M+H]$^+$

Example 34

N-(3-tert-Butyl-1-pyridin-3-yl-1H-pyrazol-5-yl)-N'-{2-[(3-isopropyl[1,2,4]triazolo[4,3-a]pyridin-6-yl)thio]benzyl}-urea

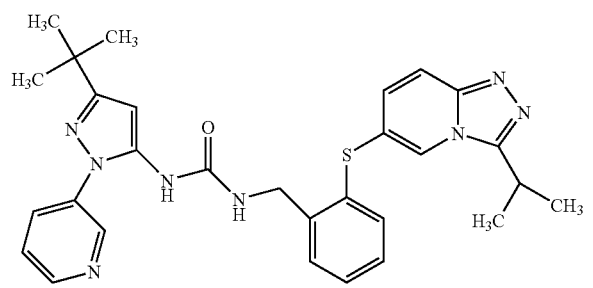

The title compound was prepared from the products of preparations 90 and 43, using a similar method to that described for preparation 121. The crude compound was purified by column chromatography using a Biotage® silica gel cartridge, eluting with dichloromethane:methanol:0.88 ammonia, 100:0:0 to 95:5:0.5. The residue was further purified by column chromatography on silica gel, eluting with ethyl acetate:methanol, 90:10, to afford the desired product in 5% yield.

$^1$HNMR (400 MHz, CD$_3$OD) δ: 1.32 (s, 9H), 1.42 (d, 6H), 3.49 (m, 1H), 4.50 (s, 2H), 6.29 (s, 1H), 7.21 (d, 1H), 7.26-7.40 (m, 4H), 7.54 (m, 1H), 7.61 (d, 1H), 7.96 (d, 1H), 8.31 (s, 1H), 8.55 (d, 1H), 8.74 (s, 1H); LRMS APCI m/z 541 [M+H]$^+$

Example 35

N-[3-tert-Butyl-1-(4-methylphenyl)-1H-pyrazol-5-yl]-N'-(2-{[3-(2-chloro-3-methoxyphenyl)[1,2,4]triazolo[4,3-a]pyridin-6-yl]thio}benzyl)urea

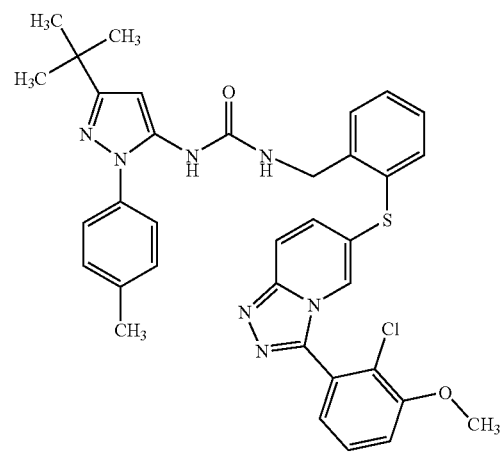

The title compound was prepared from the products of preparations 21 and 216, using the same method as that described for preparation 121. The crude compound was triturated with diethyl ether to afford the desired product as a solid in 56% yield.

$^1$HNMR (300 MHz, CDCl$_3$) δ: 1.29 (s, 9H), 2.27 (s, 3H), 3.96 (s, 3H), 4.51 (d, 2H), 5.79 (s, 1H), 6.24 (s, 1H), 6.58 (s, 1H), 6.97 (m, 1H), 7.07-7.38 (m, 10H), 7.41-7.49 (m, 1H), 7.52 (m, 1H), 7.70 (s, 1H); LCMS m/z 652.6 [M+H]$^+$

Example 36

N-[3-tert-Butyl-1-(4-methylphenyl)-1H-pyrazol-5-yl]-N'-(2-{[3-(2-chloro-3-hydroxyphenyl)[1,2,4]triazolo[4,3-a]pyridin-6-yl]thio}benzyl)urea

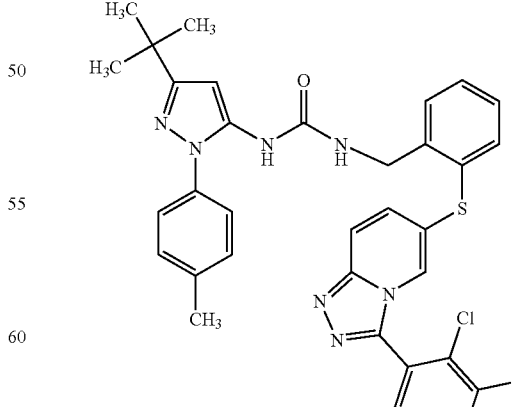

The title compound was prepared from the product of example 36, using a similar method to that described for example 72. The crude compound was re-crystallised from dichloromethane/methanol:diethyl ether, as a solid in 23% yield.

¹HNMR (300 MHz, DMSO-d₆) δ: 1.29 (s, 9H), 2.34 (s, 3H), 4.35 (d, 2H), 6.21 (m, 1H), 6.95 (m, 1H), 7.11 (m, 1H), 7.20-7.36 (m, 1H), 7.88 (m, 1H), 8.01 (m, 1H), 8.22 (m, 1H), 10.67 (s, 1H); LCMS m/z 638.6[M+H]⁺

Example 37

N-{1-[3-(2-Hydroxyethoxy)phenyl]-3-[1-(methylthio)ethyl]-1H-pyrazol-5-yl}-N'-{2-[(3-isopropyl[1,2,4]triazolo[4,3-a]pyridin-6-yl)thio]-benzyl}urea

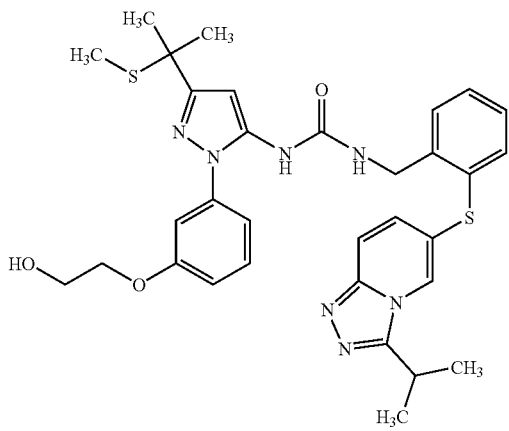

para-Toluenesulfonic acid (20 mg) was added to a solution of the product of preparation 173 (72 mg, 0.1 mmol) in methanol (10 mL) and the mixture was stirred at room temperature for 18 hours. The reaction mixture was then diluted with ethyl acetate, washed with sodium hydrogen carbonate solution, dried over magnesium sulfate and concentrated in vacuo. Purification of the residue by column chromatography on silica gel, eluting with ethyl acetate:methanol, 100:0 to 90:10, afforded the title compound as a white solid in 98% yield, 62 mg.

¹HNMR (400 MHz, DMSO-d₆) δ:1.34 (d, 6H), 1.57 (s, 6H), 1.89 (s, 3H), 3.56 (m, 1H), 3.71 (m, 2H), 4.02 (m, 2H), 4.41 (d, 2H), 4.88 (t, 1H), 6.36 (s, 1H), 6.97 (d, 1H), 7.03 (m, 2H), 7.09 (m, 2H), 7.24 (m, 2H), 7.29 (m, 2H), 7.39 (m, 1H), 7.69 (d, 1H), 8.06 (s, 1H), 8.38 (s, 1H); LRMS APCI m/z 632 [M+H]⁺

Example 38 to 42

The following compounds, of the general formula shown below were prepared by a method similar to that described for example 37, using the appropriate starting material and para-toluenesulfonic acid.

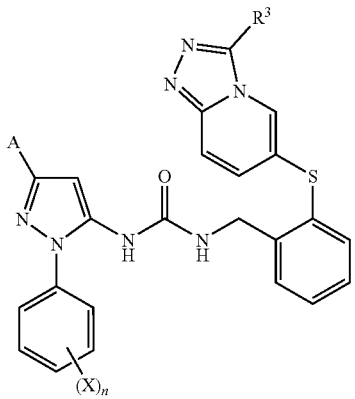

| No. | Data | Yield |
|---|---|---|
| | A = C(CH₃)₃ | |
| 38 | X = 3-(2-hydroxyethoxy), R³ = 2-chlorophenyl<br>¹HNMR(400 MHz, DMSO-d₆) δ: 1.23(s, 9 H), 3.70(q, 2 H), 4.00(t, 2 H), 4.37(d, 2 H), 4.83(t, 1 H), 6.23(s, 1 H), 6.94(d, 1 H), 6.98(m, 1 H), 7.03(m, 2 H), 7.21-7.30(m, 5 H), 7.35(m, 1 H), 7.55(m, 1 H), 7.63-7.72(m, 3 H), 7.88(d, 1 H), 8.02(s, 1 H), 8.26(s, 1 H); LRMS APCI m/z 668 [M + H]⁺ | 77% |
| 39 | X = 4-(2-hydroxyethoxy), R³ = 2-chlorophenyl<br>¹HNMR(400 MHz, DMSO-d₆) δ: 1.22(s, 9 H), 3.72(q, 2 H), 4.01(t, 2 H), 4.35(d, 2 H), 4.85(t, 1 H), 6.19(s, 1 H), 6.93(d, 1 H), 7.01(d, 2 H), 7.21-7.33(m, 7 H), 7.55(m, 1 H), 7.63-7.72(m, 3 H), 7.88(d, 1 H), 8.01(s, 1 H), 8.13(s, 1 H); LRMS APCI m/z 668 [M + H]⁺ | 51% |
| | A = (CH₃—S)C(CH₃)₂ | |
| 40 | X = 3-(2-hydroxyethoxy), R³ = 2-chlorophenyl<br>¹HNMR(400 MHz, DMSO-d₆) δ: 1.57(s, 6 H), 1.89(s, 3 H), 3.70(q, 2 H), 4.01(t, 2 H), 4.37(d, 2 H), 4.84(t, 1 H), 6.34(s, 1 H), 6.97(d, 1 H), 7.02(m, 3 H), 7.22-7.31(m, 5 H), 7.38(m, 1 H), 7.56(m, 1 H), 7.63-7.72(m, 3 H), 7.88 (d, 1 H), 8.02(s, 1 H), 8.32(s, 1 H) | 65% |
| 41 | X = 3-(2-hydroxyethoxy), R³ = 2-methoxyphenyl<br>¹HNMR(300 MHz, DMSO-d₆) δ: 1.58(s, 6 H), 1.90(s, 3 H), 3.69(m, 5 H), 4.01(t, 2 H), 4.37(d, 2 H), 4.87(t, 1 H), 6.32(s, 1 H), 6.95(d, 1 H), 7.02(m, 2 H), 7.20(m, 8 H), 7.38(m, 1 H), 7.58(m, 2 H), 7.84(m, 2 H), 8.46(s, 1 H); LCMS m/z 696 [M + H]⁺ | 80% |
| 42 | X = 3-(2-hydroxyethoxy), R³ = 2-fluorophenyl<br>¹HNMR(300 MHz, DMSO-d₆) δ: 1.58(s, 6 H), 1.90(s, 3 H), 3.69(m, 2 H), 4.00(t, 2 H), 4.35(d, 2 H), 4.91(t, 1 H), 6.28(s, 1 H), 6.91(d, 1 H), 7.05(m, 2 H), 7.28(m, 8 H), 7.44(m, 2 H), 7.67(m, 1 H), 7.85(d, 1 H), 8.19(d, 1 H), 9.08(s, 1 H); LCMS m/z 684 [M + H]⁺ | 83% |

Example 43

N-{3-tert-Butyl-1-[3-(2-hydroxyethoxy)phenyl]-1H-pyrazol-5-yl}-N'-(2-{[3-(2-fluorophenyl)[1,2,4]triazolo[4,3-a]pyridin-6-yl]thio}benzyl)urea

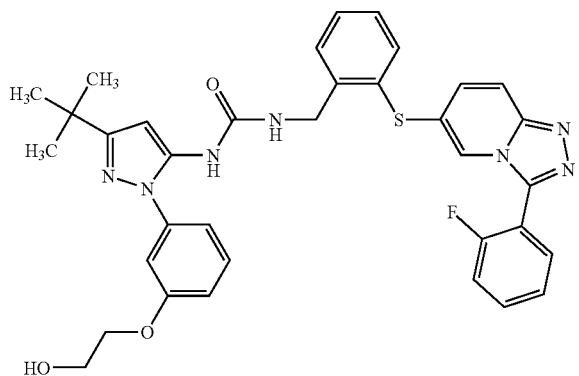

A solution of the product of preparation 219 (215 mg, 0.29 mmol) was dissolved in a mixture of acetic acid (4 mL), tetrahydrofuran (2 mL) and water (1 mL) and the resulting solution was heated to 60° C. for 18 hours. The reaction mixture was then concentrated in vacuo and the residue was purified by column chromatography on silica gel, eluting with dichloromethane:methanol, 99:1 to 92:8. The appropriate fractions were evaporated under reduced pressure and the residue was triturated with dichloromethane/diethyl ether, to afford the title compound as a white powder in 26% yield, 50.2 mg.

$^1$HNMR (400 MHz, DMSO-$d_6$) δ: 1.24 (s, 9H), 3.68 (m, 2H), 3.98 (m, 2H), 4.37 (m, 2H), 4.85 (t, 1H), 6.22 (s, 1H), 6.92 (m, 1H), 7.00-7.11 (m, 3H), 7.21-7.44 (m, 8H), 7.65 (m, 1H), 7.78 (m, 1H), 7.87 (m, 1H), 8.19 (m, 1H), 8.35 (s, 1H); LCMS m/z 652.6 [M+H]$^+$

Example 44

N-{3-tert-Butyl-1-[3-(2-hydroxyethoxy)phenyl]-1H-pyrazol-5-yl}-N'-(2-{[3-(2-isopropylphenyl)[1,2,4]triazolo[4,3-a]pyridin-6-yl]thio}benzyl)urea

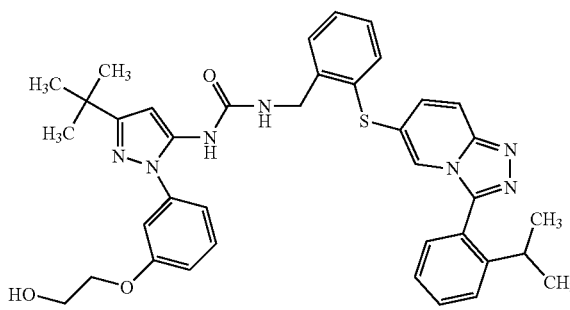

The title compound was prepared from the product of preparation 221, using the same method as that described for example 43, as a white powder in 66% yield.

$^1$HNMR (400 MHz, DMSO-$d_6$) δ: 1.07 (d, 6H), 1.24 (s, 9H), 2.75 (m, 1H), 3.68 (m, 2H), 4.00 (m, 2H), 4.35 (m, 2H), 4.86 (t, 1H), 6.21 (s, 1H), 6.90 (m, 1H), 7.01 (m, 3H), 7.16-7.36 (m, 7H), 7.47 (m, 1H), 7.58 (m, 2H), 7.86 (m, 2H), 8.31 (s, 1H); LCMS m/z 676.2 [M+H]$^+$

Example 45

N-{3-tert-Butyl-1-[3-(2-hydroxyethoxy)phenyl]-1H-pyrazol-5-yl}-N'-(2-{[3-(2-methoxyphenyl)[1,2,4]triazolo[4,3-a]pyridin-6-yl]thio}benzyl)urea

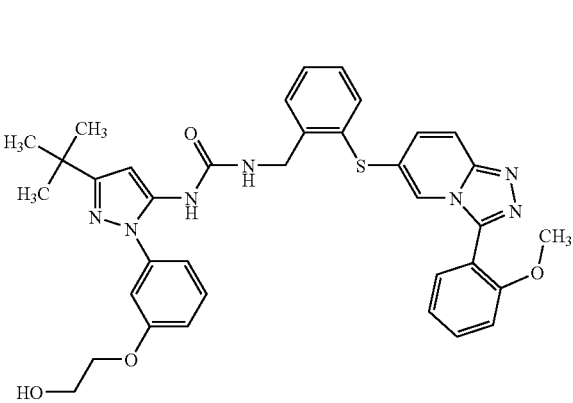

The title compound was prepared from the product of preparation 222, using the same method as that described for example 43, as a white powder in 45% yield.

$^1$HNMR (400 MHz, DMSO-$d_6$) δ: 1.25 (s, 9H), 2.75 (m, 1H), 3.68-3.70 (m, 5H), 4.01 (m, 2H), 4.35 (m, 2H), 4.86 (t, 1H), 6.22 (s, 1H), 6.94 (m, 1H), 7.01 (m, 3H), 7.13-7.34 (m, 8H), 7.57 (m, 2H), 7.85 (m, 2H), 8.31 (s, 1H); LCMS m/z 664.6 [M+H]$^+$

Example 46

N-[3-tert-Butyl-1-(4-fluorophenyl)-1H-pyrazol-5-yl]-N'-(2-{[3-(2-hydroxyphenyl)[1,2,4]triazolo[4,3-a]pyridin-6-yl]thio}benzyl)urea

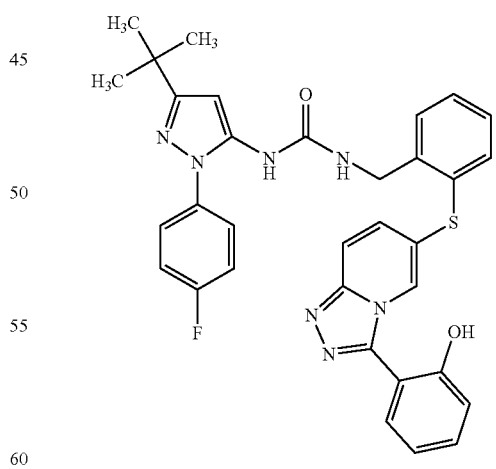

Boron tribromide (1M in dichloromethane, 1 mL, 1 mmol) was added dropwise to an ice-cold solution of the product of preparation 121 (186 mg, 0.27 mmol) in dichloromethane (10 mL) and the mixture was stirred for 10 minutes at 0° C. The reaction mixture was then diluted with dichloromethane (25 mL) and water (25 mL) and stirring continued at 0° C. for a further 10 minutes. 0.88 Ammonia (5 mL) was added and the aqueous layer was separated and extracted with dichloromethane (2×25 mL). The combined organic solution was dried over magnesium sulfate concentrated in vacuo and the residue was purified by column chromatography on silica gel, eluting with ethyl acetate:methanol, 100:0 to 95:5. The appropriate fractions were evaporated under reduced pressure and the residue was re-crystallised from ethyl acetate to afford the title compound as a pale yellow solid in 48% yield, 78 mg.

$^1$HNMR (400 MHz, DMSO-$d_6$) δ: 1.23 (s, 9H), 4.35 (d, 2H), 6.23 (s, 1H), 6.96 (m, 1H), 7.00 (t, 1H), 7.05 (d, 1H), 7.04-7.55 (m, 7H), 7.43 (m, 1H), 7.48 (dd, 2H), 7.54 (dd, 1H), 7.83 (d, 1H), 8.05 (s, 1H), 8.28 (s, 1H), 10.44 (s, 1H); LRMS APCI m/z 608 [M+H]$^+$

Examples 47 to 69

The following compounds, of the general formula shown below were prepared by a method similar to that described for example 46, using the appropriate starting material and 4-6 equivalents of boron tribromide.

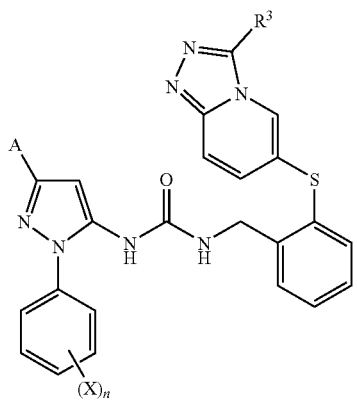

| No. | Data | Yield |
|---|---|---|
| | A = C(CH$_3$)$_3$ | |
| 47 | X = 3-F; R$^3$ = 2-(hydroxyphenyl)<br>$^1$HNMR(400 MHz, DMSO-$d_6$) δ: 1.24(s, 9 H), 4.36(d, 2 H), 6.26(s, 1 H), 7.02(m, 3 H), 7.19-7.25(m, 6 H), 7.35 (d, 2 H), 7.43(m, 1 H), 7.49(m, 1 H), 7.54(dd, 1 H), 7.83 (d, 1 H), 8.06(s, 1 H), 8.39(brs, 1 H), 10.45(s, 1 H); LRMS APCI m/z 608 [M + H]$^+$ | 30% |
| 48 | X = 4-CH$_2$CH$_3$; R$^3$ = 2-(hydroxyphenyl)<br>$^1$HNMR(400 MHz, DMSO-$d_6$) δ: 1.18(t, 3 H), 1.23(s, 9 H), 2.63(q, 2 H), 4.36(d, 2 H), 6.23(s, 1 H), 7.01(m, 2 H), 7.05 (d, 1 H), 7.17-7.36(m, 9 H), 7.43(m, 1 H), 7.54(d, 1 H), 7.83(d, 1 H), 8.06(s, 1 H), 8.26(s, 1 H), 10.46(s, 1 H); LRMS APCI m/z 618 [M + H]$^+$ | 58% |
| 49 | X = 3-CH$_2$CH$_3$; R$^3$ = 2-(hydroxyphenyl)<br>$^1$HNMR(400 MHz, DMSO-$d_6$) δ: 1.17(t, 3 H), 1.23(s, 9 H), 2.63(q, 2 H), 4.36(d, 2 H), 6.24(s, 1 H), 7.00(m, 2 H), 7.05 (d, 1 H), 7.19-7.29(m, 8 H), 7.37(m, 1 H), 7.43(m, 1 H), 7.54(d, 1 H), 7.83(d, 1 H), 8.06(s, 1 H), 8.27(s, 1 H), 10.46 (s, 1 H); LRMS APCI m/z 618 [M + H]$^+$ | 64% |
| 50 | X = 3-Cl, 4-Cl; R$^3$ = 2-(hydroxyphenyl)<br>$^1$HNMR(400 MHz, CD$_3$OD) δ: 1.31(s, 9 H), 4.48(d, 2 H), 6.26(s, 1 H), 6.97(d, 1 H), 7.03(m, 1 H), 7.27(m, 2 H), 7.31-7.39(m, 3 H), 7.45(m, 2 H), 7.54-7.59(m, 2 H), 7.70-7.74(m, 2 H), 7.82(s, 1 H); LRMS APCI m/z 658 [M + H]$^+$ | 31% |
| 51 | X = 3-CN; R$^3$ = 2-(hydroxyphenyl)<br>$^1$HNMR(400 MHz, CD$_3$OD) δ: 1.32(s, 9 H), 4.48(s, 2 H), 6.28(s, 1 H), 6.97(d, 1 H), 7.03(m, 1 H), 7.24-7.38(m, 5 H), 7.44(m, 1 H), 7.55(d, 1 H), 7.62(m, 1 H), 7.70-7.72 (m, 2 H), 7.81-7.82(m, 2 H), 7.88(s, 1 H); LRMS APCI m/z 615 [M + H]$^+$ | 47% |
| 52 | X = 4-CN; R$^3$ = 2-(hydroxyphenyl)<br>$^1$HNMR(400 MHz, CD$_3$OD) δ: 1.31(s, 9 H), 4.48(s, 2 H), 6.29(s, 1 H), 6.97(d, 1 H), 7.02(m, 1 H), 7.26-7.46(m, 6 H), 7.54(d, 1 H), 7.70-7.71(m, 3 H), 7.76-7.79(m, 2 H), 7.82(s, 1 H); LRMS APCI m/z 615 [M + H]$^+$ | 60% |
| 53 | X = H; R$^3$ = 2-(hydroxyphenyl)<br>$^1$HNMR(400 MHz, CD$_3$OD) δ: 1.31(s, 9 H), 4.48(s, 2 H), 6.29(s, 1 H), 6.98-7.04(m, 2 H), 7.23-7.33(m, 4 H), 7.36 (m, 1 H), 7.40-7.49(m, 6 H), 7.54(d, 1 H), 7.69(d, 1 H), 7.81(s, 1 H); LRMS APCI m/z 590 [M + H]$^+$ | 83% |
| 54 | X = 3-OH; R$^3$ = 2-chlorophenyl<br>$^1$HNMR(400 MHz, DMSO-$d_6$) δ: 1.22(s, 9 H), 4.37(d, 2 H), 6.21(s, 1 H), 6.75(d, 1 H), 6.86(d, 1 H), 6.87(s, 1 H), 6.89(m, 1 H), 7.22-7.30(m, 6 H), 7.55(m, 1 H), 7.63-7.72 (m, 3 H), 7.88(d, 1 H), 8.02(s, 1 H), 8.24(s, 1 H), 9.70(s, 1 H) | 48% |
| 55 | X = 3-OH; R$^3$ = 2-(hydroxyphenyl)<br>$^1$HNMR(400 MHz, DMSO-$d_6$) δ: 1.13(s, 9 H), 4.40(d, 2 H), 6.23(s, 1 H), 6.76(d, 1 H), 6.89(s, 2 H), 6.95-7.10 (m, 3 H), 7.16-7.28(m, 6 H), 7.40(m, 1 H), 7.55(d, 1 H), 7.77-7.90(m, 1 H), 8.06(s, 1 H), 8.65(s, 1 H); LRMS APCI m/z 606 [M + H]$^+$ | 50% |
| 56 | X = 3-OH; R$^3$ = 2-methylphenyl<br>$^1$HNMR(400 MHz, CDCl$_3$) δ: 1.29(s, 9 H), 2.14(s, 3 H), 4.48(d, 2 H), 6.36(s, 1 H), 6.47(d, 1 H), 6.56(brs, 1 H), 6.75(s, 1 H), 6.80(d, 1 H), 6.95(m, 2 H), 7.17(m, 2 H), 7.33(m, 7 H), 7.42(m, 1 H), 7.60(s, 1 H), 7.72(brs, 1 H); LRMS APCI m/z 604 [M + H]$^+$ | 57% |
| 57 | X = 3-OH, 5-CH$_3$; R$^3$ = HC(CH$_3$)$_2$<br>$^1$HNMR(300 MHz, DMSO-$d_6$) δ: 1.35(d, 6 H), 3.56(m, 1 H), 4.38(d, 2 H), 6.19(s, 1 H), 6.96-7.04(m, 2 H), 7.09 (dd, 1 H), 7.17-7.30(m, 5 H), 7.39(d, 1 H), 7.68(d, 1 H), 8.22(s, 1 H), 8.58(s, 1 H), 10.53(s, 1 H); LCMS m/z 590/592 [M + H]$^+$ | 59% |
| 58 | X = 3-CH$_3$; R$^3$ = 2-hydroxy-5-chlorophenyl<br>$^1$HNMR(400 MHz, DMSO-$d_6$) δ: 1.22(s, 9 H), 2.31(s, 3 H), 4.37(d, 2 H), 6.22(s, 1 H), 7.00(m, 1 H), 7.05(d, 1 H), 7.20(m, 8 H), 7.33(m, 1 H), 7.45(d, 1 H), 7.54(s, 1 H), 7.83(d, 1 H), 8.10(s, 1 H), 8.27(s, 1 H), 10.75(s, 1 H); LRMS APCI m/z 638/640 [M + H]$^+$ | 39% |
| | A = (CH$_3$—S—CH$_2$)C(CH$_3$)$_2$ | |
| 59 | X = 3-(2-hydroxyethoxy), R$^3$ = 2-(hydroxyphenyl)<br>$^1$HNMR(400 MHz, DMSO-$d_6$) δ: 1.28(s, 6 H), 1.96(s, 3 H), 2.76(s, 2 H), 3.70(m, 2 H), 4.00(t, 2 H), 4.37(d, 2 H), 4.88(brs, 1 H), 6.28(s, 1 H), 6.94(d, 1 H), 7.02(m, 5 H), 7.19(m, 3 H), 7.27(m, 2 H), 7.37(m, 1 H), 7.43(m, 1 H), 7.54(d, 1 H), 7.84(d, 1 H), 8.06(s, 1 H), 8.37(s, 1 H), 10.47 (brs, 1 H); LRMS ESI m/z 696 [M + H]$^+$ | 63% |
| 60 | X = H, R$^3$ = 2-(hydroxyphenyl)<br>$^1$HNMR(400 MHz, DMSO-$d_6$) δ: 1.39(s, 6 H), 2.00(s, 3 H), 2.83(s, 2 H), 4.56(d, 2 H), 6.35(s, 1 H), 6.85(brm, 1 H), 6.92(m, 1 H), 7.00(d, 1 H), 7.12-7.52(m, 14 H), 7.74 (brm, 1 H); LRMS ESI m/z 636 [M + H]$^+$ | 47% |
| 61 | X = 4-CH$_3$, R$^3$ = 2-(hydroxyphenyl)<br>$^1$HNMR(400 MHz, DMSO-$d_6$) δ: 1.39(s, 6 H), 2.00(s, 3 H), 2.18(s, 3 H), 2.84(s, 2 H), 4.56(d, 2 H), 6.35(s, 1 H), | 49% |

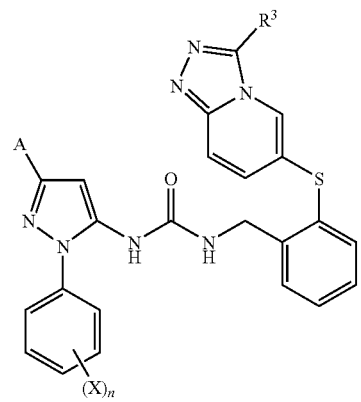

-continued

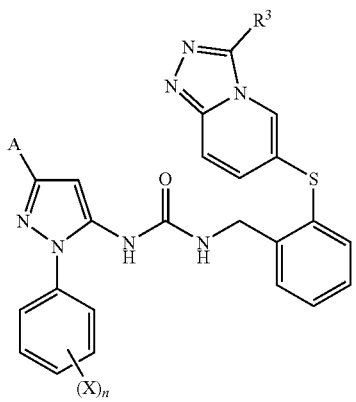

| No. | Data | Yield |
|---|---|---|
| | 6.87(brm, 1 H), 6.93(m, 1 H), 7.01-7.05(m, 3 H), 7.15(d, 1 H), 7.20-7.52(m, 10 H), 7.72(brm, 1 H); LRMS ESI m/z 650 [M + H]⁺ | |
| 62 | X = 4-F; R³ = 2-(hydroxyphenyl)<br>¹HNMR(400 MHz, CD₃OD) δ: 1.37(s, 6 H), 1.99(s, 3 H), 2.82(s, 2 H), 4.49(s, 2 H), 6.31(s, 1 H), 7.01(m, 2 H), 7.15-7.49(m, 10 H), 7.55(d, 1 H), 7.71(d, 1 H), 7.82(s, 1 H); LRMS APCI m/z 654 [M + H]⁺ | 32% |
| 63 | X = 3-F; R³ = 2-(hydroxyphenyl)<br>¹HNMR(400 MHz, CD₃OD) δ: 1.38(s, 6 H), 1.99(s, 3 H), 2.83(s, 2 H), 4.50(s, 2 H), 6.31(s, 1 H), 6.98(d, 1 H), 7.03 (m, 1 H), 7.14(m, 1 H), 7.23-7.33(m, 6 H), 7.37(d, 1 H), 7.41-7.50(m, 2 H), 7.55(d, 1 H), 7.71(d, 1 H), 7.80(s, 1 H); LRMS APCI m/z 654 [M + H]⁺ | 34% |
| 64 | X = 3-F, 4-F; R³ = 2-(hydroxyphenyl)<br>¹HNMR(400 MHz, CDCl₃) δ: 1.38(s, 6 H), 1.99(s, 3 H), 2.79(s, 2 H), 4.50(s, 2 H), 6.22(s, 1 H), 6.97(m, 2 H), 7.15-7.28(m, 6 H), 7.30-7.41(m, 5 H), 7.45(d, 1 H), 7.55(m, 1 H), 7.78(m, 1 H); LRMS APCO m/z 672 [M + H]⁺ | 19% |
| 65 | X = 3-OH; R³ = CH(CH₃)₂<br>¹HNMR(400 MHz, DMSO-d₆) δ: 1.28(s, 6 H), 1.34(d, 6 H), 1.96(s, 3 H), 2.76(s, 2 H), 3.56(m, 1 H), 4.40(d, 2 H), 6.26(s, 1 H), 6.77(d, 1 H), 6.87(m, 2 H), 7.04(m, 1 H), 7.11(d, 1 H), 7.24(m, 2 H), 7.30(m, 3 H), 7.70(d, 1 H), 8.32(s, 1 H), 8.60(s, 1 H), 9.76(s, 1 H); LRMS APCI m/z 602 [M + H]⁺ | 53% |
| 66 | X = 4-OH; R³ = CH(CH₃)₂<br>¹HNMR(400 MHz, DMSO-d₆) δ: 1.27(s, 6 H), 1.34(d, 6 H), 1.95(s, 3 H), 2.74(s, 2 H), 3.55(m, 1 H), 4.39(d, 2 H), 6.23(s, 1 H), 6.84(d, 2 H), 7.00(m, 1 H), 7.11(d, 1 H), 7.18 (d, 2 H), 7.24(m, 2 H), 7.28(m, 2 H), 7.69(d, 1 H), 8.15(s, 1 H), 8.59(s, 1 H), 9.73(s, 1 H); LRMS APCI m/z 602 [M + H]⁺ | 58% |
| | A = (CH₃—S)C(CH₃)₂ | |
| 67 | X = 3-CF₃; R³ = 2-(hydroxyphenyl)<br>¹HNMR(400 MHz, CDCl₃) δ: 1.65(s, 6 H), 1.95(s, 3 H), 4.56(d, 2 H), 6.40(d, 1 H), 6.90-7.00(m, 2 H), 7.10(brs, 1 H), 7.20-7.45(m, 8 H), 7.55(m, 2 H), 7.70(d, 1 H), 7.80 (brs, 1 H), 7.90(s, 1 H), 8.10(brs, 1 H); LRMS APCI m/z 780 [M + H]⁺ | 57% |
| 68 | X = 4-OH; R³ = 2-(hydroxyphenyl)<br>¹HNMR(400 MHz, DMSO-d₆) δ: 1.55(s, 6 H), 1.87(s, 3 H), 4.37(d, 2 H), 6.30(s, 1 H), 6.86(d, 2 H), 7.00-7.10(m, 3 H), 7.20-7.27(m, 7 H), 7.41(m, 1 H), 7.55(d, 1 H), 7.82 (d, 1 H), 8.09(s, 1 H), 8.20(s, 1 H), 9.80(brs, 1 H), 10.42 (brs, 1 H); LRMS APCI m/z 780 [M + H]⁺ | 66% |
| 69 | X = 3-Br; R³ = 2-(hydroxyphenyl)<br>¹HNMR(400 MHz, DMSO-d₆) δ: 1.58(s, 6 H), 1.88(s, 3 H), 4.35(d, 2 H), 6.35(s, 1 H), 7.00-7.07(m, 3 H), 7.19-7.26(m, 5 H), 7.40-7.46(m, 2 H), 7.50-7.60(m, 3 H), 7.69 (s, 1 H), 7.83(d, 1 H), 8.06(s, 1 H), 8.45(s, 1 H), 10.42(s, 1 H); LRMS ESI m/z 702 [M + H]⁺ | 42% |

ᵃcrude compounds were triturated with diethyl ether rather than re-crystallisation from ethyl acetate.

Example 48: Crude compound was further purified by column chromatography on silica gel, eluting with ethyl acetate:methanol, 100:0 to 95:5, followed by trituration of the residue with diethyl ether.

Example 66: Crude compound was re-crystallised from ethyl acetate/methanol

Example 70

N-(3-tert-Butyl-1-pyridin-3-yl-1H-pyrazol-5-yl)-N'-(2-{[3-(2-hydroxyphenyl)[1,2,4]triazolo[4,3-a]pyridin-6-yl]thio}benzyl)urea

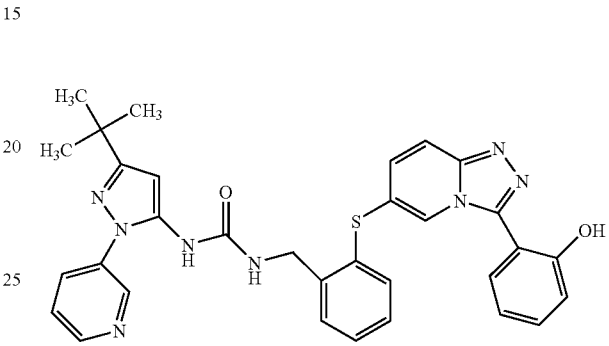

The title compound was prepared from the product of preparation 167, using the same method as that described for example 46, in 75% yield.

¹HNMR (400 MHz, CD₃OD) δ: 1.32 (s, 9H), 4.48 (s, 2H), 6.30 (s, 1H), 7.01 (m, 2H), 7.24-7.37 (m, 5H), 7.44 (m, 1H), 7.54 (m, 2H), 7.71 (d, 1H), 7.84 (s, 1H), 7.97 (d, 1H), 8.52 (d, 1H), 8.73 (s, 1H); LRMS APCI m/z 591 [M+H]⁺

Example 71

N-(3-tert-Butyl-1-pyridin-2-yl-1H-pyrazol-5-yl)-N'-(2-{[3-(2-hydroxyphenyl)[1,2,4]triazolo[4,3-a]pyridin-6-yl]thio}benzyl)urea

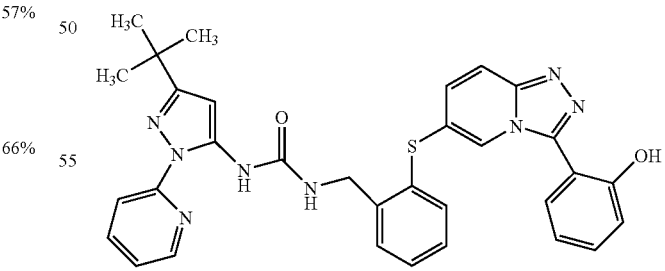

The title compound was prepared from the product of preparation 168, using the same method as that described for example 46, as a brown solid in 18% yield.

¹HNMR (400 MHz, DMSO-d₆) δ: 1.25 (s, 9H), 4.46 (s, 2H), 6.49 (s, 1H), 7.00 (m, 1H), 7.23-7.30 (m, 5H), 7.40-7.45 (m, 2H), 7.54 (d, 1H), 7.83-7.86 (m, 2H), 7.94-8.00 (m, 1H), 8.05 (m, 1H), 8.11 (s, 1H), 8.35 (m, 1H), 10.45 (s, 1H), 10.99 (s, 1H); LRMS APCI m/z 591 [M+H]+

Example 72

N-[3-tert-Butyl-1-(4-methylphenyl)-1H-pyrazol-5-yl]-N'-(2-{[3-(2-hydroxyphenyl)[1,2,4]triazolo[4,3-a]pyridin-6-yl]thio}benzyl)urea

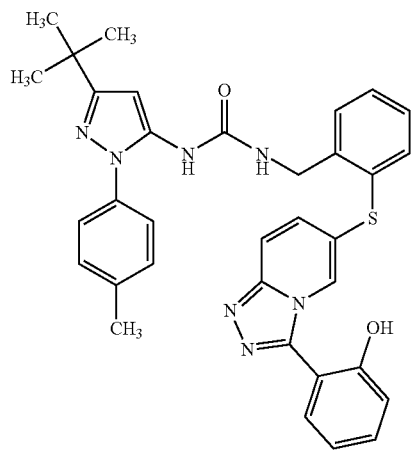

Boron tribromide (1M in dichloromethane, 5.05 mL, 5.05 mmol) was added dropwise to a solution of the product of preparation 124 (0.18 g, 0.25 mmol) in dichloromethane (2 mL) and the mixture was stirred for 18 hours at room temperature. The reaction mixture was then diluted with water (1.5 mL) and stirring continued for a further 10 minutes before 1,2-diaminoethane (1.5 mL) was added. The mixture was then stirred vigorously and acidified to pH1 with 6M hydrochloric acid. The aqueous layer was separated and re-extracted with dichloromethane (5 mL) and the combined organic solution was dried over magnesium sulfate and concentrated in vacuo. Re-crystallisation of the residue from dichloromethane:methanol, 50:50, afforded the title compound as a white solid in 36% yield.

1HNMR (300 MHz, DMSO-d6) δ: 1.29 (s, 9H), 2.34 (s, 3H), 4.39 (d, 2H), 6.25 (s, 1H), 7.02-7.59 (m, 14H), 7.81-7.91 (m, 1H), 8.08 (s, 1H), 8.28 (s, 1H), 10.53 (s, 1H); LCMS m/z 604.6 [M+H]+

Examples 73 to 79

The following compounds, of the general formula shown below were prepared by a method similar to that described for example 72, using the appropriate starting material and 4-6 equivalents of boron tribromide.

| No. | Data | Yield |
|---|---|---|
| | A = C(CH3)3 | |
| 73 | X = 3-Cl, 4-OH; R3 = HC(CH3)2<br>1HNMR(400 MHz, CDCl3) δ: 1.23(s, 9 H), 1.35(d, 6 H), 3.56(m, 1 H), 4.38(d, 2 H), 6.19(s, 1 H), 6.96-7.04(m, 2 H), 7.09(dd, 1 H), 7.17-7.30(m, 5 H), 7.39(d, 1 H), 7.68 (d, 1 H), 8.22(s, 1 H), 8.58(s, 1 H); LRMS API-ES 590/592 [M + H]+ | 59% |
| 74 | X = 3-CH2CH3,4-OH; R3 = HC(CH3)2<br>1HNMR(300 MHz, DMSO-d6) δ: 1.14(t, 3 H), 1.24(s, 9 H), 1.35(s, 6 H), 2.56(q, 2 H), 3.57(m, 1 H), 4.40(d, 2 H), 6.19 (s, 1 H), 6.86(d, 1 H), 7.00-7.14(m, 4 H), 7.22-7.30(m, 4 H), 7.68(d, 1 H), 8.13(s, 1 H), 8.59(s, 1 H), 9.63(s, 1 H); LCMS m/z 584 [M + H]+ | 90% |
| 75 | X = 3-OH, 4-CH2CH3; R3 = HC(CH3)2<br>1HNMR(300 MHz, DMSO-d6) δ: 1.15(t, 3 H), 1.24(s, 9 H), 1.35(s, 6 H), 2.56(q, 2 H), 3.56(m, 1 H), 4.41(d, 2 H), 6.22 (s, 1 H), 6.79(dd, 1 H), 6.89(d, 1 H), 7.03-7.15(m, 3 H), 7.19-7.31(m, 3 H), 7.69(d, 1 H), 8.27(s, 1 H), 8.59(s, 1 H), 9.65(s, 1 H); LCMS m/z 584 [M + H]+ | 33% |
| 76 | X = 3-OH, 4-Cl; R3 = HC(CH3)2<br>1HNMR(300 MHz, DMSO-d6) δ: 1.24(s, 9 H), 1.35(d, 6 H), 3.56(m, 1 H), 4.40(d, 2 H), 6.23(s, 1 H), 6.88(d, 1 H), 6.91(m, 1 H), 7.09(m, 2 H), 7.22-7.37(m, 4 H), 7.40-7.67(m, 1 H), 7.70(d, 1 H), 8.31(s, 1 H), 8.57(s, 1 H), 10.52(s, 1 H); LCMS m/z 590/592 [M + H]+ | 84% |
| 77 | X = 3-F, 4-F; R3 = 2-chloro-4-hydroxyphenyl<br>1HNMR(300 MHz, CDCl3) δ: 1.24(s, 9 H), 4.35(d, 2 H), 6.23(s, 1 H), 6.89-7.01(m, 3 H), 7.17-7.51(m, 6 H), 7.54-7.62(m, 3 H), 7.84(m, 1 H), 7.97(s, 1 H), 8.34(s, 1 H); LCMS m/z 660.6 [M + H]+ | 27% |
| 78 | X = 3-F, 4-F; R3 = 2-chloro-5-hydroxyphenyl<br>1HNMR(300 MHz, CDCl3) δ: 1.24(s, 9 H), 4.35(d, 2 H), 6.23(s, 1 H), 6.89-7.00(m, 3 H), 7.17-7.45(m, 6 H), 7.48-7.62(m, 3 H), 7.81(m, 1 H), 7.97(s, 1 H), 8.34(s, 1 H); LCMS m/z 660.6 [M + H]+ | 72% |
| 79 | X = 3-F, 4-F; R3 = 2-hydroxyphenyl<br>1HNMR(300 MHz, CD3OD) δ: 1.30(s, 9 H), 4.48(d, 2 H), 6.24(s, 1 H), 6.97(m, 1 H), 7.31(m, 6 H), 7.34(s, 1 H), 7.40 (m, 2 H), 7.52(dd, 1 H), 7.70(d, 1 H), 7.80(s, 1 H); LCMS m/z 624 [M + H]+ | 26% |

Example 73: The crude compound was further purified by re-crystallisation from dichloromethane/methanol: diethyl ether Example 74: The crude compound was purified by column chromatography on silica gel, eluting with dichloromethane: methanol, 98:2 to 92:8

Example 75: The crude compound was re-crystallised from dichloromethane/methanol:diethyl ether Example 78: The crude compound was purified by column chromatography on silica gel, eluting with dichloromethane: methanol, 97:3 to 94:6, followed by trituration with dichloromethane/methanol:diethyl ether (×3)

Example 79: The crude compound was purified by column chromatography on silica gel, eluting with dichloromethane:methanol, 100:0 to 95:5, followed by trituration with dichloromethane

Example 80

N-{3-tert-Butyl-1-[3-(2-hydroxyethoxy)phenyl]-1H-pyrazol-5-yl}-N'-(2-{[3-(2-hydroxyphenyl)[1,2,4]triazolo[4,3-a]pyridin-6-yl]thio}benzyl)urea

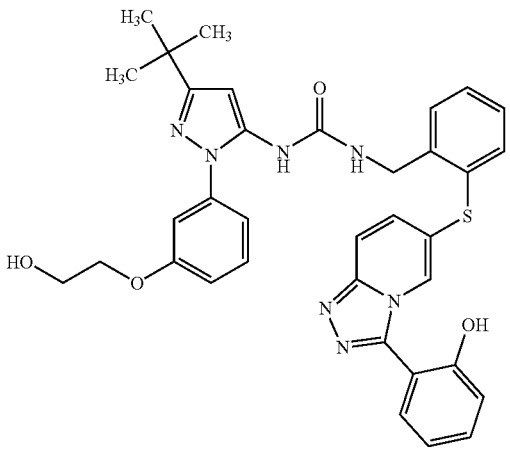

Boron tribromide (1M in dichloromethane, 1.6 mL, 1.6 mmol) was added dropwise to a solution of the product of preparation 122 (270 mg, 0.33 mmol) in dichloromethane (10 mL), cooled to −78° C. and the mixture was stirred for 90 minutes at this temperature. The reaction mixture was stirred for a further 30 minutes, allowing the temperature to rise to 25° C., and was then quenched with methanol (10 mL) and 0.88 ammonia (3 mL). The mixture was acidified with 2M hydrochloric acid and extracted with dichloromethane (3×50 mL). The combined organic solution was dried over magnesium sulfate, concentrated in vacuo and the residue was purified by column chromatography on silica gel, eluting with dichloromethane:methanol, 100:0 to 90:10. The appropriate fractions were evaporated under reduced pressure and the residue was re-crystallised from ethyl acetate/methanol to afford the title compound as a solid in 56% yield, 120 mg.

$^1$HNMR (400 MHz, DMSO-$d_6$) δ: 1.24 (s, 9H), 3.70 (m, 2H), 4.00 (t, 2H), 4.37 (d, 2H), 4.86 (m, 1H), 6.25 (s, 1H), 6.94 (dd, 1H), 7.03 (m, 5H), 7.19 (m, 3H), 7.26 (d, 2H), 7.36 (t, 1H), 7.54 (d, 1H), 7.83 (d, 1H), 8.06 (s, 1H), 8.32 (s, 1H), 10.45 (s, 1H); LRMS APCI m/z 650 [M+H]$^+$

Example 81

N-[3-tert-Butyl-1-(3-hydroxyphenyl)-1H-pyrazol-5-yl]-N'-[2-({3-[2-(2-hydroxyethoxy)phenyl][1,2,4]triazolo[4,3-a]pyridin-6-yl}thio)benzyl]urea

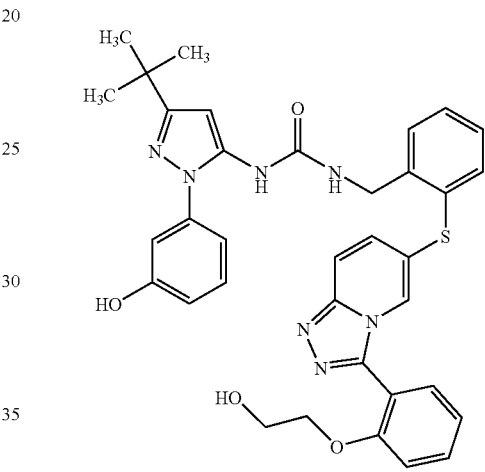

Boron tribromide (1M in dichloromethane, 1.3 mL, 1.3 mmol) was added dropwise to a solution of the product of preparation 174 (214 mg, 0.26 mmol) in dichloromethane (10 mL), at −78° C., and the mixture was stirred for 5 minutes at this temperature. The reaction mixture was then stirred for a further 5 minutes allowing the temperature to warm to 0° C. The mixture was re-cooled to −78° C., quenched with methanol (5 mL) and the temperature was allowed to rise to 25° C. The reaction mixture was then diluted with water and extracted with dichloromethane (3×40 mL). The combined organic solution was dried over magnesium sulfate, concentrated in vacuo and the residue was purified by column chromatography on silica gel, eluting with dichloromethane:methanol:0.88 ammonia, 100:0:0 to 93:7:1. The appropriate fractions were evaporated under reduced pressure and the residue was re-crystallised from ethyl acetate/methanol to afford the title compound as a solid in 47% yield, 79 mg.

$^1$HNMR (400 MHz, DMSO-$d_6$) δ: 1.23 (s, 9H), 3.52 (m, 2H), 4.06 (t, 2H), 4.36 (d, 2H), 4.72 (t, 1H), 6.22 (s, 1H), 6.76 (d, 1H), 6.88 (m, 2H), 7.01 (t, 1H), 7.14 (t, 1H), 7.17-7.28 (m,

7H), 7.58 (m, 2H), 7.82 (d, 1H), 8.12 (s, 1H), 8.28 (s, 1H), 9.73 (s, 1H); LRMS APCI m/z 650 [M+H]⁺

Example 82

N-{1-(4-Ethylphenyl)-3-[1-methyl-1-(methylthio) ethyl]-1H-pyrazol-5-yl}-N'-(2-{[3-(2-hydroxyphenyl)[1,2,4]triazolo[4,3-a]pyridin-6-yl]thio}benzyl) urea

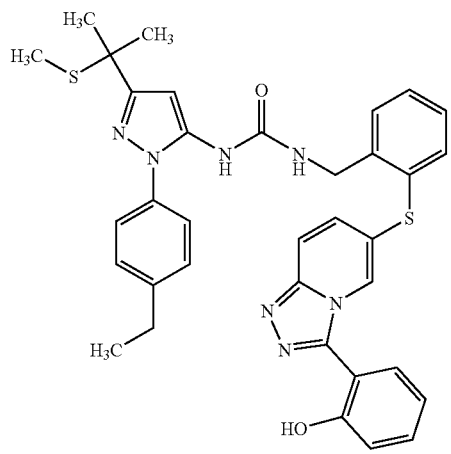

The title compound was prepared from the product of preparation 157, using the same method as that described for example 81, as a solid in 60% yield.

¹HNMR (400 MHz, CDCl₃) δ: 1.19 (t, 3H), 1.57 (s, 6H), 1.88 (s, 3H), 2.64 (q, 2H), 4.37 (d, 2H), 6.34 (s, 1H), 7.03 (m, 3H), 7.18-7.37 (m, 9H), 7.43 (m, 1H), 7.54 (d, 1H), 8.06 (s, 1H), 8.32 (s, 1H), 10.46 (s, 1H); LRMS APCI m/z 650 [M+H]⁺

Example 83

N-{1-(3-Ethylphenyl)-3-[1-methyl-1-(methylthio) ethyl]-1H-pyrazol-5-yl}-N'-(2-{[3-(2-hydroxyphenyl)[1,2,4]triazolo[4,3-a]pyridin-6-yl]thio}benzyl) urea

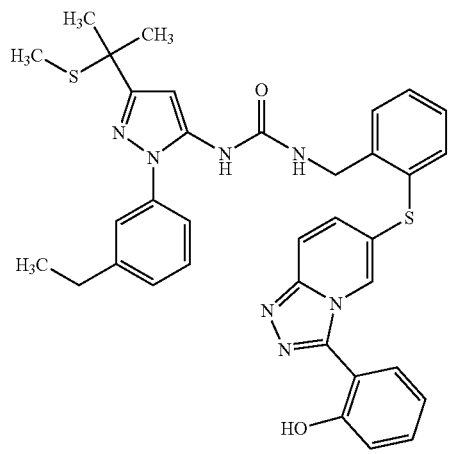

The title compound was prepared from the product of preparation 158, using the same method as that described for example 81. The crude compound was triturated with ethyl acetate/dichloromethane to afford the desired product as a solid in 52% yield.

¹HNMR (400 MHz, CDCl₃) δ: 1.17 (t, 3H), 1.57 (s, 6H), 1.89 (s, 3H), 2.64 (q, 2H), 4.37 (d, 2H), 6.35 (s, 1H), 7.01 (m, 3H), 7.05 (d, 1H), 7.19-7.29 (m, 8H), 7.39 (m, 1H), 7.44 (d, 1H), 7.54 (d, 1H), 8.06 (s, 1H), 8.33 (s, 1H), 10.45 (s, 1H); LRMS APCI m/z 650 [M+H]⁺

Example 84

N-(2-{[3-(2-Hydroxyphenyl)[1,2,4]triazolo[4,3-a] pyridin-6-yl]thio}benzyl)-N'-{1-(4-methoxy-3-methylphenyl)-3-[1-methyl-1-(methylthio)ethyl]-1H-pyrazol-5-yl}urea

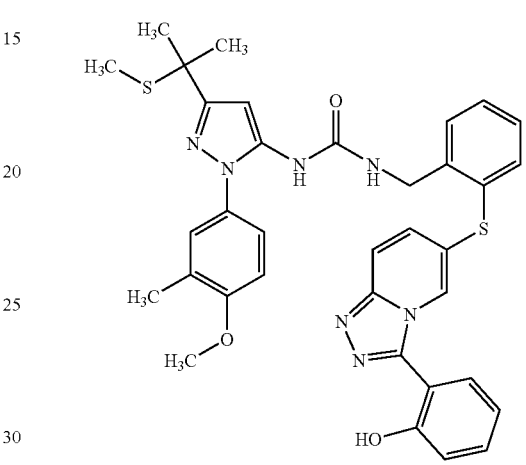

The title compound was prepared from the product of preparation 159, using the same method as that described for example 81. The crude compound was triturated with ethyl acetate to afford the desired product as a solid in 43% yield.

¹HNMR (400 MHz, CDCl₃) δ: 1.56 (s, 6H), 1.88 (s, 3H), 2.17 (s, 3H), 3.81 (s, 3H), 4.36 (d, 2H), 6.32 (s, 1H), 6.99-7.06 (m, 4H), 7.18-7.26 (m, 7H), 7.43 (m, 1H), 7.54 (d, 1H), 7.83 (d, 1H), 8.06 (s, 1H), 8.21 (s, 1H), 10.45 (s, 1H); LRMS APCI m/z 666 [M+H]⁺

Example 85

N-{1-(3-Chlorophenyl)-3-[1-methyl-1-(methylthio) ethyl]-1H-pyrazol-5-yl}-N'-(2-{[3-(2-hydroxyphenyl)[1,2,4]triazolo[4,3-a]pyridin-6-yl]thio}benzyl) urea

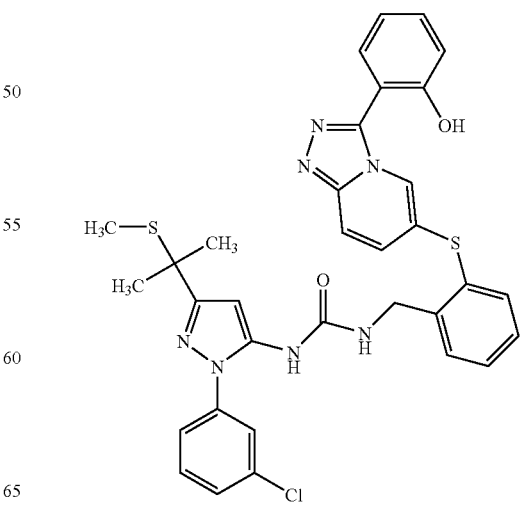

The title compound was prepared from the product of preparation 154, using the same method as that described for example 81. The crude compound was triturated with ethyl acetate to afford the desired product as a solid in 44% yield, $^1$HNMR (400 MHz, CDCl$_3$) δ: 1.55 (s, 6H), 1.88 (s, 3H), 4.35 (d, 2H), 6.35 (s, 1H), 6.87-7.32 (m, 8H), 7.34-7.62 (m, 6H), 7.82 (d, 1H), 8.05 (s, 1H), 8.50 (s, 1H), 10.50 (s, 1H); LRMS APCI m/z 608/610 [M+H]$^+$ Example 86

N-(2-{[3-(5-Chloro-2-hydroxyphenyl)[1,2,4]triazolo[4,3-a]pyridin-6-yl]thio}benzyl)-N'-[3-[1-methyl-1-(methylthio)ethyl]-1-(3-methylphenyl)-1H-pyrazol-5-yl]urea

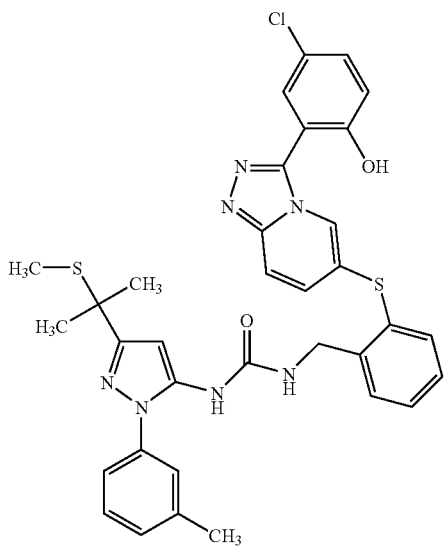

The title compound was prepared from the product of preparation 165, using a similar method to that described for example 81. The crude compound was triturated with methanol to afford the desired product as a solid in 26% yield.

$^1$HNMR (400 MHz, DMSO-d$_6$) δ: 1.56 (s, 6H), 1.87 (s, 3H), 2.34 (s, 3H), 4.36 (d, 2H), 6.35 (s, 1H), 7.02 (m, 1H), 7.05 (d, 1H), 7.22 (m, 8H), 7.36 (m, 1H), 7.47 (m, 1H), 7.55 (s, 1H), 7.83 (d, 1H), 8.10 (s, 1H), 8.31 (s, 1H), 10.75 (s, 1H); LRMS APCI m/z 608/610 [M+H]$^+$

Example 87

N-(2-{[3-(5-Chloro-2-hydroxyphenyl)[1,2,4]triazolo[4,3-a]pyridin-6-yl]thio}benzyl)-N'-[3-[1-methyl-1-(methylthio)ethyl]-1-(4-methylphenyl)-1H-pyrazol-5-yl]urea

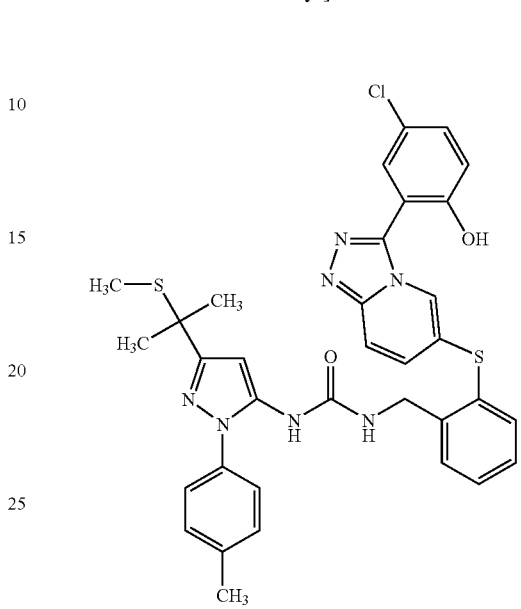

The title compound was prepared from the product of preparation 166, using a similar method to that described for example 81. The crude compound was triturated with ethyl acetate/methanol to afford the desired product as a solid in 24% yield.

$^1$HNMR (400 MHz, DMSO-d$_6$) δ: 1.56 (s, 6H), 1.87 (s, 3H), 2.34 (s, 3H), 4.36 (d, 2H), 6.33 (s, 1H), 7.01 (m, 1H), 7.05 (d, 1H), 7.25 (m, 9H), 7.47 (m, 1H), 7.54 (s, 1H), 7.83 (d, 1H), 8.11 (s, 1H), 8.27 (s, 1H), 10.75 (s, 1H); LRMS APCI m/z 608/610 [M+H]$^+$

Example 88

N-(2-{[3-(5-Chloro-2-hydroxyphenyl)[1,2,4]triazolo[4,3-a]pyridin-6-yl]thio}benzyl)-N'-[3-[1,1-dimethyl-2-(methylthio)ethyl]-1-(4-methylphenyl)-1H-pyrazol-5-yl]urea

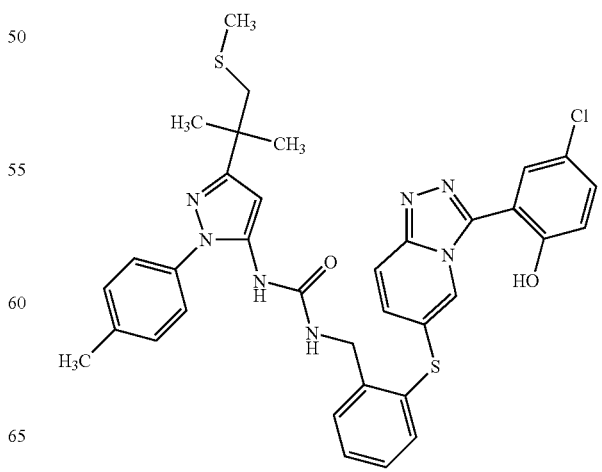

The title compound was prepared from the product of preparation 149, using a similar method to that described for example 81. The crude compound was triturated with ethyl acetate/methanol to afford the desired product as a solid in 52% yield.

¹HNMR (400 MHz, DMSO-d₆) δ: 1.26 (s, 6H), 1.95 (s, 3H), 2.33 (s, 3H), 2.77 (s, 2H), 4.36 (d, 2H), 6.27 (s, 1H), 6.98 (m, 1H), 7.06 (d, 1H), 7.16-7.35 (m, 9H), 7.47 (d, 1H), 7.55 (s, 1H), 7.84 (d, 1H), 8.12 (s, 1H), 8.27 (s, 1H), 10.78 (s, 1H); LRMS APCI m/z 684/686 [M+H]⁺

Example 89

N-(2-{[3-(2-Ethylphenyl)[1,2,4]triazolo[4,3-a]pyridin-6-yl]thio}benzyl)-N'-{1-(3-hydroxyphenyl)-3-[1-methyl-1-(methylthio)ethyl]-1H-pyrazol-5-yl}urea

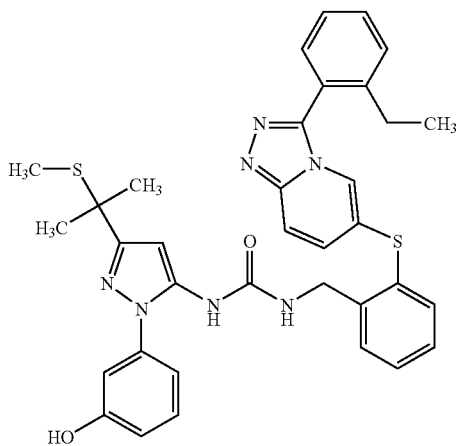

A solution of the product of preparation 228 (280 mg, 0.38 mmol) in dichloromethane (6 mL) was cooled to −78° C. Boron tribromide (1M in dichloromethane, 1.9 mL, 1.9 mmol) was added dropwise and the mixture was stirred for 20 minutes. The reaction mixture was then diluted with methanol (10 mL) and the temperature was allowed to rise to 25° C. The mixture was concentrated in vacuo and the residue was re-dissolved in dichloromethane and washed with 0.88 ammonia (2×10 mL). The organic solution was dried over magnesium sulfate, concentrated in vacuo and the residue was purified by column chromatography on silica gel, eluting with dichloromethane:methanol, 99.75:0.25 to 95:5, to afford the title compound in 59% yield, 146 mg.

¹HNMR (400 MHz, CDCl₃) δ: 0.96 (t, 3H), 1.59 (s, 6H), 1.88 (s, 3H), 2.38 (q, 2H), 4.43 (s, 2H), 6.42-6.45 (m, 2H), 6.76 (m, 2H), 6.85 (m, 1H), 6.95 (d, 1H), 7.10-7.37 (m, 8H), 7.37 (m, 1H), 7.45 (m, 1H), 7.54 (s, 1H), 8.28 (s, 1H); LRMS APCI m/z 650 [M+H]⁺

Example 90

N-{1-(4-Hydroxyphenyl)-3-[1-methyl-1-(methylthio)ethyl]-1H-pyrazol-5-yl}-N'-(2-{[3-(2-methylphenyl)[1,2,4]triazolo[4,3-a]pyridin-6-yl]thio}benzyl)urea

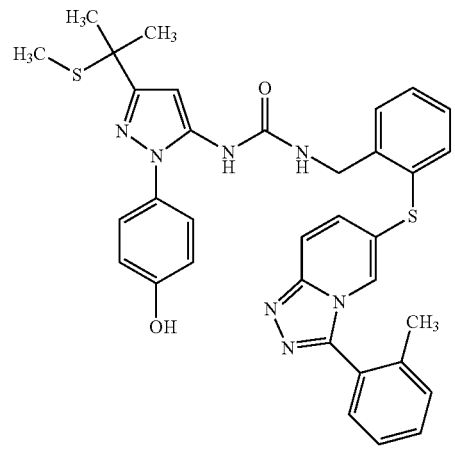

The title compound was prepared from the product of preparation 230, using a similar method to that described for example 89, as a solid in 10% yield.

¹HNMR (400 MHz, CD₃OD) δ: 1.61 (s, 6H), 1.90 (s, 3H), 2.17 (s, 3H), 4.45 (s, 2H), 6.36 (s, 1H), 6.87 (d, 2H), 7.19-7.52 (m, 11H), 7.66 (s, 1H), 7.73 (d, 1H); LRMS APCI m/z 636 [M+H]⁺

Example 91

N-{1-(3-Hydroxyphenyl)-3-[1-methyl-1-(methylthio)ethyl]-1H-pyrazol-5-yl}-N'-(2-{[3-(2-methylphenyl)[1,2,4]triazolo[4,3-a]pyridin-6-yl]thio}benzyl)urea

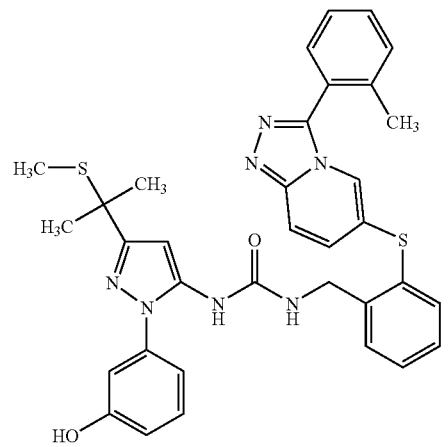

The title compound was prepared from the product of preparation 160, using a similar method to that described for example 89, as a solid in 66% yield.

¹HNMR (400 MHz, CDCl₃) δ: 162 (s, 6H), 1.91 (s, 3H), 2.15 (s, 3H), 4.47 (s, 2H), 6.44 (m, 1H), 6.48 (s, 1H), 6.76 (s, 1H), 6.82 (d, 1H), 6.93 (m, 2H), 7.04 (d, 1H), 7.18 (m, 1H), 7.24-7.45 (m, 9H), 7.58 (s, 1H), 7.98 (s, 1H); LRMS APCI m/z 636 [M+H]⁺

Example 92

N-{-(3,5-Dimethylphenyl)-3-[1-methyl-1-(methylthio)ethyl]-1H-pyrazol-5-yl}-N'-(2-{[3-(2-hydroxyphenyl)[1,2,4]triazolo[4,3-a]pyridin-6-yl]thio}benzyl)urea

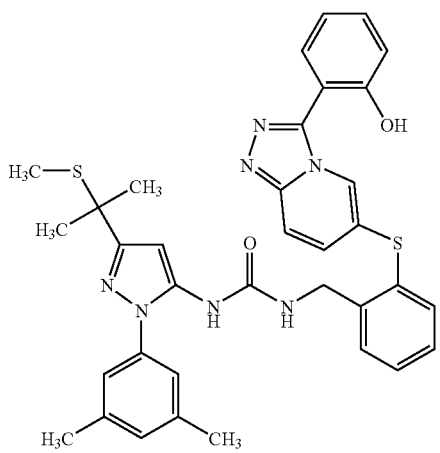

The title compound was prepared from the product of preparation 164, using a similar method to that described for example 89. The crude compound was triturated with ethyl acetate/methanol to afford the title compound as a solid in 59% yield.

¹HNMR (400 MHz, DMSO-d₆) δ: 1.37 (s, 6H), 1.89 (s, 3H), 2.30 (s, 6H), 4.37 (d, 2H), 6.44 (s, 1H), 7.02 (m, 6H), 7.10 (m, 5H), 7.42 (m, 1H), 7.54 (d, 1H), 7.81 (d, 1H), 8.05 (s, 1H), 8.30 (s, 1H), 10.45 (s, 1H); LRMS APCI m/z 650 [M+H]⁺

Example 93

N-[3-tert-Butyl-1-(3-hydroxyphenyl)-1H-pyrazol-5-yl]-N'-[2-({3-[2-(methylthio)phenyl][1,2,4]triazolo[4,3-a]pyridin-6-yl}thio)benzyl]urea

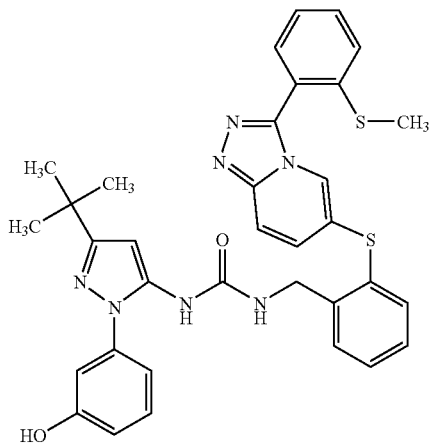

Boron tribromide (1M in dichloromethane, 0.74 mL, 0.74 mmol) was added dropwise to a solution of the product of preparation 229 (107 mg, 0.15 mmol) in dichloromethane (5 mL), at −78° C., and the mixture was stirred for 2 hours at this temperature. The reaction mixture was then quenched with methanolic ammonia (7M, 5 mL) and allowed to warm to room temperature. The mixture was diluted with water and extracted with ethyl acetate, and the organic solution was dried over magnesium sulfate and concentrated in vacuo. Purification of the residue by column chromatography on silica gel, eluting with ethyl acetate:methanol, 100:0 to 90:10, afforded the title compound as a pale yellow solid in 68% yield, 64 mg.

¹HNMR (400 MHz, DMSO-d₆) δ: 1.22 (s, 9H), 2.38 (s, 3H), 4.36 (d, 2H), 6.21 (s, 1H), 6.76 (d, 1H), 6.86 (d, 1H), 6.87 (s, 1H), 7.00 (m, 1H), 7.23-7.34 (m, 7H), 7.49-7.65 (m, 3H), 7.83 (s, 1H), 7.88 (d, 1H), 9.26 (s, 1H), 9.73 (s, 1H); LRMS APCI m/z 636 [M+H]⁺

Example 94

N-{1-(4-Fluorophenyl)-3-[1-methyl-1-(methylthio)ethyl]-1H-pyrazol-5-yl}-N'-(2-{[3-(2-hydroxyphenyl)[1,2,4]triazolo[4,3-a]pyridin-6-yl]thio}benzyl)urea

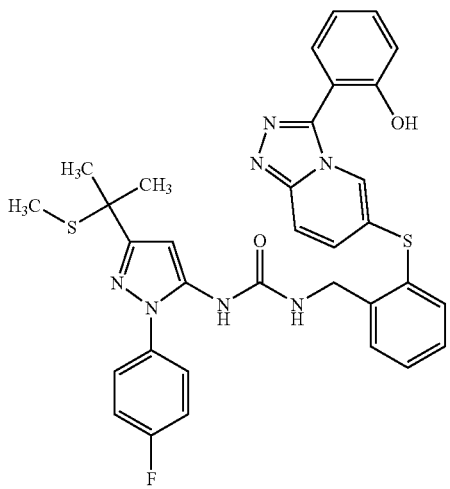

The title compound was prepared from the product of preparation 152, using the same method as that described for example 93, as a solid in 41% yield.

¹HNMR (400 MHz, DMSO-d₆) δ: 1.57 (s, 6H), 1.88 (s, 3H), 4.36 (d, 2H), 6.34 (s, 1H), 7.01 (m, 2H), 7.05 (d, 1H), 7.17-7.27 (m, 5H), 7.32 (m, 2H), 7.43 (m, 1H), 7.48-7.55 (m, 3H), 7.84 (d, 1H), 8.06 (s, 1H), 8.33 (s, 1H), 10.44 (s, 1H); LRMS APCI m/z 640 [M+H]⁺

Example 95

N-{1-(3,4-Difluorophenyl)-3-[1-methyl-1-(methylthio)ethyl]-1H-pyrazol-5-yl}-N'-(2-{[3-(2-hydroxyphenyl)[1,2,4]triazolo[4,3-a]pyridin-6-yl]thio}benzyl)urea

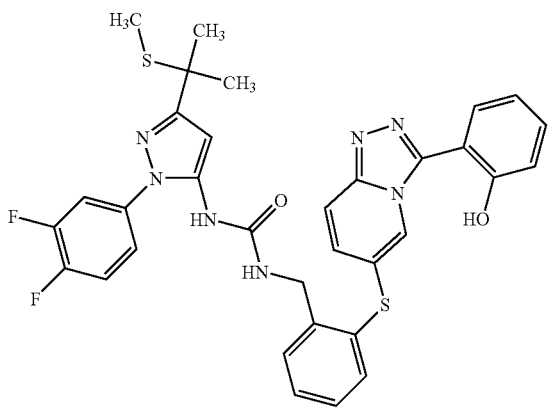

The title compound was prepared from the product of preparation 156, using the same method as that described for example 93. The crude compound was further purified by HPLC using a Phenomenex Luna C18 system, eluting with acetonitrile:water/trifluoroacetic acid (5.95:0.1):acetonitrile, 100:0 to 0:100, to afford the desired product in 3% yield.

$^1$HNMR (400 MHz, CDCl$_3$) δ: 1.65 (s, 6H), 1.94 (s, 3H), 4.52 (d, 2H), 6.40 (s, 1H), 6.80 (d, 1H), 6.91 (m, 1H), 7.00 (s, 1H), 7.12 (m, 1H), 7.19 (m, 1H), 7.25-7.42 (m, 9H), 7.61 (m, 2H), 8.71 (s, 1H)

Example 96

N-{1-(3-Fluorophenyl)-3-[1-methyl-1-(methylthio)ethyl]-1H-pyrazol-5-yl}-N'-(2-{[3-(2-hydroxyphenyl)[1,2,4]triazolo[4,3-a]pyridin-6-yl]thio}benzyl)urea

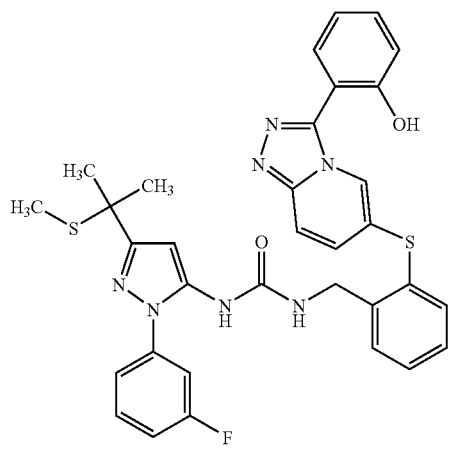

Boron tribromide (1M in dichloromethane, 0.85 mL, 0.85 mmol) was added dropwise to a solution of the product of preparation 153 (150 mg, 0.21 mmol) in dichloromethane (10 mL), cooled to −40° C., and the mixture was stirred for 20 minutes at this temperature. The reaction mixture was then quenched with methanol (5 mL) diluted with water (30 mL) and dichloromethane (30 mL) and allowed to warm to room temperature. The mixture was basified with 0.88 ammonia (5 mL) and extracted with dichloromethane (3×30 mL). The combined organic solution was dried over magnesium sulfate, concentrated in vacuo and the residue was purified by column chromatography on silica gel, eluting with dichloromethane:methanol, 100:0 to 95:5, to afford the title compound as a white solid in 45% yield, 61 mg.

$^1$HNMR (400 MHz, DMSO-d$_6$) δ: 1.58 (s, 6H), 1.89 (s, 3H), 4.36 (d, 2H), 6.37 (s, 1H), 7.00 (m, 1H), 7.04 (m, 2H), 7.18-7.27 (m, 6H), 7.36 (m, 2H), 7.43 (m, 1H), 7.53 (m, 2H), 7.83 (d, 1H), 8.06 (s, 1H), 8.44 (s, 1H), 10.44 (s, 1H); LRMS APCI m/z 640 [M+H]$^+$

Example 97

N-[3-tert-Butyl-1-(4-methoxyphenyl)-1H-pyrazol-5-yl]-N'-(2-{[3-(2-hydroxyphenyl)[1,2,4]triazolo[4,3-a]pyridin-6-yl]thio}benzyl)urea

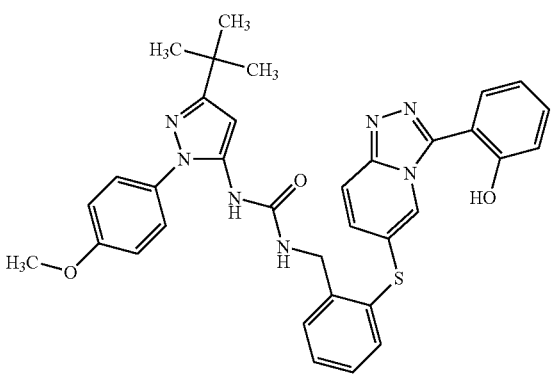

Boron tribromide (2M in dichloromethane, 0.63 mL, 1.26 mmol) was added dropwise to a solution of the product of preparation 138 (300 mg, 0.42 mmol) in dichloromethane (2.5 mL) cooled to −45° C., and the mixture was stirred for 45 minutes at this temperature. Further boron tribromide (2M in dichloromethane, 0.63 mL, 1.26 mmol) was then added and the mixture was stirred for 30 minutes at −45° C. The reaction mixture was then quenched with dimethylamine (40% in water, 2 mL) and allowed to warm to room temperature. The mixture was diluted with water (10 mL) and dichloromethane (10 mL) and the biphasic system was acidified with 4M hydrochloric acid. The aqueous layer was separated and extracted with dichloromethane (3×10 mL), and the combined organic solution was dried over sodium sulfate and concentrated in vacuo. The residue was purified by column chromatography on silica gel, eluting with dichloromethane:methanol, 100:0 to 90:10, followed by trituration with dichloromethane/diethyl ether, to afford the title compound as a white solid in 29% yield, 76.9 mg.

$^1$HNMR (300 MHz, DMSO-d$_6$) δ: 1.24 (s, 9H), 3.77 (s, 3H), 4.37 (d, 2H), 6.21 (s, 1H), 6.91-7.04 (m, 5H), 7.17-7.41

(m, 8H), 7.51 (dd, 1H), 7.81 (d, 1H), 7.92 (s, 1H), 8.03 (s, 1H), 10.60 (brs, 1H); LCMS APCI m/z 620 [M+H]+

Example 98

N-[3-tert-Butyl-1-(3-methoxyphenyl)-1H-pyrazol-5-yl]-N'-(2-{[3-(2-hydroxyphenyl)[1,2,4]triazolo[4,3-a]pyridin-6-yl]thio}benzyl)urea

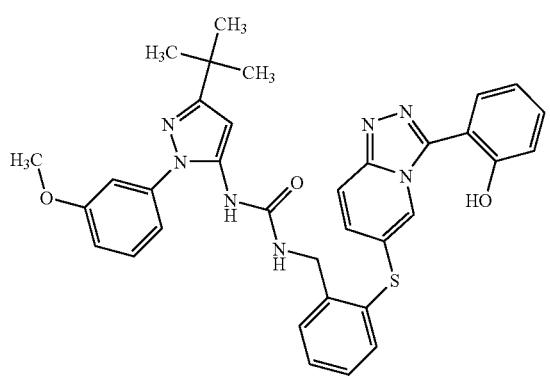

The title compound was prepared from the product of 139, using the same method as that described for example 97. The crude compound was further purified by reverse phase column chromatography on C18 silica gel, eluting with water: acetonitrile, 67:33 to 33:67, followed by trituration with dichloromethane/diethyl ether to afford the desired product in 11% yield.
$^1$HNMR (300 MHz, DMSO-$d_6$) δ: 1.25 (s, 9H), 3.76 (s, 3H), 4.37 (d, 2H), 6.24 (s, 1H), 6.90-7.06 (m, 6H), 7.18-7.25 (m, 5H), 7.32-7.45 (m, 2H), 7.53 (d, 1H), 7.82 (s, 1H), 8.04 (s, 1H), 8.33 (s, 1H), 10.40 (brs, 1H); LCMS APCI m/z 620 [M+H]+

Example 99

N-[3-(1,1-Dimethylpropyl)-1-(4-methylphenyl)-1H-pyrazol-5-yl]-N'-(2-{[3-(2-hydroxyphenyl)[1,2,4]triazolo[4,3-a]pyridin-6-yl]thio}benzyl)urea

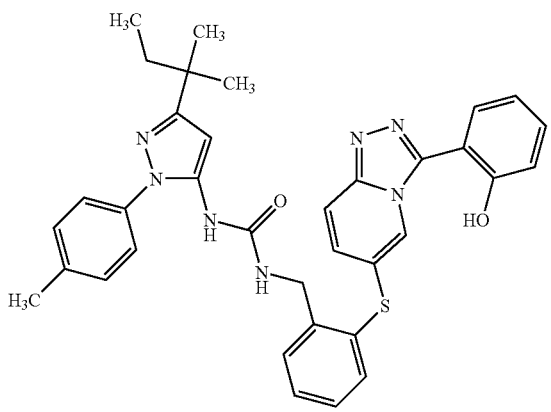

The product of preparation 141 (203 mg, 0.29 mmol) was suspended in hydrobromic acid (5.7M in glacial acetic acid, 4 mL, 22.8 mmol) and the mixture was stirred at room temperature for 18 hours. The reaction mixture was then diluted with saturated sodium hydrogen carbonate solution and extracted with dichloromethane. The organic solution was washed with brine, dried over magnesium sulfate and concentrated in vacuo. Trituration of the residue with diethyl ether afforded the title compound as a white solid in 81% yield, 144 mg.
$^1$HNMR (400 MHz, DMSO-$d_6$) δ: 0.73 (t, 3H), 1.17 (s, 6H), 1.54 (q, 2H), 2.32 (s, 3H), 4.36 (d, 2H), 6.19 (s, 1H), 6.98-7.06 (m, 2H), 7.15-7.33 (m, 10H), 7.45 (m, 1H), 7.55 (d, 1H), 7.85 (d, 1H), 8.06 (s, 1H), 8.24 (s, 1H), 10.47 (s, 1H); LRMS ESI m/z 618 [M+H]+

Example 100

N-{3-(1,1-Dimethylpropyl)-1-[3-(2-hydroxyethoxy)phenyl]-1H-pyrazol-5-yl}-N'-2-{[3-(2-hydroxyphenyl)[1,2,4]triazolo[4,3-a]pyridin-6-yl]thio}benzyl)urea

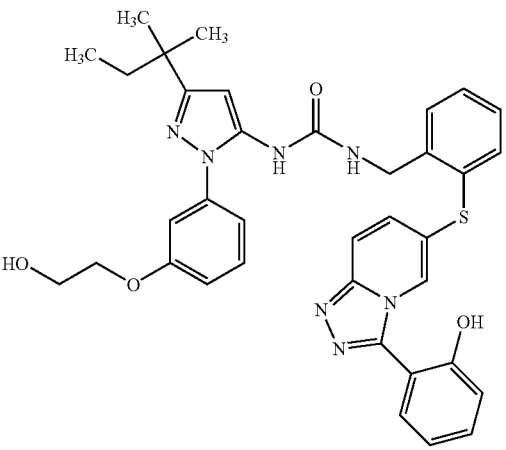

The title compound was prepared from the product of preparation 170, using a method similar to that described for example 99, as a solid in 21% yield.

$^1$HNMR (300 MHz, DMSO-$d_6$) δ: 0.76 (t, 3H), 1.20 (s, 6H), 1.56 (q, 2H), 3.70 (s, 2H), 4.01 (t, 2H), 4.37 (d, 2H), 4.86 (s, 1H), 6.21 (s, 1H), 6.94 (m, 1H), 7.05 (m, 5H), 7.23 (m, 5H), 7.38 (m, 2H), 7.53 (dd, 1H), 7.82 (d, 1H), 8.05 (s, 1H), 8.32 (s, 1H), 10.43 (s, 1H); LCMS m/z 665 [M+H]⁺

Example 101

N-[3-tert-Butyl-1-(3-fluorophenyl)-1H-pyrazol-5-yl]-N'-[2-({3-[2-(2-hydroxyethoxy)phenyl][1,2,4]triazolo[4,3-a]pyridin-6-yl}thio)benzyl]urea

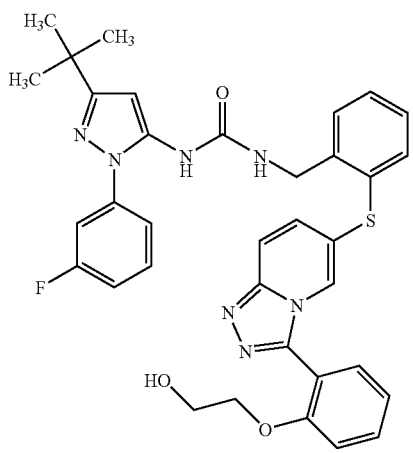

A mixture of the product of example 47 (100 mg, 0.17 mmol), 2-(2-bromoethoxy)tetrahydro-2H-pyran (30 μL, 0.20 mmol) and potassium carbonate (32 mg, 0.25 mmol) in N,N-dimethylformamide (3 mL) was heated at 60° C. for 18 hours. Further 2-(2-bromoethoxy)tetrahydro-2H-pyran (15 μL, 0.10 mmol) was added and the mixture was heated at 60° C. for 6 hours. The cooled reaction mixture was then diluted with ethyl acetate (20 mL), washed with water (10 mL) and brine (10 mL), dried over magnesium sulfate and concentrated in vacuo. The residue was dissolved in methanol (3 ml) para-toluenesulfonic acid (20 mg) was added and the mixture was stirred at room temperature for 48 hours. The reaction mixture was then diluted with ethyl acetate (20 mL), washed with water (3×10 mL), dried over magnesium sulfate and concentrated in vacuo. The residue was purified by column chromatography on silica gel, eluting with dichloromethane:methanol, 95:5 to 92:8. The residue was further purified by column chromatography on silica gel, eluting with ethyl acetate:methanol, 97.5:2.5 to 95:5, to afford the title compound as a solid in 23% yield, 24.5 mg.

¹HNMR (400 MHz, CDCl₃) δ: 1.24 (s, 9H), 3.70 (m, 2H), 4.01 (m, 2H), 4.37 (d, 2H), 6.25 (s, 1H), 6.68 (m, 1H), 6.92 (m, 2H), 7.00-7.07 (m, 5H), 7.15 (m, 1H), 7.20-7.39 (m, 4H), 7.53 (m, 2H), 7.71 (m, 1H), 7.79 (s, 1H)

Example 102

N-(2-{[3-(2-Ethylphenyl)[1,2,4]triazolo[4,3-a]pyridin-6-yl]thio}benzyl)-N'-{1-[3-(2-hydroxyethoxy)phenyl]-3-[1-methyl-1-(methylthio)ethyl]-1H-pyrazol-5-yl}urea

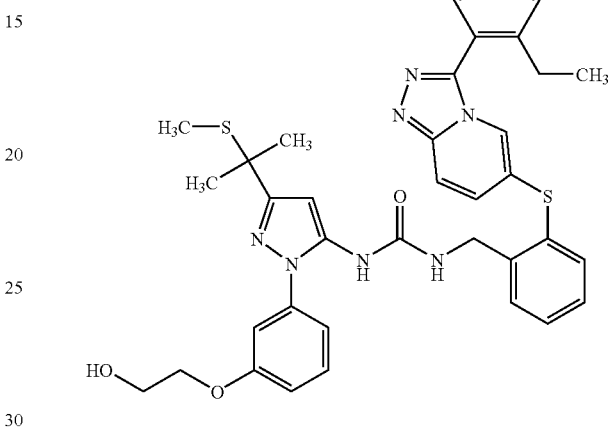

The title compound was prepared from the product of example 89, using the same method as that described for example 101, in 52% yield.

¹HNMR (400 MHz, CDCl₃) δ: 1.01 (t, 3H), 1.63 (s, 6H), 1.92 (s, 3H), 2.44 (q, 2H), 3.72 (m, 2H), 3.86 (m, 2H), 4.46 (d, 2H), 6.47 (s, 1H), 6.58 (d, 1H), 6.90-7.36 (m, 13H), 7.41 (d, 1H), 7.49 (d, 1H), 7.49 (t, 1H), 7.64 (s, 1H), 8.03 (s, 1H); LRMS APCI m/z 695 [M+H]⁺

Example 103

N-[2-({3-[2-(2-Hydroxyethoxy)phenyl][1,2,4]triazolo[4,3-a]pyridin-6-yl}thio)benzyl]-N'-[3-[1-methyl-1-(methylthio)ethyl]-1-(4-methylphenyl)-1H-pyrazol-5-yl]urea

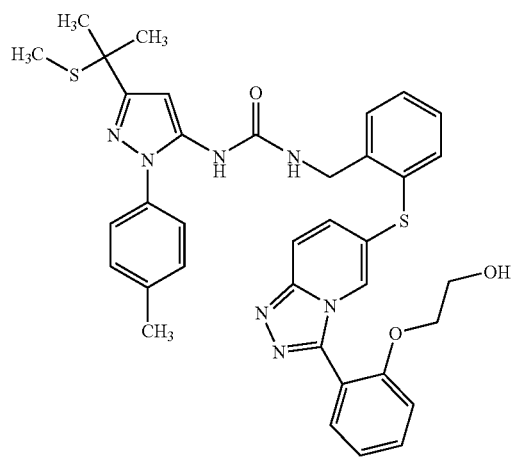

The title compound was prepared from the product of preparation 172, using a similar method to that described for example 101, in 34% yield.

¹HNMR (400 MHz, CDCl₃) δ: 1.57 (s, 6H), 1.89 (s, 3H), 2.34 (q, 2H), 3.52 (m, 2H), 4.06 (m, 2H), 4.36 (d, 2H), 4.70 (m, 1H), 6.33 (s, 1H), 6.99 (m, 1H), 7.10-7.34 (m, 11H), 7.58 (m, 2H), 7.81 (d, 1H), 8.10 (s, 1H), 8.25 (s, 1H); LRMS APCI m/z 681 [M+H]⁺

Example 104

N-{3-tert-Butyl-1-[3-(2-hydroxyethoxy)phenyl]-1H-pyrazol-5-yl}-N'-(2-{[3-(2-ethylphenyl)[1,2,4]triazolo[4,3-a]pyridin-6-yl]thio}benzyl)urea

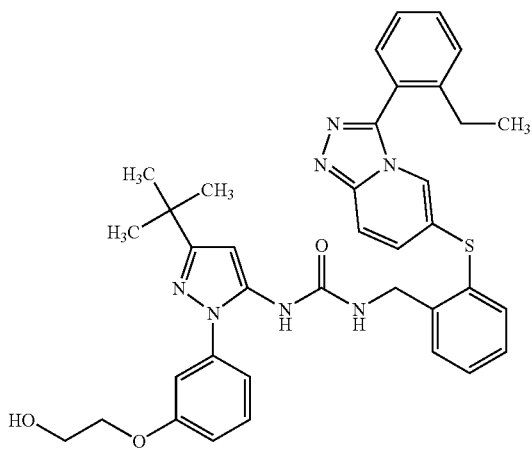

A solution of the product of preparation 204 (360 mg, 1 mmol) in dimethylsulfoxide (5 mL) was added to a solution of the product of preparation 116 (490 mg, 1 mmol) and the mixture was stirred at room temperature for 18 hours and at 50° C. for 3 hours. The reaction mixture was then cooled to room temperature, diluted with dichloromethane (10 mL) and washed with 1M hydrochloric acid (1 mL), water (10 mL), 1M sodium hydroxide (10 mL) and brine (10 mL). The organic solution was dried over magnesium sulfate and concentrated in vacuo. The residue was dissolved in methanol (5 mL), para-toluenesulfonic acid (100 mg) was added and the mixture was stirred at room temperature for 18 hours. The reaction mixture was then concentrated in vacuo and the residue was dissolved in dichloromethane (30 mL) and washed with water (2×10 mL). The organic solution was dried over magnesium sulfate, concentrated in vacuo and the residue was purified by column chromatography on silica gel, eluting with ethyl acetate:methanol, 95:5, to afford the title compound in 31% yield, 208.3 mg.

¹HNMR (400 MHz, CDCl₃) δ: 1.07 (t, 3H), 1.31 (s, 9H), 2.52 (q, 2H), 3.84 (t, 2H), 4.01 (t, 2H), 4.53 (d, 2H), 6.13 (brs, 1H), 6.33 (s, 1H), 6.75 (d, 1H), 7.01 (m, 3H), 7.21 (m, 3H), 7.26 (m, 3H), 7.36 (m, 3H), 7.45 (d, 1H), 7.52 (m, 1H), 7.57 (d, 1H), 7.71 (s, 1H); LRMS APCI m/z 662 [M+H]⁺

Example 105

N-{3-tert-Butyl-1-[3-(2-hydroxyethoxy)phenyl]-1H-pyrazol-5-yl}-N'-(2-{[3-(2-methylphenyl)[1,2,4]triazolo[4,3-a]pyridin-6-yl]thio}benzyl)urea

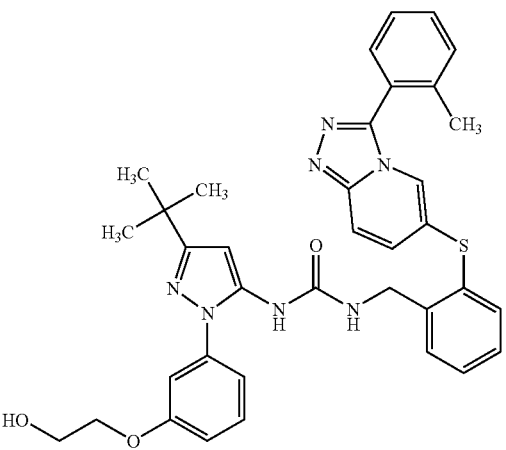

The title compound was prepared from the products of preparations 116 and 206, using the same method as that described for example 104, as a solid in 36% yield.

¹HNMR (400 MHz, CDCl₃) δ: 1.31 (s, 9H), 2.21 (s, 3H), 3.83 (m, 2H), 3.98 (m, 2H), 4.53 (d, 2H), 6.18 (brs, 1H), 6.33 (s, 1H), 6.72 (d, 1H), 7.00 (m, 3H), 7.09 (brs, 1H), 7.20 (m, 3H), 7.35 (m, 6H), 7.45 (d, 1H), 7.52 (d, 1H), 7.71 (s, 1H); LRMS APCI m/z 648 [M+H]⁺

Example 106

N-{3-tert-Butyl-1-[4-(hydroxymethyl)phenyl]-1H-pyrazol-5-yl}-N'-{2-[(3-isopropyl[1,2,4]triazolo[4,3-a]pyridin-6-yl)thio]benzyl}urea

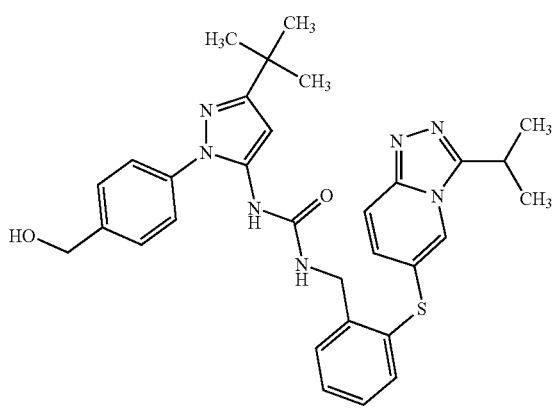

Tetraethylammonium fluoride dihydrate (60 mg, 0.40 mmol) was added to a solution of the product of preparation 136 (200 mg, 0.29 mmol) in tetrahydrofuran (5 mL) and the mixture was stirred at room temperature for 6 hours. Further tetraethylammonium fluoride dihydrate (60 mg, 0.32 mmol) was then added and the mixture was stirred at room temperature for 48 hours. The reaction mixture was concentrated in vacuo and the residue was partitioned between 1M hydrochloric acid (20 mL) and dichloromethane (20 mL). The aqueous layer was separated and extracted with dichloromethane (5×20 mL), and the combined organic solution was dried over sodium sulfate and concentrated in vacuo. Purification of the residue by column chromatography on silica gel, eluting with dichloromethane:methanol, 99:1 to 92.5:7.5, followed by trituration with dichloromethane/diethyl ether, afforded the title compound as a solid in 41% yield, 68.8 mg.

¹HNMR (300 MHz, CDCl₃) δ: 1.27 (s, 9H), 1.29 (d, 6H), 3.18 (m, 1H), 4.33 (s, 2H), 4.46 (d, 2H), 4.69 (brs, 1H), 6.30 (s, 1H), 6.87 (d, 1H), 6.95 (d, 2H), 7.07-7.25 (m, 7H), 7.36 (d, 1H), 7.74 (s, 1H), 8.04 (s, 1H); LCMS m/z 570 [M+H]⁺

Example 107

N-{1-(3-Hydroxyphenyl)-3-[1-methyl-1-(methylthio)ethyl]-1H-pyrazol-5-yl}-N'-(2-{[3-(2-methoxyphenyl)[1,2,4]triazolo[4,3-a]pyridin-6-yl]thio}benzyl)urea

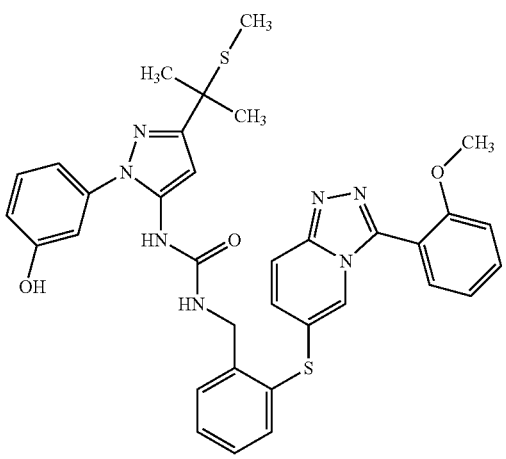

The title compound was prepared from the product of preparation 227, using a similar method as that described for example 106, as a white solid in 65% yield.)

¹HNMR (400 MHz, DMSO-d₆) δ: 1.58 (s, 6H), 1.89 (s, 3H), 3.69 (s, 3H), 4.38 (d, 2H), 6.32 (s, 1H), 6.77 (dd, 1H), 6.86 (m, 2H), 7.05 (m, 1H), 7.22 (m, 8H), 7.56 (m, 2H), 7.84 (m, 2H), 8.32 (s, 1H), 9.77 (s, 1H); LCMS m/z 652 [M+H]⁺

Example 108

N-[3-tert-Butyl-1-(3-hydroxy-4-methylphenyl)-1H-pyrazol-5-yl]-N'-{2-[(3-isopropyl[1,2,4]triazolo[4,3-a]pyridin-6-yl)thio]benzyl}urea

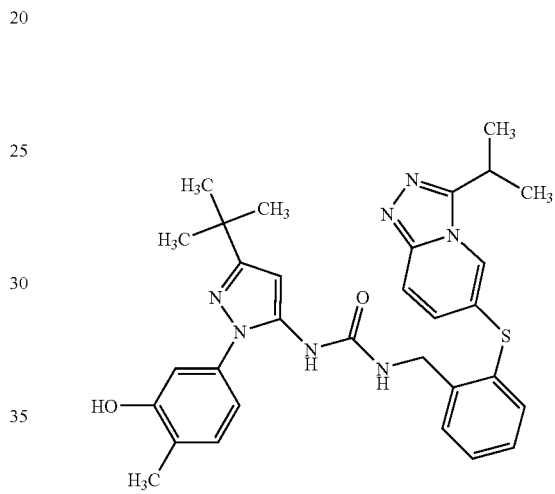

Tetraethylammonium fluoride dihydrate (2.78 g, 15.0 mmol) was added to a solution of the product of preparation 137 (951 mg, 1.39 mmol) in tetrahydrofuran (10 mL) and the mixture was stirred at room temperature for 5 minutes. The reaction mixture was then concentrated in vacuo and the residue was partitioned between 1M hydrochloric acid (25 mL) and dichloromethane (25 mL). The organic layer was separated, dried over sodium sulfate and concentrated in vacuo. Purification of the residue by column chromatography on silica gel, eluting with dichloromethane:methanol, 95:5 to 90:10, followed by trituration with dichloromethane/methanol:diethyl ether, afforded the title compound as a solid in 11% yield, 83.7 mg.

¹HNMR (300 MHz, DMSO-d₆) δ: 1.24 (s, 9H), 1.37 (d, 6H), 2.15 (s, 3H), 3.38 (m, 1H), 4.42 (d, 2H), 6.19 (s, 1H), 6.74 (d, 1H), 6.89 (s, 1H), 7.10-7.13 (m, 2H), 7.25-7.33 (m, 4H), 7.47 (m, 1H), 7.88 (m, 2H), 8.30 (s, 1H), 8.80 (s, 1H); LCMS m/z 570.6 [M+H]$^+$

Example 109

N-(2-{[3-(2-Fluorophenyl)[1,2,4]triazolo[4,3-a]pyridin-6-yl]thio}benzyl)-N'-{1-(4-hydroxyphenyl)-3-[1-methyl-1-(methylthio)ethyl]-1H-pyrazol-5-yl}urea

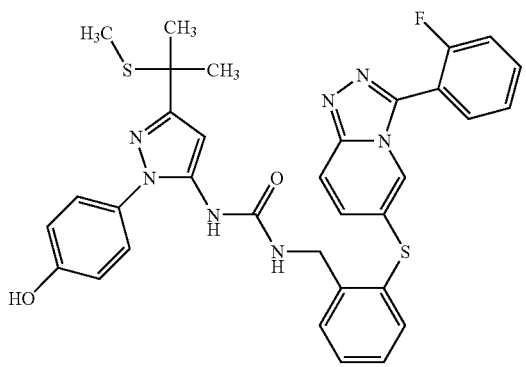

The title compound was prepared from the product of preparation 163, using a similar method as that described for example 108, as a white solid in 26% yield.

$^1$HNMR (300 MHz, DMSO-d$_6$) δ: 1.56 (s, 6H), 1.88 (s, 3H), 4.36 (d, 2H), 6.30 (s, 1H), 6.83 (d, 2H), 7.00 (m, 1H), 7.23 (m, 7H), 7.44 (m, 2H), 7.66 (m, 1H), 7.77 (m, 1H), 7.86 (d, 1H), 8.16 (d, 2H), 9.72 (s, 1H); LCMS m/z 640 [M+H]$^+$

Example 110

N-{1-(3-Hydroxyphenyl)-3-[1-methyl-1-(methylthio)ethyl]-1H-pyrazol-5-yl}-N'-{2-[(3-isopropyl[1,2,4]triazolo[4,3-a]pyridin-6-yl)thio]benzyl}urea

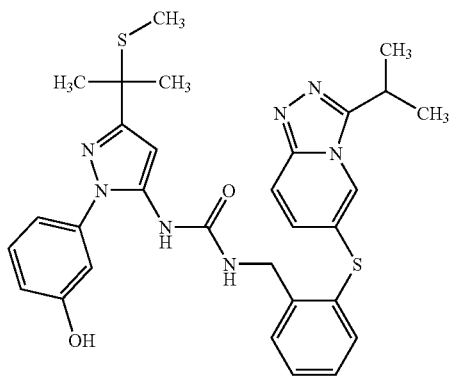

The title compound was prepared from the product of preparation 225, using a similar method as that described for example 108, as a white solid in 53% yield.

$^1$HNMR (300 MHz, DMSO-d$_6$) δ: 1.24 (s, 9H), 1.38 (d, 6H), 3.58 (m, 1H), 4.41 (d, 2H), 6.23 (s, 1H), 6.74 (m, 1H), 6.87 (m, 2H), 7.01-7.17 (m, 2H), 7.20-7.29 (m, 5H), 7.67 (m, 1H), 8.28 (m, 1H), 8.58 (m, 1H), 9.72 (s, 1H); LCMS m/z 632.6 [M+H]$^+$

Example 111

N-(2-{[3-(2-Fluorophenyl)[1,2,4]triazolo[4,3-a]pyridin-6-yl]thio}benzyl)-N'-{1-(3-hydroxyphenyl)-3-[1-methyl-1-(methylthio)ethyl]-1H-pyrazol-5-yl}urea

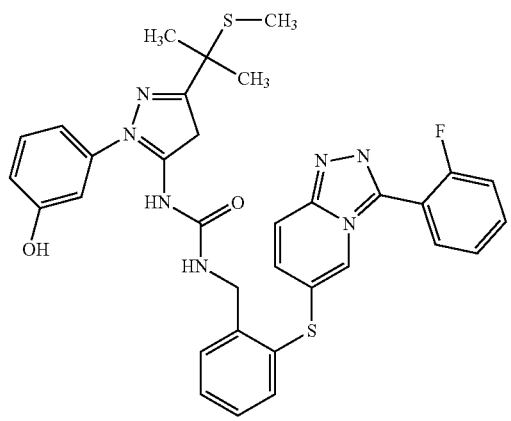

The title compound was prepared from the product of preparation 226, using a similar method as that described for example 108, as a white solid in 53% yield.

$^1$HNMR (300 MHz, DMSO-d$_6$) δ: 1.57 (s, 6H), 1.89 (s, 3H), 4.38 (d, 2H), 6.32 (s, 1H), 6.78 (dd, 1H), 6.86 (m, 2H), 7.05 (m, 1H), 7.28 (m, 6H), 7.44 (m, 2H), 7.67 (m, 1H), 7.77 (m, 1H), 7.87 (d, 1H), 8.20 (m, 1H), 8.31 (s, 1H), 9.77 (s, 1H); LCMS m/z 640 [M+H]$^+$

Example 112

N-[3-(1,1-Dimethylpropyl)-1-(3-hydroxyphenyl)-1H-pyrazol-5-yl]-N'-[2-({3-[2-(methylthio)phenyl][1,2,4]triazolo[4,3-a]pyridin-6-yl}thio)benzyl]urea

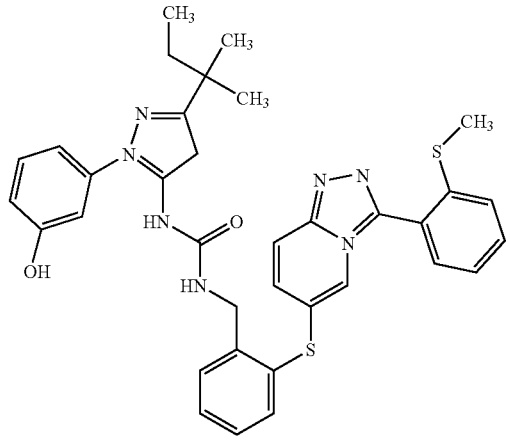

The title compound was prepared form the product of preparation 243, using a similar method as that described for example 108, as a white solid in 31% yield.

¹HNMR (300 MHz, DMSO-d₆) δ: 0.75 (t, 3H), 1.19 (s, 6H), 1.57 (q, 2H), 2.40 (s, 3H), 4.38 (d, 2H), 6.20 (s, 1H), 6.76 (d, 1H), 6.87 (m, 2H), 7.03 (m, 1H), 7.24-7.37 (m, 6H), 7.55 (m, 2H), 7.61 (m, 1H), 7.85-7.92 (m, 2H), 8.30 (m, 2H), 9.77 (s, 1H); LCMS m/z 650 [M+H]⁺

Example 113

N-[3-tert-Butyl-1-(4-hydroxyphenyl)-1H-pyrazol-5-yl]-N'-(2-{[3-(2-fluorophenyl)[1,2,4]triazolo[4,3-a]pyridin-6-yl]thio}benzyl)urea

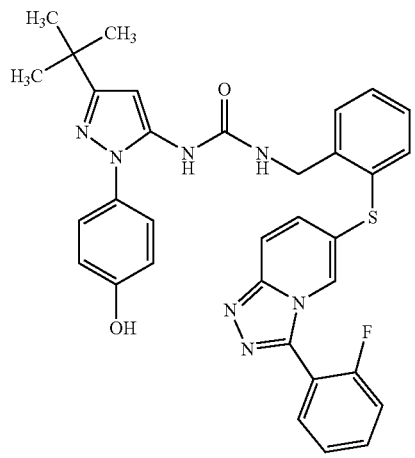

The title compound was prepared form the product of preparation 248, using the same method as that described for the preparation of example 108, as a white solid in 95% yield.
¹HNMR (300 MHz, DMSO-d₆) δ 1.23 (s, 9H), 4.37 (d, 2H), 6.14 (s, 1H), 6.85 (d, 2H), 7.18-7.30 (m, 8H), 7.39-7.49 (m, 2H), 7.68 (m, 1H), 7.76-7.87 (m, 2H), 8.19 (s, 1H), 8.38 (s, 1H), 9.87 (s, 1H); LCMS m/z 608 [M+H]⁺

Example 114

N-[3-tert-Butyl-1-(3-hydroxyphenyl)-1H-pyrazol-5-yl]-N'-[2-({3-[4-(methylthio)phenyl][1,2,4]triazolo[4,3-a]pyridin-6-yl}thio)benzyl]urea

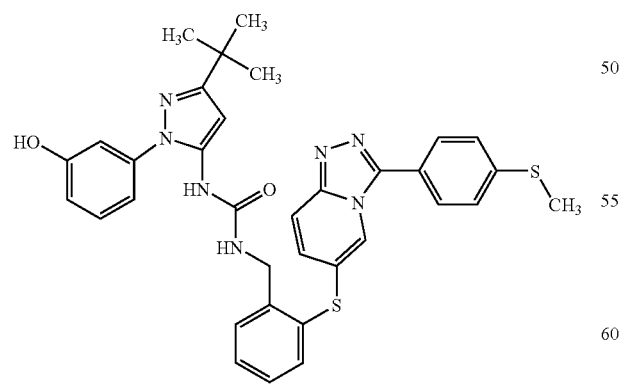

The title compound was prepared form the product of preparation 253, using the same method as that described for the preparation of example 97, as a pale yellow solid in 78% yield.

¹HNMR (400 MHz, DMSO-d₆) δ: 1.21 (s, 9H), 2.53 (s, 3H), 4.40 (d, 2H), 6.21 (s, 1H), 6.75 (d, 1H), 6.85 (d, 1H), 6.88 (s, 1H), 7.02 (m, 1H), 7.20 (d, 1H), 7.25 (m, 2H), 7.31 (m, 3H), 7.43 (d, 2H), 7.81 (d, 2H), 7.83 (d, 1H), 8.27 (s, 1H), 8.37 (s, 1H), 9.73 (s, 1H); LRMS APCI m/z 636 [M+H]⁺

Example 115

N-{1-[3-(2-Hydroxyethoxy)phenyl]-3-[1-methyl-1-(methylthio)ethyl]-1H-pyrazol-5-yl}-N'-(2-{[3-(2-isopropylphenyl)[1,2,4]triazolo[4,3-a]pyridin-6-yl]thio}benzyl)urea

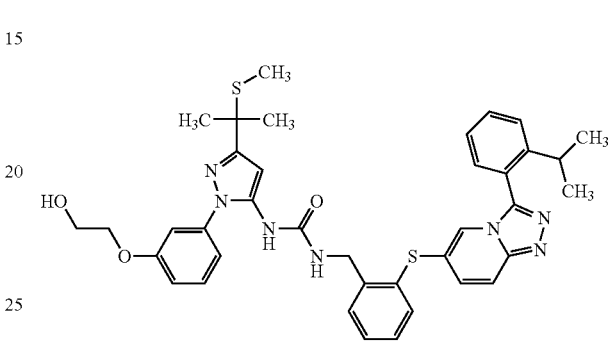

para-Toluenesulfonic acid (63 mg, 3.3 mmol) was added to a solution of the product of preparation 255 (262 mg, 3.3 mmol) in methanol (15 mL) and the mixture was stirred at room temperature for 72 hours. The reaction mixture was then diluted with water, basified with sodium hydrogen carbonate solution and the resulting precipitate was filtered off to afford the title compound as a white solid in 76% yield.
¹HNMR (300 MHz, DMSO-d₆) δ: 1.09 (d, 6H), 1.57 (s, 6H), 1.89 (s, 3H), 2.75 (m, 1H), 3.69 (s, 2H), 4.40 (d, 2H), 4.34 (d, 2H), 4.88 (brs, 1H), 6.31 (s, 1H), 6.93 (dd, 1H), 7.03 (m, 2H), 7.26 (m, 8H), 7.46 (d, 1H), 7.56 (d, 2H), 7.83 (d, 2H), 8.63 (s, 1H); LCMS m/z 708 [M+H]⁺

The following compounds have been prepared by analogy with the methods previously described.

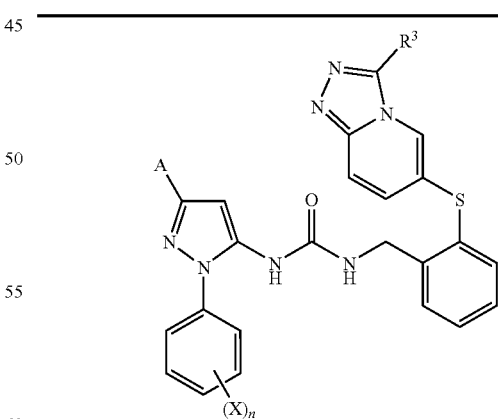

| Example No. | Definitions | LCMS m/z [M + H]⁺ |
|---|---|---|
| 116 | A = C(CH₃)₃; X = 4-CH₃; R³ = 2-benzyloxyphenyl | 694.6 |
| 117 | A = (CH₃S)C(CH₃)₂; X = 3-CF₃; R³ = CH(CH₃)₂ | 640 |

-continued

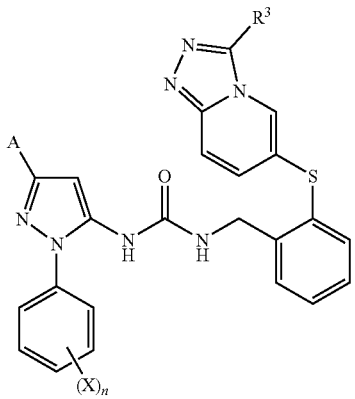

| Example No. | Definitions | LCMS m/z [M + H]+ |
|---|---|---|
| 118 | A = C(CH$_3$)$_3$; X = 4-C(O)NHCH$_3$; R$^3$ = CH(CH$_3$)$_2$ | 597.2747$^A$ |
| 119 | A = C(CH$_3$)$_3$; X = 3-F, 4-F; R$^3$ = 2-chloro-3-methoxyphenyl | 674.6 |
| 120 | A = C(CH$_3$)$_3$; X = 3-Cl, 4-Cl; R$^3$ = 2-benzyloxyphenyl | 748 |
| 121 | A = C(CH$_3$)$_3$; X = 3-CN; R$^3$ = 2-benzyloxyphenyl | 705 |
| 122 | A = C(CH$_3$)$_3$; X = 4-CN; R$^3$ = 2-benzyloxyphenyl | 705 |
| 123 | A = C(CH$_3$)$_3$; X = 3-F; R$^3$ = 2-benzyloxyphenyl | 698 |
| 124 | A = C(CH$_3$)$_3$; X = 3-benzyloxy, 5-CH$_3$; R$^3$ = CH(CH$_3$)$_2$ | 660.6 |
| 125 | A = (CH$_3$S)C(CH$_3$)$_2$; X = 4-(2-hydroxyethoxy); R$^3$ = CH(CH$_3$)$_2$ | 632 |
| 126 | A = (CH$_3$S)C(CH$_3$)$_2$; X = 4-Br; R$^3$ = CH(CH$_3$)$_2$ | 652 |
| 127 | A = (CH$_3$S)C(CH$_3$)$_2$; X = 3-Br; R$^3$ = CH(CH$_3$)$_2$ | 652 |
| 128 | A = C(CH$_3$)$_3$; X = 3-F, 4-F; R$^3$ = 2-chloro-3-hydroxyphenyl; | 660.5 |
| 129 | A = C(CH$_3$)$_3$; X = 3-CH$_3$CH$_2$, 4-OCH$_3$; R$^3$ = CH(CH$_3$)$_2$ | 598.6 |
| 130 | A = C(CH$_3$)$_3$; X = 3-OCH$_3$, 4-CH$_3$CH$_2$; R$^3$ = CH(CH$_3$)$_2$ | 598.6 |
| 131 | A = C(CH$_3$)$_3$; X = 3-OH, 5-CH$_3$CH$_2$; R$^3$ = CH(CH$_3$)$_2$ | 584.6 |
| 132 | A = (CH$_3$S)C(CH$_3$)$_2$; X = 4-OH; R$^3$ = 2-ethylphenyl; | 650.2364$^A$ |
| 133 | A = (CH$_3$S)C(CH$_3$)$_2$; X = 4-OH; R$^3$ = CH(CH$_3$)$_2$ | 588 |
| 134 | A = (CH$_3$S)C(CH$_3$)$_2$; X = 4-Br; R$^3$ = 2-hydroxyphenyl | 700 |
| 135 | A = C(CH$_3$)$_3$; X = 3-OCH$_3$, 4-Cl; R$^3$ = CH(CH$_3$)$_2$ | 604.6 |
| 136 | A = (CH$_3$S)C(CH$_3$)$_2$; X = 3-CH$_3$, 5-CH$_3$; R$^3$ = CH(CH$_3$)$_2$ | 600 |
| 137 | A = (CH$_3$S)C(CH$_3$)$_2$; X = 4-CH$_2$CH$_3$; R$^3$ = CH(CH$_3$)$_2$ | 600 |
| 138 | A = C(CH$_3$)$_3$; X = 4-(2-hydroxyethoxy); R$^3$ = 2-methoxyphenyl | 664.5 |
| 139 | A = C(CH$_3$)$_3$; X = 4-(2-hydroxyethoxy); R$^3$ = 2-isopropylphenyl | 676.6 |
| 140 | A = (CH$_3$S)C(CH$_3$)$_2$; X = 4-OH; R$^3$ = 2-methoxyphenyl | 652.6 |
| 141 | A = C(CH$_3$)$_3$; X = 4-(2-hydroxyethoxy); R$^3$ = 2-fluorophenyl | 652.6 |
| 142 | A = (CH$_3$S)C(CH$_3$)$_2$; X = 4-OH; R$^3$ = 2-isopylphenyl | 664.6 |
| 143 | A = C(CH$_3$)$_3$; X = 4-OH; R$^3$ = 2-methoxyphenyl | 620.6 |
| 144 | A = C(CH$_3$)$_3$; X = 4-OH; R$^3$ = 2-isopropylphenyl | 632.6 |
| 145 | A = C(CH$_3$)$_3$; X = 3-OH; R$^3$ = 2-methoxyphenyl | 620.6 |

-continued

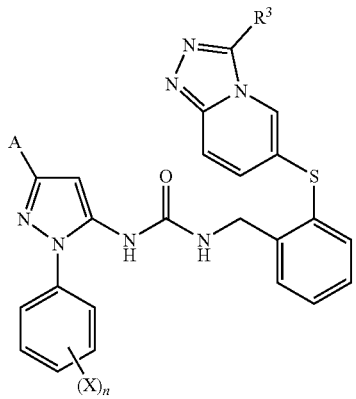

| Example No. | Definitions | LCMS m/z [M + H]+ |
|---|---|---|
| 146 | A = (CH$_3$S)C(CH$_3$)$_2$; X = 4-(2-hydroxyethoxy); R$^3$ = 2-fluorophenyl | 684.4 |
| 147 | A = (CH$_3$S)C(CH$_3$)$_2$; X = 4-(2-hydroxyethoxy); R$^3$ = 2-methoxy-phenyl | 696.5 |
| 148 | A = C(CH$_3$)$_3$; X = 3-OH; R$^3$ = 2-fluorophenyl | 608.6 |
| 149 | A = (CH$_3$S)C(CH$_3$)$_2$; X = 4-(2-hydroxyethoxy); R$^3$ = 2-isopropyl-phenyl | 708.6 |
| 150 | A = C(CH$_3$)$_3$; X = 3-OH; R$^3$ = 2-isopropylphenyl | 664.6 |
| 151 | A = (CH$_3$S)C(CH$_3$)$_2$; X = 3-CH$_3$; R$^3$ = 2-hydroxy-4-methylphenyl | 650 |
| 152 | A = (CH$_3$S)C(CH$_3$)$_2$; X = 3-CH$_3$; R$^3$ = 2-hydroxy-3-chlorophenyl | 669$^B$ |
| 153 | A = (CH$_3$S)C(CH$_3$)$_2$; X = 4-CH$_3$; R$^3$ = 2-hydroxy-3-chlorophenyl | Microanalysis found: C, 60.69; H, 4.82; N, 14.27. C$_{34}$H$_{32}$ClN$_7$O$_2$S$_2$ requires C, 60.93; H, 4.81; N, 14.63%. |
| 154 | A = (CH$_3$CH$_2$)C(CH$_3$)$_2$; X = H; R$^3$ = 2-hydroxyphenyl | 604.6 |
| 155 | A = (CH$_3$S)C(CH$_3$)$_2$; X = 4-CH$_3$; R$^3$ = 2-hydroxy-4-methylphenyl | 650 |
| 156 | A = C(CH$_3$)$_3$; X = 4-F; R$^3$ = 2-hydroxy-4-methylphenyl | 622 |
| 157 | A = C(CH$_3$)$_3$; X = 3-F; R$^3$ = 2-hydroxy-4-methylphenyl | 622 |
| 158 | A = (CH$_3$CH$_2$)C(CH$_3$)$_2$; X = 3-Cl; R$^3$ = CH(CH$_3$)$_2$ | 570.6 |
| 159 | A = C(CH$_3$)$_3$; X = 4-OH; R$^3$ = 2-chlorophenyl | 624 |
| 160 | A = C(CH$_3$)$_3$; X = 3-(2-hydroxyethoxy); R$^3$ = CH(CH$_3$)$_2$ | 600 |
| 161 | A = C(CH$_3$)$_3$; X = 3-CH$_3$; R$^3$ = 3-chloro-2-hydroxyphenyl | 638, 640 |
| 162 | A = (CH$_3$CH$_2$)C(CH$_3$)$_2$; X = 3-Cl, 4-OH; R$^3$ = CH(CH$_3$)$_2$ | 604.6 |
| 163 | A = (CH$_3$CH$_2$)C(CH$_3$)$_2$; X = 3-F; R$^3$ = 2-hydroxyphenyl | 622.6 |
| 164 | A = (CH$_3$S)C(CH$_3$)$_2$; X = 4-OH; R$^3$ = 2-chlorophenyl | 656 |
| 165 | A = (CH$_3$S)C(CH$_3$)$_2$; X = 4-CH$_3$; R$^3$ = 2-hydroxyphenyl | 637 |
| 166 | A = (CH$_3$SCH$_2$)C(CH$_3$)$_2$; X = 3-CH$_3$; R$^3$ = 2-hydroxyphenyl | 650 |
| 167 | A = C(CH$_3$)$_3$; X = 3-CH$_3$; R$^3$ = 2-hydroxyphenyl | 604 |
| 168 | A = C(CH$_3$)$_3$; X = 4-OH; R$^3$ = 2-hydroxyphenyl | 606 |
| 169 | A = C(CH$_3$)$_3$; X = H; R$^3$ = 4-carboxyphenyl | 616 |
| 170 | A = C(CH$_3$)$_3$; X = 4-CH$_3$; R$^3$ = 3-chloro-5-fluoro-2-hydroxyphenyl | 656.1997$^A$ |
| 171 | A = (CH$_3$SCH$_2$)C(CH$_3$)$_2$; X = 3-CN; R$^3$ = 2-hydroxyphenyl | 661 |

-continued

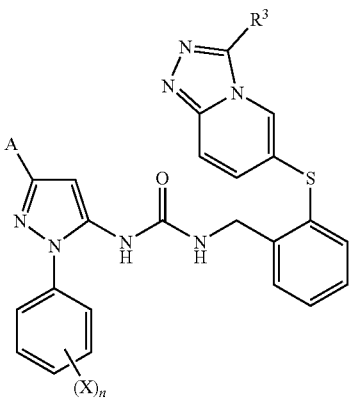

| Example No. | Definitions | LCMS m/z [M + H]⁺ |
|---|---|---|
| 172 | A = (CH₃SCH₂)C(CH₃)₂; X = 4-CN; R³ = 2-hydroxyphenyl | 661 |
| 173 | A = C(CH₃)₃; X = 4-OH; R³ = 3-(2-hydroxyethoxy)phenyl | 650 |
| 174 | A = C(CH₃)₃; X = 4-CH₃; R³ = 3-chloro-5-fluoro-4-hydroxyphenyl | 656 |
| 175 | A = C(CH₃)₃; X = 3-carboxymethoxy; R³ = CH(CH₃)₂ | 614 |
| 176 | A = (CH₃S)C(CH₃)₂; X = 3-(2-hydroxyethoxy); R³ = 2-hydroxyphenyl | 634 |
| 177 | A = (CH₃S)C(CH₃)₂; X = 4-CH₃; R³ = 2-hydroxy-6-methylphenyl | 650 |
| 178 | A = (CH₃S)C(CH₃)₂; X = 4-OH; R³ = 3-(2-hydroxyethoxy)phenyl | 682.2252ᴬ |
| 179 | A = C(CH₃)₃; X = 3-OH; R³ = 2-[(2-hydroxyethyl)thio]phenyl | 666 |

ᴬ = HRMS: m/z
ᴮ = LRMS: m/z [M − H]⁻

| Example No. | Definitions | LCMS m/z [M + H]⁺ |
|---|---|---|
| 180 | A = C(CH₃)₃; R² = pyridin-2-yl; R³ = CH(CH₃)₂ | 541 |
| 181 | A = C(CH₃)₃; R² = isoquinolin-5-yl; R³ = CH(CH₃)₂ | 591.6 |
| 182 | A = (CH₃CH₂)C(CH₃)₂; R² = pyridin-3-yl; R³ = 2-hydroxyphenyl | 605.6 |
| 183 | A = C(CH₃)₃; R² = isoquinolin-7-yl; R³ = CH(CH₃)₂ | 591.2 |

The following compounds in list² may be prepared by analogy with the methods previously described. In another embodiment of the invention, a preferred group of compounds is that in which each substituent is as specified in the list² below.

Preferably, the compound of formula (I) is selected from the list²:

N-[3-tert-butyl-1-(3-chloro-4-hydroxyphenyl)-1H-pyrazol-5-yl]-N'-[2-({3-[2-(2-hydroxyethoxy)phenyl][1,2,4]triazolo[4,3-a]pyridin-6-yl}thio)benzyl]urea N-[3-tert-butyl-1-(3-chloro-4-hydroxyphenyl)-1H-pyrazol-5-yl]-N'-[2-({3-[3-(2-hydroxyethoxy)phenyl][1,2,4]triazolo[4,3-a]pyridin-6-yl}thio)benzyl]urea N-[3-tert-butyl-1-(3-chloro-4-hydroxyphenyl)-1H-pyrazol-5-yl]-N'-[2-({3-[4-(2-hydroxyethoxy)phenyl][1,2,4]triazolo[4,3-a]pyridin-6-yl}thio)benzyl]urea N-[3-tert-butyl-1-(3-chloro-4-hydroxyphenyl)-1H-pyrazol-5-yl]-N'-[2-({3-[2-(methylthio)phenyl][1,2,4]triazolo[4,3-a]pyridin-6-yl}thio)benzyl]urea N-[3-tert-butyl-1-(3-chloro-4-hydroxyphenyl)-1H-pyrazol-5-yl]-N'-{2-[(3-isopropyl[1,2,4]triazolo[4,3-a]pyridin-6-yl)thio]benzyl}urea N-[3-tert-butyl-1-{3-chloro-4-hydroxyphenyl}-1H-pyrazol-5-yl]-N'-{2-[(3-(2-[(2-hydroxyethyl)thio]phenyl}[1,2,4]triazolo[4,3-a]pyridin-6-yl)thio]benzyl}urea N-[3-tert-butyl-1-(4-chloro-3-hydroxyphenyl)-1H-pyrazol-5-yl]-N'-[2-({3-[2-(2-hydroxyethoxy)phenyl][1,2,4]triazolo[4,3-a]pyridin-6-yl}thio)benzyl]urea N-[3-tert-butyl-1-(4-chloro-3-hydroxyphenyl)-1H-pyrazol-5-yl]-N'-[2-({3-[3-(2-hydroxyethoxy)phenyl][1,2,4]triazolo[4,3-a]pyridin-6-yl}thio)benzyl]urea N-[3-tert-butyl-1-(4-chloro-3-hydroxyphenyl)-1H-pyrazol-5-yl]-N'-[2-({3-[4-(2-hydroxyethoxy)phenyl][1,2,4]triazolo[4,3-a]pyridin-6-yl}thio)benzyl]urea N-[3-tert-butyl-1-(4-chloro-3-hydroxyphenyl)-1H-pyrazol-5-yl]-N'-[2-({3-[2-(methylthio)phenyl][1,2,4]triazolo[4,3-a]pyridin-6-yl}thio)benzyl]urea N-[3-tert-butyl-1-(4-chloro-3-hydroxyphenyl)-1H-pyrazol-5-yl]-N'-{2-[(3-isopropyl[1,2,4]triazolo[4,3-a]pyridin-6-yl)thio]benzyl}urea N-[3-tert-butyl-1-(4-chloro-3-hydroxyphenyl)-1H-pyrazole-5-yl]-N'-{2-[(3-{2-[(2-hydroxyethyl)thio]phenyl}[1,2,4]triazolo[4,3-a]pyridin-6-yl)thio]benzyl}urea N-{1-(3-chloro-4-hydroxyphenyl)-3-[1-methyl-1-(methylthio)ethyl]-1H-pyrazol-5-yl}-N'-[2-({3-[2-(2-hydroxyethoxy)phenyl][1,2,4]triazolo[4,3-a]pyridin-6-yl}thio)benzyl]urea N-{1-(3-chloro-4-hydroxyphenyl)-3-[1-methyl-1-(methylthio)ethyl]-1H-pyrazol-5-yl}-N'-[2-({3-[3-(2-hydroxyethoxy)phenyl][1,2,4]triazolo[4,3-a]pyridin-6-yl}thio)benzyl]urea N-{1-(3-chloro-4-hydroxyphenyl)-3-[1-methyl-1-(methylthio)ethyl]-1H-pyrazol-5-yl}-N'-[2-({3-[4-(2-hydroxyethoxy)phenyl][1,2,4]triazolo[4,3-a]pyridin-6-yl}thio)benzyl]urea N-{1-(3-chloro-4-hydroxyphenyl)-3-[1-methyl-1-(methylthio)ethyl]-1H-pyrazol-5-yl}-N'-[2-({3-[2-(methylthio)phenyl][1,2,4]triazolo[4,3-a]pyridin-6-yl}thio)benzyl]urea N-{1-(3-chloro-4-hydroxyphenyl)-3-[1-methyl-1-(methylthio)ethyl]-1H-pyrazol-5-yl}-N'-{2-[(3-isopropyl[1,2,4]triazolo[4,3-a]pyridin-6-yl)thio]benzyl}urea N-{1-(3-chloro-4-hydroxyphenyl)-3-[1-methyl-1-(methylthio)ethyl]-1H-pyrazol-5-yl}-N'-{2-[(3-{2-[(2-hydroxyethyl)thio]phenyl}[1,2,4]triazolo[4,3-a]pyridin-6-yl)thio]benzyl}urea N-{1-(4-chloro-3-hydroxyphenyl)-3-[1-methyl-1-(methylthio)ethyl]-1H-pyrazol-5-yl}-N'-[2-({3-[2-(2-hydroxyethoxy)phenyl][1,2,4]triazolo[4,3-a]pyridin-6-yl}thio)benzyl]urea N-{1-(4-chloro-3-hydroxyphenyl)-3-[1-methyl-1-(methylthio)ethyl]-1H-pyrazol-5-yl}-N'-[2-({3-[3-(2-hydroxyethoxy)phenyl][1,2,4]triazolo[4,3-a]pyridin-6-yl}thio)benzyl]urea N-{1-(4-chloro-3-hydroxyphenyl)-3-[1-methyl-1-(methylthio)ethyl]-1H-pyrazol-5-yl}-N'[2-({3-[4-(2-hydroxyethoxy)phenyl][1,2,4]triazolo[4,3-a]pyridin-6-yl}thio)benzyl]urea N-{1-(4-chloro-3-hydroxyphenyl)-3-[1-methyl-1-(methylthio)ethyl]-1H-pyrazol-5-yl}-N'-[2-({3-[2-(methylthio)phenyl][1,2,4]triazolo[4,3-a]pyridin-6-yl}thio)benzyl]urea N-{1-(4-chloro-3-hydroxyphenyl)-3-[1-methyl-1-(methylthio)ethyl]-1H-pyrazol-5-yl}-N'-{2-[(3-isopropyl[1,2,4]triazolo[4,3-a]pyridin-6-yl)thio]benzyl}urea N-{1-(4-chloro-3-hydroxyphenyl)-3-[1-methyl-1-(methylthio)ethyl]-1H-pyrazol-5-yl}-N'-{2-[(3-{2-[(2-hydroxyethyl)thio]phenyl}[1,2,4]triazolo[4,3-a]pyridin-6-yl)thio]benzyl}urea N-{1-(3-chloro-4-hydroxyphenyl)-3-[1,1-dimethyl-2-(methylthio)ethyl]-1H-pyrazol-5-yl}-N'-[2-({3-[2-(2-hydroxyethoxy)phenyl][1,2,4]triazolo[4,3-a]pyridin-6-yl}thio)benzyl]urea N-{1-(3-chloro-4-hydroxyphenyl)-3-[1,1-dimethyl-2-(methylthio)ethyl]-1H-pyrazol-5-yl}-N'-[2-({3-[3-(2-hydroxyethoxy)phenyl][1,2,4]triazolo[4,3-a]pyridin-6-yl}thio)benzyl]urea N-{1-(3-chloro-4-hydroxyphenyl)-3-[1,1-dimethyl-2-(methylthio)ethyl]-1H-pyrazol-5-yl}-N'-[2-({3-[4-(2-hydroxyethoxy)phenyl][1,2,4]triazolo[4,3-a]pyridin-6-yl}thio)benzyl]urea N-{1-(3-chloro-4-hydroxyphenyl)-3-[1,1-dimethyl-2-(methylthio)ethyl]-1H-pyrazol-5-yl}-N'-[2-({3-[2-(methylthio)phenyl][1,2,4]triazolo[4,3-a]pyridin-6-yl}thio)benzyl]urea N-{1-(3-chloro-4-hydroxyphenyl)-3-[1,1-dimethyl-2-(methylthio)ethyl]-1H-pyrazol-5-yl}-N'-{2-[(3-isopropyl[1,2,4]triazolo[4,3-a]pyridin-6-yl)thio]benzyl}urea N-{1-(3-chloro-4-hydroxyphenyl)-3-[1,1-dimethyl-2-(methylthio)ethyl]-1H-pyrazol-5-yl}-N'-{2-[(3-{2-[(2-hydroxyethyl)thio]phenyl}[1,2,4]triazolo[4,3-a]pyridin-6-yl)thio]benzyl}urea N-{1-(4-chloro-3-hydroxyphenyl)-3-[1,1-dimethyl-2-(methylthio)ethyl]-1H-pyrazol-5-yl}-N'-[2-({3-[2-(2-hydroxyethoxy)phenyl][1,2,4]triazolo[4,3-a]pyridin-6-yl}thio)benzyl]urea N-{1-(4-chloro-3-hydroxyphenyl)-3-[1,1-dimethyl-2-<methylthio)ethyl]-1H-pyrazol-5-yl}-N'-[2-({3-[3-(2-hydroxyethoxy)phenyl][1,2,4]triazolo[4,3-a]pyridin-6-yl}thio)benzyl]urea N-{1-(4-chloro-3-hydroxyphenyl)-3-[1,1-dimethyl-2-(methylthio)ethyl]-1H-pyrazol-5-yl}-N'-[2-({3-[4-(2-hydroxyethoxy)phenyl][1,2,4]triazolo[4,3-a]pyridin-6-yl}thio)benzyl]urea N-{1-(4-chloro-3-hydroxyphenyl)-3-[1,1-dimethyl-2-(methylthio)ethyl]-1H-pyrazol-5-yl}-N'-[2-({3-[2-(methylthio)phenyl][1,2,4]triazolo[4,3-a]pyridin-6-yl}thio)benzyl]urea N-{1-(4-chloro-3-hydroxyphenyl)-3-[1,1-dimethyl-2-(methylthio)ethyl]-1H-pyrazol-5-yl}-N'-{2-[(3-isopropyl[1,2,4]triazolo[4,3-a]pyridin-6-yl)thio]benzyl}urea N-{1-(4-chloro-3-hydroxyphenyl)-3-[1,1-dimethyl-2-(methylthio)ethyl]-1H-pyrazol-5-yl}-N'-{2-[(3-{2-[(2-hydroxyethyl)thio]phenyl}[1,2,4]triazolo[4,3-a]pyridin-6-yl)thio]benzyl}urea N-[1-(3-chloro-4-hydroxyphenyl)-3-(1,1-dimethylpropyl)-1H-pyrazol-5-yl]-N'-[2-({3-[2-(2-hydroxyethoxy)phenyl][1,2,4]triazolo[4,3-a]pyridin-6-yl}thio)benzyl]urea N-[1-(3-chloro-4-hydroxyphenyl)-3-(1,1-dimethylpropyl)-1H-pyrazol-5-yl]-N'-[2-({3-[3-(2-hydroxyethoxy)phenyl][1,2,4]triazolo[4,3-a]pyridin-6-yl}thio)benzyl]urea N-[1-(3-chloro-4-hydroxyphenyl)-3-(1,1-dimethylpropyl)-1H-pyrazol-5-yl]-N'-[2-({3-[4-(2-hydroxyethoxy)phenyl][1,2,4]triazolo[4,3-a]pyridin-6-yl}thio)benzyl]urea N-[1-(3-chloro-4-hydroxyphenyl)-3-(1,1-dimethylpropyl)-1H-pyrazol-5-yl]-N'-[2-({3-[2-(methylthio)phenyl][1,2,4]triazolo[4,3-a]pyridin-6-yl}thio)benzyl]urea N-[1-(3-chloro-4-hydroxyphenyl)-3-(1,1-dimethylpropyl)-1H-pyrazol-5-yl]-N'-{2-[(3-isopropyl[1,2,4]triazolo[4,3-a]pyridin-6-yl)thio]benzyl}urea N-[1-(3-chloro-4-hydroxyphenyl)-3-(1,1-dimethylpropyl)-1H-pyrazol-5-yl]-N'-{2-[(3-{2-[(2-hydroxyethyl)thio]phenyl}[1,2,4]triazolo[4,3-a]pyridin-6-yl)thio]benzyl}urea N-[1-(4-chloro-3-hydroxyphenyl)-3-(1,1-dimethylpropyl)-1H-pyrazol-5-yl]-N'-[2-({3-[2-(2-hydroxyethoxy)phenyl][1,2,4]triazolo[4,3-a]pyridin-6-yl}thio)benzyl]urea N-[1-(4-chloro-3-hydroxyphenyl)-3-(1,1-dimethylpropyl)-1H-pyrazol-5-yl]-N'-[2-({3-[3-(2-hydroxyethoxy)phenyl][1,2,4]triazolo[4,3-a]pyridin-6-yl}thio)benzyl]urea N-[1-(4-chloro-3-hydroxyphenyl)-3-(1,1-dimethylpropyl)-1H-pyrazol-5-yl]-N'-[2-({3-[4-(2-hydroxyethoxy)phenyl][1,2,4]triazolo[4,3-a]pyridin-6-yl}thio)benzyl]urea N-[1-(4-chloro-3-hydroxyphenyl)-3-(1,1-dimethylpropyl)-1H-pyrazol-5-yl]-N'-[2-({3-[2-(methylthio)phenyl][1,2,4]triazolo[4,3-a]pyridin-6-yl}thio)benzyl]urea N-[1-(4-chloro-3-hydroxyphenyl)-3-(1,1-dimethylpropyl)-1H-pyrazol-5-yl]-N'-{2-[(3-isopropyl[1,2,4]triazolo[4,3-a]pyridin-6-yl)thio]benzyl}urea N-[1-(4-chloro-3-hydroxyphenyl)-3-<1,1-dimethylpropyl)-1H-pyrazol-5-yl]-N'-{2-[(3-{2-[(2-hydroxyethyl)thio]phenyl}[1,2,4]triazolo[4,3-a]pyridin-6-yl)thio]benzyl}urea N-[3-tert-butyl-1-(3-cyano-4-hydroxyphenyl)-1H-pyrazol-5-yl]-N'-[2-({3-[2-(2-hydroxyethoxy)phenyl][1,2,4]triazolo[4,3-a]pyridin-6-yl}thio)benzyl]urea N-[3-tert-butyl-1-(3-cyano-4-hydroxyphenyl)-1H-pyrazol-5-yl]-N'-[2-({3-[3-(2-hydroxyethoxy)phenyl][1,2,4]triazolo[4,3-a]pyridin-6-yl}thio)benzyl]urea N-[3-tert-butyl-1-(3-cyano-4-hydroxyphenyl)-1H-pyrazol-5-yl]-N'-[2-({3-[4-(2-hydroxyethoxy)phenyl][1,2,4]triazolo[4,3-a]pyridin-6-yl}thio)benzyl]urea N-[3-tert-butyl-1-(3-cyano-4-hydroxyphenyl)-1H-pyrazol-5-yl]-N'-[2-({3-[2-methylthio)phenyl][1,2,4]triazolo[4,3-a]pyridin-6-yl}thio)benzyl]urea N-[3-tert-butyl-1-(3-cyano-4-hydroxyphenyl)-1H-pyrazol-5-yl]-N'-{2-[(3-isopropyl[1,2,4]triazolo[4,3-a]pyridin-6-yl)thio]benzyl}urea N-[3-tert-butyl-1-(3-cyano-4-hydroxyphenyl)-1H-pyrazol-5-yl]-N'-{2-[(3-{2-[(2-hydroxyethyl)thio]phenyl}[1,2,4]triazolo[4,3-a]pyridin-6-yl)thio]benzyl}urea N-{1-(3-cyano-4-hydroxyphenyl)-3-[1-methyl-1-(methylthio)ethyl]-1H-pyrazol-5-yl}-N'-[2-({3-[2-(2-hydroxyethoxy)phenyl][1,2,4]triazolo[4,3-a]pyridin-6-yl}thio)benzyl]urea N-{1-(3-cyano-4-hydroxyphenyl)-3-[1-methyl-1-(methylthio)ethyl]-1H-pyrazol-5-yl}-N'-[2-({3-[3-(2-hydroxyethoxy)phenyl][1,2,4]triazolo[4,3-a]pyridin-6-yl}thio)benzyl]urea N-{1-(3-cyano-4-hydroxyphenyl)-3-[1-methyl-1-(methylthio)ethyl]-1H-pyrazol-5-yl}-N'-[2-({3-[4-(2-hydroxyethoxy)phenyl][1,2,4]triazolo[4,3-a]pyridin-6-yl}thio)benzyl]urea N-{1-(3-cyano-4-hydroxyphenyl)-3-[1-methyl-1-(methylthio)ethyl]-1H-pyrazol-5-yl}-N'-[2-({3-[2-(methylthio)phenyl][1,2,4]triazolo[4,3-a]pyridin-6-yl}thio)benzyl]urea N-{1-(3-cyano-4-hydroxyphenyl)-3-[1-methyl-1-(methylthio)ethyl]-1H-pyrazol-5-yl}-N'-{2-[(3-isopropyl[1,2,4]triazolo[4,3-a]pyridin-6-yl)thio]benzyl}urea N-{1-(3-cyano-4-hydroxyphenyl)-3-[1-methyl-1-(methylthio)ethyl]-1H-pyrazol-5-yl}-N'-{2-[(3-{2-[(2-hydroxyethyl)thio]phenyl}[1,2,4]triazolo[4,3-a]pyridin-6-yl)thio]benzyl}urea N-{1-(3-cyano-4-hydroxyphenyl)-3-[1,1-dimethyl-2-(methylthio)ethyl]-1H-pyrazol-5-yl}-N'-[2-({3-[2-(2-hydroxyethoxy)phenyl][1,2,4]triazolo[4,3-a]pyridin-6-yl}thio)benzyl]urea N-{1-(3-cyano-4-hydroxyphenyl)-3-[1,1-dimethyl-2-(methylthio)ethyl]-1H-pyrazol-5-yl}-N'-[2-({3-[3-(2-hydroxyethoxy)phenyl][1,2,4]triazolo[4,3-a]pyridin-6-yl}thio)benzyl]urea N-{1-(3-cyano-4-hydroxyphenyl)-3-[1,1-dimethyl-2-(methylthio)ethyl]-1H-pyrazol-5-yl}-N'-[2-({3-[4-(2-hydroxyethoxy)phenyl][1,2,4]triazolo[4,3-a]pyridin-6-yl}thio)benzyl]urea N-{1-(3-cyano-4-hydroxyphenyl)-3-[1,1-dimethyl-2-(methylthio)ethyl]-1H-pyrazol-5-yl}-N'-[2-({3-[2-(methylthio)phenyl][1,2,4]triazolo[4,3-a]pyridin-6-yl}thio)benzyl]urea N-{1-(3-cyano-4-hydroxyphenyl)-3-[1,1-dimethyl-2-(methylthio)ethyl]-1H-pyrazole-5-yl}-N'-{2-[(3-isopropyl[1,2,4]triazolo[4,3-a]pyridin-6-yl)thio]benzyl}urea N-{1-(3-cyano-4-hydroxyphenyl)-3-[1,1-dimethyl-2-(methylthio)ethyl]-1H-pyrazol-5-yl}-N'-{2-[(3-{2-[(2-hydroxyethyl)thio]phenyl}[1,2,4]triazolo[4,3-a]pyridin-6-yl)thio]benzyl}urea N-[1-(3-cyano-4-hydroxyphenyl)-3-(1,1-dimethylpropyl)-1H-pyrazol-5-yl]-N'-[2-({3-[2-(2-hydroxyethoxy)phenyl][1,2,4]triazolo[4,3-a]pyridin-6-yl}thio)benzyl]urea N-[1-(3-cyano-4-hydroxyphenyl)-3-(1,1-dimethylpropyl)-1H-pyrazol-5-yl]-N'-[2-({3-[3-(2-hydroxyethoxy)phenyl][1,2,4]triazolo[4,3-a]pyridin-6-yl}thio)benzyl]urea N-[1-(3-cyano-4-hydroxyphenyl)-3-(1,1-dimethylpropyl)-1H-pyrazol-5-yl]-N'-[2-({3-[4-(2-hydroxyethoxy)phenyl][1,2,4]triazolo[4,3-a]pyridin-6-yl}thio)benzyl]urea N-[1-(3-cyano-4-hydroxyphenyl)-3-(1,1-dimethylpropyl)-1H-pyrazol-5-yl]-N'-[2-({3-[2-(methylthio)phenyl][1,2,4]triazolo[4,3-a]pyridin-6-yl}thio)benzyl]urea N-[1-(3-cyano-4-hydroxyphenyl)-3-(1,1-dimethylpropyl)-1H-pyrazol-5-yl]-N'-{2-[(3-isopropyl[1,2,4]triazolo[4,3-a]pyridin-6-yl)thio]benzyl}urea N-[1-(3-cyano-4-hydroxyphenyl)-3-(1,1-dimethylpropyl)-1H-pyrazol-5-yl]-N'-{2-[(3-{2-[(2-hydroxyethyl)thio]phenyl}[1,2,4]triazolo[4,3-a]pyridin-6-yl)thio]benzyl}urea N-{3-tert-butyl-1-[3-<2-hydroxyethoxy)phenyl]-1H-pyrazol-5-yl}-N'-(2-{[3-(5-chloro-2-hydroxyphenyl)[1,2,4]triazolo[4,3-a]pyridin-6-yl]thio}benzyl)urea N-{3-tert-butyl-1-[3-(2-hydroxyethoxy)phenyl]-1H-pyrazol-5-yl}-N'-(2-{[3-(2-chloro-5-hydroxyphenyl)[1,2,4]triazolo[4,3-a]pyridin-6-yl]thio}benzyl)urea N-{3-tert-butyl-1-[4-(2-hydroxyethoxy)phenyl]-1H-pyrazol-5-yl}-N'-(2-{[3-(5-chloro-2-hydroxyphenyl)[1,2,4]triazolo[4,3-a]pyridin-6-yl]thio}benzyl)urea N-{3-tert-butyl-1-[4-(2-hydroxyethoxy)phenyl]-1H-pyrazol-5-yl}-N'-(2-{[3-(2-chloro-5-hydroxyphenyl)[1,2,4]triazolo[4,3-a]pyridin-6-yl]thio}benzyl)urea N-(2-{[3-(5-chloro-2-hydroxyphenyl)[1,2,4]triazolo[4,3-a]pyridin-6-yl]thio}benzyl)-N'-{1-[3-(2-hydroxyethoxy)phenyl]-3-[1-methyl-1-(methylthio)ethyl]-1H-pyrazol-5-yl}urea N-(2-{[3-(2-chloro-5-hydroxyphenyl)[1,2,4]triazolo[4,3-a]pyridin-6-yl]thio}benzyl)-N'-{1-[3-(2-hydroxyethoxy)phenyl]-3-[1-methyl-1-(methylthio)ethyl]-1H-pyrazol-5-yl}urea N-(2-{[3-(5-chloro-2-hydroxyphenyl)[1,2,4]triazolo[4,3-a]pyridin-6-yl]thio}benzyl)-N'-{1-[4-(2-hydroxyethoxy)phenyl]-3-[1-methyl-1-(methylthio)ethyl]-1H-pyrazol-5-yl}urea N-(2-{[3-(2-chloro-5-hydroxyphenyl)[1,2,4]triazolo[4,3-a]pyridin-6-yl]thio}benzyl)-N'-{1-[4-(2-hydroxyethoxy)phenyl]-3-[1-methyl-1-(methylthio)ethyl]-1H-pyrazol-5-yl}urea N-(2-{[3-(5-chloro-2-hydroxyphenyl)[1,2,4]triazolo[4,3-a]pyridin-6-yl]thio}benzyl)-N'-{3-[1,1-dimethyl-2-(methylthio)ethyl]-1-[3-(2-hydroxyethoxy)phenyl]-1H-pyrazol-5-yl}urea N-(2-{[3-(2-chloro-5-hydroxyphenyl)[1,2,4]triazolo[4,3-a]pyridin-6-yl]thio}benzyl)-N'-{3-[1,1-dimethyl-2-(methylthio)ethyl]-1-[3-(2-hydroxyethoxy)phenyl]-1H-pyrazol-5-yl}urea N-(2-{[3-(5-chloro-2-hydroxyphenyl)[1,2,4]triazolo[4,3-a]pyridin-6-yl]thio}benzyl)-N'-{3-[1,1-dimethyl-2-(methylthio)ethyl]-1-[4-(2-hydroxyethoxy)phenyl)]-1H-pyrazol-5-yl}urea N-(2-{[3-(2-chloro-5-hydroxyphenyl)[1,2,4]triazolo[4,3-a]pyridin-6-yl]thio}benzyl)-N'-{3-[1,1-dimethyl-2-(methylthio)ethyl]-1-[4-(2-hydroxyethoxy)phenyl]-1H-pyrazol-5-yl}urea N-(2-{[3-(5-chloro-2-hydroxyphenyl)[1,2,4]triazolo[4,3-a]pyridin-6-yl]thio}benzyl)-N'-{3-(1,1-dimethylpropyl)-1-[3-(2-hydroxyethoxy)phenyl]-1H-pyrazol-5-yl}urea N-(2-{[3-(2-chloro-5-hydroxyphenyl)[1,2,4]triazolo[4,3-a]pyridin-6-yl]thio}benzyl)-N'-{3-(1,1-dimethylpropyl)-1-[3-(2-hydroxyethoxy)phenyl]-1H-pyrazol-5-yl}urea N-(2-{[3-(5-chloro-2-hydroxyphenyl)[1,2,4]triazolo[4,3-a]pyridin-6-yl]thio}benzyl)-N'-{3-(1,1-dimethylpropyl)-1-[4-(2-hydroxyethoxy)phenyl]-1H-pyrazol-5-yl}urea N-(2-{[3-(2-chloro-5-hydroxyphenyl)[1,2,4]triazolo[4,3-a]pyridin-6-yl]thio}benzyl)-N'-{3-(1,1-dimethylpropyl)-1-[4-(2-hydroxyethoxy)phenyl]-1H-pyrazol-5-yl}urea N-{3-tert-butyl-1-[3-(2-hydroxyethoxy)phenyl]-1H-pyrazol-5-yl}-N'-(2-{[3-(3-cyano-4-hydroxyphenyl)[1,2,4]triazolo[4,3-a]pyridin-6-yl]thio}benzyl)urea N-{3-tert-butyl-1-[4-(2-hydroxyethoxy)phenyl]-1H-pyrazol-5-yl}-N'-(2-{[3-(3-cyano-4-hydroxyphenyl)[1,2,4]triazolo[4,3-a]pyridin-6-yl]thio}benzyl)urea N-(2-{[3-(3-cyano-4-hydroxyphenyl)[1,2,4]triazolo[4,3-a]pyridin-6-yl]thio}benzyl)-N'-{1-[3-(2-hydroxyethoxy)phenyl]-3-[1-methyl-1-(methylthio)ethyl]-1H-pyrazol-5-yl}urea N-(2-{[3-(3-cyano-4-hydroxyphenyl)[1,2,4]triazolo[4,3-a]pyridin-6-yl]thio}benzyl)-N'-{1-[4-(2-hydroxyethoxy)phenyl]-3-[1-methyl-1-(methylthio)ethyl]-1H-pyrazol-5-yl}urea N-(2-{[3-(3-cyano-4-hydroxyphenyl)[1,2,4]triazolo[4,3-a]pyridin-6-yl]thio}benzyl)-N'-{3-[1,1-dimethyl-2-(methylthio)ethyl]-1-[3-(2-hydroxyethoxy)phenyl]-1H-pyrazol-5-yl}urea N-(2-{[3-(3-cyano-4-hydroxyphenyl)[1,2,4]triazolo[4,3-a]pyridin-6-yl]thio}benzyl)-N'-{3-[1,1-dimethyl-2-(methylthio)ethyl]-1-[4-(2-hydroxyethoxy)phenyl]-1H-pyrazol-5-yl}urea N-(2-{[3-(3-cyano-4-hydroxyphenyl)[1,2,4]triazolo[4,3-a]pyridin-6-yl]thio}benzyl)-N'-{3-(1,1-dimethylpropyl)-1-[3-(2-hydroxyethoxy)phenyl]-1H-pyrazol-5-yl}urea N-(2-{[3-(3-cyano-4-hydroxyphenyl)[1,2,4]triazolo[4,3-a]pyridin-6-yl]thio}benzyl)-N'-{3-(1,1-dimethylpropyl)-1-[4-(2-hydroxyethoxy)phenyl]-1H-pyrazol-5-yl}urea N-[3-tert-butyl-1-(3-hydroxyphenyl)-1H-pyrazol-5-yl]-N'-(2-{[3-(2-ethylphenyl)[1,2,4]triazolo[4,3-a]pyridin-6-yl]thio}benzyl)urea $CONR^5R^6$, heteroaryl, heterocyclyl, aryl, carbocyclyl, aryloxy, carbocyclyloxy, heteroaryloxy and heterocyclyloxy;

p is 0, 1 or 2;

$R^5$ and $R^6$ are taken separately and are each independently selected from H and $(C_1-C_4)$alkyl, said $(C_1-C_4)$alkyl being optionally substituted with one to three substituents independently selected from OH and halo, or $R^5$ and $R^6$ are taken together with the nitrogen to which they are attached to form a piperazinyl, piperidinyl, morpholinyl or pyrrolidinyl group, wherein said piperazinyl, piperidinyl, morpholinyl and pyrrolidinyl groups are each optionally substituted by one to three OH);

---

---

The invention claimed is:

1. A method of treating a disease, disorder or condition in a mammal, said method comprising administering to said mammal a therapeutically effective amount of a compound of formula (I):

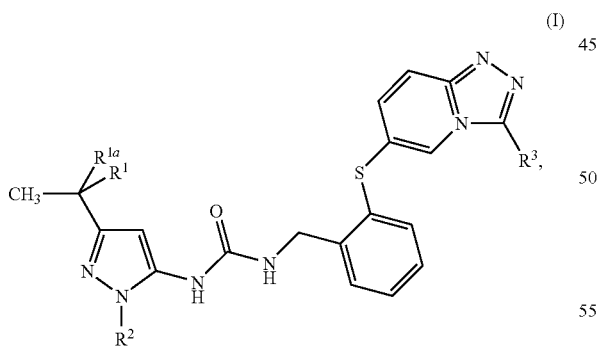

or a pharmaceutically acceptable salt thereof,
wherein:

$R^1$ is $CH_3$, $SCH_3$, $SCH_2CH_3$, $CH_2CH_3$, H or $CH_2SCH_3$;

$R^{1a}$ is $CH_3$ or $CH_2CH_3$;

$R^2$ is heteroaryl, heterocyclyl, aryl, or carbocyclyl;

$R^3$ is heteroaryl, heterocyclyl, aryl, carbocyclyl or $R^7$;

$R^7$ is $(C_1-C_6)$alkyl optionally substituted with one to three substituents independently selected from OH, halo, $NR^5R^6$, $(C_1-C_6)$alkoxy, $-S(O)_p(C_1-C_6)$alkyl, $CO_2H$, said aryl is independently phenyl or naphthyl, said phenyl or naphthyl being optionally substituted with one to three substituents independently selected from halo, $-CN$, $-CO_2H$, OH, $CONR^5R^6$, $NR^5R^6$, $R^8$ and $R^9$;

$R^8$ is independently selected from $(C_1-C_6)$alkyl, $(C_1-C_6)$alkoxy, $-CO_2(C_1-C_6)$alkyl, $-S(O)_p(C_1-C_6)$alkyl, $-CO(C_1-C_6)$alkyl and $(C_3-C_7)$cycloalkyl, wherein each $R^8$ is optionally substituted independently with one to three substituents independently selected from:

$(C_1-C_6)$alkoxy, optionally substituted with one to three substituents independently selected from OH, halo, $CO_2H$, $CONR^5R^6$ and $NR^5R^6$, $-S(O)_p(C_1-C_6)$alkyl, optionally substituted with one to three substituents independently selected from OH, halo, $CO_2H$, $CONR^5R^6$ and $NR^5R^6$,

OH, halo, $NR^5R^6$, $CO_2H$, $CONR^5R^6$, and $R^9$;

$R^9$ is heteroaryl$^2$, heterocyclyl$^2$, aryl$^2$, carbocyclyl$^2$, aryl$^2$oxy, carbocyclyl$^2$oxy, heteroaryl$^2$oxy or heterocyclyl$^2$oxy;

aryl$^2$ is phenyl or naphthyl wherein said phenyl or naphthyl in the definition of aryl$^2$ is optionally substituted with one to three substituents independently selected from halo, $-CN$, $-CO_2H$, OH, and $CONR^5R^6$;

carbocyclyl is a monocyclic or bicyclic, saturated or partially unsaturated ring system comprising from 3 to 10 ring carbon atoms, wherein said ring system is optionally substituted with one to three substituents independently selected from halo, —CN, —CO$_2$H, OH, CONR$^5$R$^6$, R$^8$ and R$^9$;

carbocyclyl$^2$ is a monocyclic or bicyclic, saturated or partially unsaturated ring system comprising from 3 to 10 ring carbon atoms, optionally substituted with one to three substituents independently selected from halo, —CN, —CO$_2$H, —OH and CONR$^5$R$^6$;

heterocyclyl and heterocyclyl$^2$ are each independently a 3- to 10-membered, saturated or partially unsaturated, monocyclic or bicyclic group comprising from 1 to 4 ring heteroatoms independently selected from N, O, and S;

heteroaryl and heteroaryl$^2$ are each independently a 5- to 10-membered, monocyclic or bicyclic aromatic group comprising from 1 to 4 ring heteroatoms independently selected from N, O, and S, provided that the total number of ring S atoms does not exceed 1, and the total number of ring O atoms does not exceed 1;

each heterocyclyl and heteroaryl group is, independently, optionally substituted on one to three ring carbon atoms with one to three substituents independently selected from halo, —CN, —CO$_2$H, OH, CONR$^5$R$^6$, R$^8$ and R$^9$, and independently optionally substituted on one to three ring nitrogen atoms with one to three substituents independently selected from H and (C$_1$-C$_6$)alkyl; and each heterocyclyl$^2$ and heteroaryl$^2$ group is, independently, optionally substituted on one to three ring carbon atoms with one to three substituents independently selected from halo, —CN, —CO$_2$H, OH and CONR$^5$R$^6$, and independently optionally substituted on one to three ring nitrogen atoms with one substituent independently selected from H and (C$_1$-C$_6$)alkyl, or a pharmaceutical composition comprising a therapeutically effective amount of a compound of formula (I) or a pharmaceutically acceptable salt thereof and a pharmaceutically acceptable diluent, carrier or adjuvant, wherein said disease, disorder or condition is selected from the group consisting of asthma, chronic or acute bronchoconstriction, small airways obstruction, emphysema, chronic obstructive pulmonary disease (COPD), bronchitis, bronchiectasis and COPD that includes chronic bronchitis.

2. A method of claim 1 wherein said asthma is selected from the group consisting of atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, non-atopic asthma, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome and bronchiolytis; said bronchitis is selected from the group consisting of acute bronchitis, acute laryngotracheal bronchitis, arachidic bronchitis, catarrhal bronchitis, croupus bronchitis, dry bronchitis, infectious asthmatic bronchitis, productive bronchitis, staphylococcus or streptococcal bronchitis and vesicular bronchitis; and said bronchiectasis is selected from the group consisting of cylindric bronchiectasis, sacculated bronchiectasis, fusiform bronchiectasis, capillary bronchiectasis, cystic bronchiectasis, dry bronchiectasis and follicular bronchiectasis.

3. A method of claim 1 wherein said disease, disorder or condition is selected from asthma and chronic obstructive pulmonary disease (COPD).

4. A method of treating a disease, disorder or condition in a mammal, said method comprising administering to said mammal a therapeutically effective amount of N-[3-tert-butyl-1-(3-chloro-4-hydroxyphenyl)-1H-pyrazol-5-yl]-N'-{2-[(3-{2-[(2-hydroxyethyl)thio]phenyl}[1,2,4]triazolo[4,3-a]pyridin-6-yl)thio]benzyl}urea, or a pharmaceutically acceptable salt thereof, or a pharmaceutical composition comprising a therapeutically effective amount of N-[3-tert-butyl-1-(3-chloro-4-hydroxyphenyl)-1H-pyrazol-5-yl]-N'-{2-[(3-{2-[(2-hydroxyethyl)thio]phenyl}[1,2,4]triazolo[4,3-a]pyridin-6-yl)thio]benzyl}urea, or a pharmaceutically acceptable salt of thereof, and a pharmaceutically acceptable diluent, carrier or adjuvant, wherein said disease, disorder or condition is selected from the group consisting of asthma, chronic or acute bronchoconstriction, small airways obstruction, emphysema, chronic obstructive pulmonary disease (COPD), bronchitis, bronchiectasis and COPD that includes chronic bronchitis.

5. A method of claim 4 wherein said asthma is selected from the group consisting of atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, non-atopic asthma, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome and bronchiolytis; said bronchitis is selected from the group consisting of acute bronchitis, acute laryngotracheal bronchitis, arachidic bronchitis, catarrhal bronchitis, croupus bronchitis, dry bronchitis, infectious asthmatic bronchitis, productive bronchitis, staphylococcus or streptococcal bronchitis and vesicular bronchitis; and said bronchiectasis is selected from the group consisting of cylindric bronchiectasis, sacculated bronchiectasis, fusiform bronchiectasis, capillary bronchiectasis, cystic bronchiectasis, dry bronchiectasis and follicular bronchiectasis.

6. A method of claim 4 wherein said disease, disorder or condition is selected from asthma and chronic obstructive pulmonary disease (COPD).

\* \* \* \* \*